(12) United States Patent
Ciotti

(10) Patent No.: US 11,369,578 B2
(45) Date of Patent: Jun. 28, 2022

(54) PERSISTENT TOPICAL ANTIMICROBIAL COMPOSITIONS AND METHODS OF USING THE SAME

(71) Applicant: BlueWillow Biologics, Inc., Ann Arbor, MI (US)

(72) Inventor: Susan Ciotti, Ann Arbor, MI (US)

(73) Assignee: BlueWillow Biologics, Inc., Ann Arbor, MI (US)

( * ) Notice: Subject to any disclaimer, the term of this patent is extended or adjusted under 35 U.S.C. 154(b) by 0 days.

(21) Appl. No.: 17/013,024

(22) Filed: Sep. 4, 2020

(65) Prior Publication Data

US 2021/0046023 A1 Feb. 18, 2021

Related U.S. Application Data

(63) Continuation-in-part of application No. 16/828,542, filed on Mar. 24, 2020, and a continuation-in-part of
(Continued)

(51) Int. Cl.
| | |
|---|---|
| *A61K 31/74* | (2006.01) |
| *A61K 31/14* | (2006.01) |
| *A61K 47/44* | (2017.01) |
| *A61K 9/00* | (2006.01) |
| *A61K 9/107* | (2006.01) |

(Continued)

(52) U.S. Cl.
CPC ............ *A61K 31/14* (2013.01); *A61K 9/0014* (2013.01); *A61K 9/0043* (2013.01); *A61K 9/1075* (2013.01); *A61K 31/34* (2013.01); *A61K 31/427* (2013.01); *A61K 31/4706* (2013.01); *A61K 31/513* (2013.01); *A61K 31/53* (2013.01); *A61K 31/685* (2013.01); *A61K 31/7064* (2013.01); *A61K 38/215* (2013.01); *A61K 45/06* (2013.01); *A61K 47/26* (2013.01); *A61K 47/34* (2013.01); *A61K 47/44* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 4,895,452 A | 1/1990 | Yiournas et al. | |
| 5,103,497 A | 4/1992 | Hicks | |
| (Continued) | | | |

FOREIGN PATENT DOCUMENTS

| | | |
|---|---|---|
| EP | 2 545 937 A1 | 1/2013 |
| WO | WO 95/31956 A1 | 11/1995 |
| (Continued) | | |

OTHER PUBLICATIONS

Wu et al., "The outbreak of COVID-19: An overview," J Chin Med Assoc, 83: 217-220 (Year: 2020).*
(Continued)

*Primary Examiner* — M Franco G Salvoza
(74) *Attorney, Agent, or Firm* — Foley & Lardner LLP

(57) ABSTRACT

The present disclosure relates to nanoemulsion compositions with certain surfactant blend ratios that impart enhanced permeability. Such compositions are useful for topical, mucosal and intranasal applications and allow for the greater delivery of one or more active agents to the application site to prevent infection by a microorganism.

19 Claims, 50 Drawing Sheets

Specification includes a Sequence Listing.

Related U.S. Application Data application No. PCT/US2019/061408, filed on Nov. 14, 2019.

(60) Provisional application No. 62/990,534, filed on Mar. 17, 2020, provisional application No. 62/767,966, filed on Nov. 15, 2018, provisional application No. 62/860,089, filed on Jun. 11, 2019.

(51) Int. Cl.

| | | |
|---|---|---|
| *A61K 31/34* | (2006.01) | |
| *A61K 31/427* | (2006.01) | |
| *A61K 31/4706* | (2006.01) | |
| *A61K 31/513* | (2006.01) | |
| *A61K 31/53* | (2006.01) | |
| *A61K 31/685* | (2006.01) | |
| *A61K 31/7064* | (2006.01) | |
| *A61K 38/21* | (2006.01) | |
| *A61K 45/06* | (2006.01) | |
| *A61K 47/26* | (2006.01) | |
| *A61K 47/34* | (2017.01) | |
| *A61P 31/14* | (2006.01) | |

(56) References Cited

U.S. PATENT DOCUMENTS

| | | | |
|---|---|---|---|
| 6,015,832 | A | 1/2000 | Baker, Jr. et al. |
| 6,506,803 | B1 | 1/2003 | Baker, Jr. et al. |
| 6,559,189 | B2 | 5/2003 | Baker, Jr. et al. |
| 6,635,676 | B2 | 10/2003 | Baker, Jr. et al. |
| 6,844,005 | B2 | 1/2005 | Wahi et al. |
| 7,314,624 | B2 | 1/2008 | Baker et al. |
| 8,163,802 | B2 | 4/2012 | Wahi |
| 9,737,497 | B2 | 8/2017 | Wahi et al. |
| 9,750,706 | B2 | 9/2017 | Wahi et al. |
| 2003/0161790 | A1 | 8/2003 | Wahi et al. |
| 2003/0223934 | A1 | 12/2003 | Wahi |
| 2004/0043041 | A1 | 3/2004 | Baker, Jr. et al. |
| 2005/0100612 | A1 | 5/2005 | Capps |
| 2009/0143477 | A1 | 6/2009 | Baker, Jr. et al. |
| 2009/0235933 | A1 | 9/2009 | Wahi |
| 2009/0246163 | A1 | 10/2009 | Wahi |
| 2009/0258946 | A1 | 10/2009 | Wahi |
| 2010/0004337 | A1 | 1/2010 | Wahi |
| 2010/0055152 | A1 | 3/2010 | Wahi |
| 2010/0226983 | A1 | 9/2010 | Sutcliffe et al. |
| 2012/0201779 | A1 | 8/2012 | Wahi |
| 2012/0276182 | A1 | 11/2012 | Baker, Jr. et al. |
| 2017/0105950 | A1 | 4/2017 | Wahi et al. |
| 2017/0181985 | A1 | 6/2017 | Wahi et al. |
| 2017/0246294 | A1* | 8/2017 | Baker, Jr. ............... A61K 39/35 |

FOREIGN PATENT DOCUMENTS

| | | | | |
|---|---|---|---|---|
| WO | WO-2005074947 | A2 * | 8/2005 | ............. A61K 31/14 |
| WO | WO 2008/137747 | A1 | 11/2008 | |
| WO | WO 2009/131995 | A1 | 10/2009 | |
| WO | WO 2009/132342 | A1 | 10/2009 | |
| WO | WO 2015/143386 | A1 | 9/2015 | |
| WO | WO 2017/201390 | A1 | 11/2017 | |

OTHER PUBLICATIONS

Pereira et al., "Benzalkonium Chlorides: Uses, Regulatory Status, and Microbial Resistance,"Appl Environ Microbiol 85(13):e00377-19 (Year: 2019).*

Rutter, "Drug absorption through the skin: a mixed blessing," Archive of Disease in Childhood, 62: 220-221 (Year: 1987).*

Alanen et al., "Measurement of hydration in the stratum corneum with the MoistureMeter and comparison with the Corneometer," *Skin Res Technol,* 10:32-37 (2004).

Avis, K. E., "Parenteral Preparations—History, Administration, Components, Production, Quality Control, Packaging, Labeling", Remington's Pharmaceutical Sciences, fifteenth edition, 1975, 1461-1487.

Chilvers et al., "The effects of coronavirus on human nasal ciliated respiratory epithelium," *European Respiratory J.,* 78:965-970 (2001).

Chmielowiec-Korzeniowska et al., *Staphylococcus aureus* carriage state in healthy adult population and phenotypic and genotypic properties of isolated strains. Postepy Dermatol Alergol., 37(2):184-189 (Apr. 2020).

Deardoff, D. L., "Isotonic Solutions—Freezing Point, Calculations, Tonicity Testing, Methods", Remington's Pharmaceutical Sciences, fifteenth edition, 1975, 1405-1412.

Franz et al., Skin: Drug Application and Evaluation or Environmental hazards, The Finite Dose Technique as a Valid in vitro Model for the Study of Percutaneous Absorption in Man, *Current Problems in Dermatology,* vol. 7, pp. 58-68 (1978).

Franz, TJ: Percutaneous absorption: on the relevance of in vitro data, J. Invest Dermatol., vol. 64, pp. 190-195 (1975).

Glezen et al., "Risk of primary infection and reinfection with respiratory syncytial virus,"Am. J. Dis. Child., 140(6):543-6 (1986).

He et al., "Temporal dynamics in viral shedding and transmissibility of COVID-19," *Nat. Med.* (2020).

International Search Report and Written Opinion issued in International Patent Application No. PCT/US2019/061408, dated Feb. 5, 2020.

Richard et al., "Influenza A viruses are transmitted via the air from the nasal respiratory epithelium of ferrets," *Nature Communications,* 11:1-11 (2020).

Serup, J., Winter, C., Blichmann, A. simple method for the study of scale pattern and effects of a moisture-qualitative and quantitative evaluation by D-Squame® tape compared with parameters of epidermal hydration. Clinical and Experimental Dermatology, 1365-2230 (1989).

Wang et al., "Detection of SARS-CoV-2 in Different Types of Clinical Specimens," *JAMA,* E1 (2020).

Zanin et al., "The interaction between respiratory pathogens and mucus," *Cell Host Microbe,* 19(2): 159-168 (2016).

Zou et al., "SARS-CoV-2 Viral Load in Upper Respiratory Specimens of Infected Patients," *N. Engl. J. Med.,* 382:1177-1179 (2020).

International Search Report and Written Opinion issued in International Patent Application No. PCT/US2021/022534, dated Jul. 6, 2021.

* cited by examiner

Figure 45
Cross-Section of Mouse Nasal Epithelium 24 Hours Post Application
GFP* Applied in
BlueWillow's Nanoemulsion
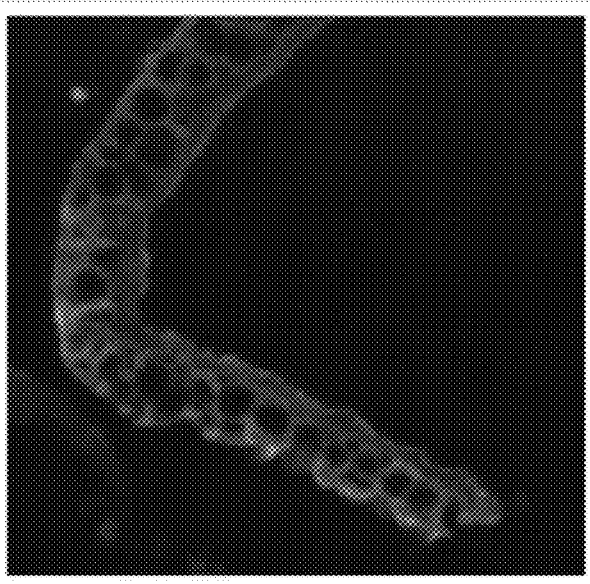
B
GFP* Applied in
Aqueous Solution
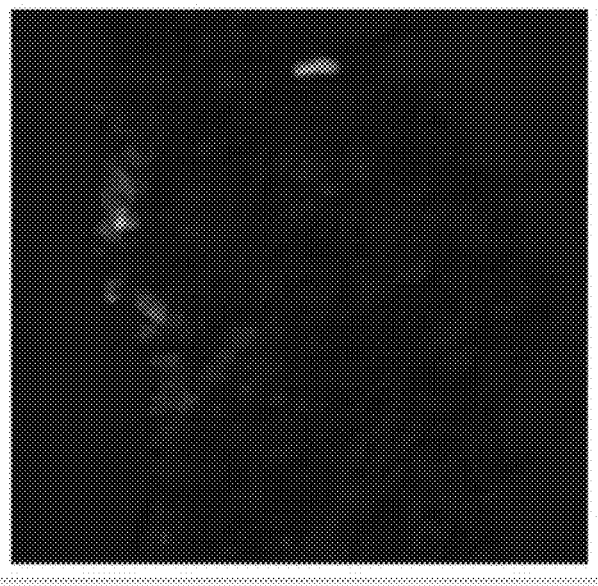
A
* Green fluorescent protein (GFP) was used to follow the material 24 hours post application.

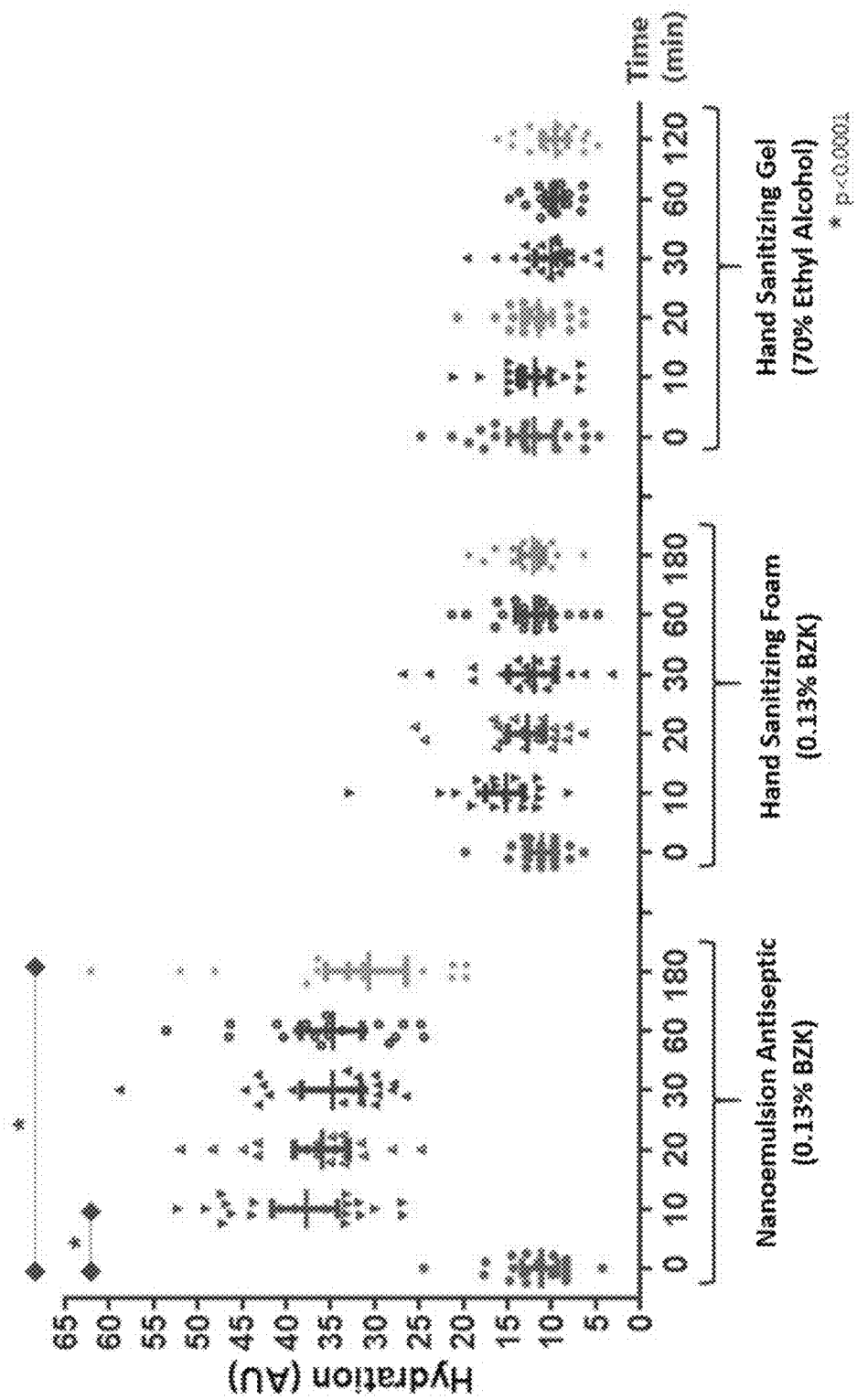

PERSISTENT TOPICAL ANTIMICROBIAL COMPOSITIONS AND METHODS OF USING THE SAME

CROSS-REFERENCE TO RELATED APPLICATIONS

This application is a continuation-in-part of U.S. patent application Ser. No. 16/828,542, filed Mar. 24, 2020, which claims priority to U.S. Provisional Patent Application No. 62/990,534, filed Mar. 17, 2020. U.S. patent application Ser. No. 16/828,542 is also a continuation-in-part of International Patent Application No. PCT/US2019/061408, filed Nov. 14, 2019, which in turn claims priority to U.S. Provisional Patent Application No. 62/860,089, filed Jun. 11, 2019, and U.S. Provisional Patent Application No. 62/767,966, filed Nov. 15, 2018. The contents of all of these applications are specifically incorporated herein by reference in their entirety.

SEQUENCE LISTING

The instant application contains a Sequence Listing which has been filed electronically in ASCII format and is hereby incorporated by reference in its entirety. Said ASCII copy, created on Jun. 14, 2021, is named 038491-0310_SL.txt and is 39019 bytes in size.

FIELD OF THE APPLICATION

The present application is directed to methods of preventing and/or decreasing the risk of microbial infection by topical administration of a persistent, long-acting antimicrobial nanoemulsion compositions.

BACKGROUND OF THE INVENTION

Nanoemulsions have been used as topical antimicrobial formulations as well as vaccine adjuvants. Prior teachings related to nanoemulsions are described in, for example, U.S. Pat. Nos. 6,015,832; 6,506,803; 6,559,189; 6,635,676; and 7,314,624. Methods of using persistent long-acting antimicrobial nanoemulsion compositions, where the site of application can be flushed with a liquid or water and the site still retains the 99.9% antimicrobial killing activity of the topically administered composition, have not been previously disclosed.

There exists a need to develop compositions useful in preventing and/or minimizing the risk of microbial infections. The present disclosure satisfies these needs.

SUMMARY OF THE INVENTION

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF DRAWINGS

FIG. 45 shows cross sections of nasal mouse epithelium 24 hours post application of green fluorescent protein (GFP) in aqueous solution (left) (FIG. 45A) and in nanoemulsion with a surfactant blend ratio of 1:9 (right) (FIG. 45B).

FIG. 50 shows skin hydration levels following one topical application of NE-BZK and two commercially available hand sanitizers.

DETAILED DESCRIPTION

I. Overview

Figure 1:
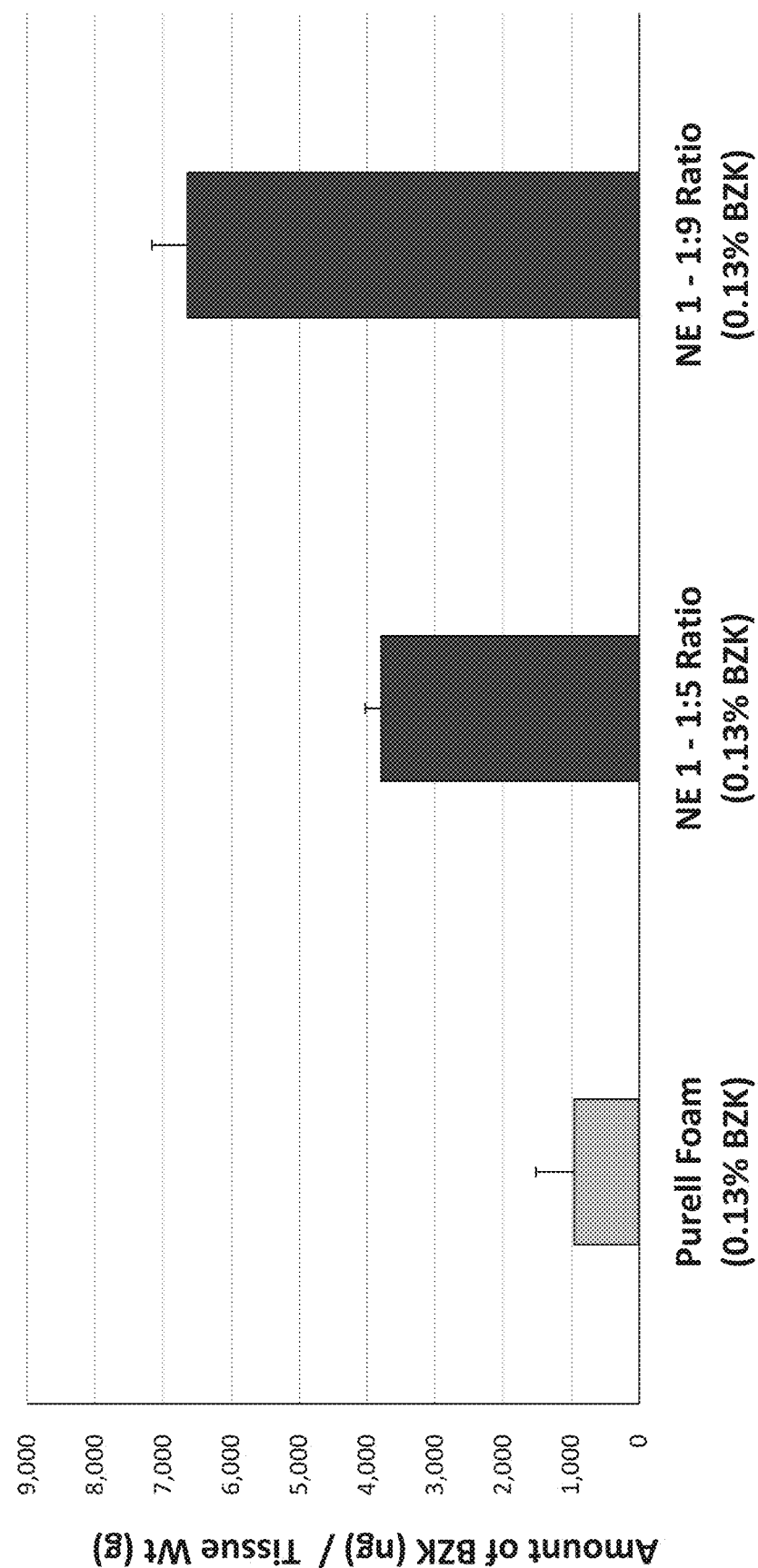
FIG. 1 shows epidermal levels of BZK (µg/g tissue) in human abdominal skin following one application (dose of 100 µl/cm$^2$, measured at 24 hours) of NE-1 formulations (0.13% BZK) with surfactant blend ratios 1:5 and 1:9 and Purell® Foam (0.13% BZK).

The present invention is directed to the surprising discovery that antibacterial nanoemulsion compositions, applied either topically, mucosally, ocularly or nasally, and comprising a quaternary ammonium compound and a nonionic surfactant, where the quaternary ammonium compound and surfactant are present in a defined ratio, exhibit highly unexpected persistence when applied to a skin or mucosal surface. The highly unexpected substantivity (e.g., "stickiness") of the compositions to a biological surface means that the compositions can function as long acting sanitizers, killing 99.9% of microorganisms present on the application site (e.g., skin or mucosal surface) at the time of application or for up to about 12 hours after application.

As described in the examples below, the compositions function to kill 99.9% of microorganisms, such as bacteria and viruses, present at the application site at the time of application. However, in contrast to non-nanoemulsion formulations comprising the same quaternary ammonium compound (e.g., such as benzakonium chloride), the compositions also kill 99.9% of microorganisms exposed to the application site for up to 12 hours after application. This "substantivity" is similar to the function of sunscreens and insect repellant, which function for a period of time after application.

At present, there is no other known or commercially available product which kills 99.9% of bacteria for a period of time after application, such as about 4, about 8, or up to about 12 hours. This property is highly desirable as it can be a useful tool in minimizing the spread of viral and bacterial diseases.

Moreover, also as detailed in the examples below, it was unexpectedly and surprisingly found that the ability to kill 99.9% of microorganisms exposed to the site of application for a period of up to about 12 hours is retained even after the site is flushed with water or another liquid, such as soap. Again, this property is analogous to a sunscreen that retains its properties even after a site of application is flushed with water (e.g., jumping in a pool or lake). There is no other known or commercially available product having this property.

Thus, in one aspect, the disclosure encompasses methods of treating and/or preventing a microbial infection, e.g., a viral or bacterial infection, comprising topically, mucosally, ocularly, or nasally (e.g., via a spray or swab) administering an antibacterial nanoemulsion composition described herein. The site of application can be, for example, mucosa, ocular, dermis, epidermis, skin, and/or squamous epithelium (the nasal vestibule is completely lined by squamous epithelium).

The antibacterial nanoemulsion comprises an aqueous phase, an oil phase comprising at least one pharmaceutically acceptable oil, at least one pharmaceutically acceptable organic solvent, and a combination of at least one a quaternary ammonium compound and at least one non-ionic surfactant, wherein the ratio of the concentration of the quaternary ammonium compound to nonionic surfactant is about 5:1 to about 1:27. In other embodiments, the ratio of the concentration of the quaternary ammonium compound to nonionic surfactant is about 1:2 to about 1:18. The significant and dramatic persistence and permeation of the nanoemulsions described herein can be compared to nanoemulsions having quaternary ammonium compound/non-ionic surfactant concentration ratios outside the narrow range disclosed herein.

This presence of a combination of a quaternary ammonium compound and a non-ionic surfactant, and in a defined concentration ratio, results in the bioadhesive nature of the nanoemulsions, which may aid in the "long acting" antimicrobial properties of the compositions.

Also encompassed by this disclosure are compositions to be used in the methods described herein.

Nanoemulsions kill viruses at concentrations that are nontoxic in humans. The nanoemulsions function by fusing with lipid bilayers of cell membranes, thereby destabilizing the lipid membrane of the microbial pathogen. In effect, the nanoemulsion "dissolves" the membrane or envelope surrounding the microbe (e.g., virus or bacteria), thus inactivating the virus or bacteria and eliminating the ability of the virus or bacteria to infect a host. The antimicrobial activity of nanoemulsions is nonspecific, unlike that of typical small molecule antimicrobial compositions, thus allowing broad-spectrum antimicrobial activity while limiting the capacity for the generation of resistance.

A key aspect of the disclosure is that the described nanoemulsions have a high permeation and residence time at the site of mucosal, ocular, or skin application, with significant microbial-killing nanoemulsion residing at the side of application for an extended period of time—e.g., about 4, about 8, or about 12 hours or more. Thus, the nanomemulsions can be routinely applied to sites of potential microbial infection, e.g., skin, nasal mucosa, ocular sites, and the mouth area, and the nanoemulsions will function to kill any microbes present at the application site, thereby preventing microbial infection. In addition, the nanoemulsion will kill microorganisms which are present at the site of nanoemulsion application, where the microorganism is present either before or after the nanoemulsion is applied. This is because the nanoemulsion will function to kill microorganisms already present prior to application and the nanoemulsion will reside at the site of application in a sufficient amount to kill microorganisms that comes into contact with the application site up to 24 hours after nanoemulsion application.

Nanoemulsion compositions may be applied periodically to mucosal, ocular, or skin surfaces of subjects at risk for microbial infection. Periodic applications will allow for constant residence of the microbial-killing nanoemulsion composition at and within the biological surface, and thus defend the subject from microbial particles contacted with these surfaces.

At present, there are no known compositions that can minimize or prevent microbial infection. The only methods currently available are barrier methods, comprising using medical grade masks that cover the nose and mouth combined with eye goggles or face shields. The present disclosure therefore satisfies an urgent need in the art.

An exemplary patient population includes subjects susceptible to exposure to microbial infections, such as healthcare workers, subjects in coronavirus quarantine zones, subjects caring for COVID-19 patients, and subjects with pre-existing conditions including but not limited to diabetes, heart conditions, or respiratory conditions such as asthma or COPD.

Microbial Infections

The nasal cavity is a primary route of entry for viral and bacterial respiratory pathogens. Recently published studies on SARS-CoV-2 highlight the prominent role of nasal epithelium in initial infection, viral replication and transmission (He et al., "Temporal dynamics in viral shedding and transmissibility of COVID-19*,*" *Nat. Med*. (2020); Zou et al., "SARS-CoV-2 Viral Load in Upper Respiratory Specimens of Infected Patients," *N. Engl. J. Med.,* 382:1177-1179 (2020); and Wang et al., "Detection of SARS-CoV-2 in Different Types of Clinical Specimens," *JAMA*, E1 (2020)).

Other highly contagious and pathogenic viruses such as influenza, respiratory syncytial virus (RSV) and human coronavirus also initiate infection via the nose (Richard et al., "Influenza A viruses are transmitted via the air from the nasal respiratory epithelium of ferrets," *Nature Communications,* 11:1-11 (2020); Glezen et al., "Risk of primary infection and reinfection with respiratory syncytial virus," Am. J. Dis. Child., 140(6):543-6 (1986); and Chilvers et al., "The effects of coronavirus on human nasal ciliated respiratory epithelium," *European Respiratory J.,* 18:965-970 (2001)).

Once inoculated, viral pathogens can spread from the nose into the lower respiratory tract, causing morbidity and mortality from lower respiratory tract disease. Bacterial pathogens, such as *Staphylococcus aureus*, can reside in nasal mucosal tissues for long periods serving as a source for infection in other areas of the host or opportunistic respiratory infections (Chmielowiec-Korzeniowska et al., "*Staphylococcus aureus* carriage state in healthy adult population and phenotypic and genotypic properties of isolated strains. Postepy Dermatol Alergol., 37(2):184-189 (April 2020)). These factors highlight the need for improved broad-spectrum protection strategies against infections acquired through the nose. The current COVID-19 pandemic has significantly raised the urgency of this need.

An exemplary nanoemulsion described herein is a nanoemulsion comprising benzalkonium chloride as the quaternary ammonium compound (NE-BZK). This composition incorporates the FDA-monographed active ingredient benzalkonium chloride (0.13% BZK) in plant oil nanodroplets emulsified in water. The nanodroplets are approximately 350 nm in size and have positively charged surfaces. Given their size, they persist following application for up to 24 hours in hair follicles, sweat glands and sebaceous glands which can harbor pathogens. While these nanodroplets are small enough to penetrate these glands of the skin, they are too large to penetrate through the epidermis and are therefore not absorbed systemically. Being positively charged, the nanodroplets repel each other which keeps the active ingredient BZK from crystallizing, which has clinical relevance in that once crystallized on the skin, BZK loses its antimicrobial activity and can cause skin irritation. The surfaces of enveloped viruses (e.g. SARS-CoV-2, influenza, RSV) and cell-walled bacteria (e.g. *Staphylococcus, Enterococcus, Pseudomonas*) are negatively charged (Zanin et al., "The interaction between respiratory pathogens and mucus," *Cell Host Microbe*, 19(2): 159-168 (2016)). Therefore, the positively charged nanodroplets in NE-BZK are attracted to these microbes, delivering the antiseptic directly to the surface of the pathogen where killing occurs.

Ethyl alcohol products comprise over 80% of skin sanitizers available in the U.S. and have been promoted by the Centers for Disease Control and Prevention as preferred for infection risk reduction (cdc.gov/coronavirus/2019-ncov/hcp/hand-hygiene.html; and Guideline for Hand Hygiene in Health-Care Settings Recommendations of the Healthcare Infection Control Practices Advisory Committee and the HICPAC/SHEA/APIC/IDSA Hand Hygiene Task Force; CDC Morbidity and Mortality Weekly Report Oct. 25, 2002/Vol. 51/No. RR-16). Aqueous 0.13% BZK preparations are also widely available. However, alcohol and water evaporate quickly after application, leading to short duration of action. In the case of aqueous 0.13% BZK, rapid evaporation of the water component leads to breakdown of the positively charged BZK-containing micelles which determine antimicrobial activity in these formulations. An alcohol-free, broad-spectrum skin antiseptic that maintains activity for many hours after application while hydrating the skin represents a significant scientific and clinical advancement.

The antiseptic, antimicrobial nanoemulsions described herein are a novel approach which can be used as an alternative to conventional topical and mucosal formulations to increase substantivity. This system comprises the active (e.g. a quaternary ammonium compound such as BZK) and upon contact with the skin, leaves behind a layer of excipients along with the active upon evaporation. The formed layer is the nanoemulsion droplet material that act a residual liquid film which is rapidly adhering to the stratum corneum. The co-surfactant in the nanoemulsion is a thermo-responsive hydrogel, which is extremely bioadhesive at the surface temperature of the skin and increases the interaction between two materials, the nanoemulsion droplets and the skin stratum corneum for a given period through interfacial forces. The advantage of these nanoemulsions over conventional semisolid formulations is that it allows treatment of larger areas of affected skin with an extended contact time and adequate substantivity.

As described in the examples below, in an exemplary nanoemulsion described herein, the incorporation of the FDA-monographed skin antiseptic 0.13% BZK in oil-in-water nanodroplets in NE-BZK confers significant advantages over typical aqueous BZK formulations. In these studies, NE-BZK demonstrated broad-spectrum in-vitro activity against every enveloped virus, gram-positive bacteria and gram-negative bacteria tested including but not limited to SARS-CoV-2, Influenza and MRSA. The pathogens against which this antiseptic demonstrated consistent greater than 4 log killing cause substantial human morbidity and mortality. The persistence of ex-vivo antimicrobial activity up to 12 hours after NE-BZK is applied and the maintenance of antimicrobial activity with dilution of NE-BZK combine with strong evidence of in-vivo skin hydration, represent a significant scientific and clinical advancement in skin antiseptics.

Viral Transmission

Coronaviruses are a family of hundreds of viruses that can cause fever, respiratory problems, and sometimes gastrointestinal symptoms. Coronavirus Disease 2019 (COVID-19) is one of seven members of this family known to infect humans, and the third in the past three decades to jump from animals to humans. Since emerging in China in December 2019, this new coronavirus has caused a global health emergency. Patient populations at risk for more serious COVID-19 disease include elderly subjects, those with weakened immune systems, and those with preexisting health conditions, such diabetes, heart disease, and asthma or other respiratory conditions such as COPD. "Elderly subjects" can be defined as subjects aged about 50 or older, aged about 55 or older, aged about 60 or older, aged about 65 or older, aged about 70 or older, aged about 75 or older, or aged about 80 or older.

Human coronaviruses most commonly spread from an infected person to others through respiratory droplets produced when an infected person coughs or sneezes, close personal contact (such as caring for or living with an infected person), or touching an object or surface with the virus on it and then touching the mouth or eyes prior to hand washing. Three human coronaviruses (SARS-CoV, MERS-CoV, and 2019-nCoV) are also thought to spread from infected animals to people through contact. The new 2019-nCoV virus spreads much more readily than the one that caused severe acute respiratory syndrome, or SARS (also a coronavirus).

Viruses such as influenza and coronavirus infect a subject by entering the nasal or respiratory tract, where they replicate in epithelial cells. Interruption of the replication process can be a tactic used to prevent infection. Moreover, coronaviruses need a period of time to replicate for successful infection. Thus, this period of time offers a window into an infection prevention strategy, as well as a method for minimizing the risk of infection.

There are two ways a coronavirus can be transmitted via air. In droplet form, the coronavirus is airborne for a few seconds after someone sneezes or coughs. A coronavirus droplet is able to travel only a short distance before gravitational forces pull it down. Someone close enough for the virus particles to reach in that brief period can therefore be infected. So can anyone who comes into contact with virus-containing droplets that fall onto a surface. The new coronavirus can survive on surfaces for several hours; hence the importance of hand-washing after touching a surface in a public place. An aerosol is a wholly different physical state: Particles are held in the air by physical and chemical forces. Fog is an aerosol; water droplets are suspended in air. The suspended particles remain for hours or more, depending on factors such as heat and humidity. If virus particles, probably on droplets of mucus or saliva, can be suspended in air for more than a few seconds, as the measles virus can, then anyone passing through that pathogenic cloud could become infected. Nevertheless, the fact that coronaviruses spread via airborne droplets demonstrates the need for more rigorous methods of preventing or minimizing the risk of infection, particularly for patent populations at greater risk for infection, or for patent populations at greater risk for significant adverse effects following infection.

II. Summary of the Experimental Results

Antimicrobial Activity is Retained Even with Extensive Nanoemulsion Dilution

Figure 48:
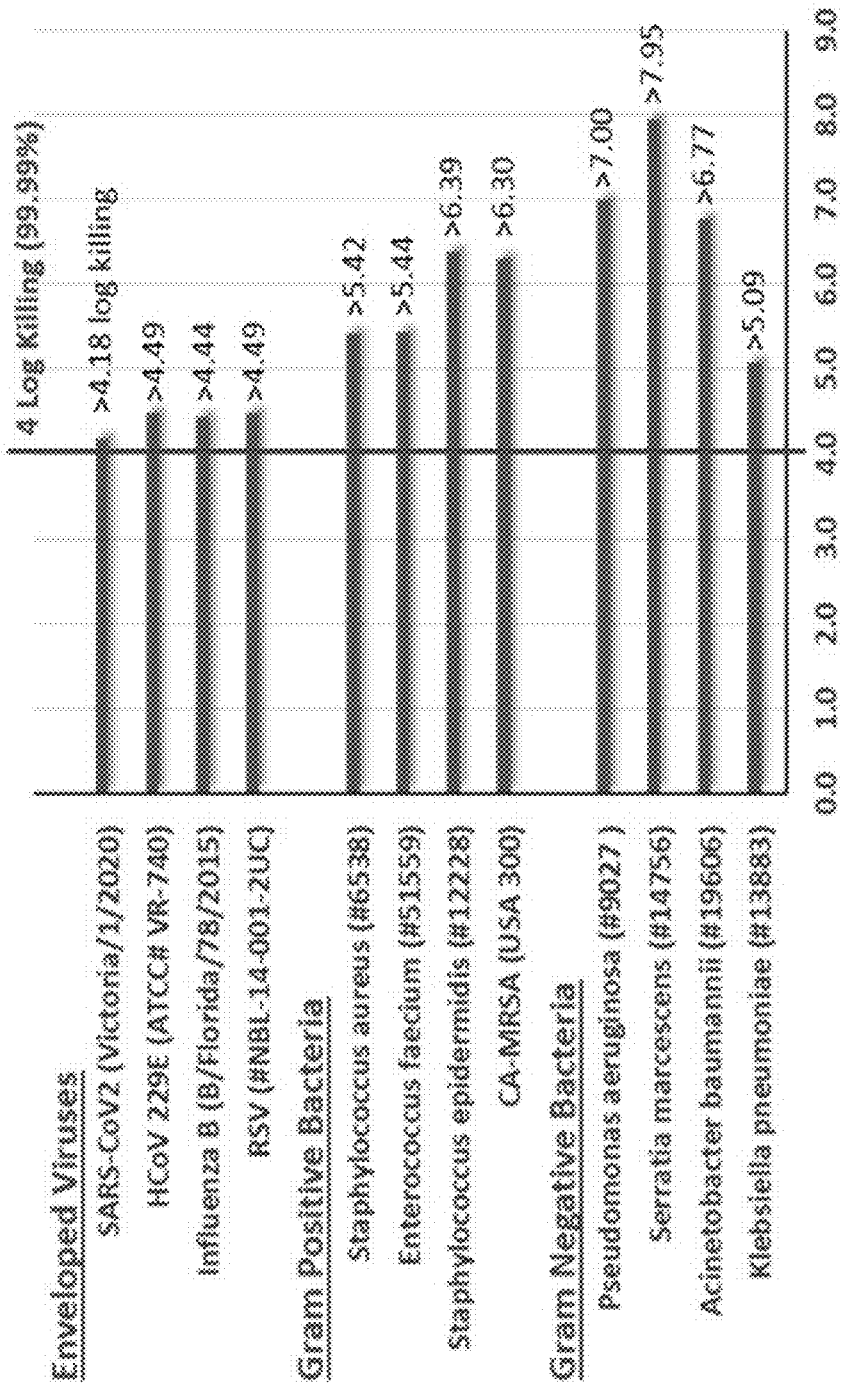
FIG. 48 shows log reduction in viral and bacterial pathogens treated with a topical, persistent antimicrobial nanoemulsion having a preferred ratio of quaternary ammonium compound:non-ionic surfactant.

Example 20 details experimental results demonstrating the persistence, or substantivity, of the antibacterial nanoemulsions when applied to a skin or mucosal surface. A nanoemulsion comprising the quaternary ammonium compound BSK at 0.13% concentration. FIG. 48 illustrates the antiviral and antibacterial activity of the nanoemulsion composition tested (NE-BZK) against several common pathogens, including the novel coronavirus SARS-CoV-2, HCoV 229E, Influenza B, RSV, *S. aureus, E. faecium, S. epidermidis*, CA-MRSA, *P. aeruginosa, S. marcescens, A. baumannii*, and *K. pneumoniae*. NE-BZK deactivated >99.99% of all viruses following five minutes of exposure (the earliest time point measured) and >99.99% of all bacterial pathogens following one minute of exposure.

Example 21 details the results of an evaluation of the antibacterial activity against human coronavirus and MRSA of an antibacterial nanoemulsion comprising BZK (NE-BZK) as compared to aqueous BZK (AQ-BZK). Antiviral activity was measured against human coronavirus (HCoV229E) in a time-kill study following 5 minutes exposure. As presented in Table 32, both the nanoemulsion antiseptic and AQ-BZK formulations achieved >99.99% killing when formulated at full strength or a 1/10 dilution. Notably, at a dilution of 1/20, the aqueous AQ-BZK formulation lost all activity while in dramatic contrast the nanoemulsion antiseptic continued to demonstrate >99.99% killing.

Additionally, four different concentrations of NE-BZK from 1/10 to 1/100 dilution were tested for in vitro antimicrobial activity against MRSA as compared to the same concentrations of AQ-BZK following 5 minutes of exposure. As presented in Table 33, both the nanoemulsion antiseptic and AQ-BZK formulation achieved >99.9999% killing when formulated at 1/10 and 1/20 dilution. However, at a 1/50 and 1/100 dilution the AQ-BZK lost activity while nanoemulsion antiseptic continued to demonstrate >99.99% killing. Dilution is an inherent process when applying any antiseptic to skin given the sweat and sebaceous glands present.

Persistence of the Antimicrobial Nanoemulsion Compositions

Figure 49:
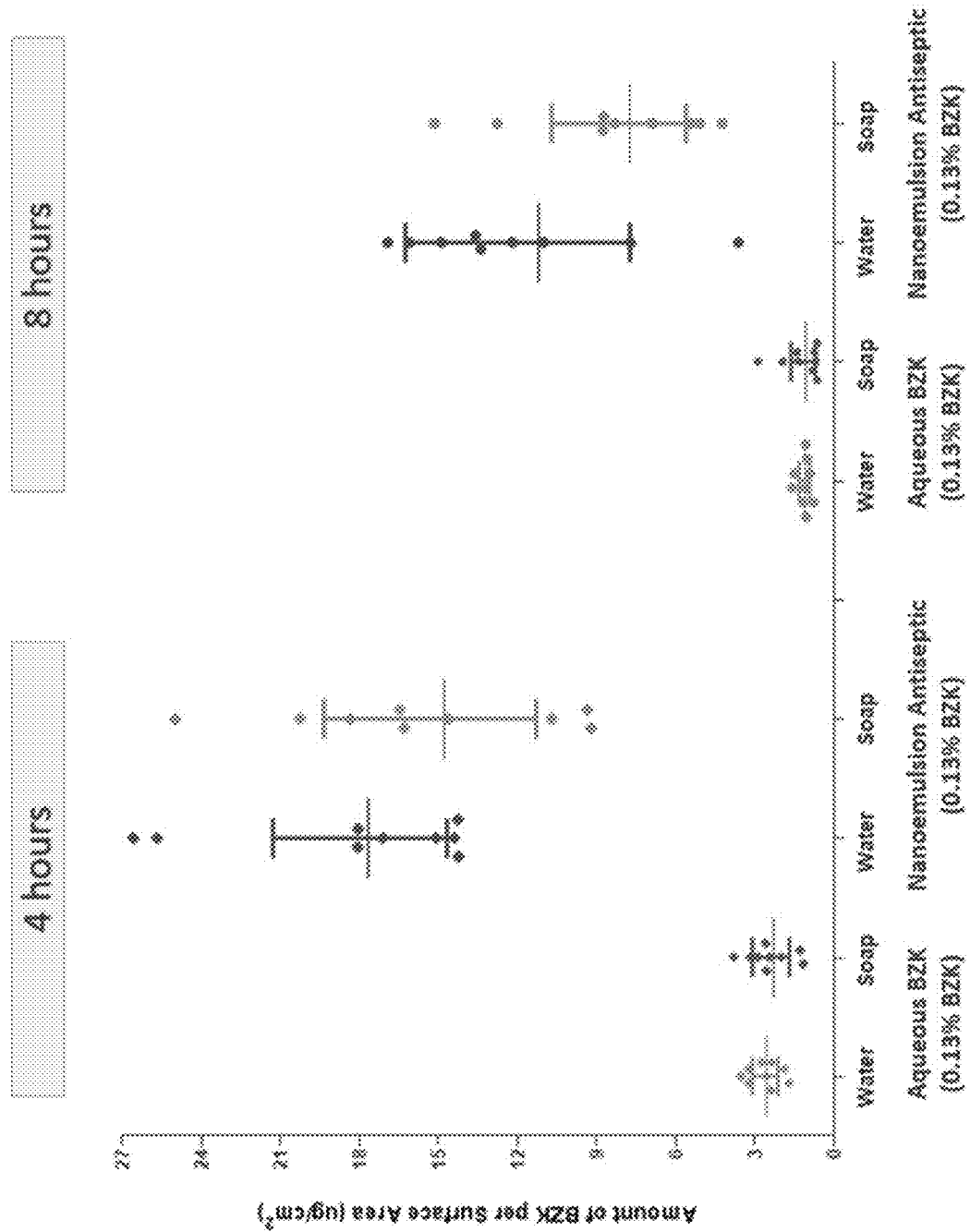
FIG. 49 shows skin substantivity of BZK from a nanoemulsion comprising BZK as compared to aqueous BZK after water and soap-water washing procedure at 4 hours and at 8 hours following application.

FIG. 49 and Table 34 shows that a model nanoemulsion comprising BZK (NE-BZK) exhibited a 5.8 and 3.8 fold increase substantivity on volunteers' skin surface at 4 hours after two washing protocols (e.g. (1) water rinse and (2) soap rub+water rinse) and 16.5 and 7.3 fold increase, respectively, after 8 hours after a two washing protocols as compared to a 0.13% AQ-BZK solution.

Moreover, it was also shown that antiviral activity is retained for an extensive period of time following application. Specifically, Example 21 details measurement of antiviral activity of the model nanoemulsion NE-BZK against human coronavirus (HCoV229E) ex vivo in a time-kill study following 15 minutes exposure of skin pre-treated with the nanoemulsion antiseptic (0.13% BZK) or AQ-BZK for 4 and 8 hours. As presented in Table 35, NE-BZK achieved >4.7% log killing at both the 4- and 8 hour time points. In contrast, aqueous BZK (AQ-BZK) exhibited only 1.5 log killing at 4 hours and below the limit of detection at 8 hours.

Next, the antimicrobial activity of the model nanoemulsion NE-BZK was measured against MRSA ex vivo in a time-kill study following 15 minutes exposure of skin pre-treated and compared to AQ-BZK (0.13% BZK) and an alcohol-based nasal sanitizer (0.62% ethyl alcohol). As presented in Table 36, NE-BZK achieved >5.2% log killing at 4, 8 and 12 hours. In contrast, aqueous BZK (AQ-BZK) formulation exhibited only 0.5 log killing at 4 hours and 0.21 log killing at 8 hours. Moreover, the alcohol-based nasal sanitizer demonstrated no antimicrobial activity at either 8 or 12 hours after application.

Permeation Correlated with Specific Surfactant Blend Concentration Ratio

Figure 2:
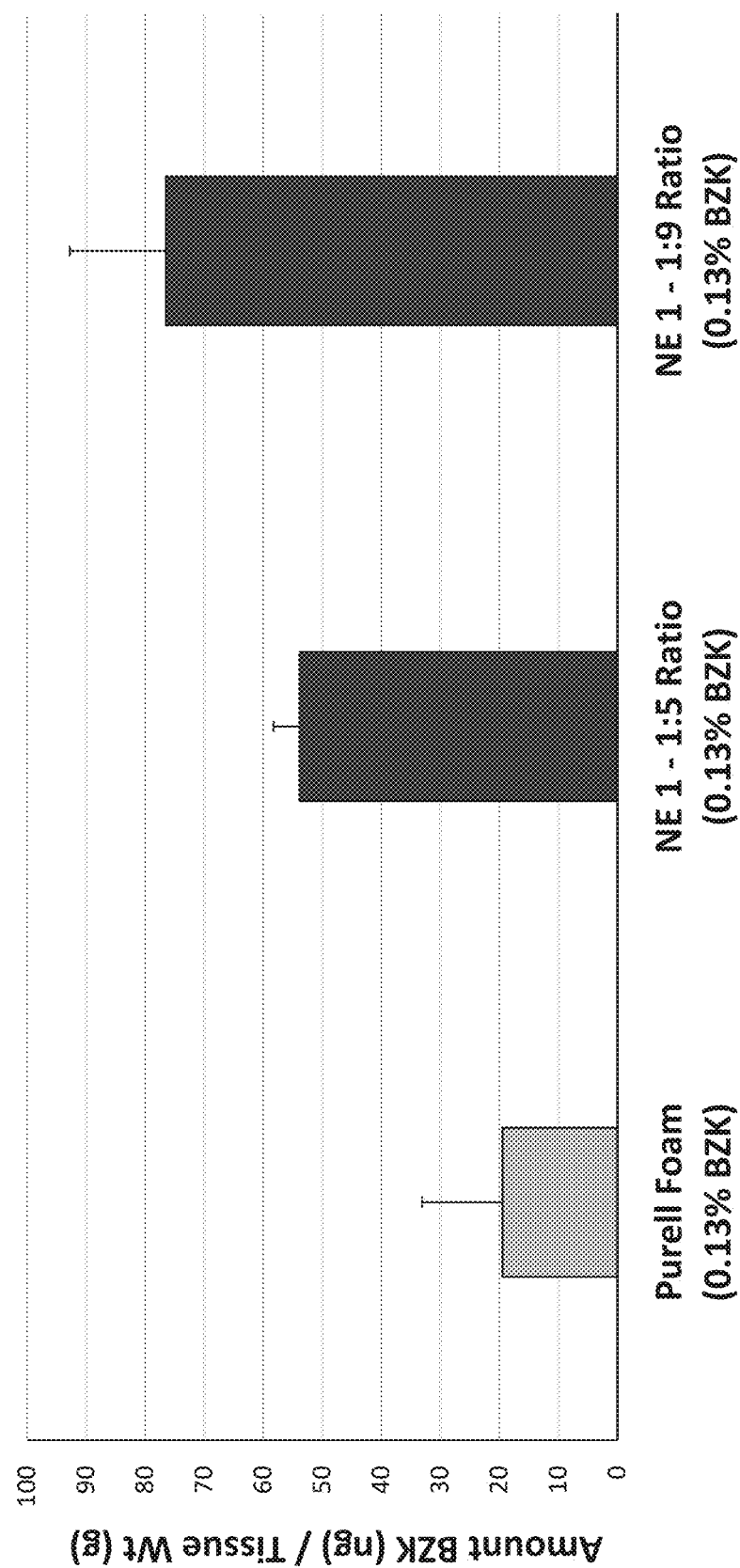
FIG. 2 shows dermal levels of BZK (µg/g tissue) in human abdominal skin following one application (dose of 100 µl/cm$^2$, measured at 24 hours) of NE-1 formulations (0.13% BZK) with surfactant blend ratios 1:5 and 1:9 and Purell® Foam.

Applicant's data clearly and unequivocally details the surprising and significant results observed with the claimed narrow range of a surfactant blend ratio. Specifically, Example 6 shows that in a comparison of a non-nanoemulsion formulation having 0.13% BKC (Purell® Foam) with nanoemulsion (NE) formulations having 0.13% BZK and surfactant blend ratios of 1:5 and 1:9, the amount of BZK delivered into human abdominal skin epidermal tissue was almost 600% higher for the nanoemulsion formulation having a 1:9 surfactant blend ratio as compared to the non-nanoemulsion formulation (6642 ng BZK/gram tissue, as compared to 953 ng BZK/gram tissue for the Purell® Foam). See also FIGS. 2 (epidermis) and 3 (dermis), showing graphs of levels of BZK (µg/g tissue) following application of one dose of 100 µl/cm$^3$ measured 24 hours after application. More specifically, after one application of 0.13% NE formulations to human skin, the nanoemulsion formulation delivered almost 4 to 7 times more BZK into the epidermis as compared to a marketed 0.13% Purell® Foam (FIG. 1). Additionally, with respect to the dermis levels, the nanoemulsion formulation delivered 3 to 4 times more BZK as compared to the marketed product, Purell® Foam, indicating that the BZK was able to penetrate into the deeper dermal levels of the skin from the nanoemulsion formulations (FIG. 2).

Figure 5:
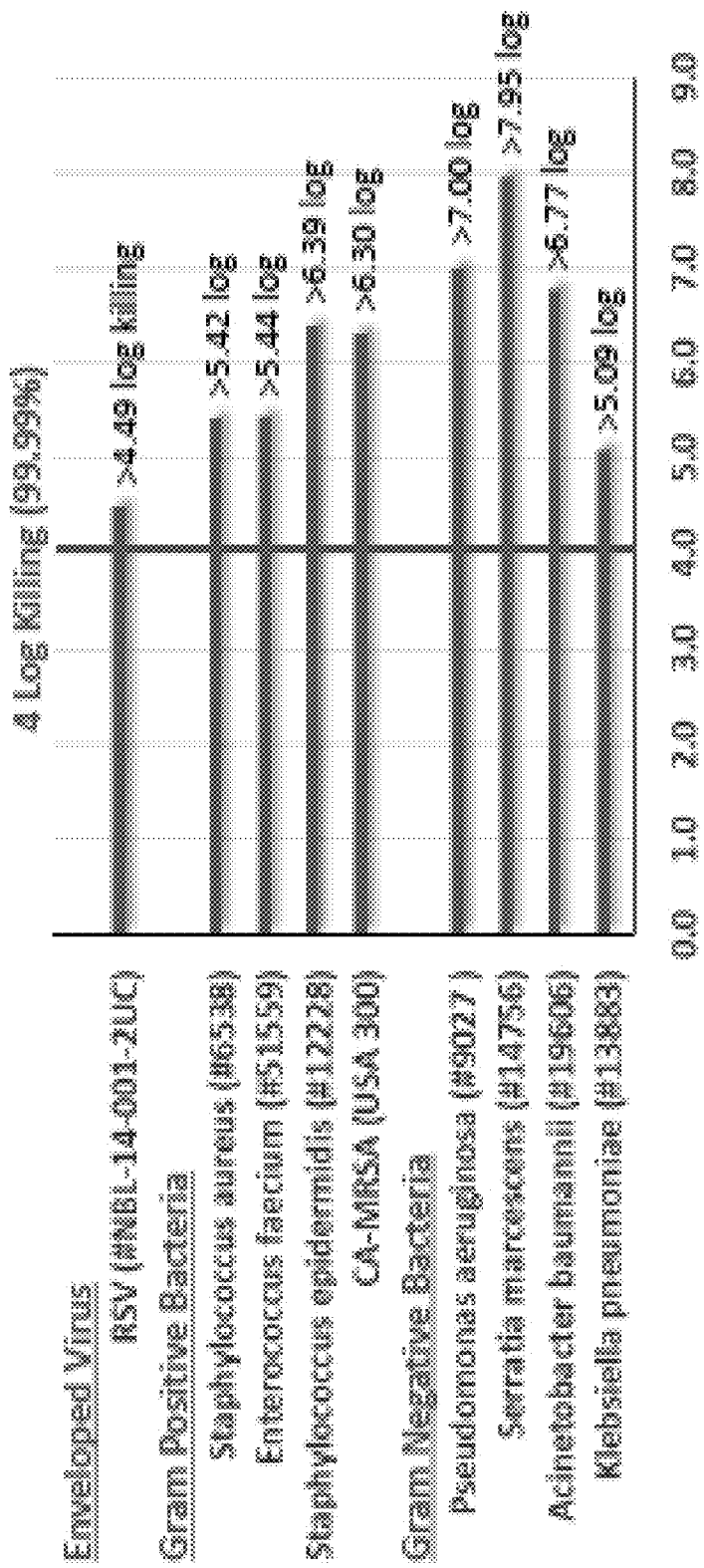
FIG. 5 shows the log killing of NE-2 (surfactant blend ratio: 1:5; 0.13% BZK) microorganisms and virus following one-minute exposure.

Antiseptics formulated using Applicant's nanoemulsion having this superior permeability have been shown by Applicant to kill 99.9% of enveloped respiratory syncytial virus (RSV), SARS-CoV2, HCoV229E, and Influenza B within one minute upon exposure (see FIGS. 5 and 48; and Examples 1 and 21). Furthermore, is has also been shown that after nanoemulsion carrying green fluorescent protein (GFP) has permeated into mouse nasal epithelium, nanoemulsion remains within the tissue for at least 24 hours post-administration (see Example 3 and FIG. 45).

As detailed herein, it was surprisingly discovered that the surfactant ratio of the nanoemulsion was critical to achieving unexpected nanoemulsion permeability. As clearly depicted in FIGS. 1 and 2, nanoemulsions having representative surfactant ratios of 1:5 and 1:9 showed dramatic and significantly greater permeation (amount of BZK (ng)/tissue weight (g)) as compared to a non-nanoemulsion formulation having the same quantity of BZK.

Figure 3:
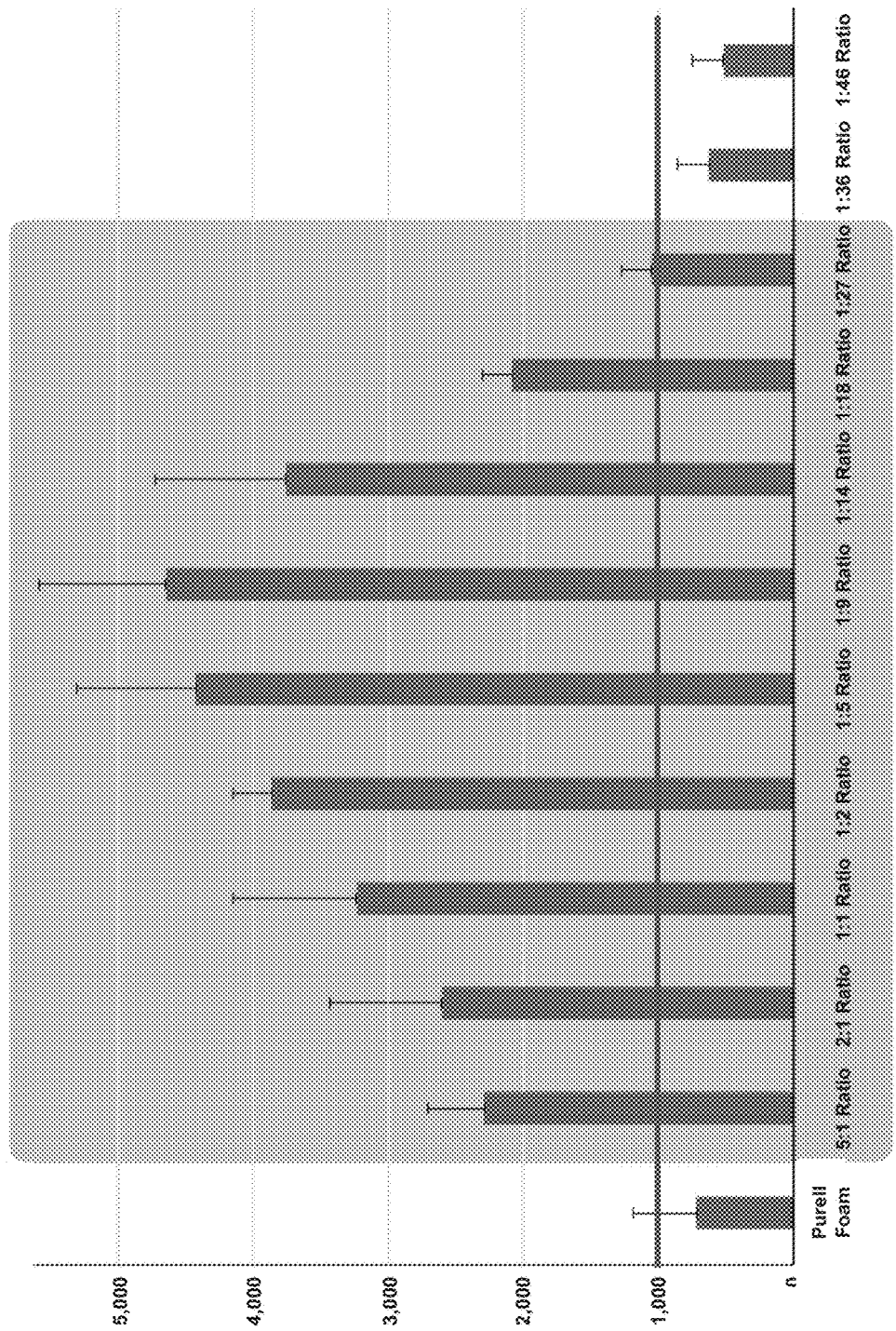
FIG. 3 shows Epidermal Skin Permeation of 0.13% BZK Formulations vs Ratio of Quaternary Ammonium Compound to Nonionic Surfactant, and epidermal levels of BZK (µg/g tissue) in human abdominal skin following one application (dose of 100 µl/cm$^2$, measured at 24 hours) of NE-1 formulations (0.13% BZK) with different surfactant blend ratios (5:1, 2:1, 1:1, 1:2, 1:5, 1:9, 1:14, 1:18, and 1:27) and Purell® Foam (0.13% BZK).
Figure 4:
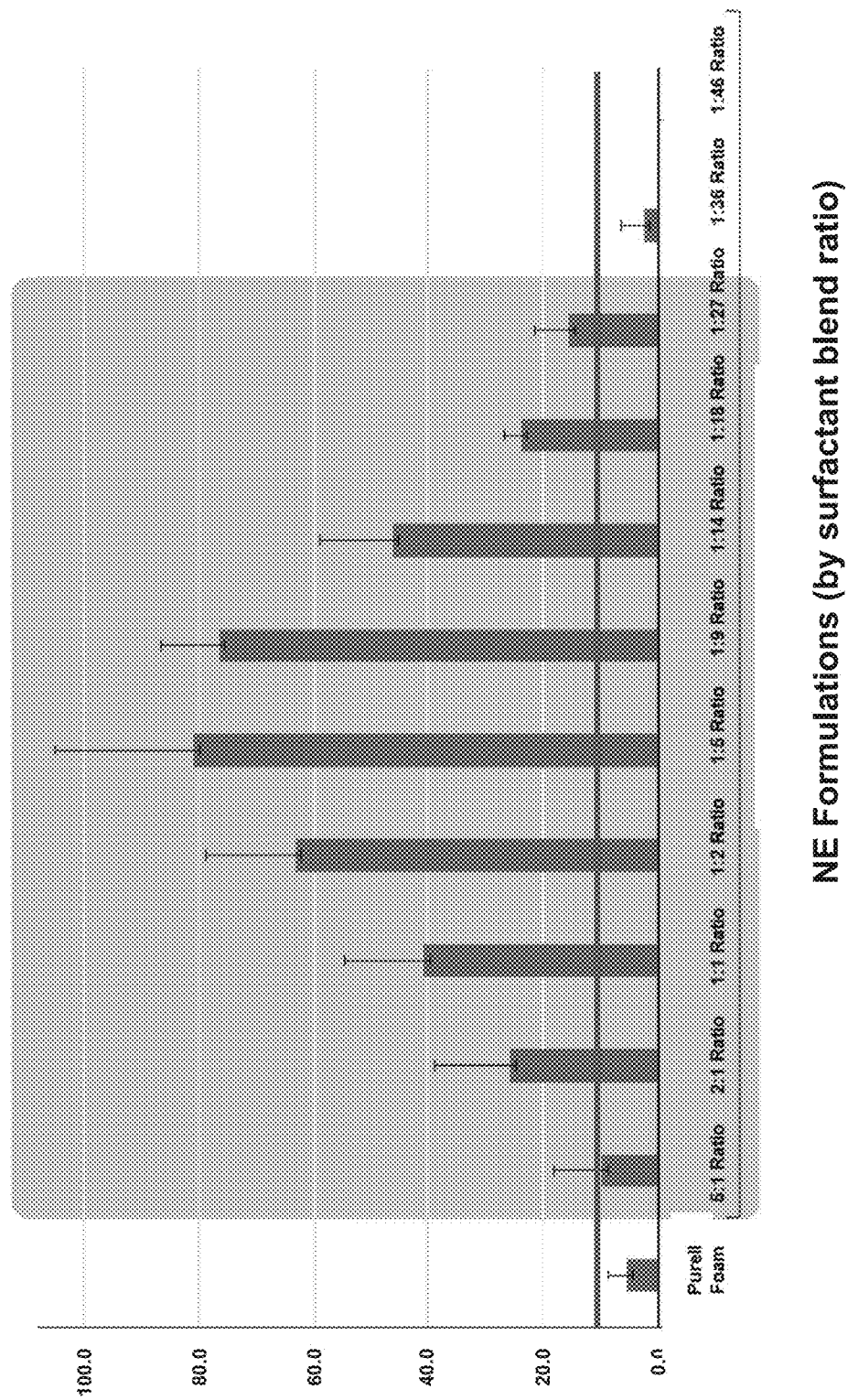
FIG. 4 shows Dermal Skin Permeation of 0.13% BZK Formulations vs Surfactant Ratio, and dermal levels of BZK (µg/g tissue) in human abdominal skin following one application (dose of 100 µl/cm$^2$, measured at 24 hours) of NE-1 formulations (0.13% BZK) with different surfactant blend ratios (5:1, 2:1, 1:1, 1:2, 1:5, 1:9, 1:14, 1:18, and 1:27) and Purell® Foam (0.13% BZK).

A clear bell curve of permeation vs. surfactant blend ratio is depicted in FIGS. 3 and 4, demonstrating that nanoemulsions having a preferred surfactant blend ratio show dramatic and significant increased permeation in the epidermis (FIG. 3) and dermis (FIG. 4) as compared to non-nanoemulsion formulations of the same quaternary ammonium compound at the same concentration (Purell® Foam), and as compared to nanoemulsion formulations having surfactant blend ratios outside the claimed range of about 5:1 up to about 1:27. Outside the claimed surfactant blend ratio, the amount of drug in the epidermis (FIG. 3) and dermis (FIG. 4) is dramatically less. The impact of the claimed narrow range of surfactant blend ratios on permeation was not known prior to the present invention.

This enhanced permeability allows for the nanoemulsion compositions described herein to deliver more of the quaternary ammonium compound to the site of application, as well as any additional therapeutic agent present in the nanoemulsion, and to also have a longer residence time at the site of application as compared to non-nanoemulsion compositions containing the same quaternary ammonium compound present at the same concentration. This property is critical to effective prevention of microbial infections.

The nanoemulsion compositions described herein can also comprise a therapeutic agent suitable for topical, mucosal, ocular, or intranasal delivery. The enhanced permeability of the nanoemulsions described herein allows for the nanoemulsion compositions to deliver more of the therapeutic agent to a site of application, and to also have a longer residence time of the therapeutic agent at the site of application, as compared to non-nanoemulsion compositions containing the same therapeutic agent at the same concentration. The site of application can be, for example, mucosa, ocular, dermis, epidermis, skin, and/or squamous epithelium (the nasal vestibule is completely lined by squamous epithelium).

Figure 10:
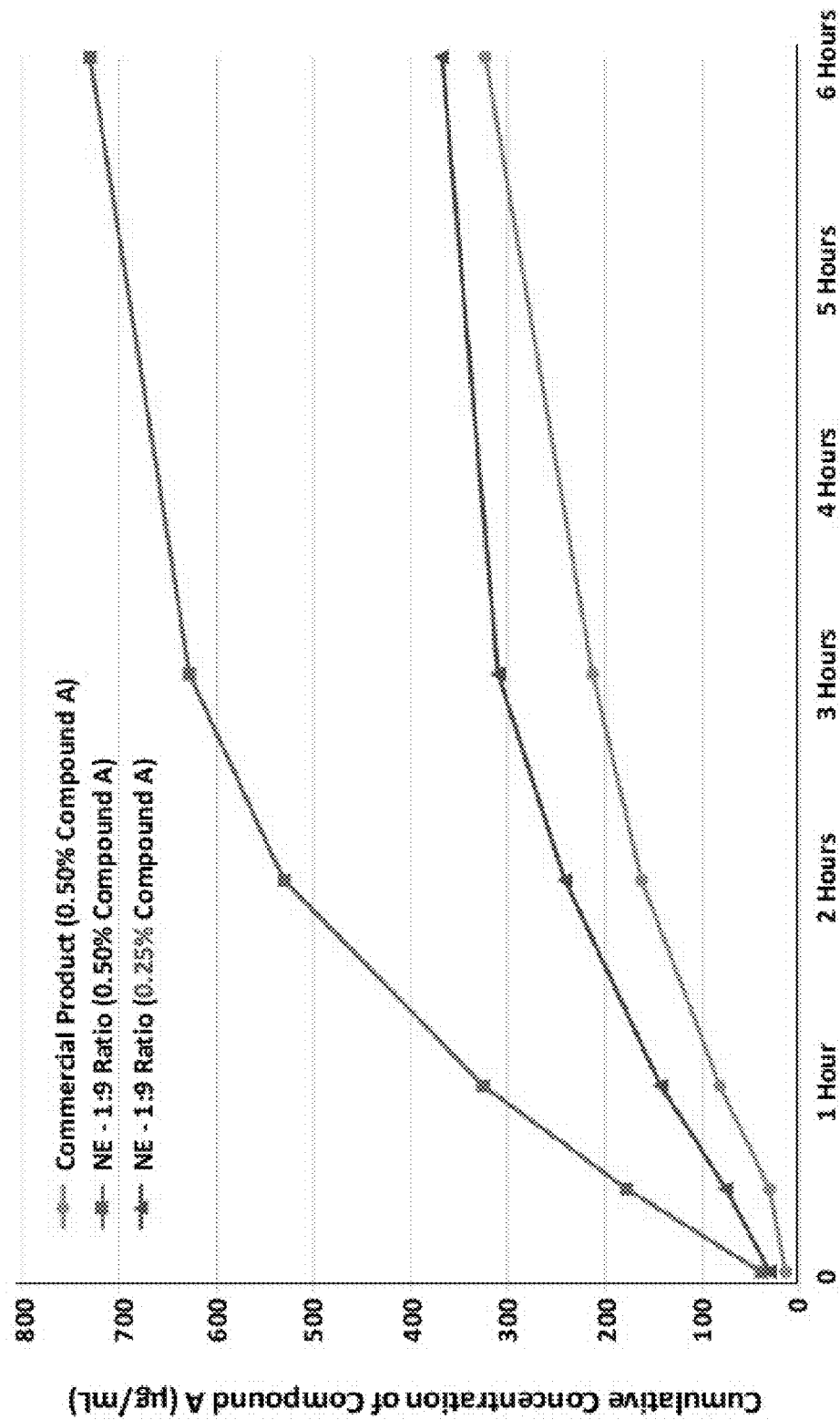
FIG. 10 shows the results of the in vitro mucin permeation studies of Compound A with the commercially available intranasal product of Compound A (0.50% Compound A) and the NE-1 (surfactant blend ratio: 1:9) with 0.50% and 0.25% of Compound A.

For example, as graphically depicted in FIG. 10, the permeation of a representative model therapeutic agent Compound A was significantly greater when present in a nanoemulsion formulation as compared to a non-nanoemulsion formulation, having the same drug concentration. In particular, the commercial product of Compound A, having a drug concentration of 50% present in non-nanoemulsion formulation, showed a cumulative concentration of Compound A (µg/mL) at 6 hours following application of about 325 µg/mL, in contrast to a concentration of about 730 µg/mL for the nanoemulsion having a surfactant ratio of 1:9 and a drug concentration of 50%, an increase in drug permeation of about 125%.

Figure 12:
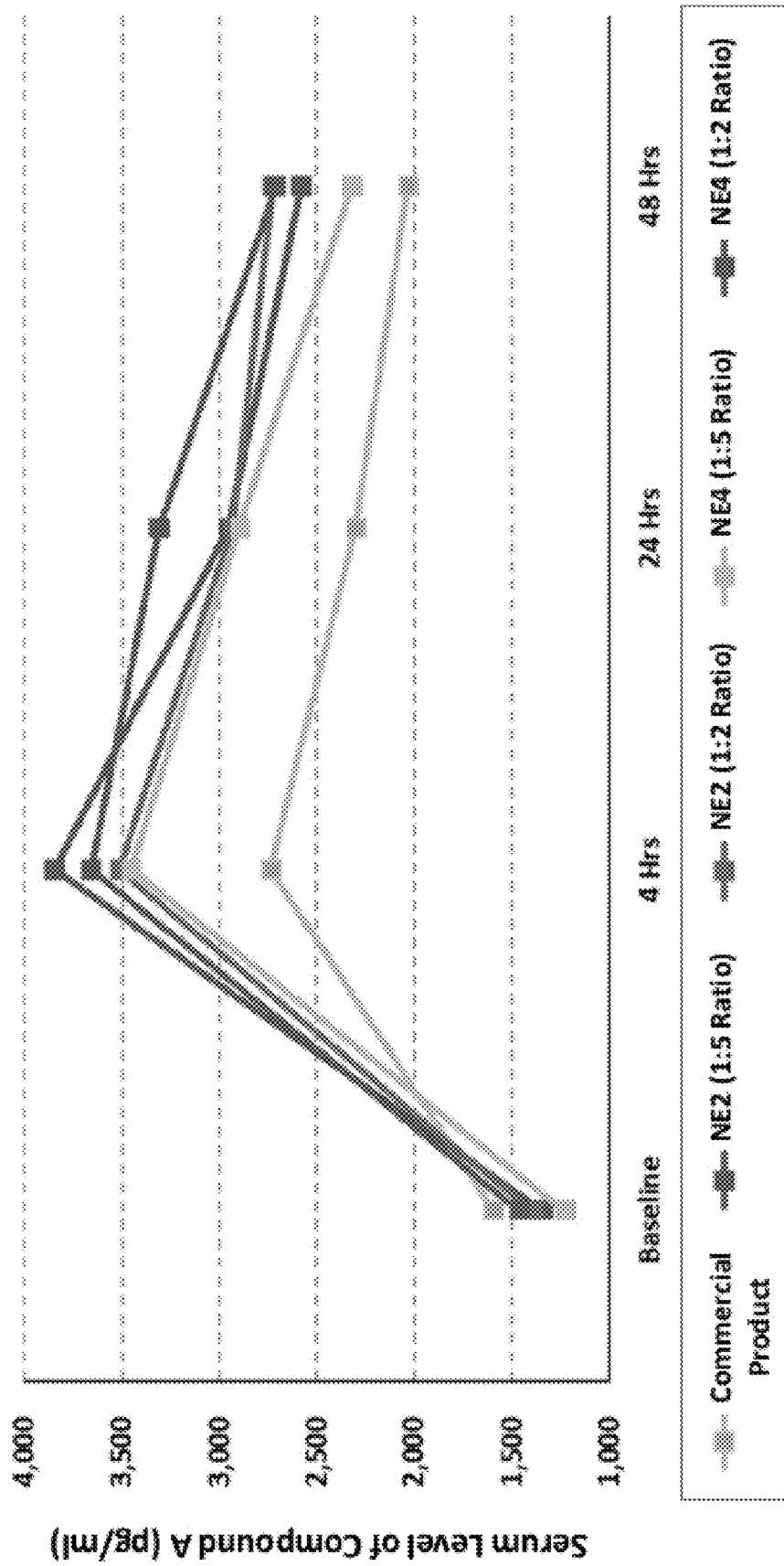
FIG. 12 shows the serum levels of Compound A following one administration with the commercially available intranasal product of Compound A (0.50% Compound A) and the NE-2 and NE-4 formulations (surfactant blend ratios: 1:5 and 1:2) with 0.50% of Compound A.

Similarly, Examples 11 and 12 show in vitro and in vivo data, respectively, for a nanoemulsion having a model Compound A incorporated within the nanoemulsion. In vitro all of the nanoemulsion formulations resulted in significantly greater serum levels of Compound A (pg/mL)—all greater than about 3500 pg/mL—as compared to the conventional, non-nanoemulsion formulation having the same compound at the same concentration; e.g., about 2750 pg/mL—a difference of about 30% (FIG. 12). The results from Example 12 demonstrate that greater mucin penetration of Compound A incorporated in a nanoemulsion measured in vitro directly correlates with Compound A penetration in the nasal epithelium in vivo when animals are intranasally treated with the NE-Compound A formulations, and leads to greater systemic drug delivery as compared to the commercially available product containing the same concentration of Compound A.

These results show that nanoemulsion formulations having a preferred surfactant blend ratio significantly enhance the permeation of a component therapeutic agent. In particular, these results show that nanoemulsion formulations having a preferred surfactant blend ratio significantly enhance the systemic absorption of a representative incorporated therapeutic agent (Compound A) in vivo as compared to a non-nanoemulsion commercial product having the same active at the same concentration. Also demonstrated is that a significantly lower amount of a therapeutic agent can be administered with any one of the nanoemulsion compositions described herein to achieve systemic absorption equivalent or greater than a non-nanoemulsion composition having the same therapeutic agent.

Provided in one aspect is a method of preventing or reducing the risk of infection in a subject caused by exposure to a microorganism, the method comprising administering a composition comprising a nanoemulsion to the skin, nasal vestibule or passages, ocular, or the mucosa of the mouth, of the subject, either before or after the microbial exposure.

The nanoemulsion composition can be repeatedly replied, such at least once every 24 hours, or periodically during a 24 hr period as described herein. Other exemplary application schedules include about once every hour, once every about 2 hours, once every about 3 hours, once every about 4 hours, once every about 5 hours, once every about 6 hours, once every about 7 hours, once every about 8 hours, once every about 9 hours, once every about 10 hours, once every about 11 hours, once every about 12 hours, once every about 13 hours, once every about 14 hours, once every about 15 hours, once every about 16 hours, once every about 17 hours, once every about 18 hours, once every about 19 hours, once every about 20 hours, once every about 21 hours, once every about 22 hours, once every about 3 hours, once every about 4 hours, once every about 5 hours, once every about 23 hours, or once every about 24 hours.

In the instance where the nanoemulsion composition is applied to the skin, nasal tissue, mucosa, and/or squamous epithelium, the enhanced permeability also results in increased skin, mucosa, and/or squamous epithelium hydration. For example, the increase in skin, mucosa, and/or squamous epithelium hydration can be about 25%, about 50%, about 75%, about 100%, about 125%, about 150%, about 175%, or about 200%, as compared to the skin, mucosa, and/or squamous epithelium hydration prior to application of the nanoemulsion.

Figure 6:
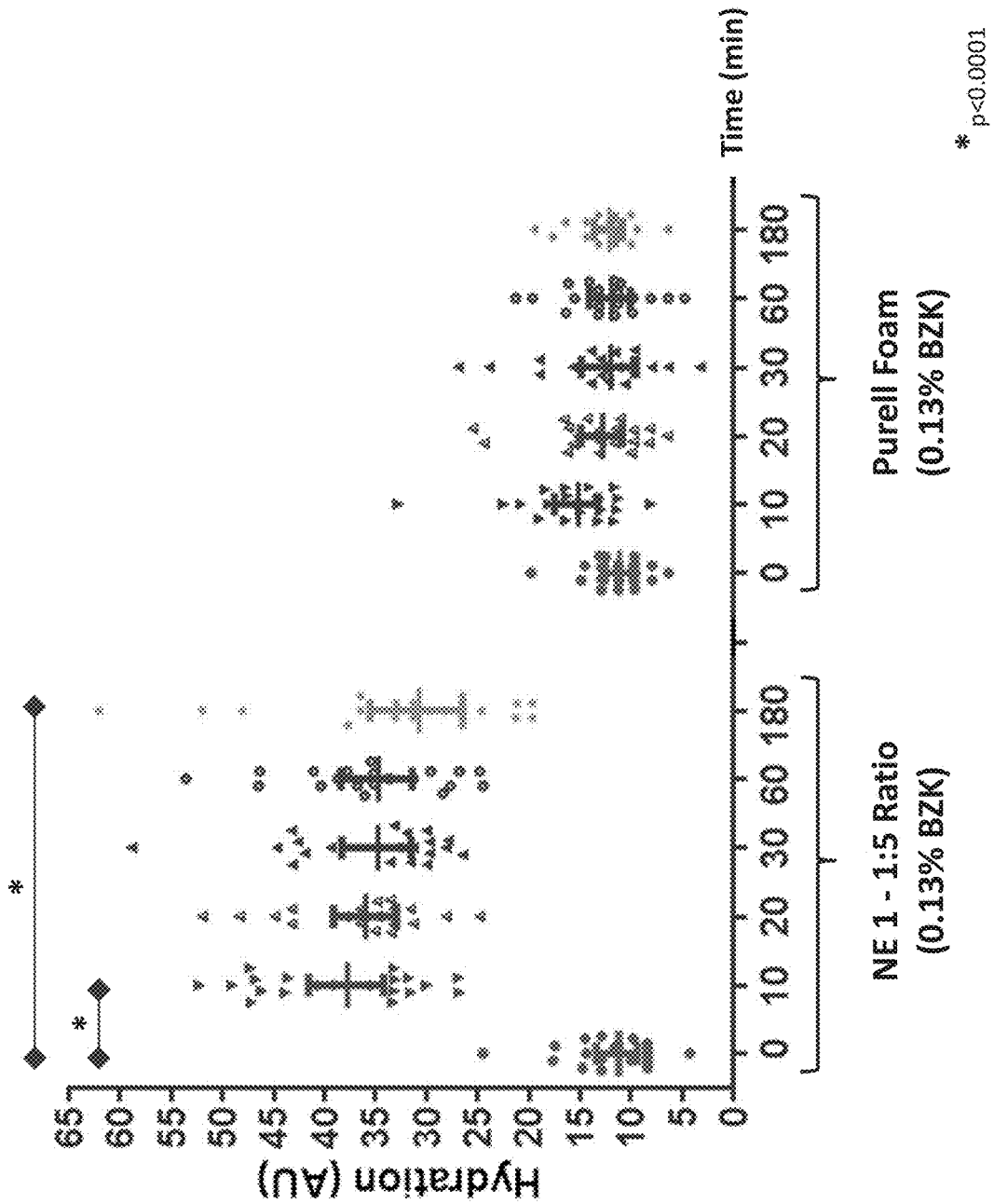
FIG. 6 shows skin hydration study results of NE-1 (surfactant blend ratio: 1:5; 0.13% BZK) and Purell® Foam (0.13% BZK).

In particular, Example 9 and FIG. 6, and Example 22 and FIG. 50, detail data showing that a nanoemulsion having a surfactant blend ratio of 1:5 and 0.13% BZK shows significant and dramatically improved hydration as compared to a non-nanoemulsion formulation comprising the same quaternary ammonium compound at the same concentration (Purell® Foam (0.13% BZK)). These results demonstrate that single application of a nanoemulsion according to the invention resulted in a significant and sustained increase in skin hydration.

Furthermore, in some embodiments, the nanoemulsions described herein with a specific surfactant blend ratio exhibit surprising and unexpected long-term stability even at high temperatures. In particular, Example 8 details data demonstrating that a nanoemulsion having a surfactant blend ratio of 1:5 was stable for 1 month even at the most extreme storage condition of 50° C. (122° F.). Additional data (not shown) demonstrates that nanoemulsions according to the invention, including nanoemulsions comprising an incorporated therapeutic agent, are stable for at least 3 months at up to 50° C., up to 12 months at 50° C., and up to 60 months at 5° C. This is highly unexpected. At severely high temperatures, emulsions are prone to rapid destabilization within a few hours to a couple of days. This data demonstrates that the tested formulations will offer key advantages for use in extremely high temperature climates. This is particularly desirable for therapeutics to be used in developing countries where refrigeration is not readily available.

III. Nanoemulsion Compositions

A nanoemulsion is a composition comprising an aqueous phase, at least one oil, and at least one organic solvent. The term "emulsion" refers to, without limitation, any oil-in-water dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases.

The nanoemulsion can comprise an aqueous phase, at least one pharmaceutically acceptable oil, at least one pharmaceutically acceptable organic solvent, at least one pharmaceutically acceptable quaternary ammonium compound selected from the group consisting of benzalkonium chloride (BZK), cetylpyridimium chloride (CPC), benzethonium chloride (BEC), dioctadecyl dimethyl ammonium chloride (DODAC), and octenidine dihydrochloride (OCT); and at least one pharmaceutically acceptable nonionic surfactant. The concentration ratio of the quaternary ammonium compound to nonionic surfactant is from about 5:1 to about 1:27.

In one embodiment, the nanoemulsion comprises droplets having an average or mean particle size diameter of less than about 1 micron or less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or less than about 100 nm. In another embodiment, the nanoemulsion comprises droplets having an average or mean particle size diameter of less than about 1000 nm. In another embodiment, the nanoemulsion comprises droplets having an average or mean particle size diameter of about 250 nm to about 1000 nm.

In some embodiments, the nanoemulsion composition described herein comprises BZK at a concentration of about 0.13%, poloxamer 407, soybean oil, EDTA, and water.

A. Aqueous Phase

The nanoemulsion composition comprises an aqueous phase. The aqueous phase may be any type of aqueous phase including, but not limited to, water (e.g., $H_2O$, distilled water, tap water), solutions (e.g., phosphate-buffered saline (PBS) solution), or any combination thereof. In some embodiments, the aqueous phase comprises water at a pH of about 4 to about 10, preferably about 6 to about 8. In some embodiments, the aqueous phase is deionized. In some embodiments, the aqueous is purified. In some embodiments, the aqueous phase is sterile and/or pyrogen free. In some embodiments, the aqueous phase is present in a concentration that is greater than about 50%, greater than about 55%, greater than about 60%, greater than about 65%, greater than about 70%, greater than about 75%, greater than about 80%, greater than about 85%, greater than about 90%, or greater than about 95%. In some embodiments, the aqueous phase is present in a concentration that is from about 50% to about 99%.

B. Oil

The nanoemulsion compositions described herein comprise at least one oil. The oil in the nanoemulsion composition described herein may be any cosmetically or pharmaceutically acceptable oil. The oil may be volatile or nonvolatile, and may be chosen from animal oil, plant oil, vegetable oil, natural oil, synthetic oil, hydrocarbon oils, silicone oils, semi-synthetic derivatives thereof, and combinations thereof. In some embodiments, the oil is an animal oil, plant oil, or a vegetable oil. In some embodiments, the oil is present in a concentration that is equal to or less than about 30%, less than about 25%, less than about 20%, less than about 15%, less than about 10%, less than about 5%, or less than about 1%. In some embodiments, the oil is present in a concentration that is from about 1% to about 30%.

Suitable oils include, but are not limited to, mineral oil, squalene oil, flavor oils, silicon oil, essential oils, water insoluble vitamins, isopropyl stearate, butyl stearate, octyl palmitate, cetyl palmitate, tridecyl behenate, diisopropyl adipate, dioctyl sebacate, menthyl anthranhilate, cetyl octanoate, octyl salicylate, isopropyl myristate, neopentyl glycol dicarpate cetols, Ceraphyls®, decyl oleate, diisopropyl adipate, $C_{12-15}$ alkyl lactates, cetyl lactate, lauryl lactate, isostearyl neopentanoate, myristyl lactate, isocetyl stearoyl stearate, octyldodecyl stearoyl stearate, hydrocarbon oils, isoparaffin, fluid paraffins, isododecane, petrolatum, argan oil, canola oil, chile oil, coconut oil, corn oil, cottonseed oil, flaxseed oil, grape seed oil, mustard oil, olive oil, palm oil, palm kernel oil, peanut oil, pine seed oil, poppy seed oil, pumpkin seed oil, rice bran oil, safflower oil, tea oil, truffle oil, vegetable oil, apricot (kernel) oil, jojoba oil (*Simmondsia chinensis* seed oil), grapeseed oil, macadamia oil, wheat germ oil, almond oil, rapeseed oil, gourd oil, soybean oil, sesame oil, hazelnut oil, maize oil, sunflower oil, hemp oil, bois oil, kuki nut oil, avocado oil, walnut oil, fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras bark oil, wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, oleic acid, linoleic acid, oleyl alcohol, isostearyl alcohol, semi-synthetic derivatives thereof, and any combinations thereof.

In some embodiments, the oil comprises soybean oil, avocado oil, squalene oil, olive oil, canola oil, corn oil, rapeseed oil, safflower oil, sunflower oil, fish oils, cinnamon bark, coconut oil, cottonseed oil, flaxseed oil, pine needle oil, silicon oil, mineral oil, essential oil, flavor oils, water insoluble vitamins, and combinations comprising one or more of the foregoing oils. In some embodiments, the oil comprises soybean oil.

C. Organic Solvent

The nanoemulsions described herein can optionally comprise at least one organic solvent. Organic solvents contemplated for use include but are not limited to $C_1$-$C_{12}$ alcohols, diols, triols, or a combination thereof. Organic phosphate solvents, alcohols and combinations thereof are also contemplated for use as organic solvents. Suitable organic phosphate solvents include, but are not limited to, dialkyl and trialkyl phosphates having one to ten carbon atoms, more preferably two to eight carbon atoms. The alkyl groups of the di- or trialkyl phosphate can all the same or the alkyl groups can be different. In one embodiment, the trialkyl phosphate is tri-n-butyl phosphate. In some embodiments, the organic solvent comprises a $C_1$-$C_{12}$ alcohol, diol, or triol, a dialkyl phosphate, a trialkyl phosphate, or a combination thereof. In some embodiments, the organic solvent is present in a concentration that is about 0.1% up to about 20%, less than about 15%, less than about 10%, less than about 5%, less than about 1%, less than about 0.5%, less than about 0.1%. In some embodiments, the organic solvent is present in a concentration that is from about 0.1% to about 5%.

Suitable organic solvents for the nanoemulsion include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and a combination thereof.

D. Quaternary Ammonium Compound

The quaternary ammonium compound may be benzalkonium chloride (BZK), cetylpyridinium chloride (CPC), benzethonium chloride (BEC), dioctadecyl dimethyl ammonium chloride (DODAC) and/or octenidine dihydrochloride (OCT). In some embodiments, the quaternary ammonium compound is a cationic surfactant or is part of a zwitterionic surfactant.

If BZK is present as the quaternary ammonium compound, then the BZK is present at a concentration of from about 0.05% to about 5.0%, or any amount in-between these two amounts. In some embodiments, the BZK is present at a concentration of from about 0.05% to about 0.40%. In some embodiments, the BZK is present at a concentration of from about 0.05% to about 0.20%. In some embodiments, the BZK is present at a concentration of from about 0.10% to about 0.20%. In some embodiments, the BZK is present at a concentration of from about 0.10% to about 0.15%. In some embodiments, the BZK is present at a concentration of about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, or about 0.40%. In some embodiments, the BZK is present at a concentration of 0.13%.

In one embodiment, the quaternary ammonium compound is monographed by the US FDA as an antiseptic for topical use. The monographed quaternary ammonium compound can be BZK.

If cetylpyridinium chloride (CPC) is present as the quaternary ammonium compound, then the CPC is present at a concentration of from about 0.05% to about 5.0%, or any amount in-between these two amounts. In some embodiments, the CPC is present at a concentration of from about 0.05% to about 0.40%. In some embodiments, the CPC is present at a concentration of from about 0.05% to about 0.20%. In some embodiments, the CPC is present at a concentration of from about 0.15% to about 0.30%. In some embodiments, the CPC is present at a concentration of from about 0.08% to about 0.15%. In some embodiments, the CPC is present at a concentration of about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, or about 0.40%. In some embodiments, the CPC is present at a concentration of 0.10%. In some embodiments, the CPC is present at a concentration of 0.20%.

If benzethonium chloride (BEC) is present as the quaternary ammonium compound, then the BEC is present at a concentration of from about 0.05% to about 5.0%, or any amount in-between these two amounts. In some embodiments, the BEC is present in a concentration of: (a) from about 0.05% to about 1%; or (b) from about 0.10% to about 0.30%. In some embodiments, the BEC is present at a concentration of about 0.05%, about 0.06%, about 0.07%, about 0.08%, about 0.09%, about 0.10%, about 0.11%, about 0.12%, about 0.13% about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, or about 0.30%. In some embodiments, the BEC is present in a concentration of about 0.2%.

If dioctadecyl dimethyl ammonium chloride (DODAC) is present as the quaternary ammonium compound, then the DODAC is present at a concentration of from about 0.05% to about 5.0%, or any amount in-between these two amounts. In some embodiments, the DODAC is present in a concentration of: (a) from about 0.05% to about 1%; or (b) from about 0.10% to about 0.40%. In some embodiments, the DODAC is present at a concentration of about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, or about 0.40%. In some embodiments, the DODAC is present in a concentration of about 0.2%.

If octenidine dihydrochloride (OCT) is present as the quaternary ammonium compound, then the OCT is present at a concentration of from about 0.05% to about 5.0%, or any amount in-between these two amounts. In some embodiments, the OCT is present in a concentration of: (a) from about 0.05% to about 1%; or (b) from about 0.10% to about 0.40%. In some embodiments, the OCT is present at a concentration of about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, or about 0.40%. In some embodiments, the OCT is present in a concentration of about 0.2%.

E. Nonionic Surfactant

The nonionic surfactants described herein are Generally Recognized as Safe (GRAS) by the US Food and Drug Administration. Exemplary useful surfactants are described in *Applied Surfactants: Principles and Applications*, Tharwat F. Tadros (Copyright 2005 WILEY-VCH Verlag GmbH & Co. KGaA, Weinheim ISBN: 3-527-30629-3), which is specifically incorporated by reference.

Suitable nonionic surfactants include polysorbate surfactants (i.e., polyoxyethylene ethers), poloxamers, or a combination thereof. Examples of polysorbate detergents include the following sold under the tradenames: TWEEN®

20, TWEEN® 21, TWEEN® 40, TWEEN® 60, TWEEN® 61, TWEEN® 65, TWEEN® 80, TWEEN® 81, and TWEEN® 85. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Examples of poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate. In some embodiments, the nonionic surfactant is polysorbate 20 (TWEEN® 20), poloxamer 407, or a combination thereof.

Nonionic surfactants can also include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N—N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl). Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-114, Triton X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or any combinations thereof.

F. Ratio of Quaternary Ammonium Compound to Nonionic Surfactant

This disclosure recognizes that the nanoemulsion compositions with certain concentration ratios of quaternary ammonium compound to nonionic surfactant provide greater delivery of the quaternary ammonium compound (or an additional active agent present in the composition) to the site of application and/or increased skin hydration when the nanoemulsions are applied to the skin as compared to non-nanoemulsion compositions comprising the same quaternary ammonium compound (or additional active agent). The ratio of the concentration of the quaternary ammonium compound to nonionic surfactant is about 5:1 to about 1:27. In some embodiments, the ratio of the concentration of the quaternary ammonium compound to nonionic surfactant is selected from the group consisting of about 5:1, about 4:1, about 3:1, about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, and about 1:27. In some embodiments, the ratio of the concentration of the quaternary ammonium compound to the nonionic surfactant is from about 4:1 to about 1:27. In some embodiments, the ratio of the concentration of the quaternary ammonium compound to the nonionic surfactant is selected from the group consisting of about 1:2, about 1:5, about 1:9, about 1:14, and about 1:18. In certain embodiments, the concentration of the quaternary ammonium compound to the nonionic surfactant is about 1:2 to about 1:18.

G. Therapeutic Agents

The nanoemulsion compositions described herein may further comprise one or more active or therapeutic agents suitable for topical, transdermal, nasal or mucosal administration. The active agents may include any active agent that kills, or inactivates a microorganism, such as a coronavirus, for example, SARS-CoV-2 (SEQ ID NO: 1). These antiviral compounds include for example, chloroquine, darunavir, galidesivir, interferon beta, lopinavir, ritonavir, remdesivir, and triazavirin, may be included.

The Examples below describe incorporation of a model therapeutic agent, Compound A, demonstrating the effectiveness of incorporating additional therapeutic agents in a nanoemulsion formulation. Compound A is a high molecular weight compound, thereby demonstrating that low molecular weight compounds can also successfully be incorporated in a nanoemulsion formulation.

In some embodiments, the therapeutic agent is present in a concentration of from about 0.01% to about 10%; from about 0.01% to about 1%; from about 0.01% to about 0.75%; and from about 0.1% to about 0.5%. In some embodiments, the therapeutic agent is present in a concentration of from about 0.01%, about 0.02%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 2%, about 3%, about 4%, about 5%, about 6%, about 7%, about 8%, about 9%, or about $10^{\%}$. For an antigen, the amount present can be from about 1 to about 250 µg/per dose.

In some embodiments, when the composition further comprises a therapeutic or active agent, after a single application of the composition topically, transdermally, nasally, or mucosally (e.g. intranasal, ocular), the composition delivers a greater amount of therapeutic agent to the dermis, epidermis, mucosa, and/or squamous epithelium as compared to a composition comprising the same therapeutic agent at the same concentration but lacking a nanoemulsion, and applied using the same method, measured at any suitable time point after application. For example, in some embodiments, after a single application of the composition to skin, mucosa, or squamous epithelium, the composition delivers at least about 25% more of the therapeutic agent to the epidermis, and/or at least about 25% more of the therapeutic agent to the dermis, and/or about 25% more of the therapeutic agent to the mucosa, and/or about 25% more of the therapeutic agent to the squamous epithelium as compared to a composition comprising the same therapeutic agent at the same concentration but lacking a nanoemulsion, and applied using the same method, measured at any suitable time point after application.

In some embodiments, when the composition further comprises a therapeutic or active agent, after a single application or administration of the composition topically, transdermally, mucosally, ocularly, or nasally, the composition delivers at least about 25%, at least about 50%, at least about 100%, at least about 125%, at least about 150%, at least about 175%, at least about 200%, at least about 225%, at least about 250%, at least about 275%, at least about 300%, at least about 325%, at least about 350%, at least about 375%, at least about 400%, at least about 425%, at least about 450%, at least about 475%, or at least about 500% more of the therapeutic agent to the dermis, epidermis, mucosa, and/or squamous epithelium as compared to a composition comprising the same therapeutic agent at the same concentration but lacking a nanoemulsion, and applied using the same method, measured at any suitable time point after application or administration.

In some embodiments, when the composition further comprises a therapeutic or active agent, after a single application or administration of the composition topically, transdermally, ocularly, nasally, or mucosally, the composition has a longer residence time at the site of application or administration as compared to a composition comprising the same therapeutic agent at the same concentration but lacking a nanoemulsion, and applied using the same method, measured at any suitable time point after application. The longer residence time can be determined by comparing the amount of the therapeutic agent present at the site of application or administration for the nanoemulsion composition as compared to the non-nanoemulsion composition, measured at any suitable time point after application. The longer residence time at the site of application can be, for example, an increase of about 30%, about 40%, about 50%, about 60%, about 70%, about 80%, about 90%, about 100%, about 125%, about 150%, about 175%, or about 200%, as compared to the residence time of the same quaternary ammonium compound, present at the same concentration, and applied using the same method, measured at any suitable time point after application or administration.

In some embodiments, when the composition further comprises a therapeutic or active agent, after a single application or administration of the composition topically, transdermally, ocularly, nasally, or mucosally, the composition delivers at least about 25% more, at least about 50% more, at least about 75% more, at least about 100% more, at least about 125% more, at least about 150% more, at least about 175% more, or at least about 200% more of the quaternary ammonium compound to the epidermis, dermis, nasal tissue, mucosa, and/or squamous epithelium as compared to a composition comprising the same therapeutic agent at the same concentration but lacking a nanoemulsion, and applied using the same method, measured at any suitable time point after application or administration.

H. Additional Ingredients

Additional compounds suitable for use in the disclosed methods or compositions include, but are not limited to, one or more solvents, such as an organic phosphate-based solvent, bulking agents, coloring agents, pharmaceutically acceptable carriers, a preservative, pH adjuster, buffer, chelating agent, an auxiliary surfactant, a suds suppressor, a detergent builder, etc. The additional compounds can be admixed into a previously formulated composition, or the additional compounds can be added to the original mixture to be further formulated. In certain of these embodiments, one or more additional compounds are admixed into an existing disclosed composition immediately prior to its use.

Suitable preservatives in the disclosed composition include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis (p-chlorophenyldiguanido) hexane), chlorphenesin (3-(-4-chlorophenoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

Suitable pH adjusters include, but are not limited to, diethyanolamine, lactic acid, monoethanolamine, triethylanolamine, sodium hydroxide, sodium phosphate, semi-synthetic derivatives thereof, and combinations thereof.

Suitable buffers include pharmaceutically acceptable buffering agents. Examples of buffering agents are disclosed in U.S. Patent Publication No. 2010/0226983

In addition, the disclosed composition can comprise a chelating agent. In one embodiment of the disclosed, the chelating agent is present in an amount of about 0.0005% to about 1%. Examples of chelating agents include, but are not limited to, ethylenediamine, ethylenediaminetetraacetic acid (EDTA), ethylene glycol-bis(β-aminoethyl ether)-N,N,N', N'-tetraacetic acid (EGTA), phytic acid, polyphosphoric acid, citric acid, gluconic acid, acetic acid, lactic acid, dimercaprol, or any combination thereof. In some embodiments, the chelating agent is ethylenediaminetetraacetic acid.

Suitable auxiliary surfactants include compounds that enhance the properties of a nanoemulsion composition. The choice of auxiliary surfactant depends on the desire of the user with regard to the intended purpose of the composition and the commercial availability of the surfactant. In one embodiment, the auxiliary surfactant is an organic, water-soluble surfactant.

Suitable suds suppressors are low-foaming co-surfactants that prevents excessive sudsing during employment of the compositions on hard surfaces. Suds suppressors are also useful in formulations for no-rinse application of the composition. Concentrations of about 0.5 vol % to about 5 vol % are generally effective. Selection of a suds suppressor depends on its ability to formulate in a nanoemulsion composition and the residue as well as the cleaning profile of the composition. The suds suppressor should be chemically compatible with the components in a nanoemulsion composition and functional at the pH of a given composition. In one embodiment the suds suppressor or composition containing a suds suppressor does not leave a visible residue on surfaces on which a composition is applied.

Low-foaming co-surfactants can be used as a suds suppressor to mediate the suds profile in a nanoemulsion composition. Examples of suitable suds suppressors include block copolymers, alkylated primary and secondary alcohols, and silicone-based materials. Exemplary block copolymers include, e.g., Pluronic® and Tetronic® (BASF Company). Alkylated alcohols include those which are ethoxylated and propoxylated, such as, tergitol (Union Carbide) or Poly-Tergent® (Olin Corp.). Silicone-based materials include DSE (Dow Corning).

Suitable detergent builders include compounds that sequester calcium and magnesium ions that might otherwise bind with and render less effective the auxiliary surfactants or co-surfactants. Detergent builders are particularly useful when auxiliary surfactants are used, and when the compositions are diluted prior to use with hard tap water, especially water having a hardness of, above about 12 grains/gallon.

The disclosed methods and compositions can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present disclosure feature nanoemulsion compositions that may readily be diluted with water or another aqueous phase to a desired concentration without impairing their desired properties.

I. Viscosity

As noted herein, in one aspect of the disclosure, a composition is provided for topical, transdermal, mucosal, ocular, or nasal application or administration. The composition comprises an oil-in-water nanoemulsion, the nanoemulsion comprising: (a) an aqueous phase; (b) at least one oil; (c) at least one quaternary ammonium compound; and (d) at least one nonionic surfactant; wherein the droplets of the nanoemulsion have a mean droplet size of less than about 1 micron; and wherein (i) the nanoemulsion is diluted resulting in a formulation of about 0.5% to about 60% nanoemulsion; (ii) the viscosity of the nanoemulsion is less than about 1000 cp; and (iii) the nanoemulsion enhances delivery of the quaternary ammonium compound into tissue by at least about 25% as compared to a solution with the same concentration of quaternary ammonium compound but lacking a nanoemulsion and as compared to a nanoemulsion with a viscosity greater than about 1000 cp. In another aspect of the disclosure, the quaternary ammonium compound is a cationic surfactant or is part of a zwitterionic surfactant.

In some embodiments, the nanoemulsion compositions described herein have a viscosity of less than about 1000 cP. In some embodiments, the nanoemulsion compositions described herein have a viscosity of less than about 900, less than about 800, less than about 700, less than about 600, less than about 500, less than about 400, less than about 300, less than about 275, less than about 250, less than about 225, less than about 200, less than about 100, less than about 75, less than about 50, less than about 25, less than about 20, less than about 10, less than about 9, less than about 8, less than about 7, less than about 6, less than about 5, less than about 4, less than about 3, less than about 2, or less than about 1.5 cP. Optionally the viscosity is greater than 0.

In some embodiments, the viscosity is from about 1 cP to about 1000 cP; or from about 1.2 cP to about 275 cP.

In some aspects, nanoemulsions described herein enhance delivery of the quaternary ammonium compound (and/or additional active/therapeutic agent) into tissue by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as compared to a solution with the same concentration of quaternary ammonium compound but lacking a nanoemulsion and as compared to a nanoemulsion with a viscosity greater than the referenced viscosity (e.g., greater than about 1000, greater than about 900, greater than about 800, . . . greater than about 300, greater than about 275 cP . . . , or greater than any other viscosity amount described herein).

J. Zeta Potential

As noted herein, in one aspect of the disclosure, a composition is provided for topical, transdermal, mucosal, nasal or ocular application or administration, the composition comprising an oil-in-water nanoemulsion, the nanoemulsion comprising: (a) an aqueous phase; (b) at least one oil; (c) at least one quaternary ammonium compound; and (d) at least one nonionic surfactant; wherein (i) the droplets of the nanoemulsion have a mean droplet size of less than about 1 micron; (ii) the nanoemulsion is diluted resulting in a formulation of about 0.5% to about 60% nanoemulsion; (iii) the zeta potential of the nanoemulsion is greater than about 20 mV; and (iv) the nanoemulsion enhances delivery of the quaternary ammonium compound (and/or additional active/therapeutic agent) into tissue by at least about 25% as compared to a solution with the same concentration of quaternary ammonium compound but lacking a nanoemulsion and as compared to a nanoemulsion with a zeta potential of less than about 20 mV. In another aspect of the disclosure, the quaternary ammonium compound is a cationic surfactant or is part of a zwitterionic surfactant.

Zeta potential is a scientific term for electrokinetic potential in colloidal dispersions. The usual units are volts (V) or millivolts (mV). From a theoretical viewpoint, the zeta potential is the electric potential in the interfacial double layer (DL) at the location of the slipping plane relative to a point in the bulk fluid away from the interface. In other words, zeta potential is the potential difference between the dispersion medium and the stationary layer of fluid attached to the dispersed particle.

In some embodiments, the nanoemulsion has a zeta potential from about 20 mV to about 40 mV; from about 40 mV to about 60 mV; from about 60 mV to about 80 mV; or from about 80 mV to about 100 mV. In other embodiments, the nanoemulsion has a zeta potential of greater than or equal to about 20 mV, about 25 mV, about 30 mV, about 35 mV, about 40 mV, about 45 mV, about 50 mV, about 55 mV, about 60 mV, about 65 mV, about 70 mV, about 75 mV, about 80 mV, about 85 mV, about 90 mV, about 95 mV, or greater than or equal to about 100 mV.

In some aspects, nanoemulsions described herein enhance delivery of the quaternary ammonium compound (and/or additional active/therapeutic agent) into tissue by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as compared to a solution with the same concentration of quaternary ammonium compound but lacking a nanoemulsion and as compared to a nanoemulsion with a zeta potential less than the referenced zeta potential (e.g., less than 20 mV, less than about 30 mV, or less than any other zeta potential amount described herein for the described nanoemulsions).

K. Entrapment of Quaternary Ammonium Compound by Oil Phase

As noted herein, in one aspect of the disclosure, a composition is provided for topical, transdermal, mucosal, ocular, or nasal application or administration, the composition comprising an oil-in-water nanoemulsion, the nanoemulsion comprising: (a) an aqueous phase; (b) at least one oil; (c) at least one quaternary ammonium compound; and (d) at least one nonionic surfactant; wherein (i) the droplets of the nanoemulsion have a mean droplet size of less than about 1 micron; (ii) the nanoemulsion is diluted resulting in a formulation of about 0.5% to about 60% nanoemulsion; (iii) at least about 33% of the quaternary ammonium compound is entrapped in the oil phase of the nanoemulsion and at least about 0.2% of the weight of the oil phase of the nanoemulsion is attributed to entrapment of the quaternary ammonium compound; and (iv) the nanoemulsion enhances delivery of the quaternary ammonium compound (and/or additional active/therapeutic agent) into tissue by at least about 25% as compared to a solution with the same concentration of quaternary ammonium compound but lacking a nanoemulsion and as compared to a nanoemulsion with less than about 0.2% of the weight of the oil phase of the nanoemulsion attributed to entrapment of the quaternary ammonium compound. In another aspect of the disclosure, the quaternary ammonium compound is a cationic surfactant or is part of a zwitterionic surfactant.

In some embodiments, (a) at least about 33% of the quaternary ammonium compound is entrapped in the oil phase of the nanoemulsion; (b) at least about 0.2% of the weight of the oil phase of the nanoemulsion is attributed to the quaternary ammonium compound; or (c) the composition satisfies both (a) and (b).

In some embodiments, at least about 0.20%, at least about 0.21%, at least about 0.22%, at least about 0.23%, at least about 0.24%, at least about 0.25%, at least about 0.26%, at least about 0.27%, at least about 0.28%, at least about 0.29%, at least about 0.30%, at least about 0.35%, at least about 0.40%, at least about 0.45%, at least about 0.50%, at least about 0.55%, at least about 0.60%, at least about 0.65%, at least about 0.70%, at least about 0.75%, at least about 0.80%, at least about 0.85%, at least about 0.90%, at least about 0.95%, at least about 1.00%, at least about 1.25%, at least about 1.40%, at least about 1.50%, at least about 2.00%, at least about 2.50%, at least about 2.75%, at least about 2.85%, at least about 3.00%, at least about 4.00%, at least about 5.00%, at least about 6.00%, at least about 7.00%, at least about 8.00%, at least about 9.00%, at least about 10.00%, at least about 11.00%, at least about 12.00%, at least about 13.00%, at least about 14.00%, at least about 15.00%, at least about 16.00%, at least about 17.00%, at least about 18.00%, at least about 19.00%, at least about 20.0%, or up to about 25% of the weight of the oil phase of the nanoemulsion is attributed to entrapment of the quaternary ammonium compound.

In some embodiments, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 55%, at least about 60%, at least about 65%, at least about 70%, at least about 75%, at least about 80%, or at least about 85% of the quaternary ammonium compound is entrapped in the oil phase of the nanoemulsion.

In some embodiments, any combination of the percentage of the quaternary ammonium compound entrapped in the oil phase of the nanoemulsion described herein (e.g., about 33%, about 35%, etc.) can be combined with any percentage of the weight of the oil phase of the nanoemulsion attributed to entrapment of the quaternary ammonium compound described herein (e.g., at least about 0.2% up to about 25%).

In some embodiments, (a) at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, or at least about 50% of the quaternary ammonium compound is entrapped in the oil phase of the nanoemulsion; (b) at least about 0.20% of the weight of the oil phase of the nanoemulsion is attributed to entrapment of the quaternary ammonium compound; or (c) the composition satisfies both (a) and (b).

In some embodiments, (a) at least about 70% of the quaternary ammonium compound is entrapped in the oil phase of the nanoemulsion; (b) at least about 0.2% of the weight of the oil phase of the nanoemulsion is attributed to entrapment of the quaternary ammonium compound; or (c) the composition satisfies both (a) and (b). In some embodiments, (a) at least about 90% of the quaternary ammonium compound is entrapped in the oil phase of the nanoemulsion; (b) at least about 0.2% of the weight of the oil phase of the nanoemulsion is attributed to entrapment of the quaternary ammonium compound; or (c) the composition satisfies both (a) and (b).

In some embodiments, (a) at least about 33% of the quaternary ammonium compound is entrapped in the oil phase of the nanoemulsion; (b) at least about 0.4% of the weight of the oil phase of the nanoemulsion is attributed to entrapment of the quaternary ammonium compound; or (c) the composition satisfies both (a) and (b). In some embodiments, (a) at least about 33% of the quaternary ammonium compound is entrapped in the oil phase of the nanoemulsion; (b) at least about 0.6% of the weight of the oil phase of the nanoemulsion is attributed to entrapment of the quaternary ammonium compound; or (c) the composition satisfies both (a) and (b). In some embodiments, (a) at least about 33% of the quaternary ammonium compound is entrapped in the oil phase of the nanoemulsion; (b) at least about 0.8% of the weight of the oil phase of the nanoemulsion is attributed to entrapment of the quaternary ammonium compound; or (c) the composition satisfies both (a) and (b). In some embodiments, (a) at least about 33% of the quaternary ammonium compound is entrapped in the oil phase of the nanoemulsion; (b) at least about 1.0% of the weight of the oil phase of the nanoemulsion is attributed to entrapment of the quaternary ammonium compound; or (c) the composition satisfies both (a) and (b).

In some aspects, nanoemulsions described herein enhance delivery of the quaternary ammonium compound (and/or additional active/therapeutic agent) into tissue by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as compared to a solution with the same concentration of quaternary ammonium compound but lacking a nanoemulsion and as compared to a nanoemulsion with a less than about 0.20% of the weight of the oil phase of the nanoemulsion attributed to entrapment of the quaternary ammonium compound.

L. Average or Mean Particle Size Diameter and Stability Thereof

The nanoemulsion compositions described herein have droplets having an average or mean particle size diameter of about 250 nm to about 1000 nm. In some embodiments, the droplets have an average or mean particle size diameter of about 250 nm to about 600 nm. In some embodiments, the droplets have an average or mean particle size diameter of about 300 nm to about 600 nm. In some embodiments, the droplets have an average or mean particle size diameter of about 150 nm or less, about 200 nm or less, about 250 nm or less, about 260 nm or less, about 270 nm or less, about 280 nm or less, about 290 nm or less, about 300 nm or less, about 310 nm or less, about 320 nm or less, about 330 nm or less, about 340 nm or less, about 350 nm or less, about 360 nm or less, about 370 nm or less, about 380 nm or less, about 390 nm or less, about 400 nm or less, about 410 nm or less, about 420 nm or less, about 430 nm or less, about 440 nm or less, about 450 nm or less, about 460 nm or less, about 470 nm or less, about 480 nm or less, about 490 nm or less, about 500 nm or less, about 510 nm or less, about 520 nm or less, about 530 nm or less, about 540 nm or less, about 550 nm or less, about 560 nm or less, about 570 nm or less, about 580 nm or less, about 590 nm or less, or about 600 nm or less.

In some embodiments, the mean droplet size of the nanoemulsion does not change by more than about 10% after centrifuging the nanoemulsion at a speed of about 200,000 rpm for about one hour. In other embodiments, the mean droplet size of the nanoemulsion does not change by more than about 9%, more than about 8%, more than about 7%, more than about 6%, more than about 5%, more than about 4%, more than about 3%, more than about 2%, more than about 1%, more than about 0.9%, more than about 0.8%, more than about 0.7%, more than about 0.6%, more than about 0.5%, more than about 0.4%, more than about 0.3%, or more than about 0.2%, after centrifuging the nanoemulsion at a speed of about 200,000 rpm for about one hour.

In some aspects, nanoemulsions described herein enhance delivery of the quaternary ammonium compound (and/or additional active/therapeutic agent) into tissue by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, as compared to a solution with the same concentration of quaternary ammonium compound but lacking a nanoemulsion and as compared to a nanoemulsion with a change in mean droplet size, following centrifuging the nanoemulsion at a speed of about 200,000 rpm for about one hour, of greater than about 10%.

M. Stability of Nanoemulsion Compositions

The nanoemulsion compositions described herein are stable. In certain embodiments, the nanoemulsion compositions herein demonstrate stability even under storage conditions at high temperatures (e.g., about 50° C.). In some embodiments, the nanoemulsion compositions described herein are thermostable. In some embodiments, the compositions are stable for at least about 1 month, at least about 2, at least about 3, at least about 4, at least about 5, at least about 6, at least about 12, at least about 24, at least about 30, at least about 36, at least about 42, at least about 48, at least about 54, or at least about 60 months at about 5° C., about 25° C., about 40° C., and/or about 50° C. In some embodiments, the compositions are stable for at least about 3 months at about 5° C., about 25° C., about 40° C., and/or about 50° C. In some embodiments, the compositions are stable for at least about 60 months at 5° C. In other embodiments the compositions are stable for at least about 12 months at 50° C.

Further, because the nanoemulsion compositions of the invention are highly thermostable, the nanoemulsion compositions can be autoclaved without losing the structural or chemical integrity of the compositions. This is desirable as sterile formulations may be preferable for some disease indications and/or patient populations.

In one embodiment, stability of a nanoemulsion according to the invention is measured by a lack of a substantial increase in average particle size over time and/or upon exposure to elevated temperatures. A "lack of a substantial increase in average particle size" of a nanoemulsion can mean a particle size growth of less than about 30%, less than about 25%, less than about 20%, less than about 15%, less than about 10%, less than about 5%, or less than about 3%. The period of time over which stability is measured can be any suitable period of time, such as about 1 month, at least about 2, at least about 3, at least about 4, at least about 5, at least about 6, at least about 12, at least about 24, at least about 30, at least about 36, at least about 42, at least about 48, at least about 54, or at least about 60 months.

In yet another embodiment, stability is measured by the ability of the composition upon exposure to elevated temperatures, and/or prolonged storage, to exhibit minimal particle aggregation formation and/or retain at an at least 80% label claim of an active agent and/or of the quaternary ammonium compound present in the nanoemulsion. Time points for measurement can be as described above. Other label claim thresholds can be about 85%, about 90%, or about 95% (see e.g. the methodology of Example 8).

N. Antimicrobial Activity

The nanoemulsion compositions described herein have antiviral activity. In some embodiments, the composition is non-toxic in human and animals. In some embodiments, the composition kills at least about 99.9% of microorganisms (i.e., coronaviruses) following a 60 second exposure using the ASTM E2315-16 Standard Guide for Assessment of Antimicrobial Activity Using a Time-Kill Procedure.

The microorganism killed by the nanoemulsion can be a virus, bacteria, fungus or yeast. In addition, the bacteria can be a gram negative or gram positive bacteria.

In some embodiments, the microorganism are selected from a coronavirus selected from the group consisting of an Alphacoronavirus; a Colacovirus such as Bat coronavirus CDPHE15; a Decacovirus such as Bat coronavirus HKU10 or Rhinolophus ferrumequinum alphacoronavirus HuB-2013; a Duvinacovirus such as Human coronavirus 229E; a Luchacovirus such as Lucheng Rn rat coronavirus; a Minacovirus such as a Ferret coronavirus or Mink coronavirus 1; a Minunacovirus such as Miniopterus bat coronavirus 1 or Miniopterus bat coronavirus HKU8; a Myotacovirus such as Myotis ricketti alphacoronavirus Sax-2011; a nyctacovirus such as Nyctalus velutinus alphacoronavirus SC-2013; a Pedacovirus such as Porcine epidemic diarrhea virus or Scotophilus bat coronavirus 512; a Rhinacovirus such as Rhinolophus bat coronavirus HKU2; a Setracovirus such as Human coronavirus NL63 or NL63-related bat coronavirus strain BtKYNL63-9b; a Tegacovirus such as Alphacoronavirus 1; a Betacoronavirus; a Embecovirus such as Betacoronavirus 1, Human coronavirus OC43, China Rattus coronavirus HKU24, Human coronavirus HKU1 or Murine coronavirus; a Hibecovirus such as Bat Hp-betacoronavirus Zhejiang2013; a Merbecovirus such as Hedgehog coronavirus 1, Middle East respiratory syndrome-related coronavirus (MERS-CoV), Pipistrellus bat coronavirus HKU5 or Tylonycteris bat coronavirus HKU4; a Nobecovirus such as Rousettus bat coronavirus GCCDC1 or Rousettus bat coronavirus HKU9, a Sarbecovirus such as a Severe acute respiratory syndrome-related coronavirus, Severe acute respiratory syndrome coronavirus (SARS-CoV) or Severe acute respiratory syndrome coronavirus 2 (SARS-CoV-2, COVID-19); a Deltacoronavirus; an Andecovirus such as Wigeon coronavirus HKU20; a Buldecovirus such as Bulbul coronavirus HKU11, Porcine coronavirus HKU15, Munia coronavirus HKU13 or White-eye coronavirus HKU16; a Herdecovirus such as Night heron coronavirus HKU19; a Moordecovirus such as Common moorhen coronavirus HKU21; a Gammacoronavirus; a Cegacovirus such as Beluga whale coronavirus SW1; and an Igacovirus such as Avian coronavirus.

O. Quaternary Ammonium Compound Delivery

In some embodiments, after a single application of the composition, the composition delivers at least 25% more of the quaternary ammonium compound to the epidermis, and/or at least 25% more of the quaternary ammonium compound to the dermis, and/or at least 25% more of the quaternary ammonium compound to the mucosa, and/or at least 25% more of the quaternary ammonium compound to the squamous epithelium as compared to a composition comprising the same quaternary ammonium compound at the same concentration but lacking a nanoemulsion, measured at any suitable time point after application, such as 24 hours after application.

In some embodiments, after a single application of the composition, the composition has a longer residence time at the site of application as compared to a composition comprising the same quaternary ammonium compound at the same concentration but lacking a nanoemulsion, wherein the longer residence time is determined by comparing the amount of the quaternary ammonium compound present at the site of application for the nanoemulsion composition as compared to the non-nanoemulsion composition.

In some embodiments, after a single application of the composition, the composition delivers at least about 1.25×, at least about 1.5×, at least about 1.75×, at least about 2×, at least about 2.25×, at least about 2.5×, at least about 2.75×, at least about 3×, at least about 3.25×, at least about 3.5×, at least about 3.75×, at least about 4×, at least about 5×, at least about 6×, at least about 7×, at least about 8×, at least about 9×, or at least about 10× more of the quaternary ammonium compound to the epidermis, dermis, mucosa, and/or squamous epithelium as compared to a composition comprising the same quaternary ammonium compound at the same concentration but lacking a nanoemulsion.

In some embodiments, after a single application of the composition, the composition delivers at least about 25%, at least about 50%, at least about 100%, at least about 125%, at least about 150%, at least about 175%, at least about 200%, at least about 225%, at least about 250%, at least about 275%, at least about 300%, at least about 325%, at least about 350%, at least about 375%, at least about 400%, at least about 425%, at least about 450%, at least about 475%, or at least about 500% more of the quaternary ammonium compound to the epidermis, dermis, mucosa, and/or squamous epithelium as compared to a composition comprising the same quaternary ammonium compound at the same concentration but lacking a nanoemulsion. In some embodiments, after a single application of the composition, the composition delivers from about 25% to about 500% more of the quaternary ammonium compound to the epidermis, dermis, mucosa, and/or squamous epithelium as compared to a composition comprising the same quaternary ammonium compound at the same concentration but lacking a nanoemulsion.

In some embodiments, when the composition is applied to skin, mucosa and/or squamous epithelium, the composition results in increased skin, mucosa and/or squamous epithelium hydration as compared to a composition comprising the same quaternary ammonium compound at the same concentration but lacking a nanoemulsion.

In some embodiments, the increase in skin, mucosa and/or squamous epithelium hydration is from about 50% to about 1000%. In some embodiments, the increase in skin, mucosa and/or squamous epithelium hydration is about 50%, about 75%, about 100%, about 125%, about 150%, about 175%, about 200%, about 225%, about 250%, about 275%, about 300%, about 325%, about 350%, about 375%, about 400%, about 425%, about 450%, about 475%, about 500%, about 525%, about 550%, about 575%, about 600%, about 625%, about 650%, about 675%, about 700%, about 725%, about 750%, about 775%, about 800%, about 825%, about 850%, about 875%, about 9000%, about 925%, about 950%, about 975%, or about 1000%.

IV. Pharmaceutical Compositions

The nanoemulsions of the present disclosure may be formulated into pharmaceutical compositions that are administered in a therapeutically effective amount to a subject and may further comprise one or more suitable, pharmaceutically-acceptable excipients, additives, or preservatives. Suitable excipients, additives, and/or preservatives are well known in the art.

Suitable pharmaceutically acceptable excipients or pharmaceutically acceptable carriers, may include solvents, dispersion media, coatings, isotonic and absorption delaying agents and the like, and combinations comprising one or more of the foregoing carriers as described, for instance, in *Remington's Pharmaceutical Sciences,* 15th Ed. Easton: Mack Publishing Co. pp. 1405-1412 and 1461-1487 (1975), and The National Formulary XIV 14th Ed., Washington: American Pharmaceutical Association (1975). Suitable carriers include, but are not limited to, calcium carbonate, carboxymethylcellulose, cellulose, citric acid, dextrate, dextrose, ethyl alcohol, glucose, hydroxymethylcellulose, lactose, magnesium stearate, maltodextrin, mannitol, microcrystalline cellulose, oleate, polyethylene glycols, potassium diphosphate, potassium phosphate, saccharose, sodium diphosphate, sodium phosphate, sorbitol, starch, stearic acid and its salts, sucrose, talc, vegetable oils, water, and combinations comprising one or more of the foregoing carriers. Except insofar as any conventional media or agent is incompatible with the emulsions of the present invention, their use in therapeutic compositions is contemplated. Supplementary active ingredients also can be incorporated into the compositions.

For topical applications, pharmaceutically acceptable carriers can take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly used in pharmaceutical compositions for topical and mucosal administration.

By the phrase "therapeutically effective amount" it is meant any amount of the composition that is effective in killing or inhibiting the growth of any one of the microorganisms described herein.

Topical administration includes administration to the skin, mucosa, and squamous epithelium, including surface of the hair follicle and pilosebaceous unit. In some embodiments, the composition enters the epidermis, dermis, mucosa, squamous epithelium, or any combination thereof. In some embodiments, the composition permeates the epidermis and dermis via the follicular route using skin pores and hair follicles. In some embodiments, the composition diffuses through the skin, skin pores, nail, scalp, hair follicles, lateral or proximal folds, nail, hyponichium, or a combination thereof.

Pharmaceutically acceptable dosage forms for administration include, but are not limited to, ointments, creams, liquids, emulsions, lotions, gels, bioadhesive gels, aerosols, pastes, foams, or in the form of an article or carrier, such as a bandage, insert, syringe-like applicator, pessary, powder, talc or other solid, cleanser, and agents that favor penetration within the pilosebaceous gland. In some embodiments, the composition is administered in the form of a liquid, lotion, cream, ointment, salve, or spray.

The pharmaceutical compositions may be formulated for immediate release, sustained release, controlled release, delayed release, or any combinations thereof, into the epidermis or dermis, with no systemic absorption. In some embodiments, the formulations may comprise a penetration-enhancing agent for enhancing penetration of the nanoemulsion through the stratum corneum and into the epidermis or dermis. Suitable penetration-enhancing agents include, but are not limited to, alcohols such as ethanol, triglycerides and aloe compositions. The amount of the penetration-enhancing agent may comprise from about 0.5% to about 40% by weight of the formulation.

The pharmaceutical compositions may be applied in a single administration or in multiple administrations. The pharmaceutical compositions can be applied for any suitable time period, such as 1× or multiples times per day. The compositions can be applied for at least once a week, at least twice a week, at least once a day, at least twice a day, multiple times daily, multiple times weekly, biweekly, at least once a month, or any combination thereof. The pharmaceutical compositions are applied for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years. Between applications, the application area may be washed to remove any residual nanoemulsion.

In some embodiments, the compositions described herein are formulated for mucosal delivery, for example by contacting any one of the compositions described herein to a nasal mucosal epithelium, a bronchial or pulmonary mucosal epithelium, oral mucosa, or ocular application. In some embodiments, the compositions described herein are formulated for intranasal delivery, (e.g., nasal mucosal delivery or intranasal mucosal delivery).

V. Dermal Wipes and Swabs

Also provided herein in one aspect is a nasal swab, or wipe impregnated or saturated with or incorporating any one of the nanoemulsions described herein. In the methods of the invention, administration comprises contacting the nasal swab or wipe to the subject. For example, a wipe impregnated with a nanoemulsion can be used to sanitize a subject's hands or any other surface that may come in contact with a microorganism, such as a coronavirus. In some embodiments, the nasal swab, or wipe dispenses a greater amount of the quaternary ammonium compound and/or incorporated active or therapeutic agent to an application site, as compared to a nasal swab or wipe impregnated or saturated with or incorporating a composition comprising the same quaternary ammonium compound and/or incorporated active or therapeutic agent at the same concentration but lacking a nanoemulsion.

In some embodiments, the nasal swab or wipe dispenses about 20% to about 100% more of the quaternary ammonium compound and/or incorporated active or therapeutic agent to an application site, as compared to a nasal swab or wipe impregnated or saturated with or incorporating a composition comprising the same quaternary ammonium compound and/or incorporated active or therapeutic agent at the same concentration but lacking a nanoemulsion. In some embodiments, the nasal swab or wipe dispenses about 20%, about 25%, about 30%, about 35%, about 40%, about 45%, about 50%, about 55%, about 60%, about 65%, about 70%, about 75%, about 80%, about 85%, about 90%, about 95%, or about 100% more of the quaternary ammonium compound and/or incorporated active or therapeutic agent to an application site, as compared to a nasal swab or wipe impregnated or saturated with or incorporating a composition comprising the same quaternary ammonium compound and/or incorporated active or therapeutic agent at the same concentration but lacking a nanoemulsion.

As detailed in Example 10, a comparison of a wipe saturated with a non-nanoemulsion formulation and compared to a wipe saturated with a nanoemulsion formulation revealed that the nanoemulsion-saturated wipe released much more of the component active agent (e.g., the cationic active agent). It is theorized that the active agent in the non-nanoemulsion formulation binds to the fibers or compounds in the wipe, preventing a significant portion of the active agent from being deposited on the surface or skin where the wipe is applied. This lack of active agent deposition is undesirable, as the result is a reduced effectiveness—e.g., a reduced effectiveness in antimicrobial activity when the wipe is used for disinfection.

In another embodiment, encompassed is a nasal swab, dropper, or spray for use with any nanoemulsion composition described herein. The nasal swab, dropper, or spray can be impregnated or saturated with or incorporating the any nanoemulsion composition described herein, or the nasal swab, dropper, or spray can be packaged in a kit with a container comprising a nanoemulsion composition described herein, with the swab being exposed to the nanoemulsion prior to use. Such swabs are useful to prevent and/or minimize infections in hospital settings.

A nasal spray comprising a nanoemulsion according to the invention can also be used to treat and/or prevent viral infections originating in the nasal cavities. Moreover, both the nasal swab, dropper, and spray are hydrating, as hydration is a feature of the nanoemulsions described herein. Thus, the swab and spray will hydrate the nasal mucosa, as well as be antiviral.

VI. Methods

The methods of the invention are useful in preventing or reducing the risk of infection in a subject caused by exposure to a coronavirus, the method comprising administering to the nasal vestibule or passages, ocular region, or mouth mucosa of the subject, either before or after the exposure, a composition comprising a nanoemulsion as disclosed herein.

In some embodiments, the composition or enters the epidermis, dermis, mucosa, squamous epithelium, or any combination thereof. In some embodiments, the composition, wipe, and/or swab permeates into the epidermis, dermis, mucosa, and/or squamous epithelium via the follicular route using skin pores and hair follicles. In some embodiments, the composition, wipe, and/or swab diffuses through the skin, skin pores, nail, scalp, hair follicles, lateral or proximal folds, nail, hyponichium, or a combination thereof.

One benefit of the nanoemulsions, wipes and swabs described herein is that use of the compositions, wipes and/or swabs does not result or produce drug-resistant viruses. This is because the mechanism of action in killing the viruses does not result in drug-resistant viruses. In particular, nanoemulsions lyse viral pathogens such as coronaviruses upon contact, thereby overcoming existing resistance mechanisms. The appearance of drug-resistant (DR) viral strains in the community is a crucial development, and is associated with increased morbidity, mortality, healthcare costs, and antibiotic/antiviral use.

Methods of Manufacture: The nanoemulsions of the invention can be formed using classic emulsion forming techniques. See e.g., U.S. 2004/0043041. In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water or PBS. The nanoemulsions of the invention are stable, and do not deteriorate even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, to that of a liquid and can be applied topically, transdermally, mucosally, ocularly, or nasally by any pharmaceutically acceptable method as stated above, e.g., by hand, or nasal drops/spray, or via any other pharmaceutically acceptable method.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. The nanoemulsion of the invention can be provided in many different types of containers and delivery systems.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles and any suitable pressurized spray device. Such spray bottles may be suitable for example for delivering the nanoemulsions intranasally or via inhalation.

VII. Definitions

The following definitions are provided to facilitate understanding of certain terms used throughout this specification.

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, the disease being treated and the subject being treated. Single or multiple administrations can be carried out with the dose level and pattern being selected by the treating physician. Suitable dosage formulations and methods of administering the agents are known in the art.

The terms "buffer" or "buffering agents" refer to materials which when added to a solution, cause the solution to resist changes in pH.

A used herein, "quaternary ammonium compound" refers to a compound containing an ammonium moiety. The ammonium moiety may include four bonds to a positively charged nitrogen atom.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

The terms "chelator" or "chelating agent" refer to any materials having more than one atom with a lone pair of electrons that are available to bond to a metal ion.

As used herein, the term "intranasal(ly)" refers to application of the compositions of the present disclosure to the surface of the skin and mucosal cells and tissues of the nasal passages, e.g., nasal mucosa, sinus cavity, nasal turbinates, or other tissues and cells which line the nasal passages.

As used herein, the term "microorganism" refers to without limitation, bacteria, viruses, bacterial spores, molds, fungi, and the like. Also included are biological microorganisms that are capable of producing an undesirable effect upon a host animal, and includes, for example, without limitation, bacteria, viruses, bacterial spores, molds, fungi, and the like. This includes all such biological microorganisms, regardless of their origin or of their method of production The term "nanoemulsion," as used herein, includes small oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The present disclosure contemplates that one skilled in the art will appreciate this distinction when necessary for understanding the specific embodiments herein disclosed.

The terms "pharmaceutically acceptable" or "pharmacologically acceptable," as used herein, refer to compositions that do not substantially produce adverse allergic or adverse immunological reactions when administered to a host (e.g., an animal or a human). Such formulations include any pharmaceutically acceptable dosage form. Examples of such pharmaceutically acceptable dosage forms include, but are not limited to, dips, sprays, seed dressings, stem injections, lyophilized dosage forms, sprays, and mists. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like.

As used herein, the term "topical(ly)" refers to application of the compositions of the present disclosure to the surface of the skin, mucosal, and squamous epithelium cells and tissues (e.g., buccal, lingual, sublingual, masticatory, respiratory or nasal mucosa, nasal turbinates and other tissues and cells which line hollow organs or body cavities). As used herein "topical(ly)" is in reference to application to the surface of the skin.

As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

The term "stable" when referring to a "stable nanoemulsion" means that the nanoemulsion retains its structure as an emulsion. A desired nanoemulsion structure, for example, may be characterized by a desired size range, macroscopic observations of emulsion science (is there one or more layers visible, is there visible precipitate), pH, and a stable concentration of one or more the components.

The term "surfactant" refers to any molecule having both a polar head group, which energetically prefers solvation by water, and a hydrophobic tail which is not well solvated by water. The term "cationic surfactant" refers to a surfactant with a cationic head group.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The terms "treatment," "treating," or any variation thereof includes reducing, ameliorating, or eliminating (i) one or more specified symptoms and/or (ii) one or more symptoms or effects of a specified disorder. The terms "prevention," "preventing," or any variation thereof includes reducing, ameliorating, or eliminating the risk of developing (i) one or more specified symptoms and/or (ii) one or more symptoms or effects of a specified disorder.

The disclosed is further described by reference to the following examples, which are provided for illustration only. The disclosed is not limited to the examples, but rather includes all variations that are evident from the teachings provided herein. All publicly available documents referenced herein, including but not limited to U.S. patents, are specifically incorporated by reference.

EXAMPLES

Example 1—Time Kill Study

The purpose of this example was to evaluate the antiviral antimicrobial properties of the nanoemulsions according to the invention.

The antiviral activity of the nanoemulsion formulations described (see e.g., Tables 5-7 below) were assessed by inoculating the test samples with a suspension of RSV viral particles at a final concentration of $1-3\times10^6$ PFU/mL. At a predetermined exposure time an aliquot was removed and naturized by diluting into EMEM media containing 2% FBS. Residual concentration of active virus particles in treated sample was determined quantitively using a qualified plaque assay described in ATP-12-213.01-Plaque Assay of Respiratory Syncytial Virus. Briefly, serially diluted sample were plated on to Vero cells grown overnight at 80-9-% confluency. Plates were incubated for 4-6 days at 37° C. under 5% CO2. After completion of incubations plates were fixed in pre-chilled methanol and immuno stained using anti RSV antibody. Number of PFU recovered from the test sample was converted into log 10 format and compared to an initial starting concentration to determine a log reduction.

The antimicrobial activity of the nanoemulsion formulations described were assessed according to the procedures described in ASTM E2315-16-Standard Guide for Assessment of Antimicrobial Activity Using a Time-Kill Procedure.

Using the method described in the Standard Guide, a sample of the test formulation was inoculated with a suspension of a test viral particle or organism. At the exposure (contact) time, an aliquot was removed, neutralized in BPB+ and plated onto TSA agar to be quantitatively assayed for surviving test viral particle or organisms. The plates were incubated for 24 hours and the survivors were enumerated. Plate counts were converted into log 10 format and compared to an initial starting population to determine log reduction.

Table 1 shows the in vitro 60 second time kill studies for each of the nanoemulsion formulations indicated (P407=Poloxamer 407; TW20=Tween 20). The results indicate that formulation changes did not impact killing and that each of the tested formulations completely killed all of the organism tested. Additionally, FIG. 5 shows that the NE-2 (surfactant blend ratio: 1:5) demonstrates rapid killing (60 second exposure time) of gram+, gram-bacteria.

TABLE 1

Log killing of selected microorganisms following one-minute exposure to each formulation.

| Formulation | Purell ® Foam | NE-1 (Surfactant Blend Ratio: 1:2) | NE-1 (Surfactant Blend Ratio: 1:5) | NE-1 (Surfactant Blend Ratio: 1:9) | NE-2 (Surfactant Blend Ratio: 1:5) | NE-3 (Surfactant Blend Ratio: 1:6) |
|---|---|---|---|---|---|---|
| Quaternary ammonium compound % | 0.13% BZK | 0.13% BZK | 0.13% BZK | 0.13% BZK | 0.13% BZK | 0.10% CPC |
| Nonionic Surfactant % | — | 0.30% P407 | 0.59% P407 | 1.18% P407 | 0.59% TW20 | 0.59% P407 |
| Surfactant Blend Ratio | — | 1:2 | 1:5 | 1:9 | 1:5 | 1:6 |
| 60 Second Log Killing* Enveloped Virus: | | | | | | |
| RSV (# NBL-14-001-2UC) | >3.49 | >4.49 | >3.49 | >2.59 | >4.49 | >3.49 |
| Gram-Positive Bacteria: | | | | | | |
| CA-MRSA (USA 300) | >6.30 | >6.30 | >6.30 | >6.30 | >6.30 | >6.30 |
| *Enterococcus faecium* (#51559) | >5.44 | >5.44 | >5.44 | >5.44 | >5.44 | >5.44 |
| *Staphylococcus epidermidis* (#12228) | >6.39 | >6.39 | >6.39 | >6.39 | >6.39 | >6.39 |
| Gram-Negative Bacteria: | | | | | | |
| *Acinetobacter baumannii* (#19606) | >6.77 | >6.77 | >6.77 | >6.77 | >6.77 | >6.77 |

TABLE 1-continued

Log killing of selected microorganisms following one-minute exposure to each formulation.

| Formulation | Purell® Foam | NE-1 (Surfactant Blend Ratio: 1:2) | NE-1 (Surfactant Blend Ratio: 1:5) | NE-1 (Surfactant Blend Ratio: 1:9) | NE-2 (Surfactant Blend Ratio: 1:5) | NE-3 (Surfactant Blend Ratio: 1:6) |
|---|---|---|---|---|---|---|
| *Serratia marescens* (#14756) | >7.95 | >7.95 | >7.95 | >7.95 | >7.95 | >7.95 |
| *Klebsiella pneumoniae* (#13883) | >5.09 | >5.09 | >5.09 | >5.09 | >5.09 | >5.09 |

*a greater than symbol (>) indicates that 100% of the bacteria sample was killed.

Example 2—Permeation Study

The goal of this study was to investigate the permeation of benzalkonium chloride (BZK) from various different nanoemulsions via human skin in-vitro permeation studies.

Nanoemulsions comprising 0.13% BZK were topically applied to dermatomed cadaver human skin in a Franz diffusion cell chamber and compared against each other and against a marketed non-nanoemulsion product comprising the same concentration of BZK, 0.13% (Purell® Foam). Permeation was measured by HPLC in the epidermis and dermis 24 hours after a single topical dose.

The in vitro human cadaver skin model has proven to be a valuable tool for the study of percutaneous absorption of topically applied compounds. The model uses human cadaver skin mounted in specially designed diffusion chambers that allow the skin to be maintained at a temperature and humidity that match typical in vivo conditions. A finite dose of formulation is applied to the epidermal layer, e.g., the outer surface of the skin, and compound absorption is measured by monitoring the compound's rate of appearance in the receptor solution bathing the dermal surface of the skin. Data defining total absorption, rate of absorption, as well as skin content can be accurately determined in this model. The method has historic precedent for accurately predicting in vivo percutaneous absorption kinetics. Franz, T J, "Percutaneous absorption: on the relevance of in vitro data," *J. Invest. Dermatol.*, 64:190-195 (1975).

Cryopreserved, dermatomed human cadaver abdominal skin from a 67-year-old Caucasian female donor was used in permeation studies and obtained from Science Care (Phoenix, Ariz.) organ donor bank. Cadaver skin was stored in aluminum foil pouches at −70° C. until use. At the time of use, the skin was thawed by placing the sealed pouch in 37° C. water for approximately five minutes. Thawed skin was removed from the pouch and cut into circular discs (30 mm diameter) to fit between the donor and receiver sides of the permeation chambers.

Percutaneous absorption was measured using the in-vitro cadaver skin finite dose technique. Franz et al., "The finite dose technique as a valid in vitro model for the study of percutaneous absorption in man," In *Skin: Drug Application and Evaluation of Environmental Hazard, Current Problems in Dermatology*, vol. 7, G, edited by Simon et al., pp 58-68 (Basel, Switzerland, S. Karger, 1978). The receptor compartment was filled with 7.0 mL of distilled water, comprising 10% (v/v) ethanol in water, and was placed in the donor compartment and left open to ambient laboratory conditions. The receptor compartment spout was covered with a Teflon screw cap to minimize evaporation of the receptor solution.

Correctly-sized human abdominal skin was placed onto the opening on the permeation cell. All cells were individually clamped with a clamp-support and placed in a heating bath which was maintained at 37° C. by a circulating water bath on the outside of the cells. The receptor compartment was maintained at 37° C. with the water bath and magnetic stirring. The surface temperature of the skin was appropriately 32° C. as determined by an IR surface temperature probe. The illustration and parameters for the diffusion study are shown in Table 2.

TABLE 2

Parameters for the human skin study using diffusion cell methodology.

| | |
|---|---|
| Apparatus | Diffusion cell apparatus |
| Membrane | Human Abdominal Skin Lot #09-03010, female (Caucasian) |
| Replicates | 5 |
| Duration | 24 hours |
| Dosing Surface Area | 1.13 cm$^2$ |
| Dose | 113 μL |
| Dose per Surface Area | 100 μL/cm$^2$ |
| Dosing Frequency | QD, Once |
| Test Formulations | 0.13% NE-1; 013% BZK NE-2 0.13% BZK in Purell® Foam |
| Concentrations | 0.13% BZK |
| Cell Volume | 7.0 mL |
| Receptor Solution | Distilled water, pH 7 with 10% (v/v) ethanol in water |
| Receptor Sampling Volume | 2 mL |
| .Receptor Sampling Time | 24 hours |
| Extraction Solvent | 200 proof Ethanol |
| Surface Wash | 1 mL rinse with 70% ethanol/water solution, 4 times with cotton swabs dipped in 70% ethanol/water solution |
| Assay Method | HPLC |
| Samples Collected | Surface wash, epidermis, dermis, and receptor samples |

The skin was equilibrated for a period of 30 minutes before applying a 113 μL dose (over a dosing area of 1.13 cm$^2$) of the test formulations onto the epidermal surface of the donor chamber of the diffusion cells using a positive displacement pipette. The exposed dosing epidermal surface area was 1.13 cm$^2$. Twenty-four hours after the application of the first dose, the surface of the skin was rinsed with 1 ml of 70% ethanol/water solution and then cleaned with a 70% ethanol-soaked cotton swab, four times. Following alcohol swabbing, the donor cap was removed, and the skin was removed from the apparatus. The epidermis was removed from the dermis via a scraping method and placed in a tarred scintillation vial. A punch biopsy was taken through the dermis and placed in a tarred scintillation vial. Weights of dermis and epidermis were recorded. The epidermal and dermal tissues were extracted with a 200 proof ethanol solution, sonicated for 30 minutes, filtered through a 25 mm, 0.45 µm PTFE membrane syringe filter into HPLC vials and assayed using HPLC. The excess skin portion was placed in scintillation vial with the surface swabs. One mL of the receptor solution was also sampled at 24 hours from the receptor of each cell and filtered through a 0.45 µm PTFE (25 mm) membrane syringe filter. The filtrates were collected in HPLC snap cap vials.

An assay of BZK, extracted from human skin samples, was determined accordingly. This determination was performed on a HPLC equipped with UV detector set at 254 nm. The HPLC column, reverse phase, used was Phenomenix, Luna Conn., 250×4 mm, 5 µm at 55° C. The mobile phase composition was acetate buffer and acetonitrile (ACN) in the ratio of 40:60 in isocratic mode. The method was qualified for linearity and for specificity. Experimental conditions are tabulated below in Table 3.

TABLE 3

Experimental conditions for HPLC analysis of BZK samples extracted from human skin samples.

| | |
|---|---|
| HPLC System | LC System: Shitnadzu LC-20AT |
| | Software: LC Solutions |
| | Communications Bus Module: |
| | Shimadzu CBM-20A |
| | UV-VIS Detector: |
| | Shimadzu SPD-20AV |
| | Column Oven: CTO-20AC |
| Mobile Phase | Acetate Buffer: CAN (40:60) |
| Column | Phenomenix, Luna 5 µ, CN, 100 Å, 250 × 4 mm |
| Chromatograph | Isocratic method |
| Data Acquisition | Acquisition Channel I |
| Detector Wavelength | 254 nm |
| Column Temperature | 25° C. |
| Injection Volume | 100 µL |
| Flow Rate | 2 mL/min |
| Run Time | 15 minutes |
| Bracketing Standard | 160 µg/mL |

The amount of BZK that permeated into the epidermis, dermis, and the receptor compartment (at 24 hours after first dose) was determined by HPLC. The concentration of BZK in the dosing area was determined with respect to a standard preparation. The level of BZK each skin area is represented as the amount per wet tissue weight (ng/grams) the standard deviation. The number of replicas used in the calculation was 5 for each formulation.

The amount of BZK delivered into the human abdominal skin epidermal tissue was the highest with NE-2 (Surfactant Blend Ratio 1:9), with 6642 ng BZK/gram tissue, as compared to 953 ng BZK/gram tissue for the Purell® Foam with the same percentage of 0.13% BZK (0.13%) in each formulation, e.g., equivalent to a 597% increase in permeation with the nanoemulsion formulation having a 1:9 surfactant blend ratio. Similarly, the nanoemulsion having a 1:5 surfactant blend ratio showed an about 300% increase in permeation as compared to the non-nanoemulsion formulation (Purell® Foam).

Figure 44A:
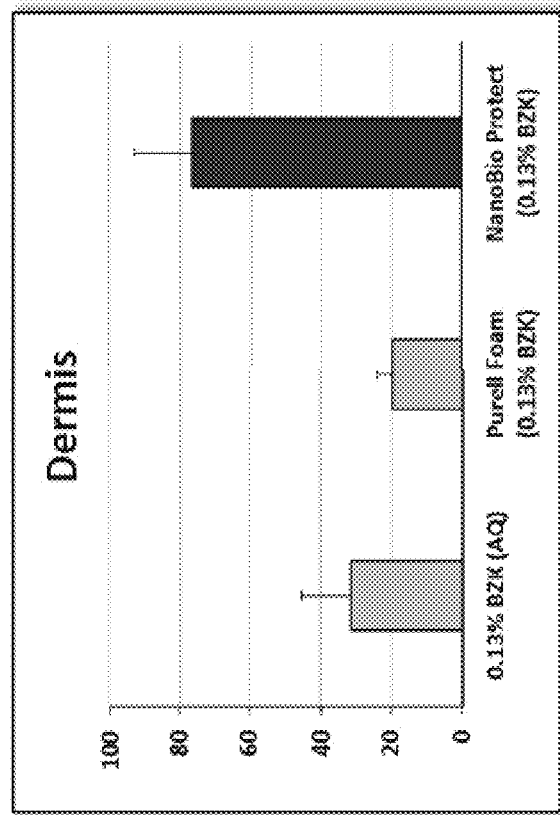
FIG. 44A shows epidermal levels of BZK (μg/g tissue) in human abdominal skin following one application (dose of 100 μl/cm$^2$, measured at 24 hours) of NE-1 formulations (NanoBio protect) (0.13% BZK) with a surfactant blend ratio of 1:9, Purell® Foam (0.13% BZK), and aqueous 0.13% BZK.
Figure 44B:
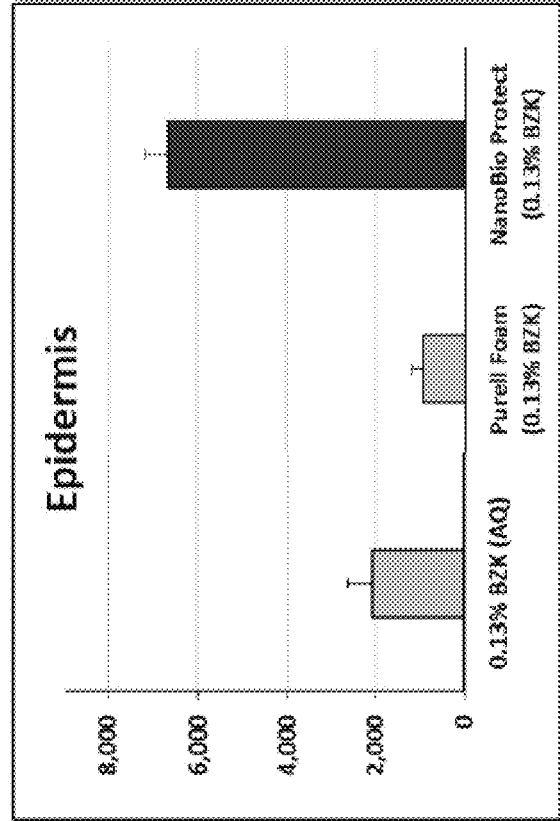
FIG. 44B shows dermal levels of BZK (μg/g tissue) in human abdominal skin following one application (dose of 100 μl/cm$^2$, measured at 24 hours) of NE-1 formulations (0.13% BZK) with a surfactant blend ratio of 1:9, Purell® Foam (0.13% BZK), and aqueous 0.13% BZK.

After one application of 0.13% NE formulations to human skin, this formulation delivered almost 4 to 7 times more BZK into the epidermis as compared to a marketed 0.13% Purell® Foam. With respect to the dermis levels, the nanoemulsion formulation delivered 3 to 4 times more BZK as compared to the marketed product, Purell® Foam, indicating the BZK was able to penetrate into the deeper dermal levels of the skin from the nanoemulsion formulations. There were no detectable levels of BZK in the receptor for any of the formulations tested. Table 4 summarizes these results. FIG. 44A graphically shows the epidermal levels of BZK (µg/g tissue) in human abdominal skin following one application (dose of 100 µl/cm$^2$, measured at 24 hours), and FIG. 44B shows the dermal levels of BZK (µg/g tissue) in human abdominal skin following one application (dose of 100 µl/cm$^2$, measured at 24 hours).

As clearly depicted in FIGS. 45A and 45B, nanoemulsions showed dramatic and significantly greater permeation (amount of BZK (ng)/tissue weight (g)) as compared to a non-nanoemulsion formulation having the same quantity of BZK.

TABLE 3A

Composition of Aqueous BZK Solution (0.13% BZK) shown in FIG. 44

| Formulation Excipients | 0.13% (w/w) Aqueous Solution |
|---|---|
| Purified Water | 99.87 |
| BZK | 0.13 |
| Total | 100% |

TABLE 4

Percutaneous absorption of BZK into human skin (FIG. 44).

| Formulation | Aqueous Solution (0.13% BZK) | Purell Foam (0.13% BZK) | 20% NE (1:9 ratio) (0.13% BZK) |
|---|---|---|---|
| Epidermis | 2101 ± 562 | 953 ± 235 | 6642 ± 1554 |
| Dermis | 32 ± 13 | 20 ± 4 | 77 ± 10 |
| Receptor | 0 | 0 | 0 |

Epidermal and dermal humans skin summary amount of BZK (µg) per weight tissue (g): mean of replicates±SD). Receptor is total amount of BZK (µg): mean of replicates±SD).

As clearly depicted in Tables 4 (FIG. 44) and 4A (FIGS. 2 and 3), the nanoemulsion showed dramatic and significantly greater permeation of BZK (amount of BZK (µg)/tissue weight (g) as compared to anon-nanoemulsion formulation having the same quantity of BZK. See also FIGS. 2 and 3.

TABLE 4A

Percutaneous absorption of BZK into human skin over 24 hours from a single topical application.

| | Formulation | | |
|---|---|---|---|
| | Purell Foam (0.13% BZK) | NE 1-1:5 Ratio (0.13% BZK) | NE 1-1:9 Ratio (0.13% BZK) |
| | | Amount | |
| | µg/g | µg/g | µg/g |
| Epidermis | 953 ± 235 | 3794 ± 525 | 6642 ± 1554 |
| Dermis | 20 ± 4 | 54 ± 16 | 77 ± 10 |
| Receptor | 0 | 0 | 0 |
| Number of Replica | 4 | 4 | 4 |

Epidermal and dermal human skin summary (amount of BZK (ng) per surface area (cm²): mean of replicates±SD; amount of BZK (μg) per weight tissue (g): mean of replicates±SD).

Example 3—Penetration of Topical Nanoemulsion Formulations

This example shows that green fluorescent protein (a visual marker) when formulated with NE was delivered into intact human nasal mucosa and laterally diffused in the mucosa 24 hours after topical application shown in FIG. 45. In particular, FIG. 45A shows that when an aqueous solution is applied topically, no GFP is delivered into the skin (left panel). FIG. 45B, right panel is the NE+GFP and shows the distribution of GFP in the epidermis and dermis.

Example 4—Protection in Mice from Lethal Influenza Challenge

Figure 46:
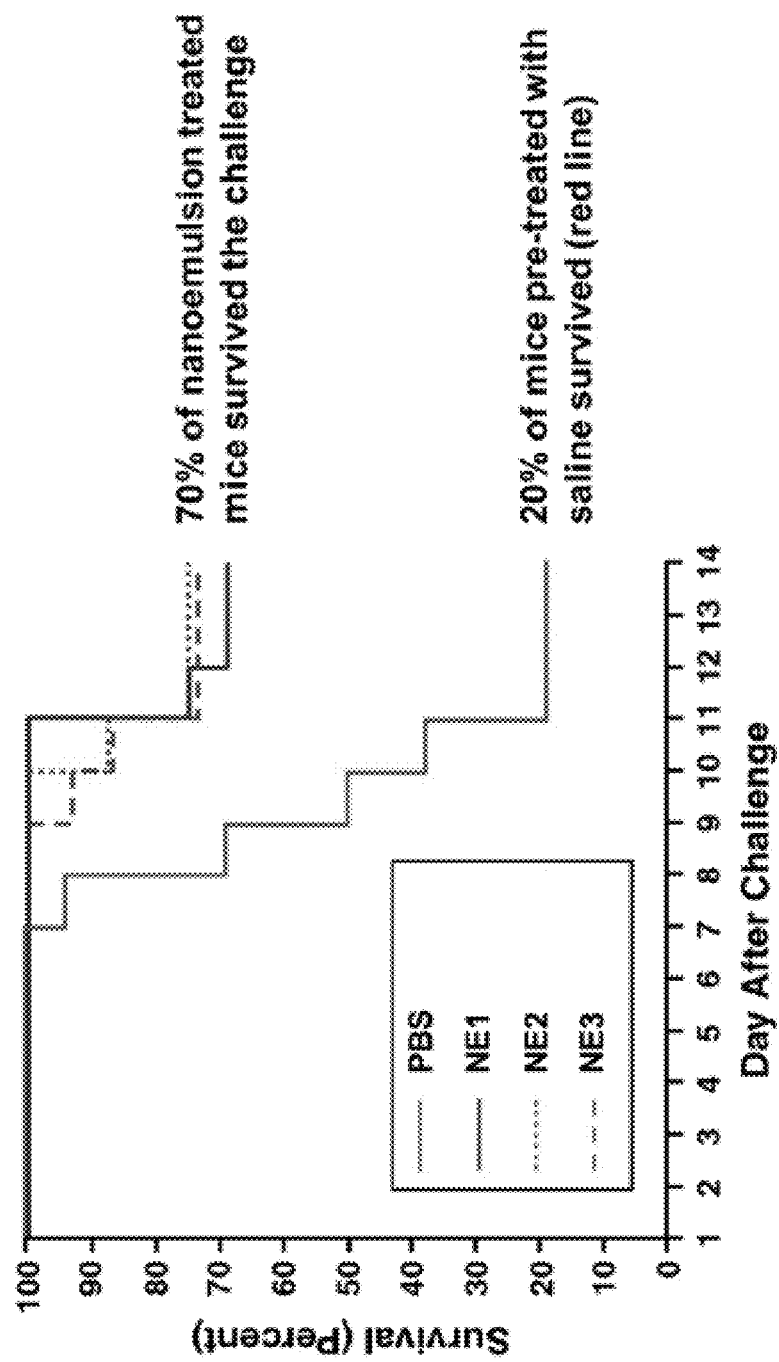
FIG. 46 shows nasal nanoemulsion antiseptic formulations (NE1, NE2, and NE3, having different surfactant ratios) significantly enhanced survival in mice that were challenged with a lethal dose of influenza virus 90 minutes after application. Pretreatment of mouse nares with three nanoemulsion formulations followed by five minute exposure to aerosolized influenza A virus at a concentration of 5×10$^5$ pfu/ml was performed to determine the ability of these compounds to protect mice against inhaled virus particles. Control mice were pretreated with an intranasal application of PBS. 81.25% (13/16) of mice pretreated with PBS died, while 31.91% (15/47) of mice pretreated with nanoemulsion died.
Figure 47:
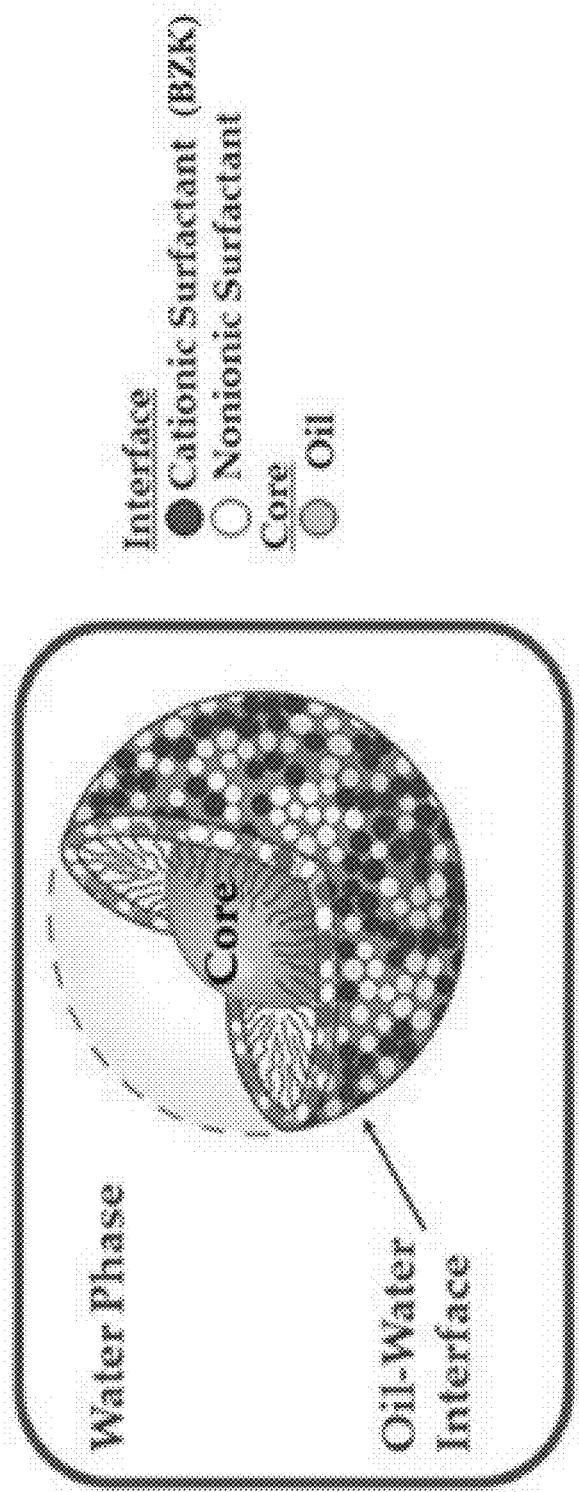
FIG. 47 shows that in a nanoemulsion, the active or quaternary ammonium compound (e.g., BZK) resides at the interface between the oil and water phases of the nanodroplets, with the hydrophobic tail distributed in the oil core and the polar cationic head group residing at the water phase.

FIG. 46 shows nasal nanoemulsion antiseptic formulations (NE1, NE2, and NE3, having different surfactant ratios) significantly enhanced survival in mice that were challenged with a lethal dose of influenza virus 90 minutes after application. Pretreatment of mouse nares with three nanoemulsion formulations followed by five minute exposure to aerosolized influenza A virus at a concentration of $5 \times 10^5$ pfu/ml was performed to determine the ability of these compounds to protect mice against inhaled virus particles. Control mice were pretreated with an intranasal application of PBS. 81.25% (13/16) of mice pretreated with PBS died, while 31.91% (15/47) of mice pretreated with nanoemulsion died.

The results shown in FIG. 46 are a graph of survival (percent) vs day after challenge. 70% of nanoemulsion-treated mice (NE1, NE2 and NE3) survived the challenge, whereas in contrast only 20% of saline treated mice survived the challenge.

Example 5—Nanoemulsion Test Formulations

The purpose of this example was to prepare several test nanoemulsions having different surfactant blend ratios.

The nanoemulsion test formulations comprised 0.13% BZK or 0.10% CPC, and were made using conventional homogenization techniques. The compositions of the BZK or CPC formulations are listed in Tables 5, 6, and 7 as NE-1, NE-2, and NE-3 formulations, respectively.

To manufacture the nanoemulsion, the water soluble ingredients are first dissolved in water. The oil is then added and the mixture is mixed using high shear homogenization and/or microfluidization until a viscous white emulsion is formed. The emulsion may be further diluted with water to yield the desired concentration of emulsion or quaternary ammonium compound.

Nanoemulsions used in this study are oil-in-water o/w) emulsions with mean droplet diameters of 300-600 nm. BZK or CPC resides at the interface between the oil and water phases. The hydrophobic tail of the surfactant distributes in the oil core and its polar head group resides in the water phase.

The nanoemulsions described herein are made from surfactants approved for human consumption and common food substances and are 'Generally Recognized as Safe' (GRAS) by the FDA. These emulsions are produced by mixing a water-immiscible oil phase into an aqueous phase. The two phases (aqueous phase and oil phase) are combined and processed to yield an emulsion. The emulsion is further processed to achieve the desired particle size.

TABLE 5

NE-1 formulations with 0.13% BZK.

| Formulation Excipients | NE-1 (Surfactant Blend Ratio: 1:2) | NE-1 (Surfactant Blend Ratio: 1:5) | NE-1 (Surfactant Blend Ratio: 1:9) | NE-1 (Surfactant Blend Ratio: 1:14) | NE-1 (Surfactant Blend Ratio: 1:18) | NE-1 (Surfactant Blend Ratio: 1:27) |
|---|---|---|---|---|---|---|
| Purified Water | 95.744 | 91.805 | 83.929 | 76.047 | 68.2 | 58.458 |
| BZK | 0.13 | 0.13 | 0.13 | 0.13 | 0.13 | 0.13 |
| Poloxamer 407 | 0.296 | 0.592 | 1.184 | 1.776 | 2.368 | 3.552 |
| Glycerol | 0.504 | 1.008 | 2.016 | 3.024 | 4.032 | 6.048 |
| Soybean Oil | 3.139 | 6.279 | 12.558 | 18.837 | 25.116 | 37.674 |
| EDTA | 0.186 | 0.186 | 0.186 | 0.186 | 0.186 | 0.186 |
| Total | 100% | 100% | 100% | 100% | 100% | 100% |

The above percentages are wt/wt, unless otherwise noted.

TABLE 6

NE-2 formulations with 0.13% BZK.

| Formulation Excipients | NE-2 (Surfactant Blend Ratio: 1:5) | NE-2 (Surfactant Blend Ratio: 1:9) |
|---|---|---|
| Purified Water | 91.805 | 83.929 |
| BZK | 0.13 | 0.13 |
| Tween 20 | 0.597 | 1.184 |
| Glycerol | 1.008 | 2.016 |

TABLE 6-continued

NE-2 formulations with 0.13% BZK.

| Formulation Excipients | NE-2 (Surfactant Blend Ratio: 1:5) | NE-2 (Surfactant Blend Ratio: 1:9) |
|---|---|---|
| Soybean Oil | 6.279 | 12.558 |
| EDTA | 0.186 | 0.186 |
| Total | 100% | 100% |

The above percentages are wt/wt, unless otherwise noted.

TABLE 7

NE-3 formulations with 0.10% CPC.

| Formulation Excipients | NE-3 (Surfactant Blend Ratio: 1:6) | NE-3 (Surfactant Blend Ratio: 1:12) |
|---|---|---|
| Purified Water | 91.835 | 83.956 |
| CPC | 0.1 | 0.1 |
| Poloxamer 407 | 0.592 | 1.184 |
| Glycerol | 1.008 | 2.016 |
| Soybean Oil | 6.279 | 12.558 |
| EDTA | 0.186 | 0.186 |
| Total | 100% | 100% |

The above percentages are wt/wt, unless otherwise noted.

Example 6—Permeation Study

The goal of this study was to investigate the permeation of benzalkonium chloride (BZK) from various different nanoemulsions via human skin in-vitro permeation studies.

Nanoemulsions comprising 0.13% BZK were topically applied to dermatomed cadaver human skin in a Franz diffusion cell chamber and compared against each other and against a marketed non-nanoemulsion product comprising the same concentration of BZK, 0.13% (Purell® Foam). Permeation was measured by HPLC in the epidermis and dermis 24 hours after a single topical dose.

The in vitro human cadaver skin model has proven to be a valuable tool for the study of percutaneous absorption of topically applied compounds. The model uses human cadaver skin mounted in specially designed diffusion chambers that allow the skin to be maintained at a temperature and humidity that match typical in vivo conditions. A finite dose of formulation is applied to the epidermal layer, e.g., the outer surface of the skin, and compound absorption is measured by monitoring the compound's rate of appearance in the receptor solution bathing the dermal surface of the skin. Data defining total absorption, rate of absorption, as well as skin content can be accurately determined in this model. The method has historic precedent for accurately predicting in vivo percutaneous absorption kinetics. Franz, T J, "Percutaneous absorption: on the relevance of in vitro data," *J. Invest. Dermatol.*, 64:190-195 (1975).

Cryopreserved, dermatomed human cadaver abdominal skin from a 67-year-old Caucasian female donor was used in permeation studies and obtained from Science Care (Phoenix, Ariz.) organ donor bank. Cadaver skin was stored in aluminum foil pouches at −70° C. until use. At the time of use, the skin was thawed by placing the sealed pouch in 37° C. water for approximately five minutes. Thawed skin was removed from the pouch and cut into circular discs (30 mm diameter) to fit between the donor and receiver sides of the permeation chambers.

Percutaneous absorption was measured using the in-vitro cadaver skin finite dose technique. Franz et al., "The finite dose technique as a valid in vitro model for the study of percutaneous absorption in man," In *Skin: Drug Application and Evaluation of Environmental Hazards, Current Problems in Dermatology*, vol. 7, G, edited by Simon et al., pp 58-68 (Basel, Switzerland, S. Karger, 1978). The receptor compartment was filled with 7.0 mL of distilled water, comprising 10% (v/v) ethanol in water, and was placed in the donor compartment and left open to ambient laboratory conditions. The receptor compartment spout was covered with a Teflon screw cap to minimize evaporation of the receptor solution. Correctly-sized human abdominal skin was placed onto the opening on the permeation cell. All cells were individually clamped with a clamp-support and placed in a heating bath which was maintained at 37° C. by a circulating water bath on the outside of the cells. The receptor compartment was maintained at 37° C. with the water bath and magnetic stirring. The surface temperature of the skin was appropriately 32° C. as determined by an IR surface temperature probe. The illustration and parameters for the diffusion study are shown in Table 8.

TABLE 8

Parameters for the human skin study using diffusion cell methodology.

| | |
|---|---|
| Apparatus | Diffusion cell apparatus |
| Membrane | Human Abdominal Skin Lot# 09-03010, female (Caucasian) |
| Replicates | 5 |
| Duration | 24 hours |
| Dosing Surface Area | 1.13 cm$^2$ |
| Dose | 113 µL |
| Dose per Surface Area | 100 µL/cm$^2$ |
| Dosing Frequency | QD, Once |
| Test Formulations | 0.13% NE-1; 013% BZK NE-2 0.13% BZK in Purell ® Foam |
| Concentrations | 0.13 % BZK |
| Cell Volume | 7.0 mL |
| Receptor Solution | Distilled water, pH 7 with 10% (v/v) ethanol in water |
| Receptor Sampling Volume | 2 mL |
| Receptor Sampling Time | 24 hours |
| Extraction Solvent | 200 proof Ethanol |
| Surface Wash | 1 mL rinse with 70% ethanol/water solution, 4 times with cotton swabs dipped in 70% ethanol/water solution |
| Assay Method | HPLC |
| Samples Collected | Surface wash, epidermis, dermis, and receptor samples |

The skin was equilibrated for a period of 30 minutes before applying a 113 µL dose (over a dosing area of 1.13 cm$^2$) of the test formulations onto the epidermal surface of the donor chamber of the diffusion cells using a positive displacement pipette. The exposed dosing epidermal surface area was 1.13 cm$^2$. Twenty-four hours after the application of the first dose, the surface of the skin was rinsed with 1 ml of 70% ethanol/water solution and then cleaned with a 70% ethanol-soaked cotton swab, four times. Following alcohol swabbing, the donor cap was removed, and the skin was removed from the apparatus. The epidermis was removed from the dermis via a scraping method and placed in a tarred scintillation vial. A punch biopsy was taken through the dermis and placed in a tarred scintillation vial. Weights of dermis and epidermis were recorded. The epidermal and dermal tissues were extracted with a 200 proof ethanol solution, sonicated for 30 minutes, filtered through a 25 mm, 0.45 µm PTFE membrane syringe filter into HPLC vials and assayed using HPLC. The excess skin portion was placed in scintillation vial with the surface swabs. One mL of the receptor solution was also sampled at 24 hours from the receptor of each cell and filtered through a 0.45 µm PTFE (25 mm) membrane syringe filter. The filtrates were collected in HPLC snap cap vials.

An assay of BZK, extracted from human skin samples, was determined accordingly. This determination was performed on a HPLC equipped with UV detector set at 254 nm. The HPLC column, reverse phase, used was Phenomenex, Luna Conn., 250×4 mm, 5 µm at 55° C. The mobile phase composition was acetate buffer and acetonitrile (ACN) in the ratio of 48:52 in isocratic mode. The method was qualified for linearity and for specificity. Experimental conditions are tabulated below in Table 9.

TABLE 9

Experimental conditions for HPLC analysis of BZK samples extracted from human skin samples.

| | |
|---|---|
| HPLC System | LC System: Shimadzu LC-20AT |
| | Software: LC Solutions |
| | Communications Bus Module: Shimadzu CBM-20A |
| | UV-VIS Detector: Shimadzu SPD-20AV |
| | Column Oven: CTO-20AC |
| Mobile Phase (v/v or v/v/v) | Acetate Buffer: ACN (48:52) |
| Column | Phenomenix, Lima 5µ, CN, 100 Å, 250 × 4 mm |
| Detector Wavelength | 254 nm |
| Column Temperature | 30° C. |
| Injection Volume | 100 µL |
| Flow Rate | 2 mL/min |
| Run Time | 15 minutes |
| Bracketing Standard | 160 µg/mL |

ACN = Acetonitrile

The amount of BZK that permeated into the epidermis, dermis, and the receptor compartment (at 24 hours after first dose) was determined by HPLC. The concentration of BZK in the dosing area was determined with respect to a standard preparation. The level of BZK each skin area is represented as the amount per wet tissue weight (ng/grams) the standard deviation. The number of replicas used in the calculation was 5 for each formulation.

The amount of BZK delivered into the human abdominal skin epidermal tissue was the highest with NE-2 (Surfactant Blend Ratio 1:9), with 6642 ng BZK/gram tissue, as compared to 953 ng BZK/gram tissue for the Purell® Foam with the same percentage of 0.13% BZK (0.13%) in each formulation, e.g., equivalent to a 597% increase in permeation with the nanoemulsion formulation having a 1:9 surfactant blend ratio. Similarly, the nanoemulsion having a 1:5 surfactant blend ratio showed an about 300% increase in permeation as compared to the non-nanoemulsion formulation (Purell® Foam).

After one application of 0.13% NE formulations to human skin, this formulation delivered almost 4 to 7 times more BZK into the epidermis as compared to a marketed 0.13% Purell® Foam. With respect to the dermis levels, the nanoemulsion formulation delivered 3 to 4 times more BZK as compared to the marketed product, Purell® Foam, indicating the BZK was able to penetrate into the deeper dermal levels of the skin from the nanoemulsion formulations. There were no detectable levels of BZK in the receptor for any of the formulations tested. Table 10 summarizes these results. FIG. 1 graphically shows the epidermal levels of BZK (µg/g tissue) in human abdominal skin following one application (dose of 100 µl/cm$^2$, measured at 24 hours), and FIG. 2 shows the dermal levels of BZK (µg/g tissue) in human abdominal skin following one application (dose of 100 µl/cm$^2$, measured at 24 hours).

As clearly depicted in FIGS. 2 and 3, nanoemulsions having surfactant ratios of 1:5 and 1:9 showed dramatic and significantly greater permeation (amount of BZK (ng)/tissue weight (g)) as compared to a non-nanoemulsion formulation having the same quantity of BZK.

TABLE 10

Percutaneous absorption of BZK into human skin over 24 hours from a single topical application.

| | Formulation | | |
|---|---|---|---|
| | Purell Foam (0.13% BZK) | NE 1-1:5 Ratio (0.13% BZK) | NE 1-1:9 Ratio (0.13% BZK) |
| | Amount | | |
| | µg/g | µg/g | µg/g |
| Epidermis | 953 ± 235 | 3794 ± 525 | 6642 ± 1554 |
| Dermis | 20 ± 4 | 54 ± 16 | 77 ± 10 |
| Receptor | 0 | 0 | 0 |
| Number of Replica | 4 | 4 | 4 |

Epidermal and dermal human skin summary (amount of BZK, per surface area (cm$^2$): mean of replicates ± SD; amount of BZK (µg) per weight tissue (g): mean of replicates ± SD).

Example 7—Expanded Ex Vivo Skin Permeation Study

Following the ex vivo skin permeation study outlined in Example 6, the following 0.13% BZK NE-1 formulations were evaluated against the Purell® Foam using the same methodology of Example 6:

TABLE 11

0.13% BZK NE-1 Formulations Tested
NE-1 Ratio (0.13% BZK)

5:1
2:1
1:1
1:2
1:5 (repeated from Example 6)
1:9 (repeated from Example 6)
1:14
1:18
1:27
1:36
1:46

FIG. 3 graphically shows the epidermal levels of BZK (µg/g tissue) in human abdominal skin following one application (dose of 100 µl/cm$^2$, measured at 24 hours) of the different NE-1 formulations with different surfactant blend ratios and Purell® Foam. FIG. 4 shows the dermal levels of BZK (µg/g tissue) in human abdominal skin following one application (dose of 100 µl/cm$^2$, measured at 24 hours) of different NE-1 formulations with different surfactant blend ratios and Purell® Foam.

The results were significant and unexpected, with a clear bell curve regarding permeation vs surfactant blend ratio demonstrating that a narrow range of a surfactant blend ratio shows dramatic increased permeation. Outside the claimed surfactant blend ratio of about 5:about 1 and ranging up to about 1:about 27, the amount of drug in the epidermis (FIG.

3) and dermis (FIG. 4) is dramatically less. The impact of the claimed narrow range of surfactant blend ratios on permeation was not known prior to the present invention.

Example 8—High Temperature Stability

The purpose of this example was to demonstrate the stability at high temperatures of nanoemulsions having a preferred surfactant blend ratio.

Stability at extremely high temperatures (e.g. 50° C.; 122° F.) in robust packaging components (e.g. PET plastic bottles with sprayers, not glass vials) would provide significant advantages for extremely hot climates.

NE-2 (Surfactant Blend Ratio: 1:5; 0.13% BZK) was produced at a 4 kg scale and placed on stability at 5° C., 25° C., 40° C., and 50° C. (122° F.). Table 12 shows that NE-2 (Surfactant Blend Ratio: 1:5; 0.13% BZK) is stable for 1 month even at the most extreme storage condition of 50° C. (122° F.). This is highly unexpected. At severely high temperatures, emulsions are prone to rapid destabilization within a few hours to a couple of days. This data demonstrates that the nanoemulsion formulations having the claimed surfactant blend ratio will offer key advantages for use in extremely high temperature climates.

The BZK Potency was determined with RP-HPLC, as described previously (e.g. permeation section). The appearance was determined via a visual assessment of color, creaming, settling and phase separation with predetermined acceptance criteria. The particle size and polydispersity index (PdI) of the sample were measured by dynamic light scattering using photon correlation spectroscopy with Malvern Zetasizer Nano Z90 (Malvern Instruments, Worcestershire, UK), according to S 208.01 version 1: Particle Sizing (Malvern). All measurements were carried out at 25° C. after appropriate dilution with double distilled 0.22 μm filtered water.

Example 9—In Vivo Skin Hydration Study

The purpose of this example was to evaluate the effect on skin hydration of nanoemulsions having a preferred surfactant blend ratio.

Two skin areas were tested in vivo, which were the human forearm and backarm. Two test formulations were tested: NE-1 (surfactant blend ratio: 1:5; 0.13% BZK) and Purell® Foam (0.13% BZK). 1 mL of each formulation was applied with rubbing for twenty seconds. Skin hydration was measured 5 times with a Delfin Moisture meter at 10, 20, 30, 60, and 180 minutes after application, with lower readings indicate lower skin hydration levels.

FIG. 6 shows skin hydration study results of NE-1 (surfactant blend ratio: 1:5; 0.13% BZK) and Purell® Foam (0.13% BZK), with the figure clearly and unequivocally showing significant and dramatically improved hydration with nanoemulsion formulations according to the invention as compared to a non-nanoemulsion formulation comprising the same quaternary ammonium compound at the same concentration. These results demonstrate that single application of NE-1 resulted in a significant and sustained increase in skin hydration.

Example 10—Wipe Dispensing Study

The objective of this study was to compare the NE formulations comprising BZK described herein to other products comprising the same amount of BZK but lacking a nanoemulsion. Two different wipe materials were tested: spunlace washcloth and airlaid washcloth. Three test formulations comprising the same amount of BZK were tested: (i) an aqueous solution of 0.13% BZK; (ii) NE-1 (surfactant blend ratio: 1:9; 0.13% BZK); and (iii) Purell® Foam (0.13% BZK). The wipes were saturated with consistent volumes of each tested formulation and the amount of BZK dispensed was measured at the following three time points—initial, 2 hours and 5 days.

TABLE 12

Summary of NE-2 (Surfactant Blend Ratio: 1:9) stability summary.

| Stability Condition | Time (months) | Appearance (Pass/Fail) | pH (3-6) | BZK Potency (90-110% Label Claim) | Mean Particle Size (nm) (250-500 nm) | Polydispersity Index (<0.25) | Viscosity (cP) (cP > 1.0) |
|---|---|---|---|---|---|---|---|
| Lot X-2112: 20% NE-2 (0.13% BZK) Stored in PET Slim Line Cylinder Bottles with Fine mis-sprayers | | | | | | | |
| Initial | 0 | Pass | 4.73 | 99.3 | 315.4 ± 0.2 | 0.151 ± 0.058 | 2.13 |
| 5° C./4° F. | 1 | Pass | 4.64 | 101.5 | 320.8 ± 4.1 | 0.195 ± 0.016 | 2.12 |
| 25° C./77° F. | 1 | Pass | 4.57 | 100.4 | 326.9 ± 5.5 | 0.190 ± 0.004 | 2.17 |
| 40° C./104° F. | 1 | Pass | 4.55 | 101.2 | 337.6 ± 3.5 | 0.220 ± 0.004 | 2.17 |
| 50° C./122° F. | 1 | Pass | 4.55 | 103.7 | 335.7 ± 6.2 | 0.193 ± 0.003 | 2.20 |
| 5° C./41° F. | 3 | Pass | 4.65 | 103.1 | 291.4 ± 4.2 | 0.121 ± 0.008 | 2.09 |
| 25° C./77° F. | 3 | Pass | 4.58 | 98.9 | 314.9 ± 1.2 | 0.158 ± 0.024 | 2.23 |
| 40° C./104° F. | 3 | Pass | 4.51 | 100.0 | 319.3 ± 4.0 | 0.143 ± 0.033 | 2.24 |
| 50° C./122° F. | 3 | Pass | 3.46 | 99.6 | 320.0 ± 3.1 | 0.185 ± 0.016 | 2.35 |

The data shows that no significant particle growth was observed at higher temperatures, demonstrating the stability of the formulation.

Rapid killing of pathogen demonstrated above coupled with stability at extremely high temperatures (shown in Table 12) makes this technology an ideal fit for extremely high temperature climates.

Figure 7:
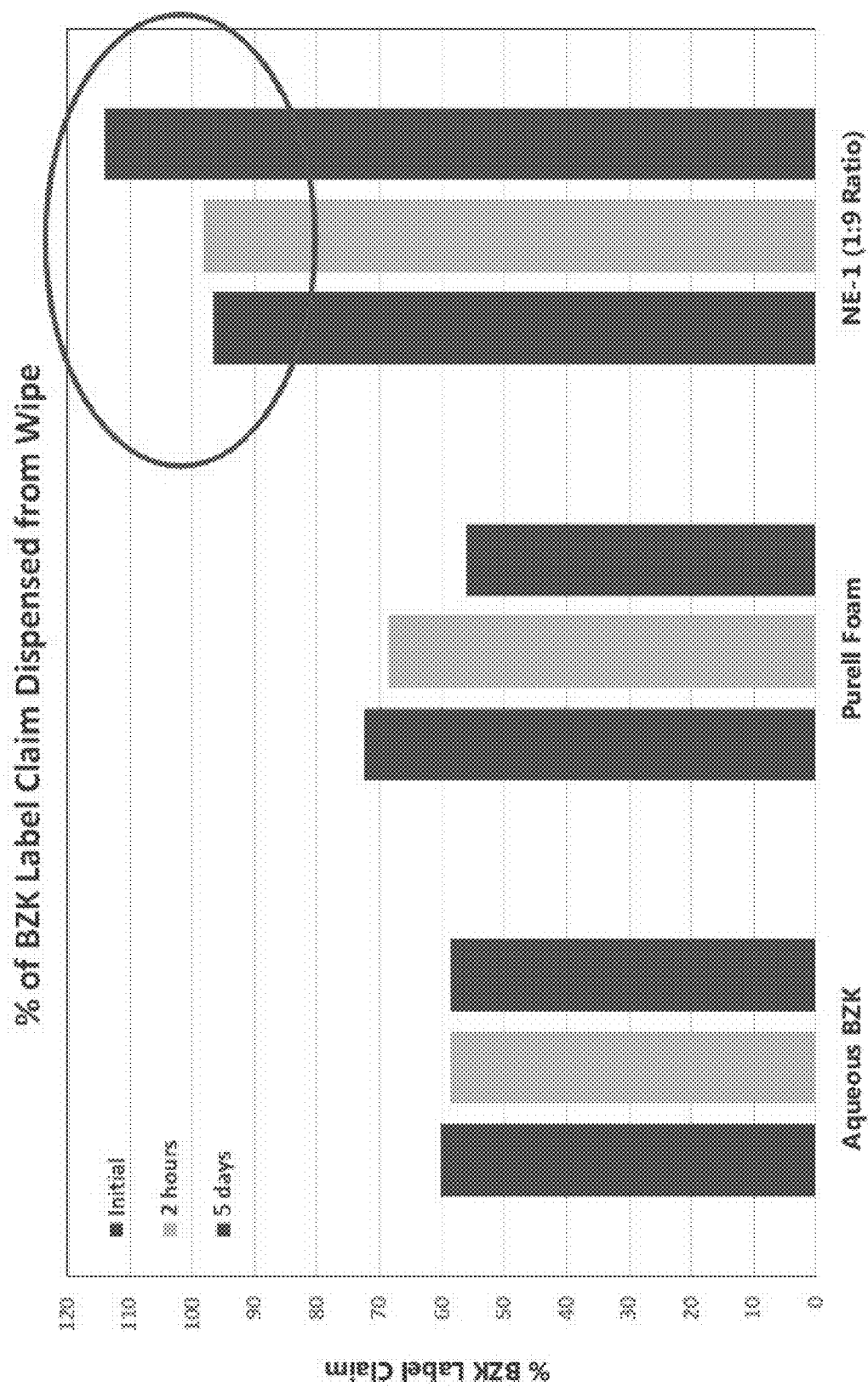
FIG. 7 shows the % of BZK dispensed from the wipe (spunlace washcloth) with aqueous BZK (0.13% BZK), NE-1 (surfactant blend ratio: 1:9; 0.13% BZK), and Purell® Foam (0.13% BZK) at the following time points: initial, 2 hours and 5 days.

FIG. 7 shows the percent (%) of BZK dispensed from the wipe (spunlace washcloth) with aqueous BZK (0.13% BZK), NE-1 (surfactant blend ratio: 1:9; 0.13% BZK), and Purell® Foam (0.13% BZK) at the following time points: initial, 2 hours and 5 days. The results graphically depicted in the figure show that the aqueous BZK and Purell® Foam formulations had significantly less compound (BSK) dispensed from the wipe as compared to the nanoemulsion formulation. This result is significant, as the goal of a wipe-dispensed product is to dispense as much drug as possible. Retention of drug in a wipe is contrary to the goal of drug dispension.

In particular, FIG. 7 (spunlace washcloth) shows that the nanoemulsion formulation dispensed over 95% of the BZK label claim from the wipe at each of the tested time points, with over a 110% measurement at 5 days. In contrast, the aqueous BZK formulation had a high BZK % label claim of 60% at the initial time point, and the Purell® Foam formulation had a high of an initial % BZK label claim of about 73%, also at the initial time point.

Figure 8:
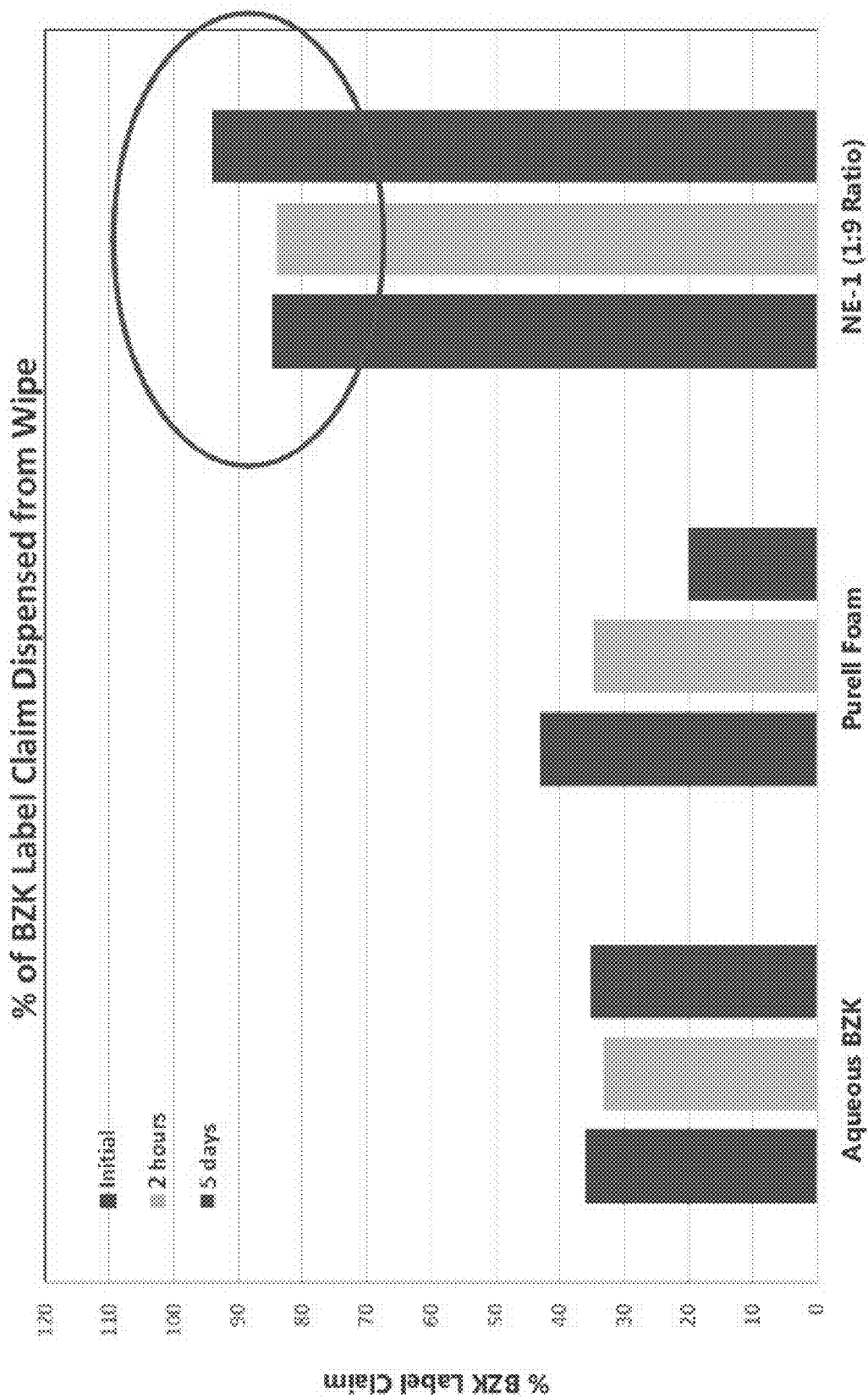
FIG. 8 shows the % of BZK dispensed from the wipe (airlaid washcloth) with aqueous BZK (0.13% BZK), NE-1 (surfactant blend ratio: 1:9; 0.13% BZK), and Purell® Foam (0.13% BZK) at the following time points: initial, 2 hours and 5 days.

FIG. 8 (airlaid washcloth) shows the % of BZK dispensed from the wipe with aqueous BZK (0.13% BZK), NE-1 (surfactant blend ratio: 1:9; 0.13% BZK), and Purell® Foam (0.13% BZK) at the following time points: initial, 2 hours and 5 days. The data shown in the figure demonstrates that the nanoemulsion formulation dispensed about 85% of the % BZK label claim at the initial and 2 hour test points, and about 95% of the % BZK label claim at 5 days. In contrast, the aqueous BZK formulation had a high of about a 35% of the % BZK label claim at the initial test point, with the percentage decreasing at the 2 hour and 5 day test points. Similarly, the Purell® Foam formulation had a high of just over 40% of the % BZK label claim at the initial time point, with decreasing amounts at the 2 hour (35%) and 5 day (20%) time points.

These results demonstrate that the wipes comprising the nanoemulsion formulations with preferred surfactant blend ratios significantly dispensed more BZK than non-emulsion formulations of the same active (BZK) present at the same concentration (0.13%).

Example 11—In Vitro Mucin Permeation Study

The objective of this study was to compare the in vitro permeation of Compound A, a therapeutic compound, across a mucin layer (as a surrogate for the nasal mucous) using a commercially available intranasal product and the nanoemulsion emulsion formulations described herein.

Porcine stomach mucin type III (a mixture of different mucins) and HEPES (4-(2-Hydroxyethyl)piperazine-1-ethanesulfonic acid, N-(2-Hydroxyethyl)piperazine-N'-(2-ethanesulfonic acid) were purchased from Sigma-Aldrich (St. Louis, Mo.). Transwell® membranes (6.5 mm diameter inserts, 3.0 μm pore size in polycarbonate membrane) were purchase from Corning Incorporated (Kennebunk Me.). 24 well plates were purchased from VWR (Radnor, Pa.).

Figure 9:
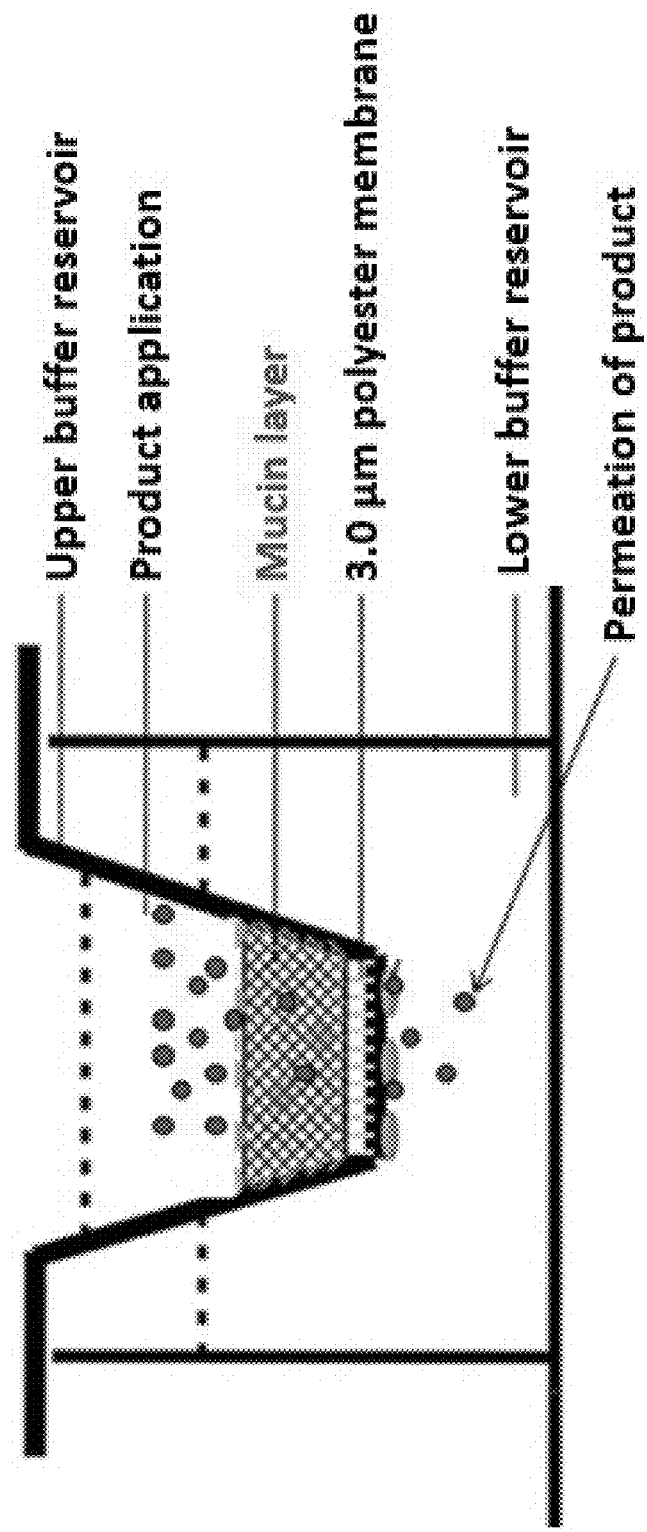
FIG. 9 shows a diagram of the mucin coated Transwell® membrane in a 24 well plate.

Porcine gastric mucin type III was rehydrated at 10 mg/mL in 1 mM HEPES, pH 7 at 25° C. for 30 minutes. Transwell® membranes were coated with 10 mg/mL mucin in 1 mM HEPES, pH 7 overnight at 37° C. hanging in a lower buffer reservoir (1 mM HEPES, pH 7). Mucin coated Transwell® membranes were moved to a fresh reservoir containing 600 μL of fresh 1 mM HEPES buffer, pH 7, at 37° C. 100 μL of NE-1 (surfactant blend ratio of 1:9)+Compound A (0.25% or 0.5%) or a commercial product containing Compound A (0.5%) was added to the top of each Transwell® membrane (as shown in FIG. 9) and incubated at 37° C.

At pre-determined timepoints, the lower buffer reservoir solution was removed and replaced with 600 μL of fresh buffer. Compound A was measured by RP-HPLC analysis in reservoir samples. Each formulation was tested in triplicate.

TABLE 13

NE-1 formulations with Compound A.

| Formulation Excipients | NE-1 (Surfactant Blend Ratio: 1:9; 0.50% Compound A) | NE-1 (Surfactant Blend Ratio: 1:9; 0.25% Compound A) |
| --- | --- | --- |
| Buffer | 88.414 | 83.664 |
| BZK | 0.12 | 0.12 |
| Poloxamer 407 | 1.184 | 1.184 |
| Glycerol | 2.224 | 2.224 |
| Soybean Oil | 12.558 | 12.558 |
| EDTA | 0.5 | 0.25 |
| Total | 100% | 100% |

*Buffer contains 0.4% sodium citrate and 0.15% citric acid in purified water.
The above percentages are wt/wt, unless otherwise noted.

FIG. 10 shows the results of the in vitro mucin permeation studies of Compound A with the commercially available intranasal product of Compound A (0.50% Compound A) and the NE-1 (surfactant blend ratio: 1:9) with 0.50% and 0.25% of Compound A. As graphically depicted in FIG. 10, the permeation of Compound A was greater when present in a nanoemulsion formulation as compared to a non-nanoemulsion formulation. In particular, the commercial product of Compound A, having a drug concentration of 50%, showed a cumulative concentration of compound A (μg/mL) at 6 hours following application of about 325 μg/mL, in contrast to a concentration of about 730 μg/mL for the nanoemulsion having a surfactant ratio of 1:9 and a drug concentration of 50%, an increase in drug permeation of 125%.

These results show that nanoemulsion formulations having a preferred surfactant blend ratio significantly enhance the permeation of a component therapeutic agent.

Example 12—In Vivo Rat Study

The objective of this study was to compare the serum levels of Compound A following intranasal administration of a commercially available intranasal product and nanoemulsion formulations described herein.

Sprague-Dawley rats were purchased from Charles River Laboratories (Wilmington, Mass.; Source; Stock #400) and were 6 weeks old upon arrival. Rats were housed in specific pathogen-free conditions. All procedures were approved by the University Committee on the Use and Care of Animals (UCUCA) at the University of Michigan (ULAM IVAC #: IV1060). Animals were housed in ventilated racks, 3 rats per cage. The in-life duration of the study included 50 μL intranasal administration (25 μL per nare) of each test formulation to three separate rats, timed bleeds, and euthanasia of the animals. The intranasal administration was performed under brief anesthesia.

The test formulations included: (1) a commercial product with 0.5% Compound A (a representative therapeutic agent) or (2) nanoemulsion formulated with either 0.25% or 0.5% Compound A (NE-2 with surfactant blend ratio of 1:2, 1:5, 1:9, and NE-4 with surfactant blend ratio of 1:2 and 1:5).

Blood was collected pre-dose at 72 hours, and then bled at 4 hours, 24 hours and 48 hours week postdose. Blood collection was approximately 1.0 mL in volume and allowed for sufficient serum to allow for analyze and measure of Compound A. Animals were monitored daily by IVAC and husbandry staff and any observations recorded on data sheets. Animals were monitored closely for reactions to test articles. There were no significant reactions that occurred as defined by the University Committee on Care and Use of Animals (UCUCA) humane endpoint guidelines. Upon euthanasia, animals were bled via cardiac puncture; with blood provided for analysis of Compound A.

TABLE 14

NE-2 and NE-4 formulations with Compound A.

| Formulation Excipients | NE-2 (Surfactant Blend Ratio: 1:2; 0.50% Compound A) | NE-2 (Surfactant Blend Ratio: 1:5; 0.50% Compound A) | NE-2 (Surfactant Blend Ratio: 1:5; 0.25% Compound A) | NE-2 (Surfactant Blend Ratio: 1:9; 0.50% Compound A) | NE-4 (Surfactant Blend Ratio: 1:2; 0.50% Compound A) | NE-4 (Surfactant Blend Ratio: 1:5; 0.50% Compound A) |
|---|---|---|---|---|---|---|
| Buffer* | 95.389 | 91.397 | 91.647 | 83.414 | 95.608 | 91.836 |
| BZK | 0.12 | 0.12 | 0.12 | 0.12 | 0.12 | 0.12 |
| Tween 80 | 0.296 | 0.592 | 0.592 | 1.184 | 0.296 | 0.592 |
| Glycerol | 0.556 | 1.112 | 1.112 | 2.224 | — | — |
| Ethanol | — | — | — | — | 0.3365 | 0.673 |
| Soybean Oil | 3.1395 | 6.279 | 6.279 | 12.558 | 3.1395 | 6.279 |
| EDTA | 0.5 | 0.5 | 0.25 | 0.5 | 0.5 | 0.5 |
| Total | 100% | 100% | 100% | 100% | 100% | 100% |

*Buffer contains 0.4% sodium citrate and 0.15% citric acid in purified water.
The above percentages are wt/wt, unless otherwise noted.

Compound A concentration in rat serum was determined using a competitive enzyme linked immunoassay performed by chemiluminescence at Texas A&M Veterinary Medical Diagnostic Laboratory (College Station, Tex.). Briefly, a ICN Pharmaceuticals SimulTRAC-SNB kit uses purified intrinsic factor. The R SimuTRAC-SNB is used for the simultaneous quantitative determination of Compound A in serum. This assay did not require boiling and utilizes both 57Cobalt and 125Iodine. In competitive protein binding, the binder should have an equal affinity for the standard and the substance which is present in the rat serum sample. The unlabeled Compound A competes with its labeled species for the limited number of available binding sites on its specific binder, thus reducing the amount of labeled Compound A bound. Therefore, the level of radioactivity bound is inversely related to the concentration in the rat serum sample or standard.

Figure 11:
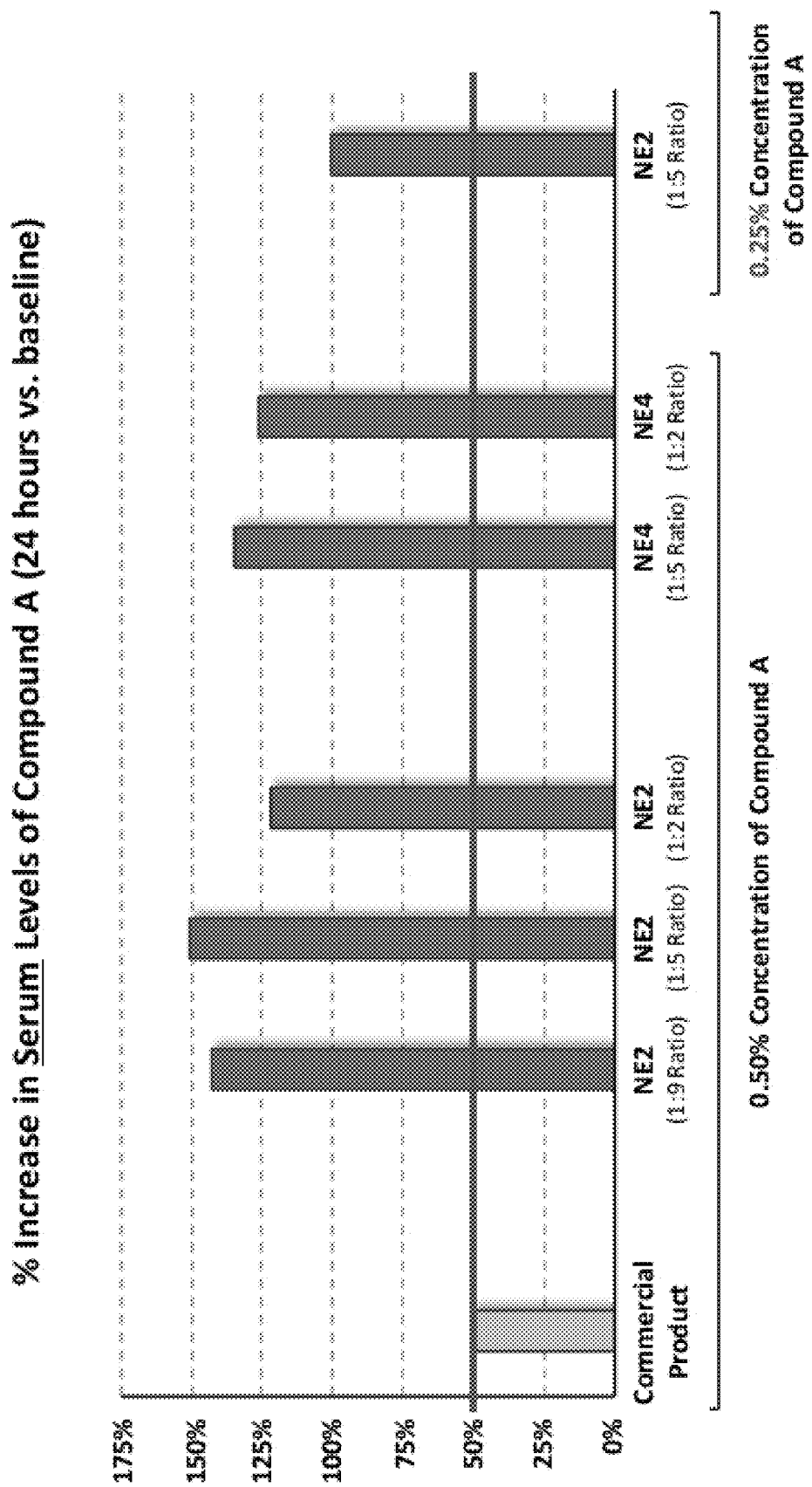
FIG. 11 shows the % increase in serum levels of Compound A following intranasal administration with the commercially available intranasal product of Compound A (0.50% Compound A) and the NE-2 (surfactant blend ratios: 1:9, 1:5, and 1:2) and NE-4 (surfactant blend ratios: 1:5 and 1:2) formulations with 0.50% or 0.25% of Compound A.

FIG. 11 shows the % increase in serum levels of Compound A following intranasal administration with the commercially available intranasal product of Compound A (0.50% Compound A) and the NE-2 (surfactant blend ratios: 1:9, 1:5, and 1:2) and NE-4 formulations (surfactant blend ratios: 1:5 and 1:2) with 0.50% or 0.25% of Compound A. In particular and as shown in FIG. 11, the non-nanoemulsion product of Compound A had a 50 percent (%) increase in serum levels of Compound A at 24 hours vs baseline. This is in contrast to increases of up to 150% for a nanoemulsion having the same drug concentration and a surfactant ratio of 1:5. Most surprisingly, a nanoemulsion having a surfactant ratio of 1:5 and half the quantity of drug, e.g., 0.25% concentration, showed a 100% increase in serum levels of the drug—a doubling of the increase shown with that observed for the commercial non-nanoemulsion product having twice as much drug (50% drug concentration).

These results show that nanoemulsion formulations having preferred surfactant ratios delivered significant amounts of an incorporated therapeutic agent when administered intranasally, as all of the tested nanoemulsion formulations resulted in an increase in serum levels of the drug of over 100%.

FIG. 12 shows the serum levels of Compound A following one intranasal administration with the commercially available intranasal product of Compound A (0.50% Compound A) and the NE-2 and NE-4 formulations (surfactant blend ratios: 1:5 and 1:2) with 0.50% of Compound A. All of the nanoemulsion formulations resulted in significantly greater serum levels of Compound A (pg/mL)—all greater than about 3500 pg/mL—as compared to the conventional, non-nanoemulsion formulation—about 2750 pg/mL—a difference of about 30%.

The results from Examples 11 and 12 taken together demonstrate that greater mucin penetration of Compound A measured in vitro directly correlates with Compound A penetration in the nasal epithelium in vivo when animals are intranasally treated with the NE-Compound A formulations and leads to greater systemic drug delivery as compared to the commercially available product containing the same concentration of Compound A.

These results show that the nanoemulsion formulations when administered intranasally significantly enhanced the systemic absorption of a representative incorporated therapeutic agent (Compound A) in vivo as compared to a non-nanoemulsion commercial product having the same active at the same concentration. Also demonstrated is that a significantly lower level of Compound A can be administered with an intranasal formulation with any one of the nanoemulsion compositions described herein to achieve systemic absorption equivalent or greater than the commercial product. Similar results are expected with other active agents that are formulated with the any one of the nanoemulsion compositions described herein for intranasal use.

Example 13—Antimicrobial Activity on Human Skin

The purpose of this example was to evaluate the antimicrobial effectiveness of a nanoemulsion according to the invention on human skin.

The nanoemulsion tested had a surfactant ratio of 1:9 and a BZK amount of 0.13% (NE-1 from Table 5, supra). The positive control was 3M Skin and Nasal Antiseptic Povidone-Iodine Solution 5% (w/w) USP REF 192401 Lot 0006461182 (Exp 2020-06-21) (St Paul, Minn.). The negative control was PBS (1×).

Materials and Reagents: (1) Human abdominal skin, dermatomed 700-1000 μm (Science Care, Aurora, Colo.). Donor Information: C111551, Sex: Female, Age: 45, Wt.: 170, Race: Caucasian, Negative/Non-reactive for HsAG, HCV, HIV; (2) 70% (v/v) Alcohol (Ethyl alcohol, 200 proof-Absolute Anhydrous (no denaturants) USP Grade Pharmco-Apper, Brookfield, Conn.; (3) Sterile Water for Injection, Rocky Mountain Biologicals, West Jordan, Utah); (4) 6 mm biopsy punch sterile (Sklar Instruments, West Chester, Pa.); (5) Scalpel sterile (Integra, Life Sciences, York, N.Y.); (6) RPMI Medium 1640 (1x) (Gibco, Life Technologies, Grand Island, N.Y.); (7) Human serum off the clot Type AB (PAA Laboratories, Dartmouth, Mass.); (8) 0.4 μm pore size cell culture inserts sterile, count 24 (Corning Inc., Durham, N.C.); (9) 6-well cell culture plates sterile, count 4 (Corning Inc., Durham, N.C.); (10) 48-well cell culture plates sterile, count 1 (Corning Inc., Durham, N.C.); (11) *S. aureus* (USA300 Methicilin-Resistant *Staphylococcus aureus* (MRSA), clinical isolates) (University of Dentistry and Medicine of New Jersey); (12) TSA (Tryptic Soy Agar) plates (IPM Scientific, Inc., Sykesville, Md.). PBS (1x) (Corning Inc., Durham, N.C.); (13) Butterfield's Buffer (Hardy Diagnostics, Santa Maria, Calif.); (14) T Shaped spreader sterile (Coran Diagnostics Inc, Murrieta, Calif.); (15) Microplate Shaker (VWR, Radnor, Pa.); (16) Incubator Water Jacketed, C02 (Therma Scientific Forma, Grand Island, N.Y.); and (17) Pipettes with sterile tips.

Procedure: Skin Preparation: Each test formulation was done in triplicate. Decolonization of normal flora was achieved by drying the surface of the specimen and swabbing the area with 70% alcohol twice for 30 seconds. 24 explants of uniform size were obtained using a sterile 6-mm biopsy punch on the skin donor. The skin surface area was ~28.27 mm$^2$.

12 tissue explants were placed in a 50 mL sterile conical tube and washed with 15 mL of RPMI 1640 (antibiotics-free) medium for 1 minute with gentle swirling. The skin explants were then placed stratum corneum side up on a 0.4 μm cell culture insert in a 6-well plate with 1 mL of RPMI1640 (antibiotics-free) medium. 12 tissue explants were placed in a 50 mL sterile conical tube and washed with 15 mL RPMI 1640 (antibiotics-free) medium plus 2% human serum for 1 minute with gentle swirling. The skin explants were placed stratum corneum side up on a 0.4 μm cell culture insert in a 6-well plate with 1 mL RPMI640 (antibiotics-free) medium. 1.2 mL/well of the appropriate medium (e.g. RPMI 1640 (antibiotics-free) medium+/−2% (v/v) human serum was placed into 6-well plate and placed in an incubator at 37° C. and 7% $CO_2$.

*S. aureus* Bacteria: *S. aureus* was inoculated into a TSA plate and incubated overnight at 37° C. and 7% $CO_2$. A single colony of *S. aureus* was chosen from the TSA plate and resuspended in RPMI 1640 (antibiotics-free) medium to a concentration of approximately 5×10 CFU/mL to be used as the inoculum.

Infection of Skin Explants: 2 μL of *S. aureus* inoculum were applied onto the stratum corneum side of each piece of skin (1×10$^6$ CFU/tissue disc). Incubated for 2 hours at 37° C. and 7% $CO_2$.

Topical Application of Test Formulations to Skin Explant: After *S. aureus* infection, 50 μL of each test formulation was applied on top of skin surface of three skin explants with a pipette. After 30 seconds, another 50 μL of the test formulation was applied for a total dosing volume of 100 μL. Incubated for 1 hour at 37° C. and 7% $CO_2$. Wash Skin Explants: 1 mL of PBS (1x) was applied in each insert to wash the tissue for 10 seconds, while swirling the plate gently to wash the tissues. 1 mL wash was removed from each insert and discarded. Incubate Skin Extracts: incubation was continued for 1 hour at 37° C. and 7% $CO_2$.

Neutralize & Recover (Bacterial (CFU) Enumeration): The infected skin explants were removed from each cell insert and transferred to a 48-well plate containing 250 μL Butterfield's Buffer (neutralization medium) per well. The 48-well plate containing skin explants was placed on a Microplate Shaker for 4 minutes at 500 rpm. The suspension was removed and serially diluted 4 times in PBS and then spread onto TSA plates using a T-shaped sterile spreader. The TSA plates were incubated for 48 hours at 37° C. and 7% $CO_2$. The colonies were then counted, with the results shown in Table 15 below.

Skin explants infected with MSRA and then treated with the nanoemulsion test formulation showed a significant log reduction of >5.1 as compared to the negative control, PBS. The nanoemulsion formulation showed the same log reduction as compared to the positive control, 3M Skin and Nasal antiseptic containing 5% Povidone Iodine.

TABLE 15

| | Test Formulations | | | |
|---|---|---|---|---|
| Log CPU/Log Reduction | RPMI Medium Tested | Nanoemulsion (0.13% BZK) | 3M Nasal Antiseptic (5% Povidone-Iodine) | PBS (1X) Negative control |
| Log CFU recovered Log Reduction | With 2% (v/v) Human Serum | <0.4 >5.1 | <0.4 >5.1 | 5.5 NA |
| Log CFU recovered Log Reduction | Without Serum | <0.4 >5.1 | <0.4 >5.1 | 5.5 NA |

Example 14—Additional Ex Vivo Skin Permeation Study with Topical Agents

The purpose of this example was to evaluate the delivery of several topical agents with a nanoemulsion according to the invention using the ex vivo skin permeation study outlined in Example 6 and the actives for each study were analyzed according the experimental conditions show in Tables 16-18.

TABLE 16

Experimental conditions for HPLC analysis of actives extracted from human skin samples.

| Actives | Benzethonium chloride (BEC) | Terbinafine Hydrochloride | Miconazole Nitrate | Hydrocortisone |
|---|---|---|---|---|
| HPLC System | LC System: Shimadzu LC-20AT Software: LC Solutions Communications Bus Module: | | LC System: Waters Software: Empower Detector: 2497 Dual λ Absorbance Detector | |

TABLE 16-continued

Experimental conditions for HPLC analysis of actives extracted from human skin samples.

| Actives | Benzethonium chloride (BEC) | Terbinafine Hydrochloride | Miconazole Nitrate | Hydrocortisone |
|---|---|---|---|---|
| | Shimadzu CBM-20A UV-VIS Detector: Shimadzu SPD-20AV Column Oven: CTO-20AC | Separation Module: Waters 2695 | | |
| Mobile Phase (v/v or v/v/v) | Acetate Buffer:ACN (48:52) | PO4 Buffer: MeOH:THF (52:40:8) | Acetate Buffer:ACN: MeOH (2:3:5) | ACN:Water (40:60) |
| Column | Phenomenex, Luna 5μ, CN, 100 Å 250 × 4 mm | Agilent, Zorbax 300 SB C-18, 150 × 4.6 mm, 3.5 μm | Waters Symmetry C8 5μ, 3.9 × 150 mm | Waters Symmetry C18 5 μm, 3.9 × 1.50 mm |
| Detector Wavelength | 215 nm | 770 nm | 230 nm | 254 nm |
| Column Temperature | 30° C. | 35° C. | 25° C. | 25° C. |
| Injection Volume | 100 μL | 20 μL | 20 μL | 20 μL |
| Flow Rate | 2 mL/min | 1 mL/min | 1 mL/min | 1 mL/minutes |
| Run Time | 12 minutes | 10 minutes | 10 minutes | 10 minutes |
| Standard | 50 μg/ml | 12.5 μg/mL | 60 μg/mL | 12 μg/mL |

TABLE 17

Experimental conditions for HPLC analysis of actives extracted from human skin samples.

| Actives | Salicylic Acid | Adapalene | PCMX | Chlorhexidine Gluconate |
|---|---|---|---|---|
| HPLC System | | LC System: Waters Software: Empower Detector: 2497 Dual λ Absorbance Detector Separation Module: Waters 2695 | | |
| Mobile Phase (v/v or v/v/v) | Water:MeOH:HAc (60:40:1) | ACN:THF TPA:Water (350:430:0.3:220) | ACN:Water: H3PO4 (100:100:0.2) | PO4 Buffer:ACN (70:30) |
| Column | Thermo Hypersil ODS 5 μm, 4.6 × 100 mm | Thermo Hypersil ODS 5 μm, 4.6 × 250 mm | Waters Symmetry C18 5 μm, 3.9 × 150 mm | Waters Symmetry C18 5 μm, 3.9 × 150 mm |
| Detector Wavelength | 234 nm | 735 nm | 280 nm | 239 nm |
| Column Temperature | 35° C. | 45° C. | 25° C. | 40° C. |
| Injection Volume | 20 μL | 20 μL | 50 μL | 10 μL |
| Flow Rate | 0.7 mL/minutes | 1 mL/minutes | 1 mL/minutes | 1 mL/minutes |
| Run Time | 10 minutes | 10 minutes | 10 minutes | 6 minutes |
| Standard | 60 μg/mL | 40 μg/mL | 100 μg/mL | 40 μg/mL |

PO4 Buffer = Phosphate Buffer
ACN = Acetonitrile
MeOH = Methanol
HAc = Acetic Acid
THF = Tetrahydrofuran
H3PO4 = Phosphoric Acid

TABLE 18

Experimental conditions for HPLC analysis

| Agent | Peanut Extract |
|---|---|
| HPLC System | LC System: Waters Software: Empower Detector: 2497 Dual λ Absorbance Detector Separation Module: Waters 2695 |
| Mobile Phase | A 0.1% TFA in Water B: 100% Acetonitrile |
| Column | Waters Symmetry C18 5 m, 3.9 × 150 mm |
| Detector Wavelength | 280 nm |
| Column Temperature | 25° C. |
| injection Volume | 20 μL |
| Flow Rate | 1.5 mL/min |

TABLE 18-continued

Experimental conditions for HPLC analysis

| Agent | Peanut Extract |
|---|---|
| Run Time | 26 minutes |
| Standard | NA |

Terbinafine Delivery: The nanoemulsion tested had a surfactant ratio of 1:9 and a terbinafine amount of 1.0% as shown in the below table. This nanoemulsion was evaluated against the Lamisil AT® (1% terbinafine) using the same methodology of Example 6:

TABLE 19

NE formulatons with Terbinafine.

| Formulation Excipients | NE-1 (Surfactant Blend Ratio: 1:9; 1% Terbinafine) |
|---|---|
| Water | 76.3972 |
| Terbinafine Hydrochloride | 1.0 |
| BZK | 0.13 |
| Poloxamer 407 | 1.184 |
| Glycerol | 2.016 |
| Soybean Oil | 12.558 |
| Ethanol | 6.70 |
| EDTA | 0.0148 |
| Total | 100% |

Figure 13:
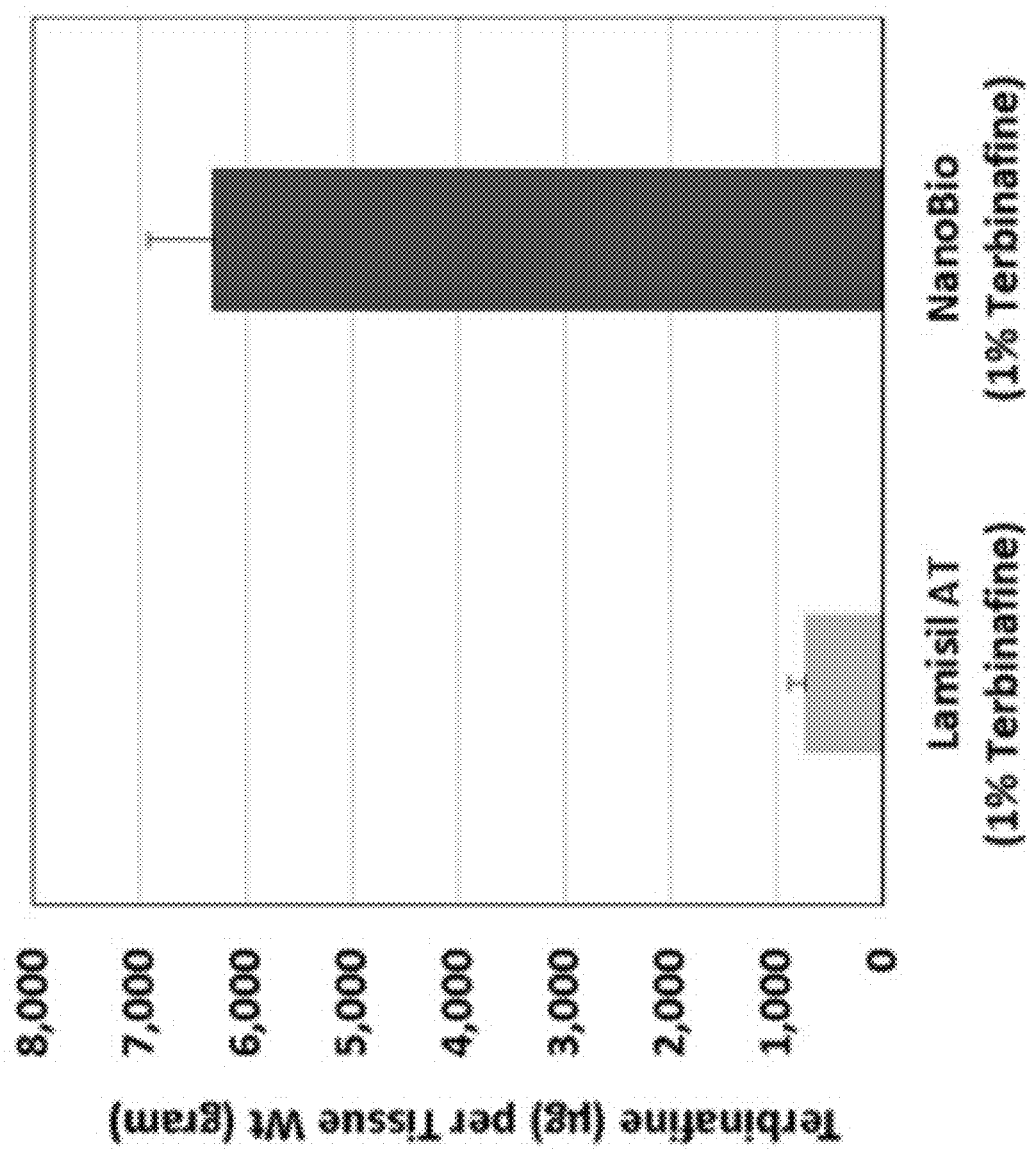
FIG. 13 shows the epidermal levels of terbinafine (µg/g tissue) in human abdominal skin following one application (dose of 100 µl/cm$^2$, measured at 24 hours) of the NE-1 formulation (surfactant ratio of 1:9 with 1% terbinafine) with Lamisil AT® (1% terbinafine).
Figure 14:
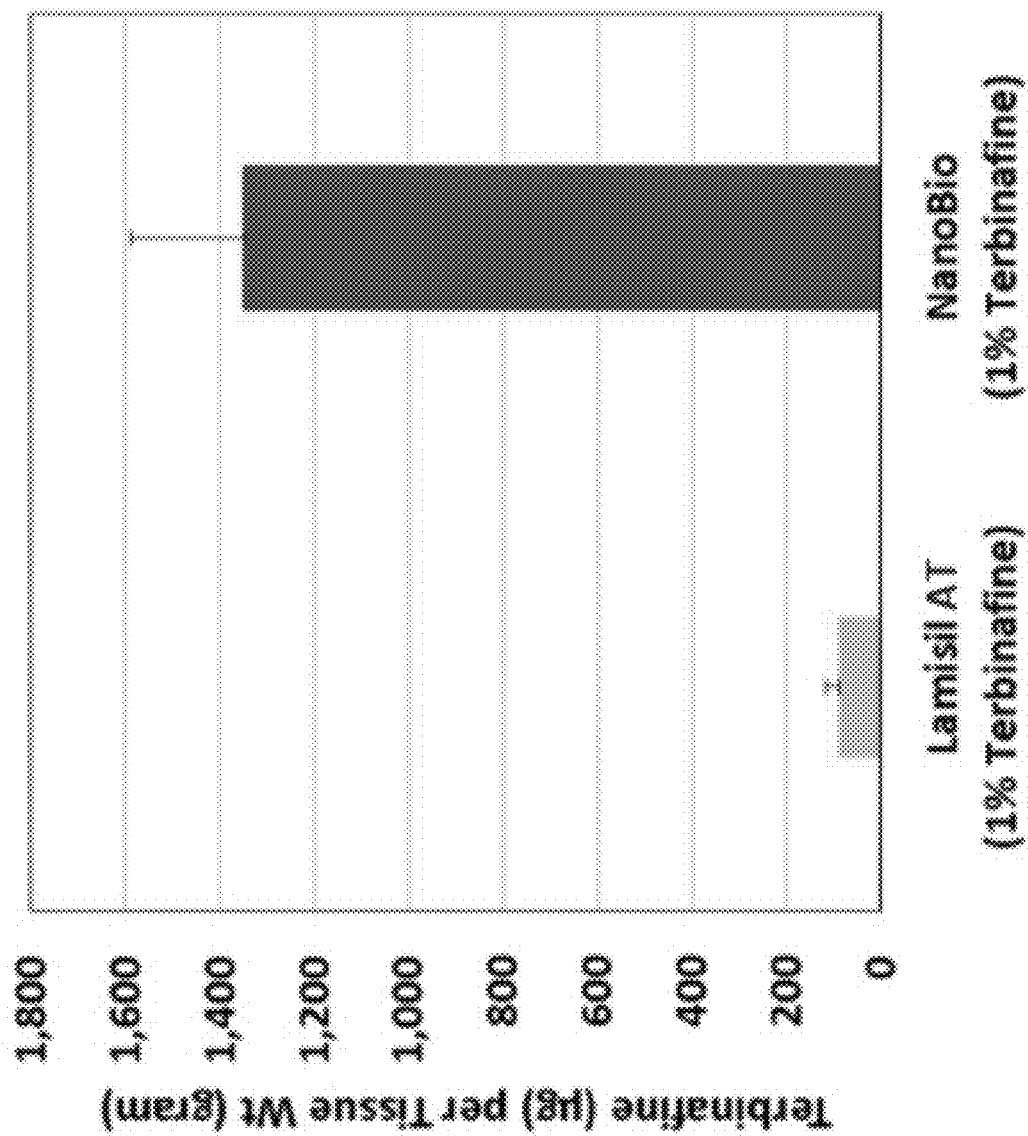
FIG. 14 shows the dermal levels of terbinafine (µg/g tissue) in human abdominal skin following one application (dose of 100 µl/cm$^2$, measured at 24 hours) of NE-1 formulation (surfactant ratio of 1:9 with 1% terbinafine) with Lamisil AT® (1% terbinafine).

FIG. 13 shows the epidermal levels of terbinafine ($\mu$g/g tissue) in human abdominal skin following one application (dose of 100 $\mu$l/cm$^2$, measured at 24 hours) of the NE-1 formulation (surfactant ratio of 1:9 with 1% terbinafine) with Lamisil AT® (1% terbinafine). FIG. 14 shows the dermal levels of terbinafine ($\mu$g/g tissue) in human abdominal skin following one application (dose of 100 $\mu$l/cm$^2$, measured at 24 hours) of NE-1 formulation (surfactant ratio of 1:9 with 1%/terbinafine) with Lanmisil AT® (1% terbinafine).

Figure 15:
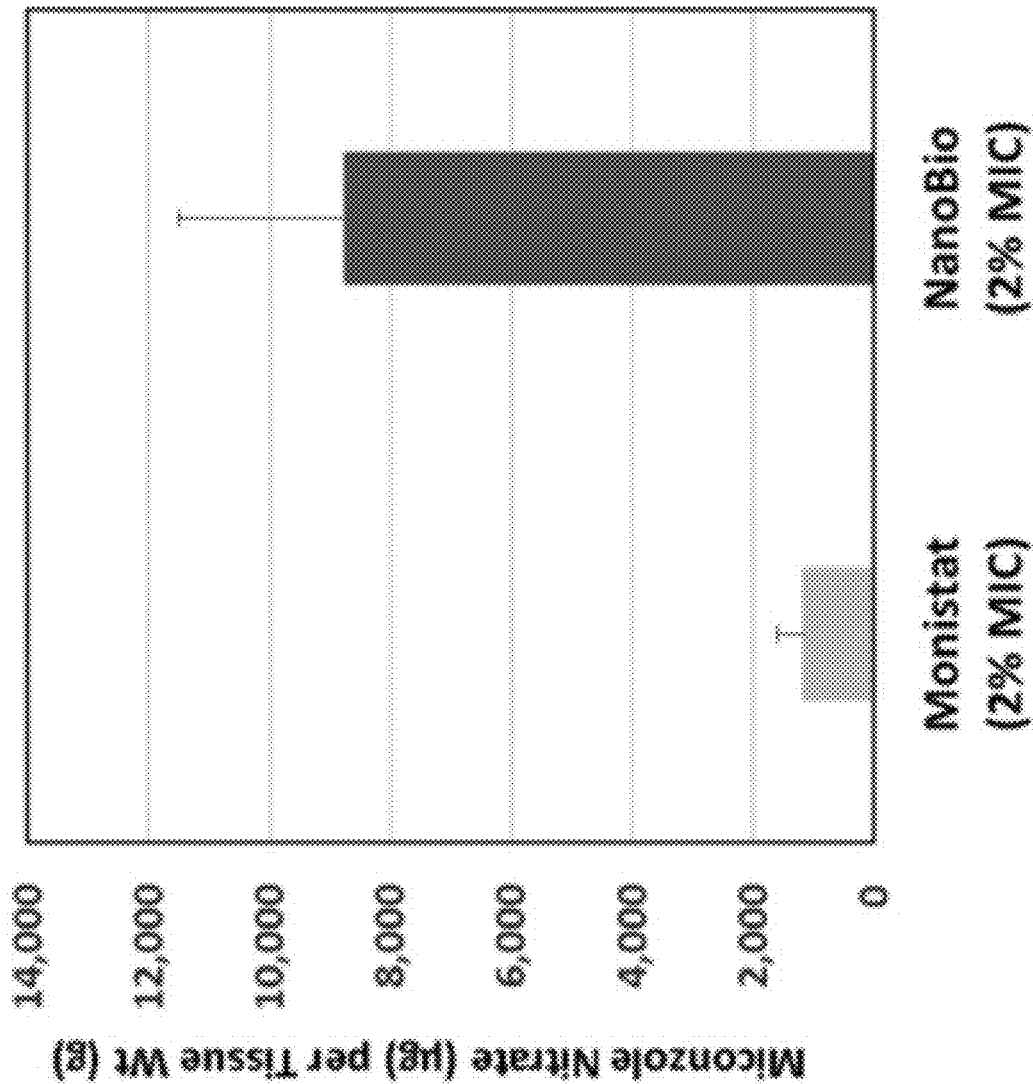
FIG. 15 shows the epidermal levels of miconazole (μg/g tissue) in human abdominal skin following one application (dose of 100 μl/cm², measured at 24 hours) of the NE-1 formulation (surfactant ratio of 1:12 with 2% miconazole) with Monistat® (2% miconazole).

As clearly depicted in FIGS. 14 and 15, the nanoemulsions having surfactant ratios of 1:9 showed dramatic and significantly greater permeation (amount of terbinafine ($\mu$g)/tissue weight (g)) as compared to a non-nanoemulsion formulation having the same quantity of terbinafine.

Miconazole Delivery: The nanoemulsion tested had a surfactant ratio of 1:12 and a miconazole amount of 2.0% as shown in the below table. This nanoemulsion was evaluated against the Monistat® (2% miconazole) using the same methodology of Example 6:

TABLE 20

NE formulations with Miconazole.

| Formulation Excipients | NE-1 (Surfactant Blend Ratio: 1:12; 2% Miconazole) |
|---|---|
| Water | 75.4272 |
| Miconazole Nitrate | 2.0 |
| BZK | 0.10 |
| Poloxamer 407 | 1.184 |
| Glycerol | 2.016 |
| Soybean Oil | 12.558 |
| Ethanol | 6.70 |
| EDTA | 0.0148 |
| Total | 100% |

Figure 16:
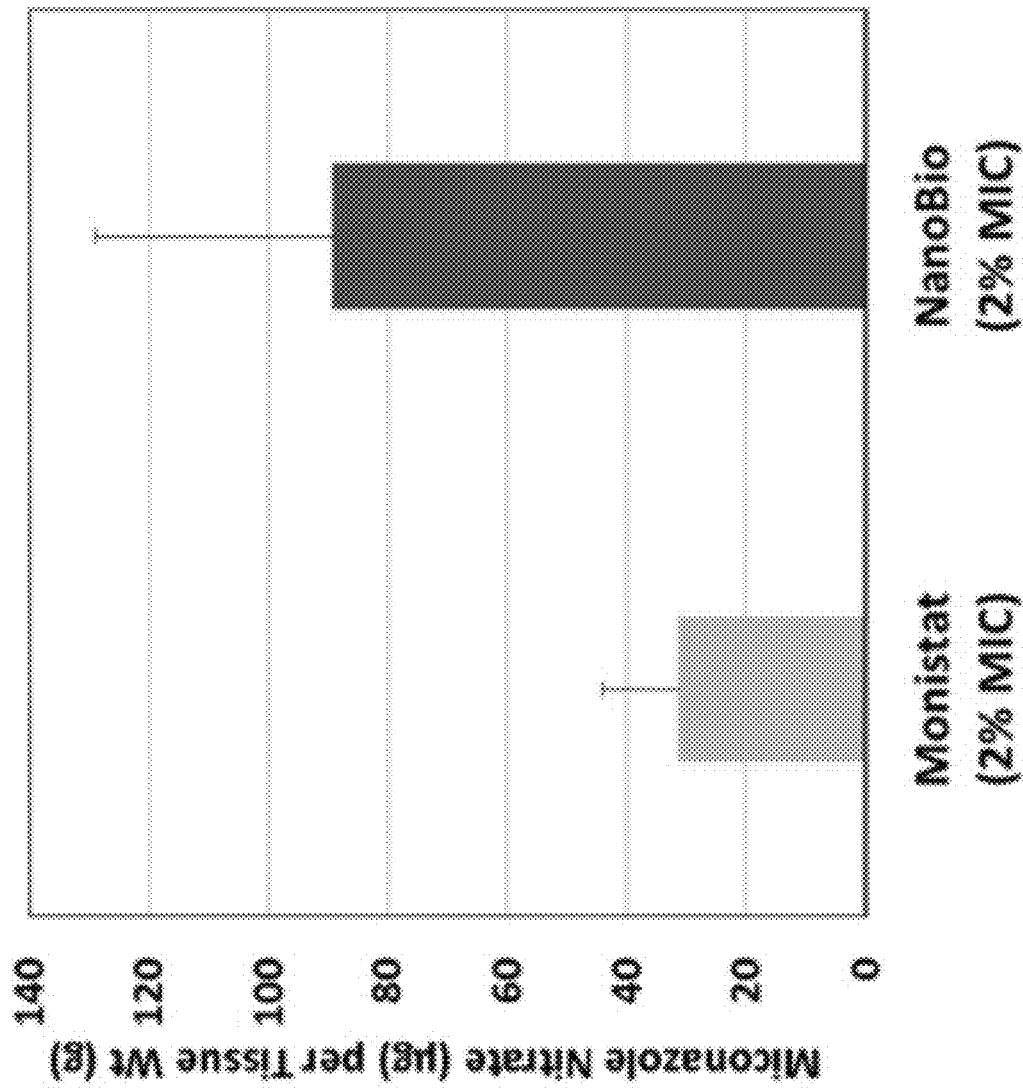
FIG. 16 shows the dermal levels of miconazole (μg/g tissue) in human abdominal skin following one application (dose of 100 μl/cm², measured at 24 hours) of NE-1 formulation (surfactant ratio of 1:12 with 2% miconazole) with Monistat® (2% miconazole).

FIG. 15 graphically shows the epidermal levels of miconazole ($\mu$g/g tissue) in human abdominal skin following one application (dose of 100 $\mu$l/cm$^2$, measured at 24 hours) of the NE-1 formulation (surfactant ratio of 1:12 with 2% miconazole) with Monistat® (2% miconazole). FIG. 16 shows the dermal levels of miconazole ($\mu$g/g tissue) in human abdominal skin following one application (dose of 100 $\mu$l/cm$^2$, measured at 24 hours) of NE-1 formulation (surfactant ratio of 1:12 with 2% miconazole) with Monistat® (2% miconazole).

Figure 17:
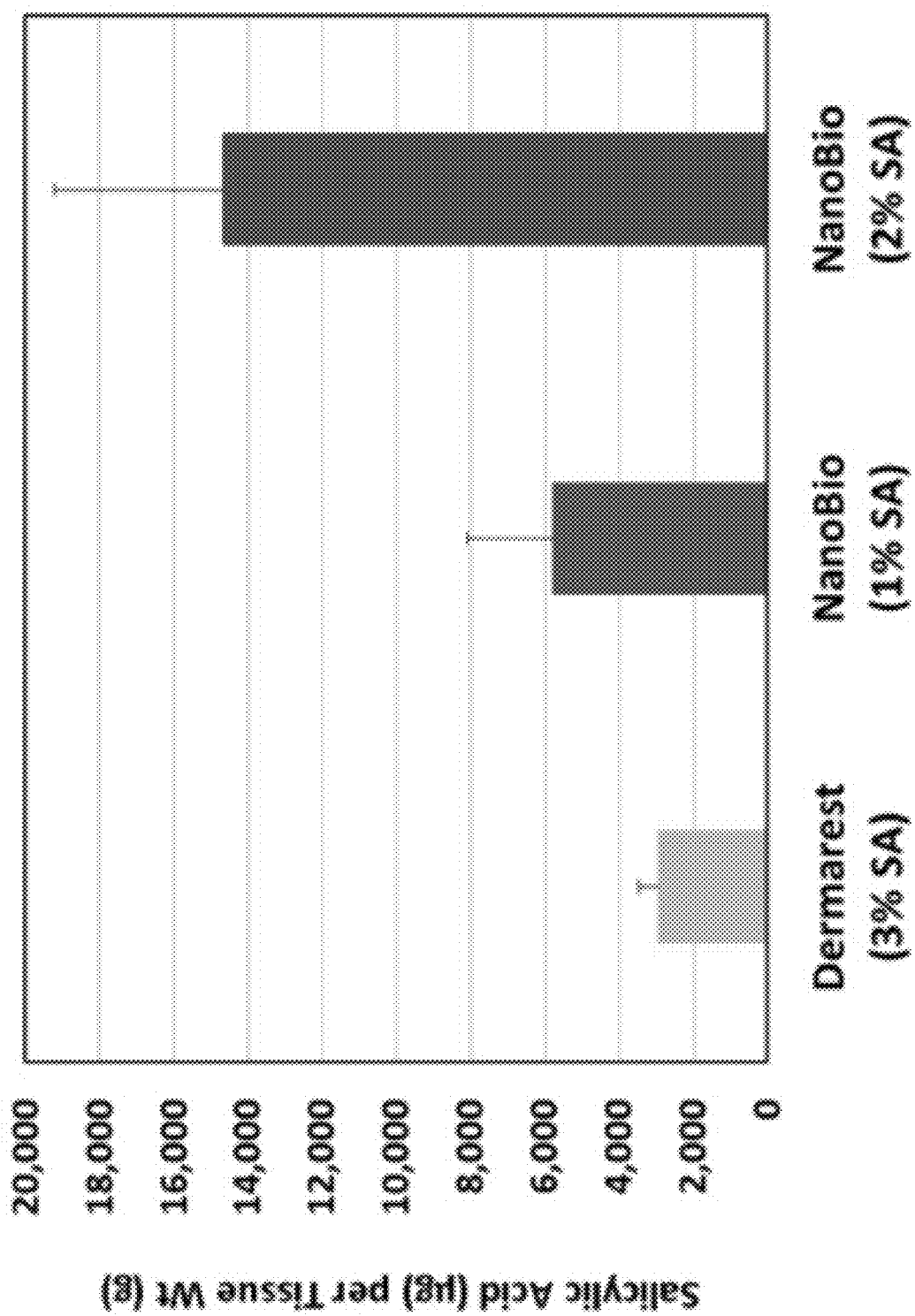
FIG. 17 shows the epidermal levels of salicylic acid (μg/g tissue) in human abdominal skin following one application (dose of 100 μl/cm², measured at 24 hours) of the NE-1 formulation (surfactant ratio of 1:12 with 1% and 2% salicylic acid) with Dermarest® (3% salicylic acid).

As clearly depicted in FIGS. 16 and 17, the nanoemulsion having surfactant ratio of 1:12 showed dramatic and significantly greater permeation (amount of miconazole ($\mu$g)/tissue weight (g)) as compared to a non-nanoemulsion formulation having the same quantity of miconazole.

Salicyclic Acid Delivery: The nanoemulsions tested had a surfactant ratio of 1:12 and a salicylic acid amounts of 1.0% and 2.0% as shown in the below table. These nanoemulsions was evaluated against the Dermarest® (3% salicylic acid) using the same methodology of Example 6:

TABLE 21

NE formulations with Salicylic Acid.

| Formulation Excipients | NE-1 (Surfactant Blend Ratio: 1:12; 1% Salicylic Acid) | NE-1 (Surfactant Blend Ratio: 1:12; 2% Salicylic Acid) |
|---|---|---|
| Water | 76.4272 | 75.4272 |
| Salicylic Acid | 1.0 | 2.0 |
| BZK | 0.1 | 0.1 |
| Poloxamer 407 | 1.184 | 1.184 |
| Glycerol | 2.016 | 2.016 |
| Soybean Oil | 12.558 | 12.558 |
| Ethanol | 6.7 | 6.7 |
| EDTA | 0.0148 | 0.0148 |
| Total | 100% | 100% |

FIG. 17 graphically shows the epidermal levels of salicylic acid ($\mu$g/g tissue) in human abdominal skin following one application (dose of 100 $\mu$l/cm$^2$, measured at 24 hours) of the NE-1 formulation (surfactant ratio of 1:12 with 1% and 2 salicylic acid) with Dermarest® (3% salicylic acid).

As clearly depicted in FIG. 17, the nanoemulsions having surfactant ratio of 1:12 showed dramatic and significantly greater permeation (amount of salicylic acid ($\mu$g)/tissue weight (g)) as compared to anon-nanoemulsion formulation having the greater quantity of salicylic acid.

Hydrocortisone Delivery: The nanoemulsion tested had a surfactant ratio of 1:9 and a hydrocortisone amount of 1.0% as shown in the below table. This nanoemulsion was evaluated against the Cortizone-10® (1% hydrocortisone) using the same methodology of Example 6:

TABLE 22

NE formulations with Hydrocortisone.

| Formulation Excipients | NE-1 (Surfactant Blend Ratio: 1:9; 1% Hydrocortisone) |
|---|---|
| Water | 76.3972 |
| Hydrocortisone | 1 |
| BZK | 0.13 |
| Poloxamer 407 | 1.184 |
| Glycerol | 2.016 |
| Soybean Oil | 12.558 |
| Ethanol | 6.7 |
| EDTA | 0.0148 |
| Total | 100% |

Figure 18:
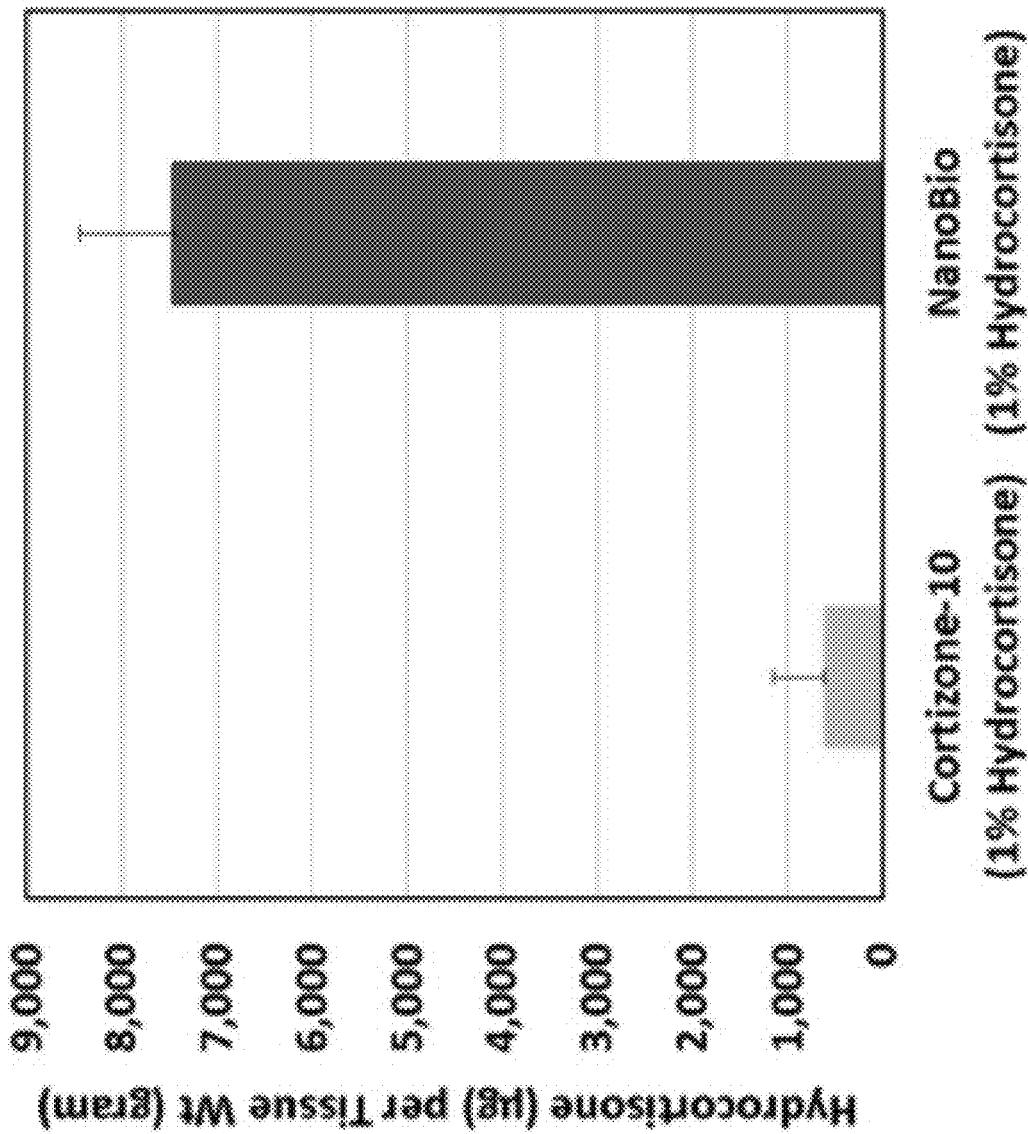
FIG. 18 shows the epidermal levels of hydrocortisone (μg/g tissue) in human abdominal skin following one application (dose of 100 μl/cm², measured at 24 hours) of the NE-1 formulation (surfactant ratio of 1:9 with 1% hydrocortisone) with Cortizone-10® (1% hydrocortisone).
Figure 19:
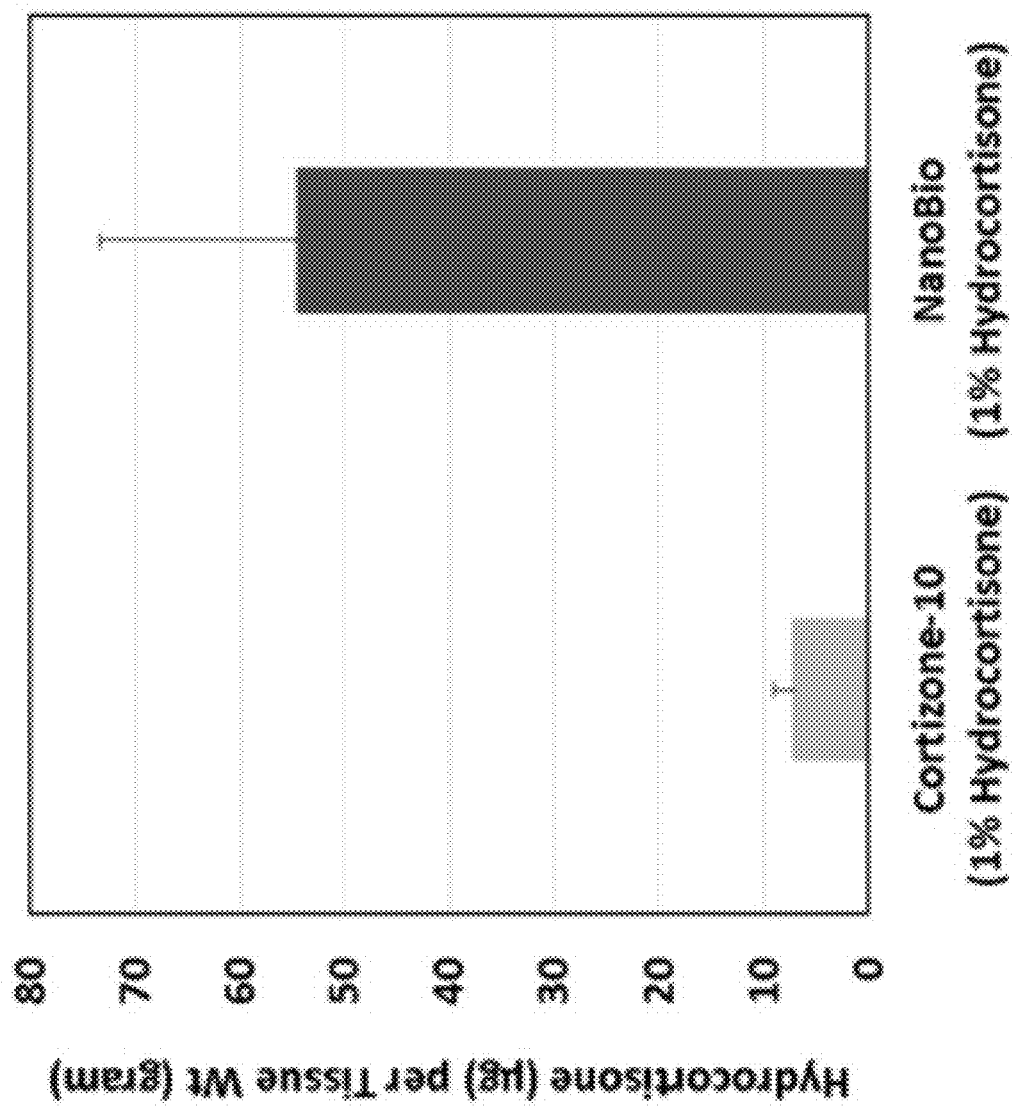
FIG. 19 shows the dermal levels of hydrocortisone (μg/g tissue) in human abdominal skin following one application (dose of 100 μl/cm², measured at 24 hours) of NE-1 formulation (surfactant ratio of 1:9 with 1% hydrocortisone) with Cortizone-10® (1% hydrocortisone).

FIG. 18 graphically shows the epidermal levels of hydrocortisone (μg/g tissue) in human abdominal skin following one application (dose of 100 μl/cm$^2$, measured at 24 hours) of the NE-1 formulation (surfactant ratio of 1:9 with 1% hydrocortisone) with Cortizone-10® (1% hydrocortisone). FIG. 19 shows the dermal levels of hydrocortisone (μg/g tissue) in human abdominal skin following one application (dose of 100 μl/cm$^2$, measured at 24 hours) of NE-1 formulation (surfactant ratio of 1:9 with 1% hydrocortisone) with Cortizone-10® (1% hydrocortisone).

As clearly depicted in FIGS. 18 and 19, the nanoemulsion having a surfactant ratio of 1:9 showed dramatic and significantly greater permeation (amount of hydrocortisone (μg)/tissue weight (g)) as compared to a non-nanoemulsion formulation having the same quantity of hydrocortisone.

Retinoid Delivery: The nanoemulsion tested had a surfactant ratio of 1:9 and a retinoid (adapalene) amount of 0.1% as shown in the below table. This nanoemulsion was evaluated against the Differin® Gel (0.1% adapalene) using the same methodology of Example 6:

TABLE 23

NE formulations with Adapalene.

| Formulation Excipients | NE-1 (Surfactant Blend Ratio: 1:9; 0.1% Adapalene) |
|---|---|
| Water | 77.2972 |
| Adapalene | 0.1 |
| BZK | 0.13 |
| Poloxamer 407 | 1.184 |
| Glycerol | 2.016 |
| Soybean Oil | 12.558 |
| Ethanol | 6.7 |
| EDTA | 0.0148 |
| Total | 100% |

Figure 20:
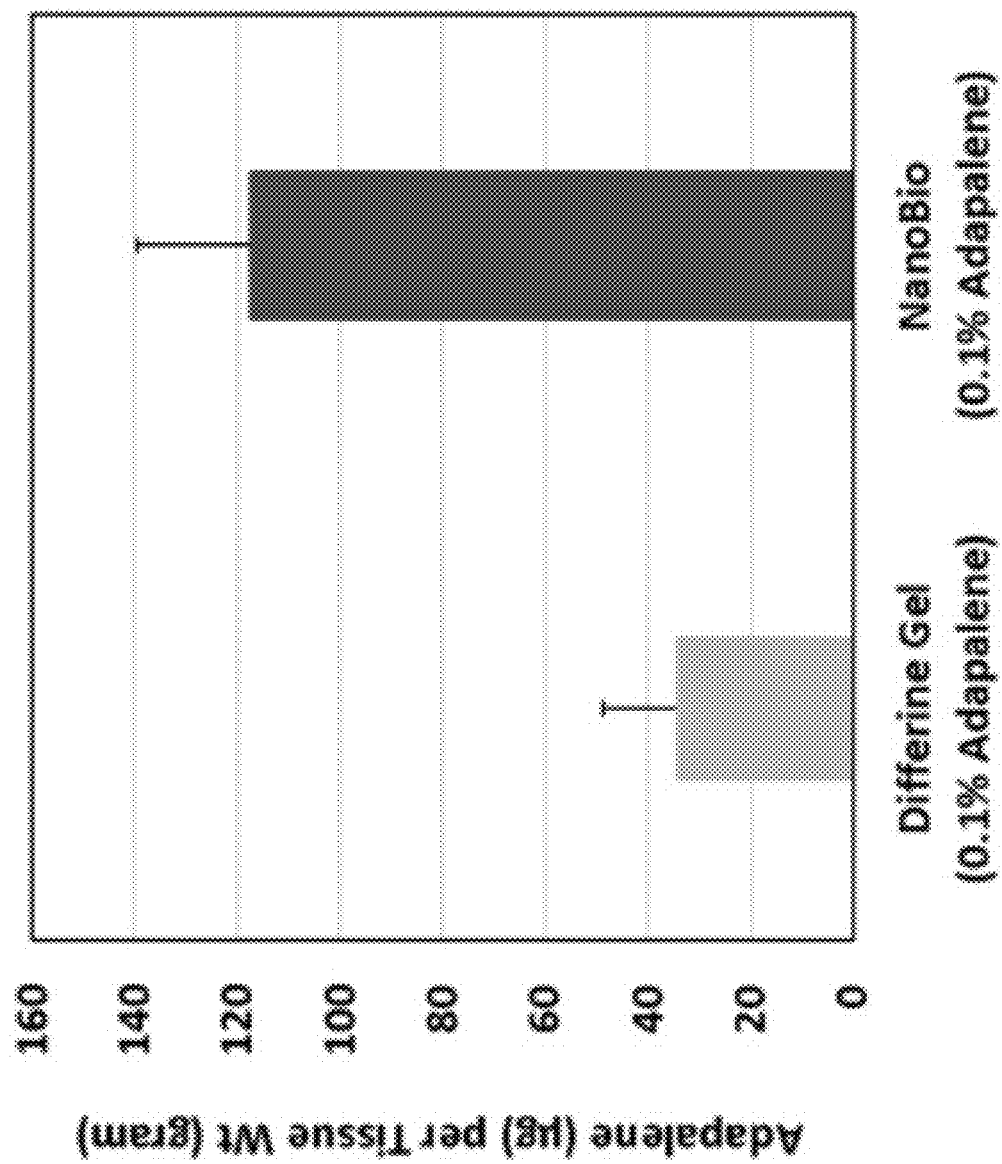
FIG. 20 shows the epidermal levels of adapalene (μg/g tissue) in human abdominal skin following one application (dose of 100 μl/cm², measured at 24 hours) of the NE-1 formulation (surfactant ratio of 1:9 with 0.1% adapalene) with Differin® (0.1% adapalene).
Figure 21:
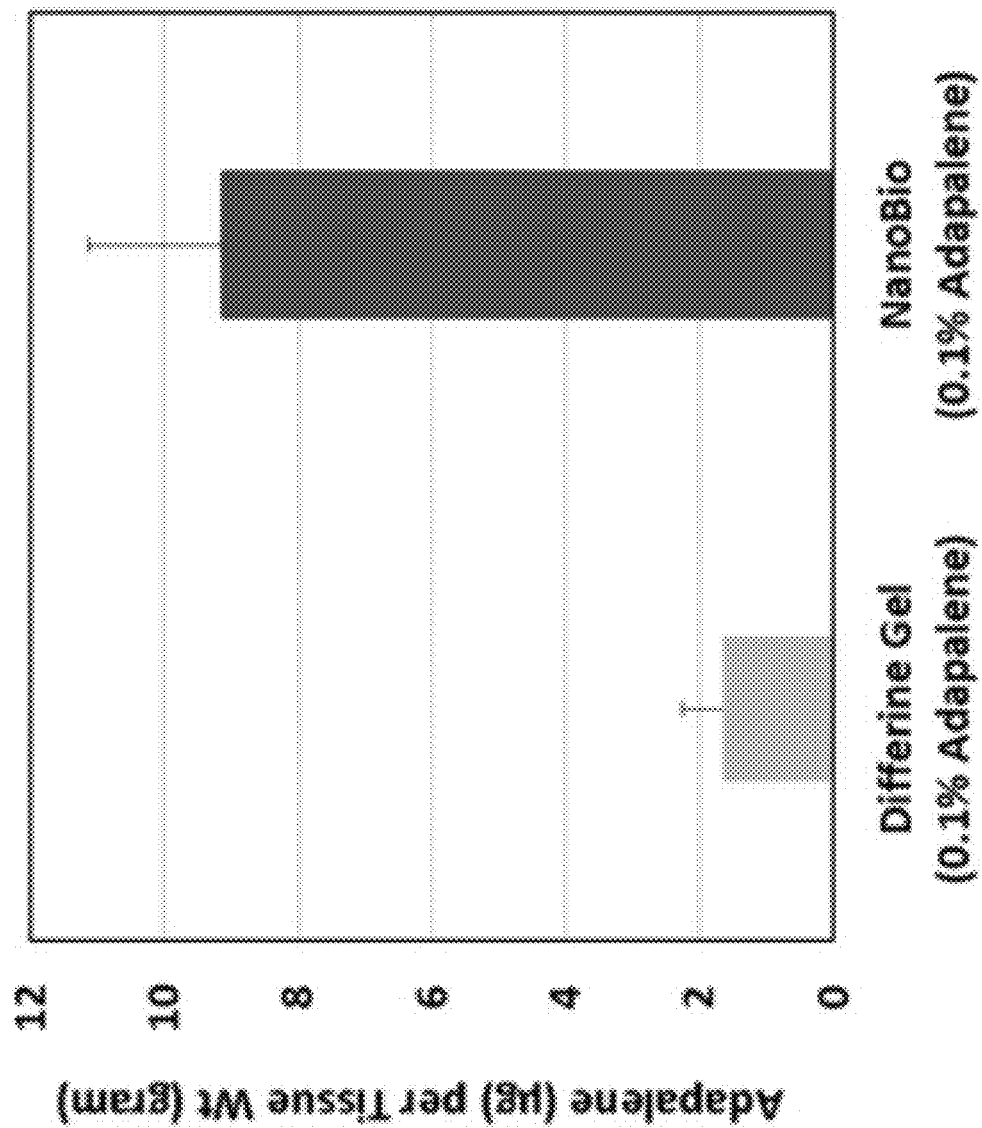
FIG. 21 shows the dermal levels of adapalene (μg/g tissue) in human abdominal skin following one application (dose of 100 μl/cm², measured at 24 hours) of NE-1 formulation (surfactant ratio of 1:9 with 0.1% adapalene) with Differin® (0.1% adapalene).
Figure 22:
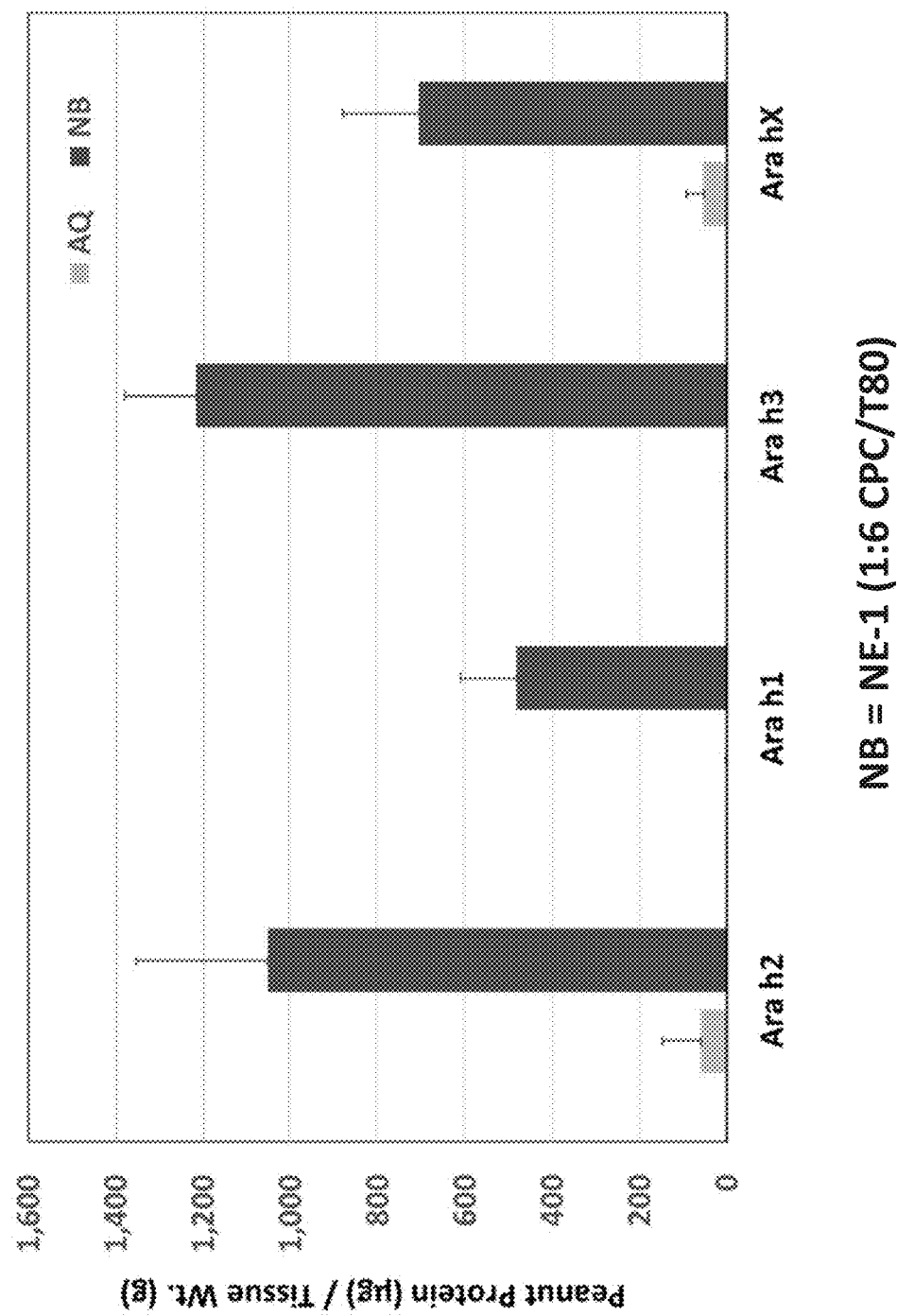
FIG. 22 shows the epidermal levels of peanut proteins Ara h2, Ara h1, Ara h3, and Ara hX (μg/g tissue) in human abdominal skin following one application (occluded dose of 100 μl/cm², measured at 18 hours) of the NE-1 formulation (surfactant ratio of 1:6 with 0.1% peanut protein) with an aqueous formulation (0.1% peanut protein).
Figure 23:
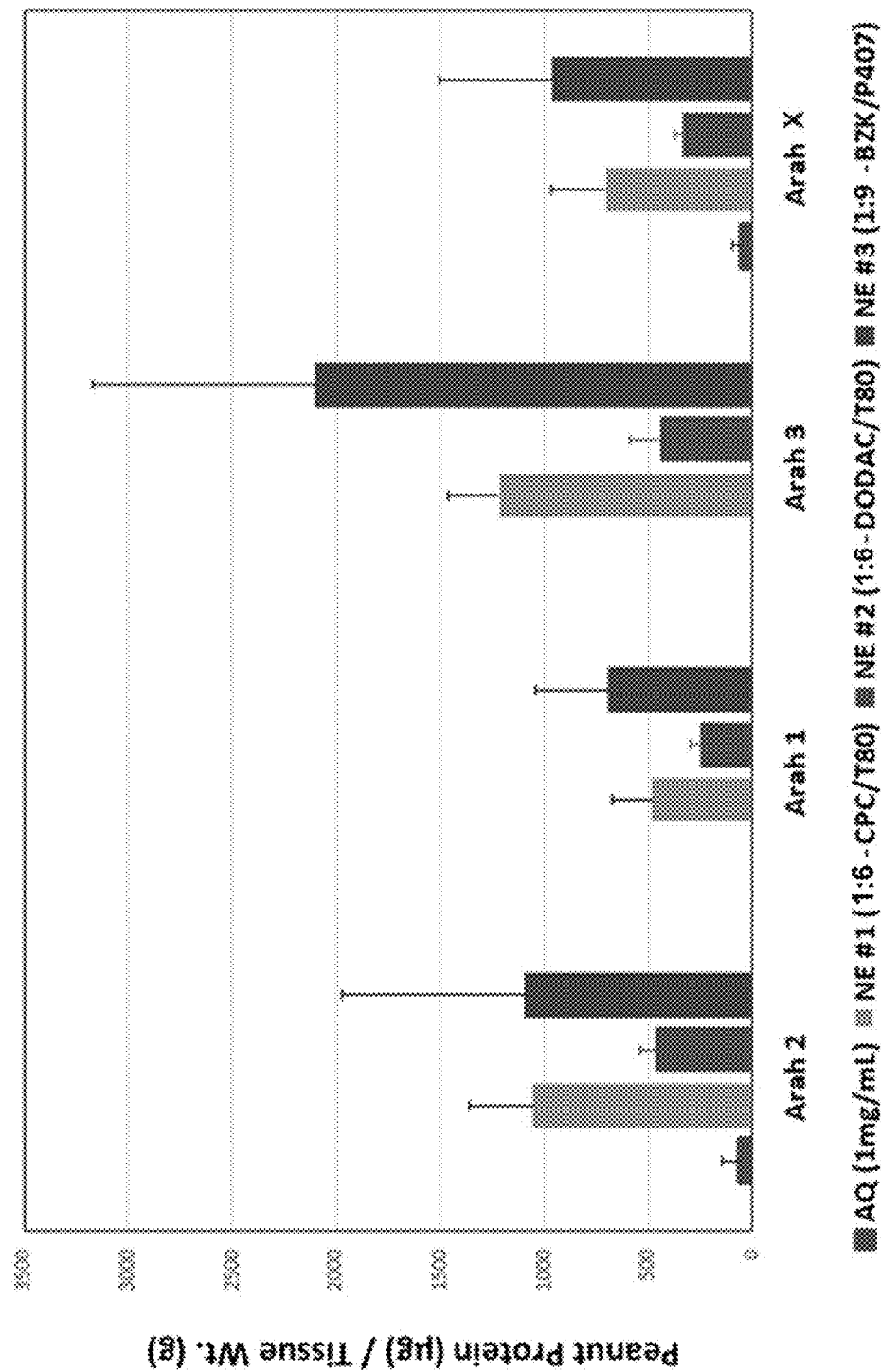
FIG. 23 shows the dermal levels of peanut proteins Ara h2, Ara h1, Ara h3, and Ara hX (μg/g tissue) in human abdominal skin following one application (occluded dose of 100 μl/cm², measured at 18 hours) of NE-1 formulation (surfactant ratio of 1:6), NE-2 formulation (surfactant ratio of 1:6), and NE-3 formulation (surfactant ratio of 1:9) with 0.1% peanut protein with aqueous formulation (0.1% peanut protein).

FIG. 20 graphically shows the epidermal levels of adapalene (μg/g tissue) in human abdominal skin following one application (dose of 100 μl/cm$^2$, measured at 24 hours) of the NE-1 formulation (surfactant ratio of 1:9 with 0.1% adapalene) with Differin® (0.1% adapalene). FIG. 21 shows the dermal levels of adapalene (μg/g tissue) in human abdominal skin following one application (dose of 100 μl/cm$^2$, measured at 24 hours) of NE-1 formulation (surfactant ratio of 1:9 with 0.1% adapalene) with Differin® (0.1% adapalene).

As clearly depicted in FIGS. 20 and 21, the nanoemulsion having surfactant ratio of 1:9 showed dramatic and significantly greater permeation (amount of adapalene (μg)/tissue weight (g)) as compared to a non-nanoemulsion formulation having the same quantity of adapalene.

Topical Protein Delivery: The nanoemulsions tested had a surfactant ratio of 1:6 and 1:9 and a peanut extract protein amount of 0.1% as shown in the below table, where each of the following peanut proteins were used: Ara h2, Ara h1, Ara h3 and Ara hX. This nanoemulsion was evaluated against an aqueous formulation (0.1% peanut protein) using the same methodology of Example 6:

TABLE 24

NE-1, NE-2 and NE-3 formulations with Peanut Extract Protein.

| Formulation Excipients | NE-1 (Surfactant Blend Ratio: 1:6; 0.1% Peanut Extract Protein)* | NE-2 (Surfactant Blend Ratio: 1:6; 0.1% Peanut Extract Protein) | NE-3 (Surfactant Blend Ratio: 1:9; 0.1% Peanut Extract Protein) |
|---|---|---|---|
| Buffer (PBS 1X) | 84.6 | 84.6 | 83.9972 |
| Peanut Extract Protein* | 0.1 | 0.1 | 0.1 |
| CPC | 0.212 | — | — |
| DODAC | — | 0.212 | — |
| BZK | — | — | 0.13 |
| Tween 80 | 1.184 | 1.184 | — |
| Poloxamer 407 | — | — | 1.184 |
| Glycerol | — | — | 2.016 |
| Ethanol | 1.346 | 1.346 | — |
| Soybean Oil | 12.558 | 12.558 | 12.558 |
| EDTA | — | — | 0.0148 |
| Total | 100% | 100% | 100% |

*Peanut Extract Protein = one of the following: Ara h2, Ara h1, Ara h3 and Ara hX FIG. 22 graphically shows the epidermal levels of peanut proteins Ara h2, Ara h1, Ara h3, and Ara hX (μg/g tissue) in human abdominal skin following one application (occluded dose of 100 μl/cm$^2$, measured at 18 hours) of the NE-1 formulation (surfactant ratio of 1:6 with 0.1%0 peanut protein) with an aqueous formulation (0.1% peanut protein). FIG. 23 shows the dermal levels of peanut proteins Ara h2, Ara h1, Ara h3, and Ara hX (μg/g tissue) inhuman abdominal skin following one application (occluded dose of 100 μl/cm$^2$, measured at 18 hours) of NE-1 formulation (surfactant ratio of 1:6), NE-2 formulation (surfactant ratio of 1:6), and NE-3 formulation (surfactant ratio of 1:9) using three different quaternary ammonium compounds and two different nonionic surfactants combined with 0.1% peanut protein) with aqueous formulation (0.1% peanut protein).

As clearly depicted in FIGS. 22 and 23, each of the nanoemulsions having surfactant ratios of 1:6 and 1:9 showed dramatic and significantly greater permeation (amount of peanut protein (μg)/tissue weight (g)) as compared to a non-nanoemulsion formulation having the same quantity of peanut protein. Furthermore, by interchanging the three quaternary ammonium compounds and two nonionic surfactants in the nanoemulsion formulations tested in FIG. 23 and still achieving significantly greater permeation in each case as compared to a non-nanoemulsion formulation, the importance of the concentration ratio of the quaternary ammonium compound to the nonionic surfactant as opposed to the specific surfactants used in each formulation is demonstrated.

Topical BEC Delivery: The nanoemulsion tested had a surfactant ratio of 1:6 and a BEC amount of 0.2% as shown in the below table. This nanoemulsion was evaluated against an aqueous formulation (0.2% BEC), New-Skin® spray (0.2% BEC), and CVS Liquid Bandage (0.2% BEC) using the same methodology of Example 6:

TABLE 25

NE formulations BEC.

| Formulation Excipients | NE (Surfactant Blend Ratio: 1:6; 0.2% BEC) |
|---|---|
| Water | 83.953 |
| BEC | 0.20 |
| Poloxamer 407 | 1.184 |
| Ethanol | 1.346 |
| Soybean Oil | 12.558 |
| EDTA | 0.7588 |
| Total | 100% |

Figure 24:
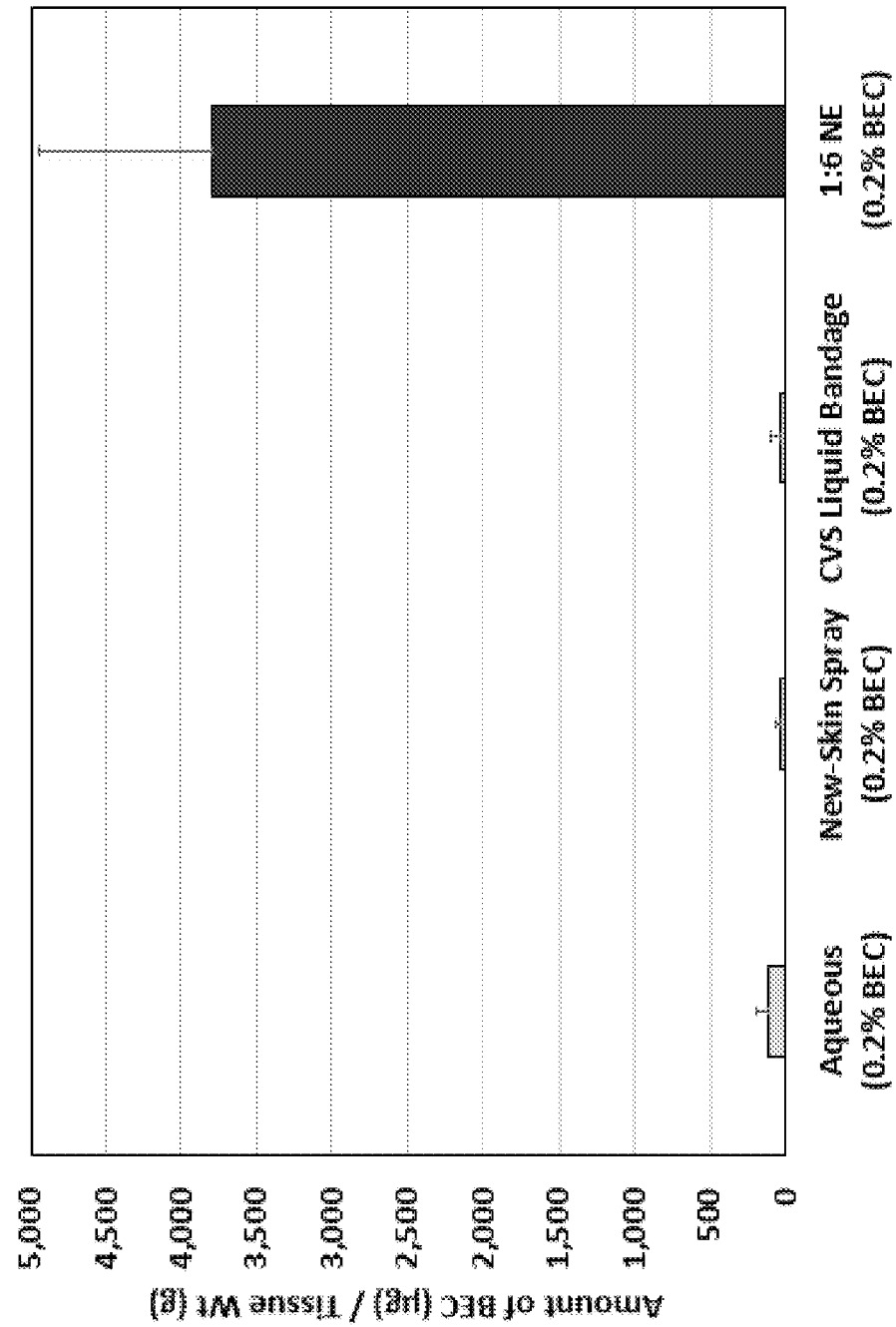
FIG. 24 shows the epidermal levels of BEC (μg/g tissue) in human abdominal skin following one application (single dose of 100 μl/cm², measured at 24 hours) of the NE formulation (surfactant ratio of 1:6 with 0.2% BEC) with an aqueous formulation (0.2% BEC), New-Skin® spray (0.2% BEC), and CVS Liquid Bandage (0.2% BEC).
Figure 25:
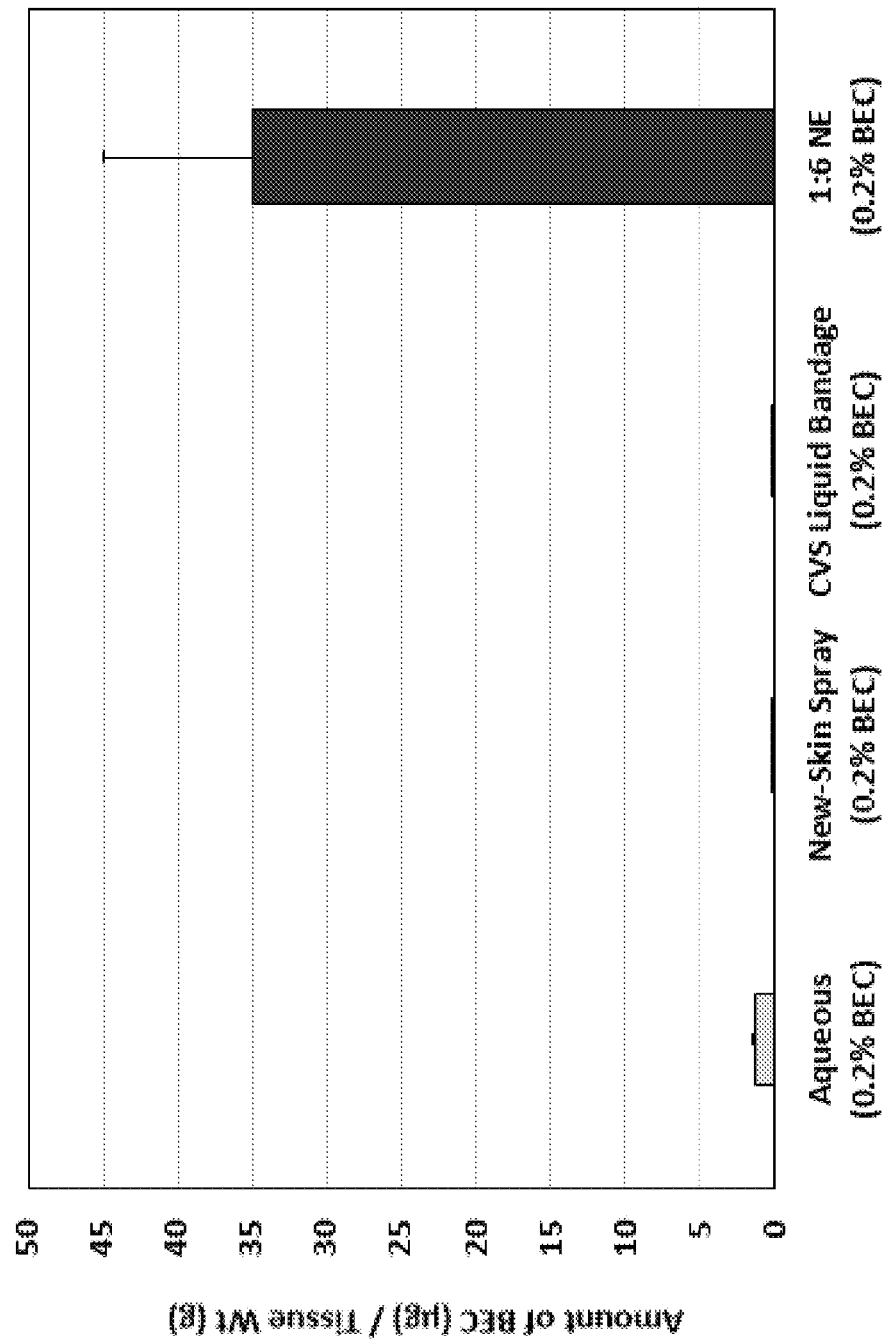
FIG. 25 shows the dermal levels of BEC (μg/g tissue) in human abdominal skin following one application (single dose of 100 μl/cm², measured at 24 hours) of the NE formulation (surfactant ratio of 1:6 with 0.2% BEC) with an aqueous formulation (0.2% BEC), New-Skin® spray (0.2% BEC), and CVS Liquid Bandage (0.2% BEC).

FIG. 24 graphically shows the epidermal levels of BEC (μg/g tissue) in human abdominal skin following one application (single dose of 100 μl/cm$^2$, measured at 24 hours) of the NE formulation (surfactant ratio of 1:6 with 0.2% BEC) with an aqueous formulation (0.2% BEC), New-Skin® spray (0.2% BEC), and CVS Liquid Bandage (0.2% BEC). FIG. 25 graphically shows the dermal levels of BEC (μg/g tissue) in human abdominal skin following one application (single dose of 100 μl/cm$^2$, measured at 24 hours) of the NE formulation (surfactant ratio of 1:6 with 0.2% BEC) with an aqueous formulation (0.2% BEC), New-Skin® spray (0.2% BEC), and CVS Liquid Bandage (0.2% BEC).

As clearly depicted in FIGS. 24 and 25, the nanoemulsion having surfactant ratio of 1:6 showed dramatic and significantly greater permeation (amount of BEC (μg)/tissue weight (g)) as compared to a non-nanoemulsion formulation having the same quantity of BEC.

Topical Chloroxylenol (para-chloro-meta-xylenol; PCMX) Delivery: The nanoemulsion tested had a surfactant ratio of 1:6 and a PCMX amount of 3% as shown in the below table. This nanoemulsion was evaluated against an 70% ethanol formulation (3% PCMX) using the same methodology of Example 6:

TABLE 26

NE formulation with BEC and PCMX.

| Formulation Excipients | NE (Surfactant Blend Ratio: 1:6; 3% PCMX) |
|---|---|
| Water | 83.951 |
| PCMX | 3.0 |
| BEC | 0.2 |
| Poloxamer 407 | 1.184 |
| Ethanol | 1.346 |
| Soybean Oil | 9.56 |
| EDTA | 0.7588 |
| Total | 100% |

Figure 26:
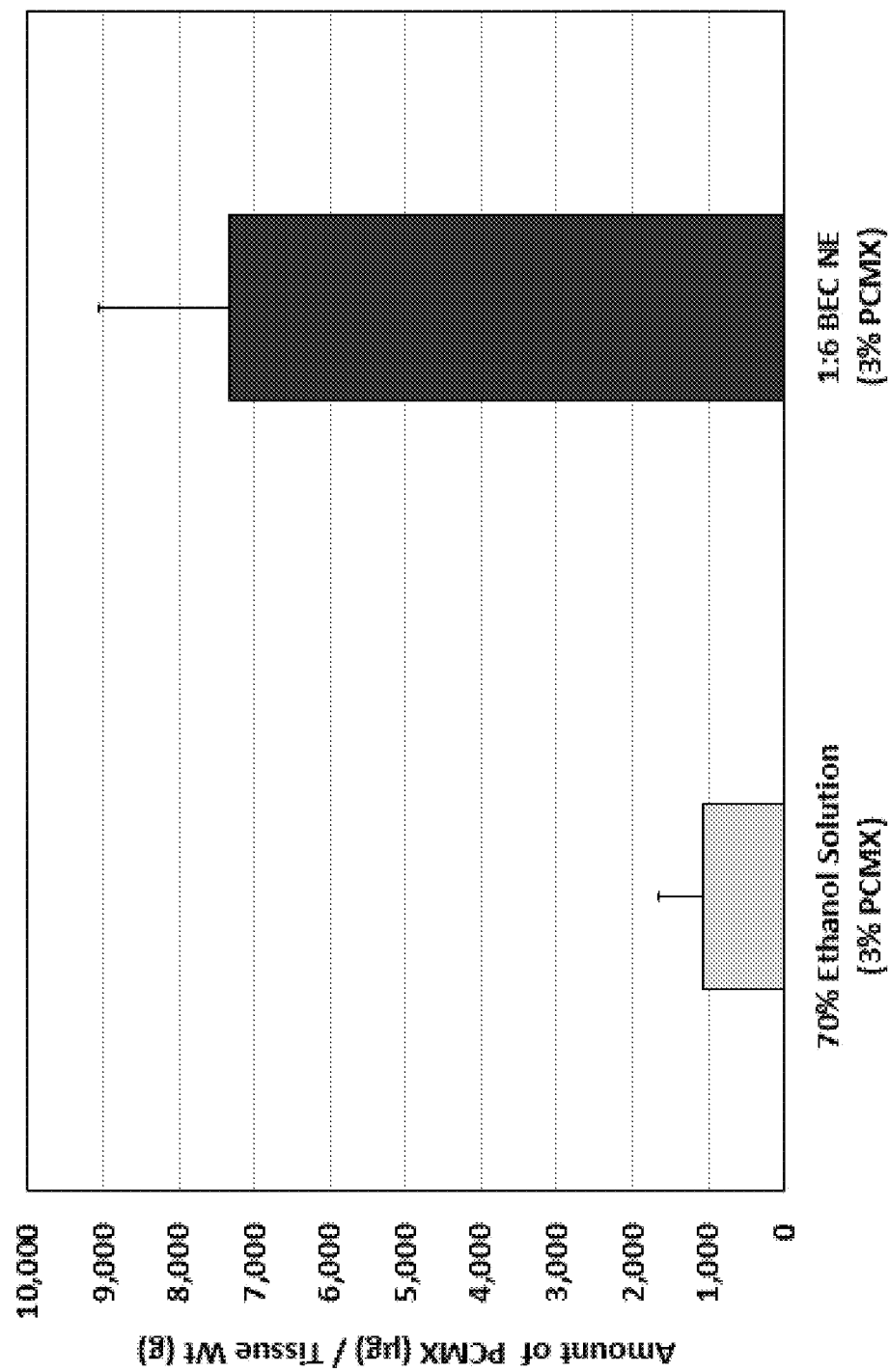
FIG. 26 shows the epidermal levels of PCMX (μg/g tissue) in human abdominal skin following one application (single dose of 100 μl/cm², measured at 24 hours) of the NE formulation (surfactant ratio of 1:6 with 3.0% PCMX) with an 70% ethanol formulation (3% PCMX).
Figure 27:
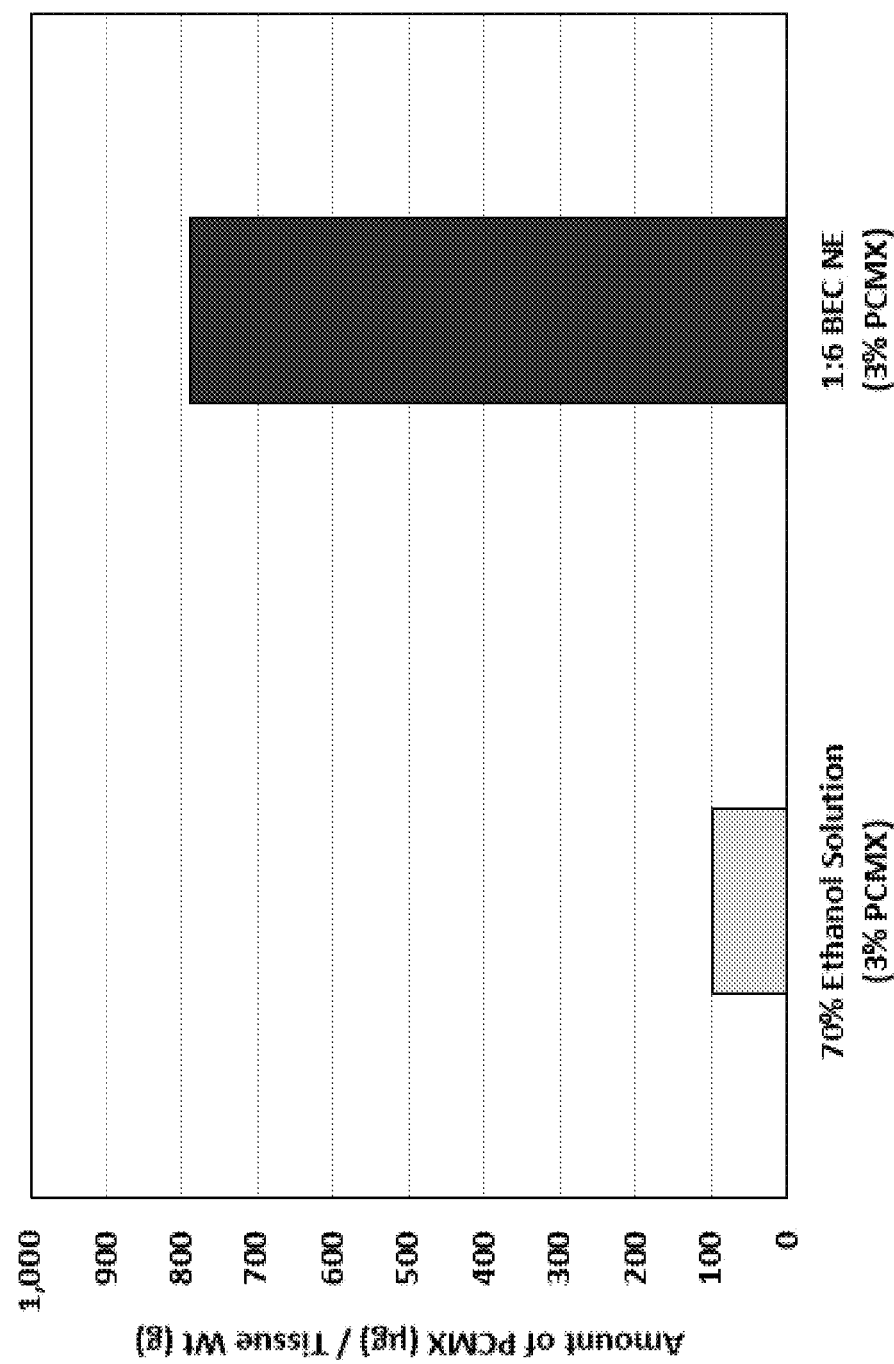
FIG. 27 shows the dermal levels of PCMX (μg/g tissue) in human abdominal skin following one application (single dose of 100 μl/cm², measured at 24 hours) of the NE formulation (surfactant ratio of 1:6 with 3.0% PCMX) with an 70% ethanol formulation (3% PCMX).

FIG. 26 graphically shows the epidermal levels of PCMX (μg/g tissue) in human abdominal skin following one application (single dose of 100 μl/cm$^2$, measured at 24 hours) of the NE formulation (surfactant ratio of 1:6 with 3.0% PCMX) with an 70% ethanol formulation (3% PCMX). FIG. 27 graphically shows the dermal levels of PCMX (μg/g tissue) in human abdominal skin following one application (single dose of 100 μl/cm$^2$, measured at 24 hours) of the NE formulation (surfactant ratio of 1:6 with 3.0% PCMX) with an 70% ethanol formulation (3% PCMX).

As clearly depicted in FIGS. 26 and 27, the nanoemulsion having surfactant ratio of 1:6 showed dramatic and significantly greater permeation (amount of PCMX (μg)/tissue weight (g)) as compared to a non-nanoemulsion formulation having the same quantity of PCMX.

Chlorhexidine Delivery: The nanoemulsion tested had a surfactant ratio of 1:9 and a chlorhexidine amount of 2.0% as shown in the below table. This nanoemulsion was evaluated against the 70% isopropanol (IPA) solution containing 2% chlorhexidine using the same methodology of Example 6.

TABLE 27

NE formulation with Chlorhexidine

| Formulation Excipients | NE-1 (Surfactant Blend Ratio: 1:9; 2% Chlorhexidine) |
|---|---|
| Water | 81.911 |
| Chlorhexidine Gluconate | 2.0 |
| BZK | 0.13 |
| Poloxamer 407 | 1.184 |
| Glycerol | 2.016 |
| Soybean Oil | 12.558 |
| EDTA | 0.201 |
| Total | 100% |

Figure 28:
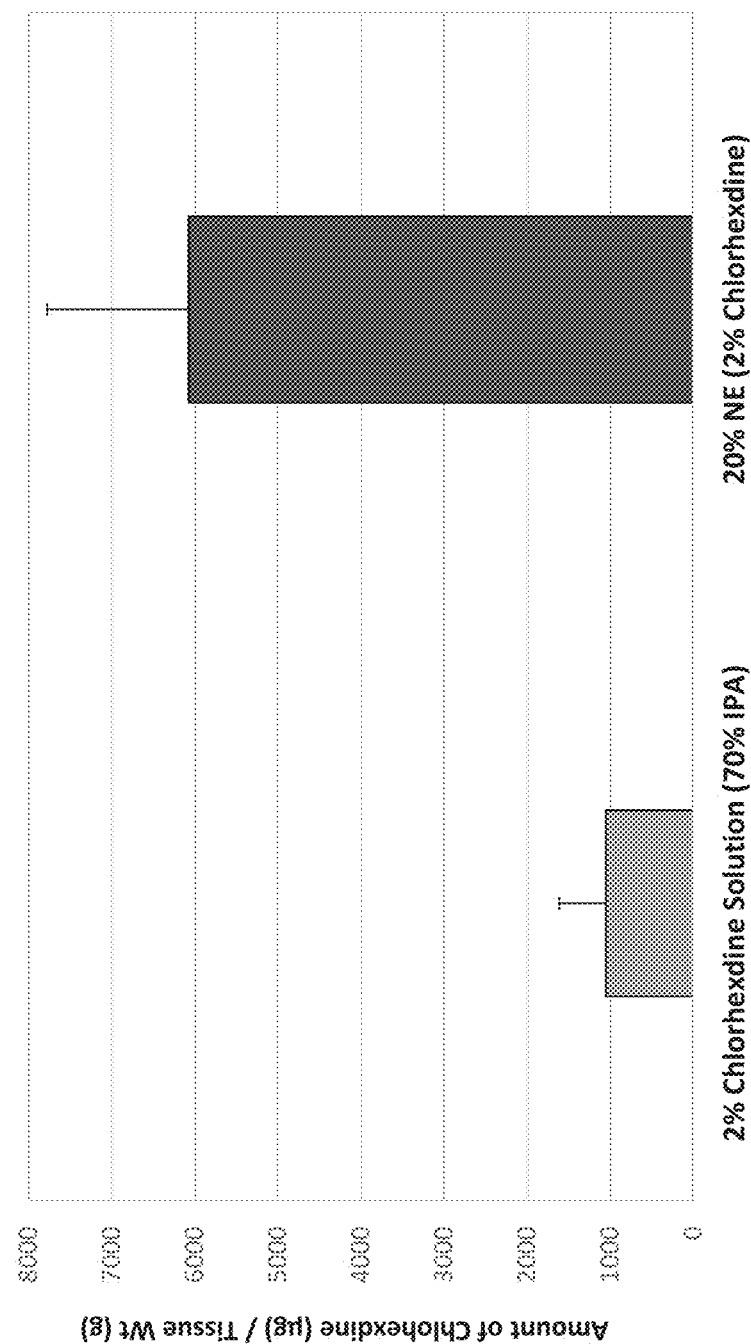
FIG. 28 shows the epidermal levels of chlorhexidine (μg/g tissue) in human abdominal skin following one application (dose of 100 μl/cm², measured at 24 hours) of the NE-1 formulation (surfactant ratio of 1:9 with 2% chlorhexidine) with a 70% IPA solution containing 2% chlorhexidine.
Figure 29:
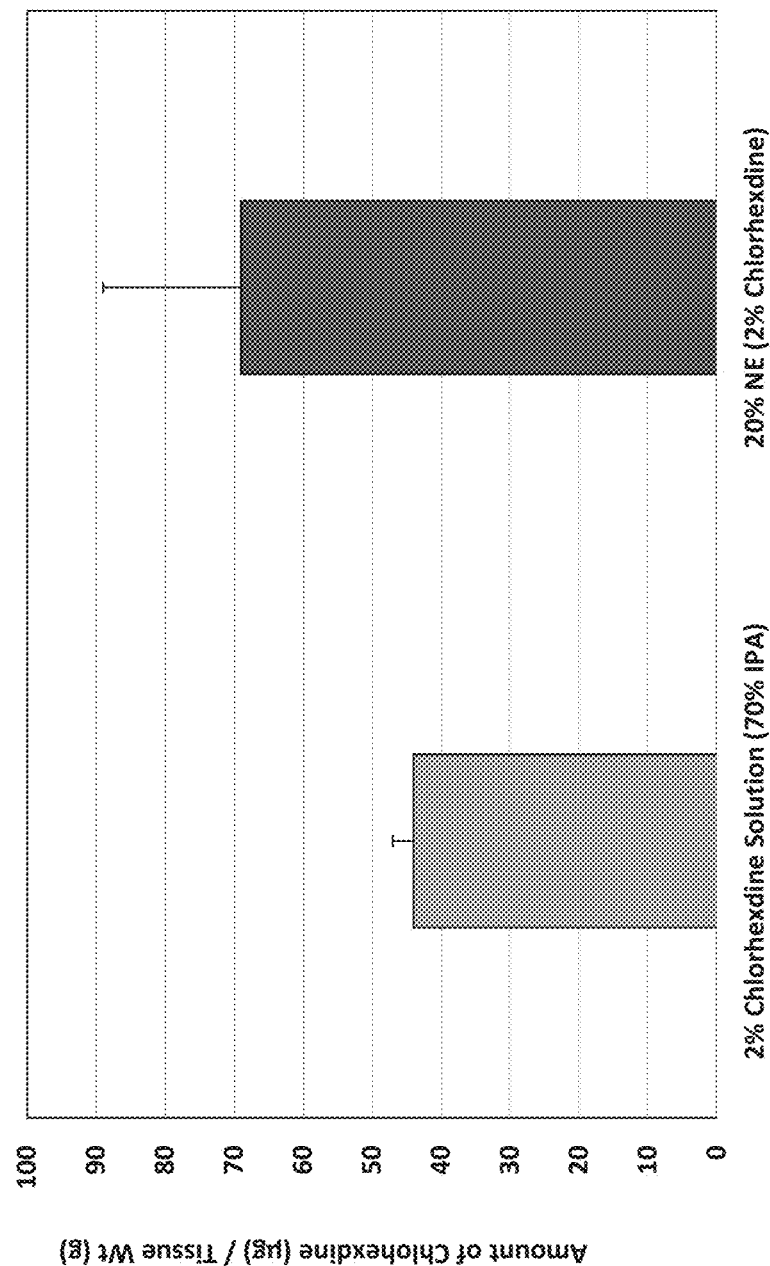
FIG. 29 shows the dermal levels of chlorhexidine (μg/g tissue) in human abdominal skin following one application (dose of 100 μl/cm², measured at 24 hours) of NE-1 formulation (surfactant ratio of 1:9 with 2% chlorhexidine) with a 70% IPA solution containing 2% chlorhexidine.

FIG. 28 shows the epidermal levels of chlorhexidine (μg/g tissue) in human abdominal skin following one application (dose of 100 μl/cm$^2$, measured at 24 hours) of the NE-1 formulation (surfactant ratio of 1:9 with 2% chlorhexidine) with a 70% IPA solution containing 2% chlorhexidine. FIG. 29 shows the dermal levels of chlorhexidine (μg/g tissue) in human abdominal skin following one application (dose of 100 μl/cm$^2$, measured at 24 hours) of NE-1 formulation (surfactant ratio of 1:9 with 2% chlorhexidine) with a 70% IPA solution containing 2% chlorhexidine.

As clearly depicted in FIGS. 28 and 29, the nanoemulsions having surfactant ratios of 1:9 showed dramatic and significantly greater permeation (amount of chlorhexidine (μg)/tissue weight (g)) as compared to a non-nanoemulsion formulation having the same quantity of chlorhexidine.

Example 15—Determination of Viscosity of Samples

The purpose of this example was to measure the viscosity of different nanoemulsions and to correlate the viscosity with improved epidermal and dermal permeation of the component quaternary ammonium compound.

To determine the viscosity the nanoemulsion (NE) samples ranging from 0.5% NE to 100% NE, Brookfield Viscometers Models LV and RV (Brookfield Engineering Laboratories. Inc., USA) were used. Prior to taking the viscosity reading, the viscometers and NE samples were allowed come to 22.0±1° C. Each NE sample was placed in a BD Falcon™ 50 mL Conical Centrifuge Tube wide enough to properly cover the specified spindle. The tube containing the NE sample was placed under the spindle and centered to the immersion line. For NE samples 0.5% NE to 60% NE, a LV viscometer using an UL adaptor was used. The viscosity of each NE sample was measured at a property speed of either 100, 50 or 1 rpm. The viscosity (cP) readings were recorded. The 80% NE sample was measured using a LV viscometer using a LV2 spindle at a speed of 3 rpm. Due to tremendous increase in viscosity of the 100% NE sample, an RV viscosity with a F spindle at 100 rpm was used to determine the viscosity.

Figure 30:
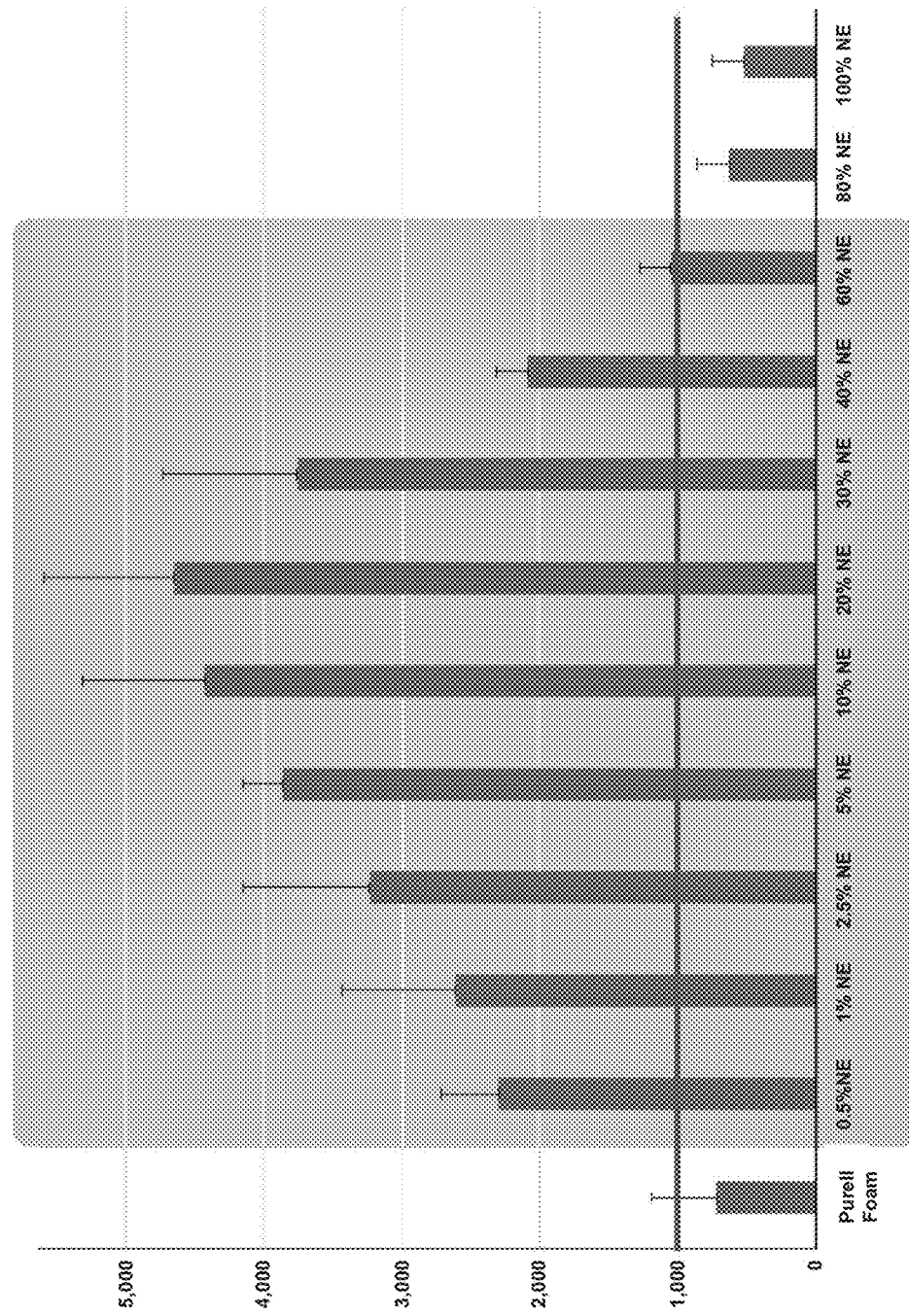
FIG. 30 shows Epidermal Skin Permeation of 0.13% BZK Formulations vs NE %, Epidermal levels of BZK (μg/g tissue) in human abdominal skin after one application (dose of 100 μl/cm², measured at 24 hours) and epidermal permeability results for nanoemulsion formulations of various nanoemulsion concentrations (0.5%, 1%, 2.5%, 5%, 10%, 20%, 30%, 40%, and 60%) and Purell® Foam (0.13% BZK).
Figure 31:
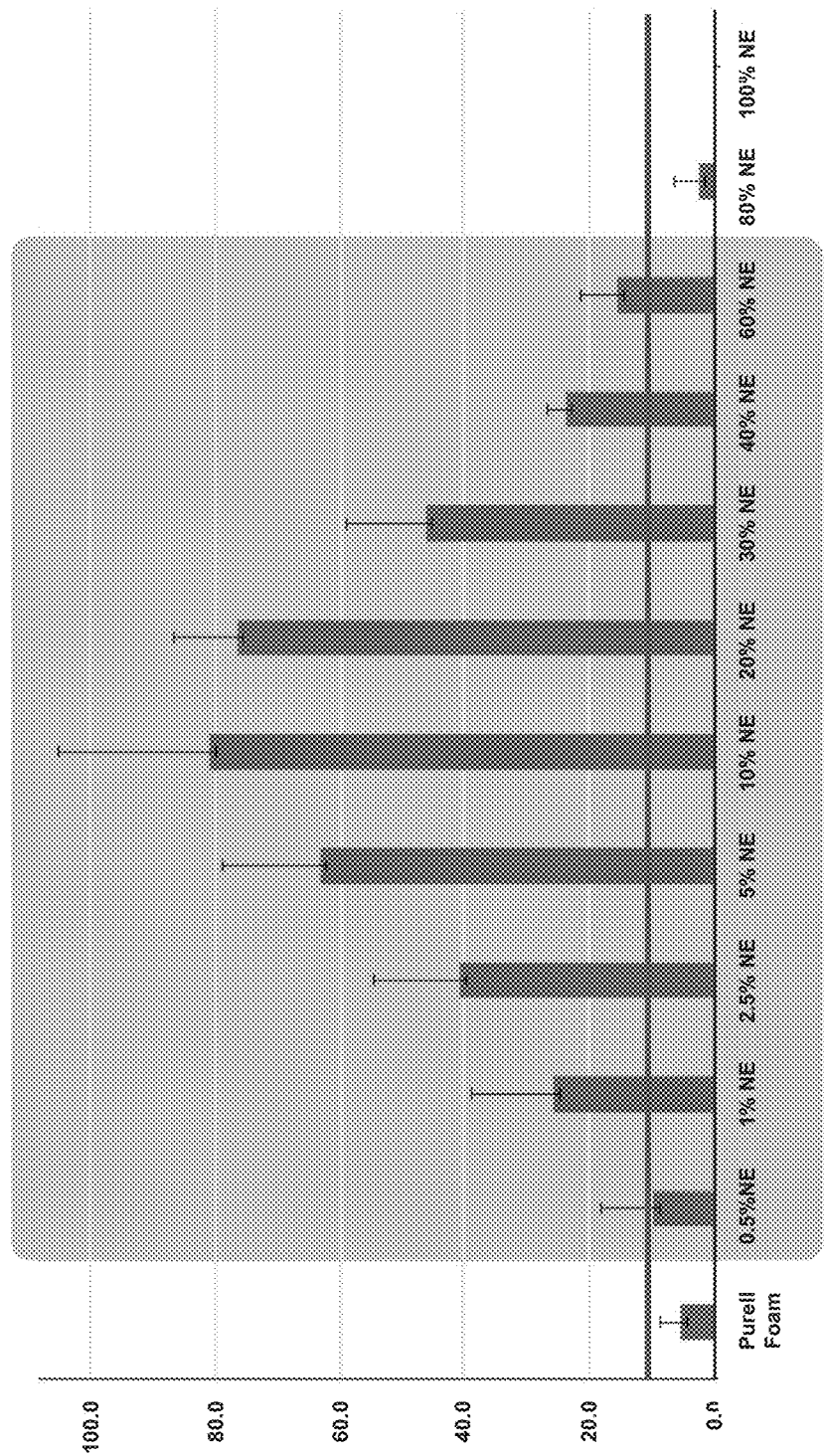
FIG. 31 shows Dermal Skin Permeation of 0.13% BZK Formulations vs NE %, dermal levels of BZK (μg/g tissue) in human abdominal skin after one application (dose of 100 μl/cm², measured at 24 hours), and dermal permeability results for nanoemulsion formulations of various nanoemulsion concentrations (0.5%, 1%, 2.5%, 5%, 10%, 20%, 30%, 40%, and 60%) and Purell® Foam (0.13% BZK).
Figure 32:
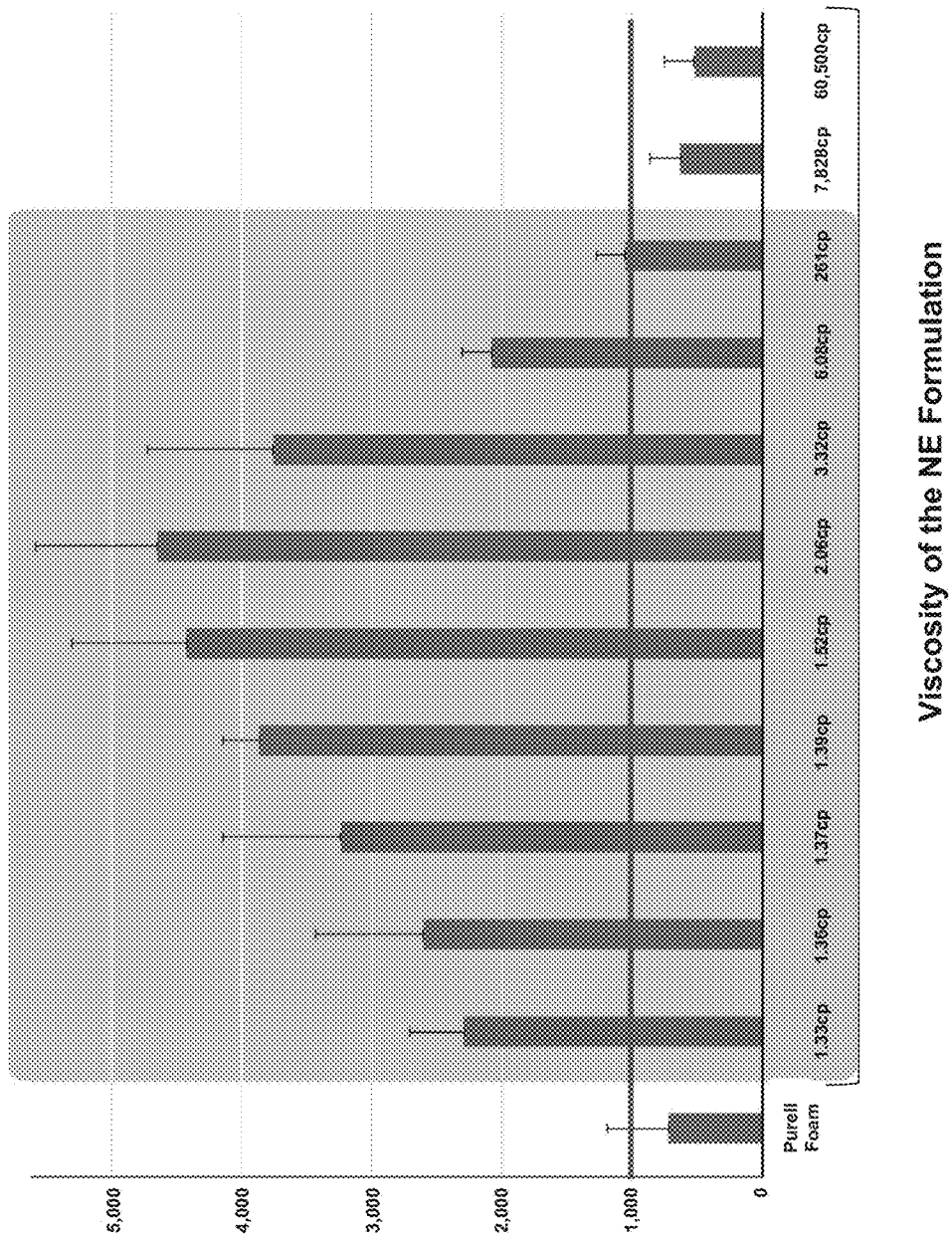
FIG. 32 shows Epidermal Skin Permeation of 0.13% BZK Formulations vs Viscosity, epidermal levels of BZK (μg/g tissue) in human abdominal skin after one application (dose of 100 μl/cm², measured at 24 hours), and epidermal permeability results for nanoemulsion formulations relative to their viscosity (1.33 cp, 1.36 cp, 1.37 cp, 1.39 cp, 1.52 cp, 2.06 cp, 3.32 cp, 6.08 cp, and 261 cp) and Purell® Foam (0.13% BZK).
Figure 33:
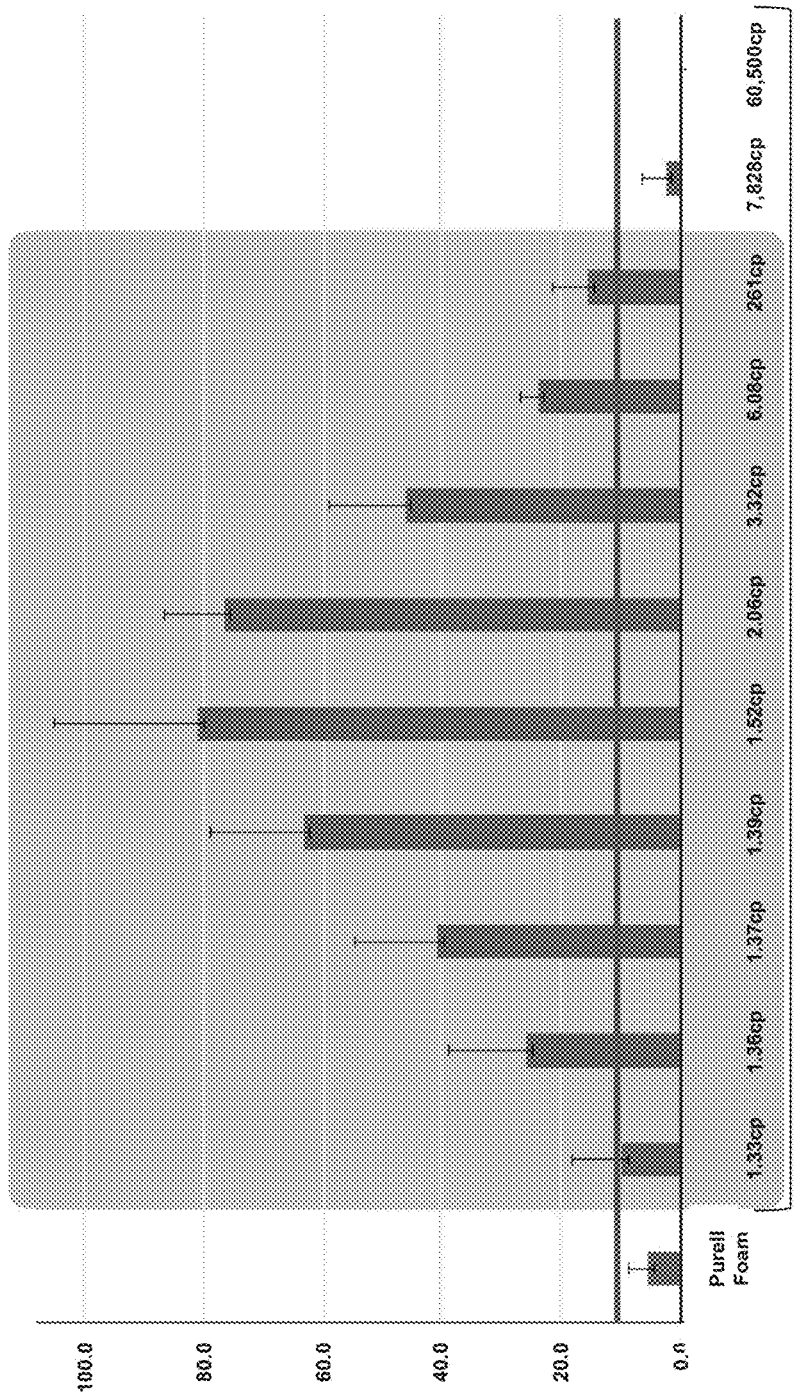
FIG. 33 shows Dermal Skin Permeation of 0.13% BZK Formulations vs Viscosity, dermal levels of BZK (μg/g tissue) in human abdominal skin after one application (dose of 100 μl/cm², measured at 24 hours), and dermal permeability results for nanoemulsion formulations relative to their viscosity (1.33 cp, 1.36 cp, 1.37 cp, 1.39 cp, 1.52 cp, 2.06 cp, 3.32 cp, 6.08 cp, and 261 cp) and Purell® Foam (0.13% BZK).
Figure 34:
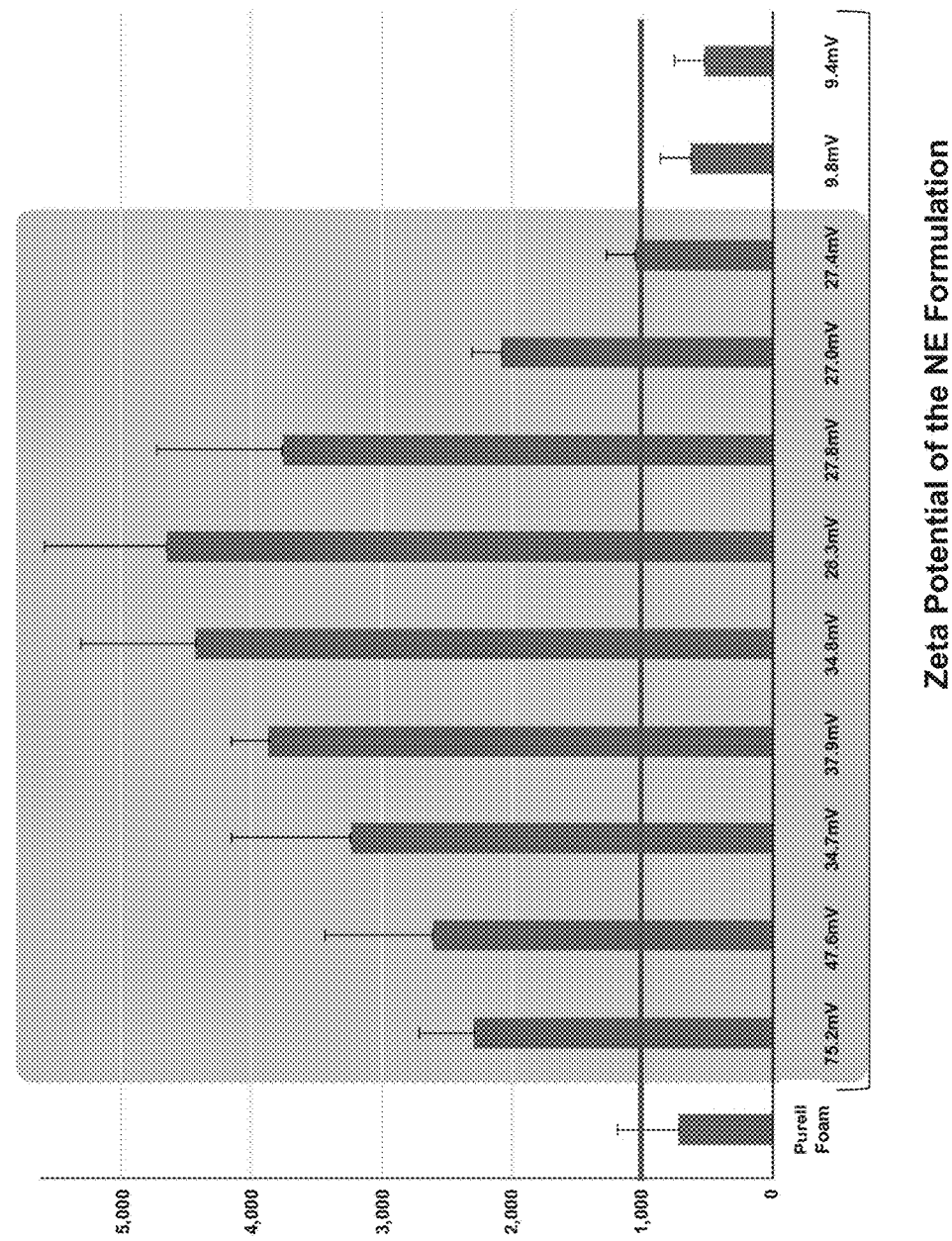
FIG. 34 shows Epidermal Skin Permeation of 0.13% BZK Formulations vs Zeta potential, epidermal levels of BZK (μg/g tissue) in human abdominal skin after one application (dose of 100 μl/cm², measured at 24 hours), and epidermal permeability results for nanoemulsion formulations relative to their zeta potential (75.2 mV, 47.6 mV, 34.7 mV, 34.8 mV, 28.3 mV, 27.8 mV, 27.0 mV, 27.4 mV) and Purell® Foam (0.13% BZK).
Figure 35:
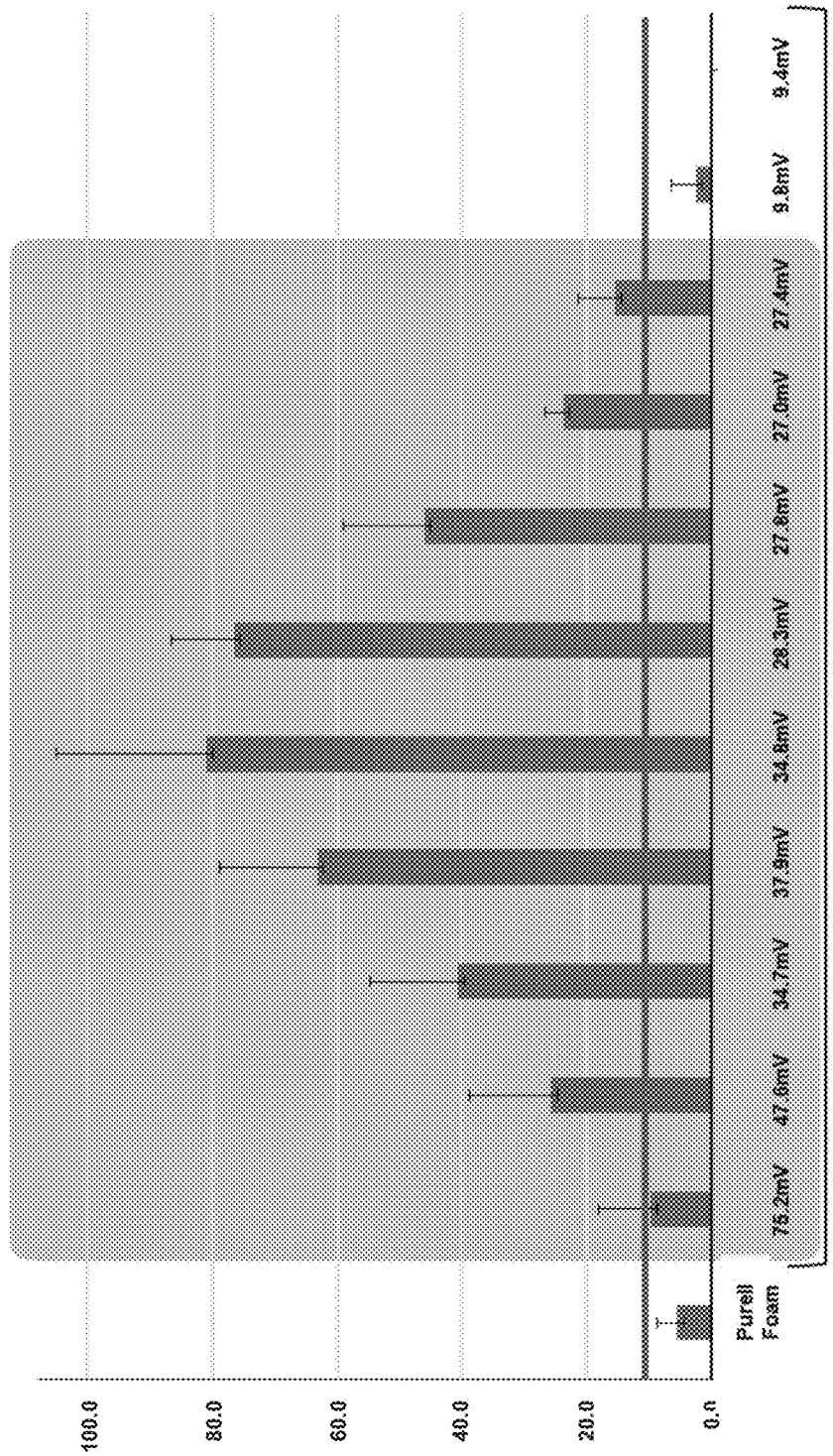
FIG. 35 shows Dermal Skin Permeation of 0.13% BZK Formulations vs Zeta Potential, dermal levels of BZK (μg/g tissue) in human abdominal skin after one application (dose of 100 μl/cm², measured at 24 hours), and dermal permeability results for nanoemulsion formulations relative to their zeta potential (75.2 mV, 47.6 mV, 34.7 mV, 34.8 mV, 28.3 mV, 27.8 mV, 27.0 mV, 27.4 mV) and Purell® Foam (0.13% BZK).
Figure 36:
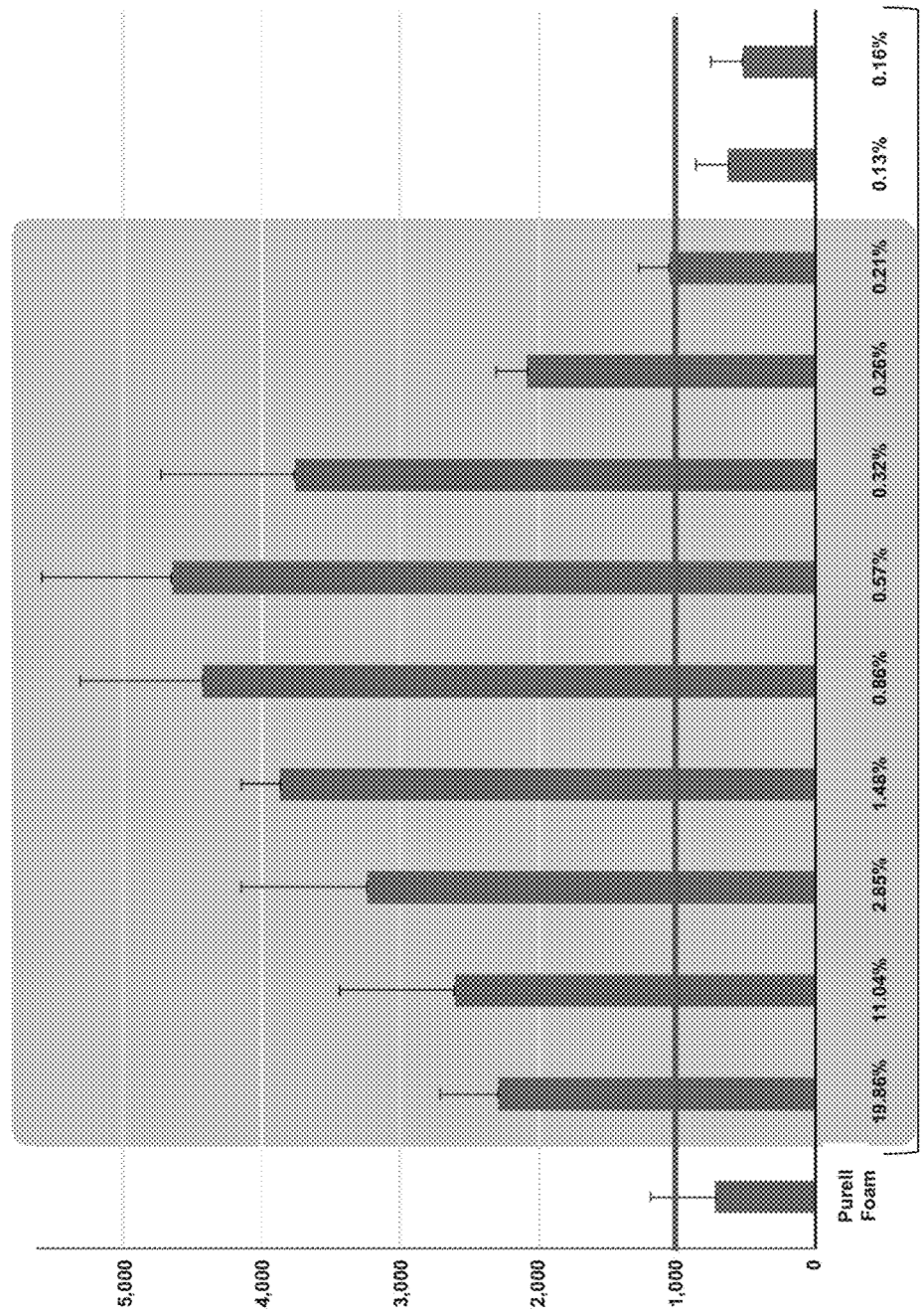
FIG. 36 shows Epidermal Skin Permeation of 0.13% BZK Formulations vs Weight of Oil Attributed to Quaternary Ammonium Entrapment, epidermal levels of BZK (μg/g tissue) in human abdominal skin after one application (dose of 100 μl/cm², measured at 24 hours), and epidermal permeability results for nanoemulsion formulations relative to their entrapment of the quaternary ammonium salt (19.86%, 11.04%, 2.85%, 1.48%, 0.86%, 0.57%, 0.32%, 0.26%, 0.21%) and Purell® Foam (0.13% BZK).
Figure 37:
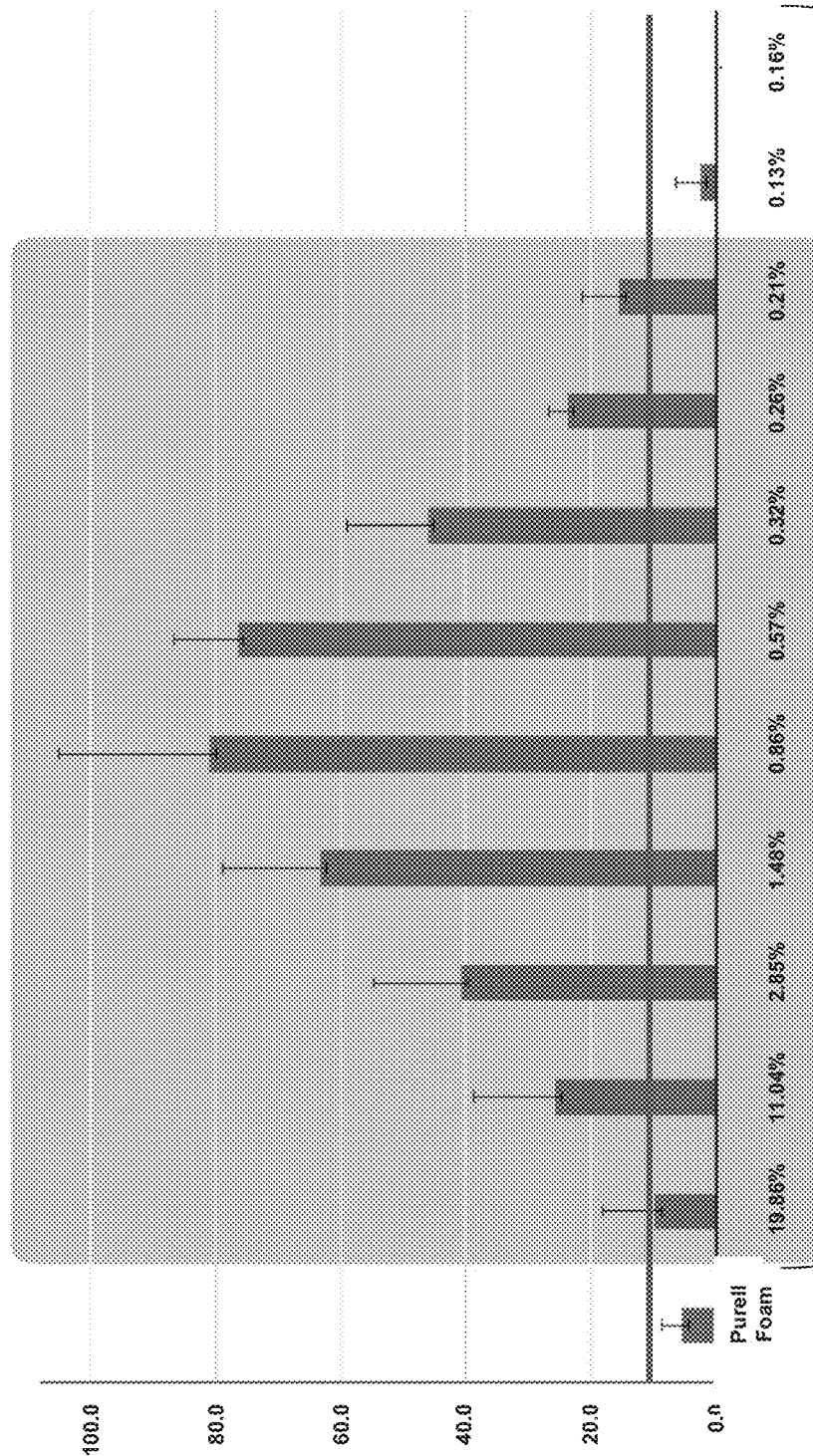
FIG. 37 shows Dermal Skin Permeation of 0.13% BZK Formulations vs Weight of NE Attributed to Quaternary Ammonium Compound, dermal levels of BZK (μg/g tissue) in human abdominal skin after one application (dose of 100 μl/cm$^2$, measured at 24 hours), and dermal permeability results for nanoemulsion formulations relative to their entrapment of the quaternary ammonium salt (19.86%, 11.04%, 2.85%, 1.48%, 0.86%, 0.57%, 0.32%, 0.26%, 0.21%) and Purell® Foam (0.13% BZK).

FIG. 30 shows epidermal permeability results, and FIG. 31 shows dermal permeability results, for nanoemulsion formulations of various nanoemulsion concentrations, and FIG. 32 shows epidermal permeability, and FIG. 33 shows dermal permeability for nanoemulsions having various viscosities. Nanoemulsions falling within the preferred viscosity range of the present disclosure shown in the shaded box have significant and dramatic increased permeability as compared to the nanoemulsion formulations outside the viscosity range of the disclosure.

Example 16—Particle Size Analysis Polydispersity Index (PdI) and Zeta Potential

The purpose of this example was to measure the zeta potential of different nanoemulsions and to correlate the zeta potential with improved epidermal and dermal permeation of the component quaternary ammonium compound.

The mean particle size (Z-AVE), polydispersity index (PdI) and zeta potential were determined for samples by dynamic light scattering using photon correlation spectroscopy in a Malvern Zetasizer Nano ZS90 (Malvern Instruments, Worcestershire, UK). For particle size, the test sample of nanoemulsion diluted was to 1% final nanoemulsion concentration. For zeta potential, the test sample of nanoemulsion diluted was to 0.1% final nanoemulsion concentration. All measurements were carried out at 25° C. after appropriate dilution with double distilled 0.2 μm filtered water.

FIG. 34 shows epidermal permeability results, and FIG. 35 shows dermal permeability results, for nanoemulsion formulations within preferred zeta potential range and outside the scope of the disclosure relative to the formulation's zeta potential. Nanoemulsions of the disclosure shown in the shaded box show significant and dramatic increased permeability as compared to the nanoemulsion formulations outside the claimed zeta potential range.

Example 17—Centrifugation Study to Determine Quaternary Ammonium Compound Entrapment The purpose of this example was to measure the amount of quaternary ammonium compound present in the oil phase of the NE, and to correlate the results with improved epidermal and dermal permeation of the component quaternary ammonium compound.

The amount of BZK in the external (aqueous phase) the nanoemulsion was determined. The experiment required separation of the nanoemulsion droplets from the external aqueous phase of the formulation using centrifugation while maintaining emulsion droplet structure (i.e. intact droplets in close proximity to each other) and not to cause coalescence (fusing of the droplets and then measuring the concentration of quaternary ammonium compound.

Approximately 5 grams of the nanoemulsion samples was placed into pre-weighed centrifuge tubes. The weight of nanoemulsion in each tube varied slightly to balance the centrifuge tubes in the rotor. The actual weight of the centrifuged emulsion was determined by the difference of the weight of the filled tube from the empty tube. The samples were centrifuged at 30,000 rpm for 30 minutes.

The nanoemulsion droplets concentrate at the top of the tube and the clear aqueous phase below the emulsion droplets. Images depicting nanoemulsion sample after centrifugation are shown in FIG. 43. Image taken under normal lighting conditions (left) and corresponding negative image (right). The negative image illustrates the clarity of the aqueous phase. A portion of the aqueous phase was removed from the tube with a 26-gauge needle and syringe without distributing the top layer of the nanoemulsion droplets. The sample of the aqueous phase was than assayed for BZK using RP-HPLC. The concentration of BZK in the extracted aqueous phase, the weight of the nanoemulsion in each tube and the percentage of the aqueous phase verses the oil phase was used to determine the entrapment of the quaternary ammonium compound in the oil phase of the nanoemulsion.

FIG. 38 shows epidermal permeability results, and FIG. 39 shows dermal permeability results, for nanoemulsion formulations falling within the disclosure and outside the scope of the disclosure relative to the formulation's entrapment of the quaternary ammonium compound in the oil phase of the nanoemulsion. Nanoemulsions falling within the disclosure are shown in the shaded box and show significant and dramatic increased permeability as compared to the nanoemulsion formulations outside the range of the disclosure (e.g., 80% and 100% nanoemulsion (NE)) and a current commercial formulation (Purell®).

Example 18—Centrifugation on Particle Size Stability of Nanoemulsion Formulations The purpose of this example was to measure the stability of droplet size of various nanoemulsions following centrifugation, and to correlate the results with improved epidermal and dermal permeation of the component quaternary ammonium compound.

Nanoemulsion samples were placed under a very high centrifugal force and long duration to force the nanoemulsion droplets from the external aqueous phase to come near each other. If the interface of the nanoemulsion droplets is not strong, the droplets will coalescence (fusing of the droplets) and the mean particle size will be effected.

Approximately 5 grams of the nanoemulsion samples was placed into pre-weighed centrifuge tubes. The weight of nanoemulsion in each tube varied slightly in order to balance the centrifuge tubes in the rotor. The actual weight of the centrifuged emulsion is determined by the difference of the weight of the filled tube from the empty tube. The samples were centrifuged at 200,000 rpm for 1 hour. The emulsion droplets concentrate at the top of the tube and the clear aqueous phase below the emulsion droplets. Following centrifugation, droplets are re-distributed in the external aqueous phase by simple shaking and the particle size distribution determined using the Malvern Zetasizer. The mean particle size was determined before and after centrifugation as shown below in Table 28 and the % change in the mean was determined. A change of more than 10% was considered unstable.

TABLE 28

| Mean particle size of nanoemulsion compositions | | | |
|---|---|---|---|
| % NE | Mean Particle Size (initial) | Mean Particle Size (After centrifugation) | % Change |
| 0.5% | 630.9 ± 2.8 | 631.0 ± 8.2 | 0.2 |
| 1% | 201.7 ± 2.0 | 197.3 ± 4.9 | 2.0 |
| 2.5% | 196.2 ± 1.8 | 195.0 ± 0.9 | 0.5 |
| 5% | 213.6 ± 2.3 | 208.5 ± 2.7 | 1.8 |
| 10% | 240.7 ± 3.2 | 233.4 ± 0.4 | 2.9 |

TABLE 28-continued

Mean particle size of nanoemulsion compositions

| % NE | Mean Particle Size (initial) | Mean Particle Size (After centrifugation) | % Change |
|------|------|------|------|
| 20% | 317.8 ± 2.4 | 310.3 ± 1.6 | 2.2 |
| 30% | 361.2 ± 5.0 | 382.3 ± 6.7 | 5.4 |
| 40% | 423.2 ± 5.3 | 423.9 ± 13.2 | 0.2 |
| 60% | 425.2 ± 4.9 | 423.0 ± 1.8 | 0.5 |
| 80% | 412.8 ± 3.5 | 543.7 ± 5.6 | 23 |
| 100% | 366.5 ± 1.1 | 432.6 ± 4.5 | 15 |

Figure 38:
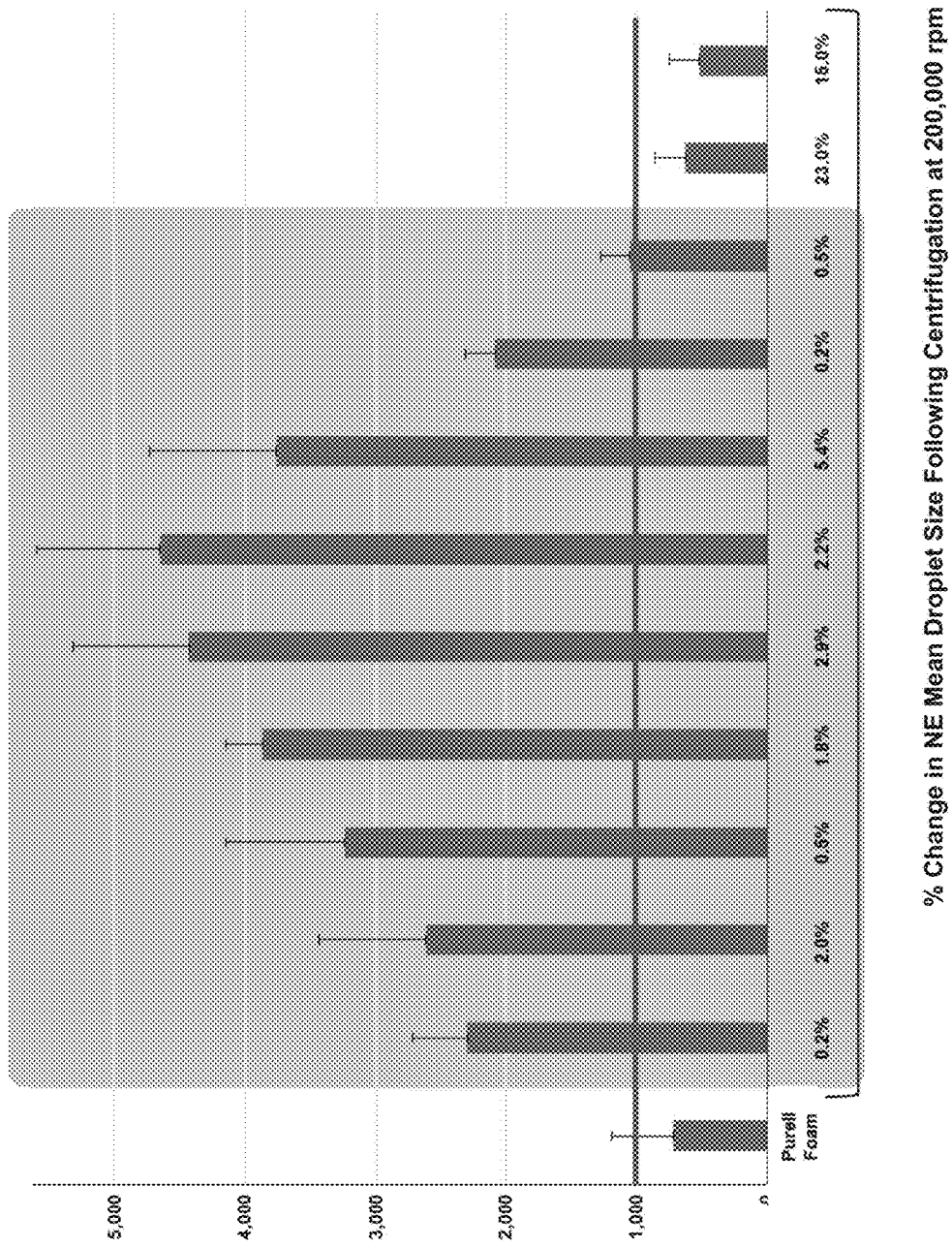
FIG. 38 shows Epidermal Skin Permeation of 0.13% BZK Formulations vs % Δ in NE Droplet Size, epidermal levels of BZK (μg/g tissue) in human abdominal skin after one application (dose of 100 μl/cm$^2$, measured at 24 hours), and epidermal permeability results for nanoemulsion formulations of the disclosure relative to the formulation's stability as measured by the percent (%) change in mean droplet size following prolonged centrifugation (0.2%, 2.0%, 0.5%, 1.8%, 2.9%, 2.2%, 5.4%, 0.2%, 0.5%) and Purell® Foam (0.13% BZK).
Figure 39:
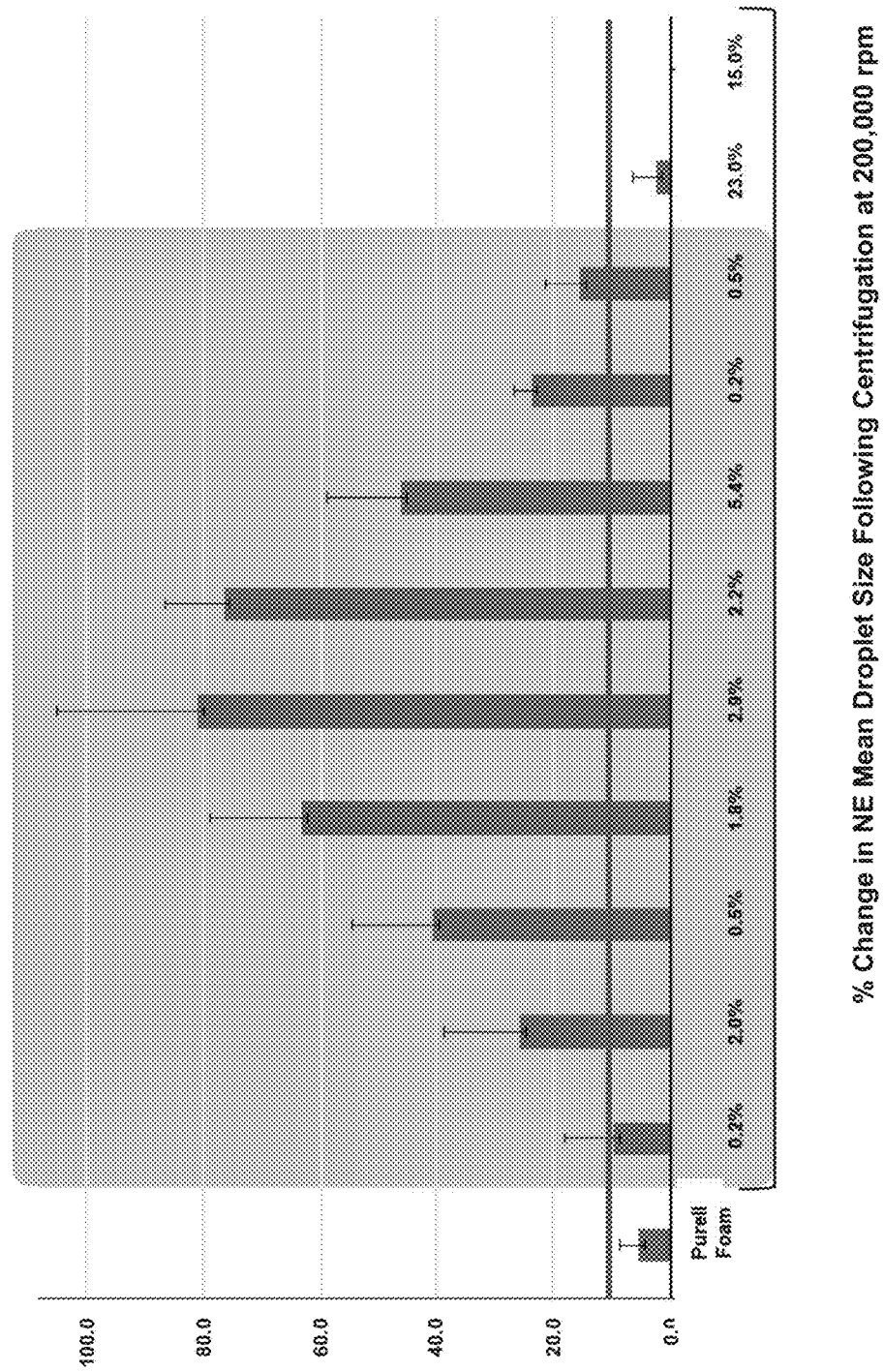
FIG. 39 shows Dermal Skin Permeation of 0.13% BZK Formulations vs % Δ in NE Droplet Size After Centrifugation, dermal levels of BZK (μg/g tissue) in human abdominal skin after one application (dose of 100 μl/cm$^2$, measured at 24 hours), and dermal permeability results for nanoemulsion formulations of the disclosure relative to the formulation's stability as measured by the percent (%) change in mean droplet size following prolonged centrifugation (0.2%, 2.0%, 0.5%, 1.8%, 2.9%, 2.2%, 5.4%, 0.2%, 0.5%) and Purell® Foam (0.13% BZK).
Figure 40:
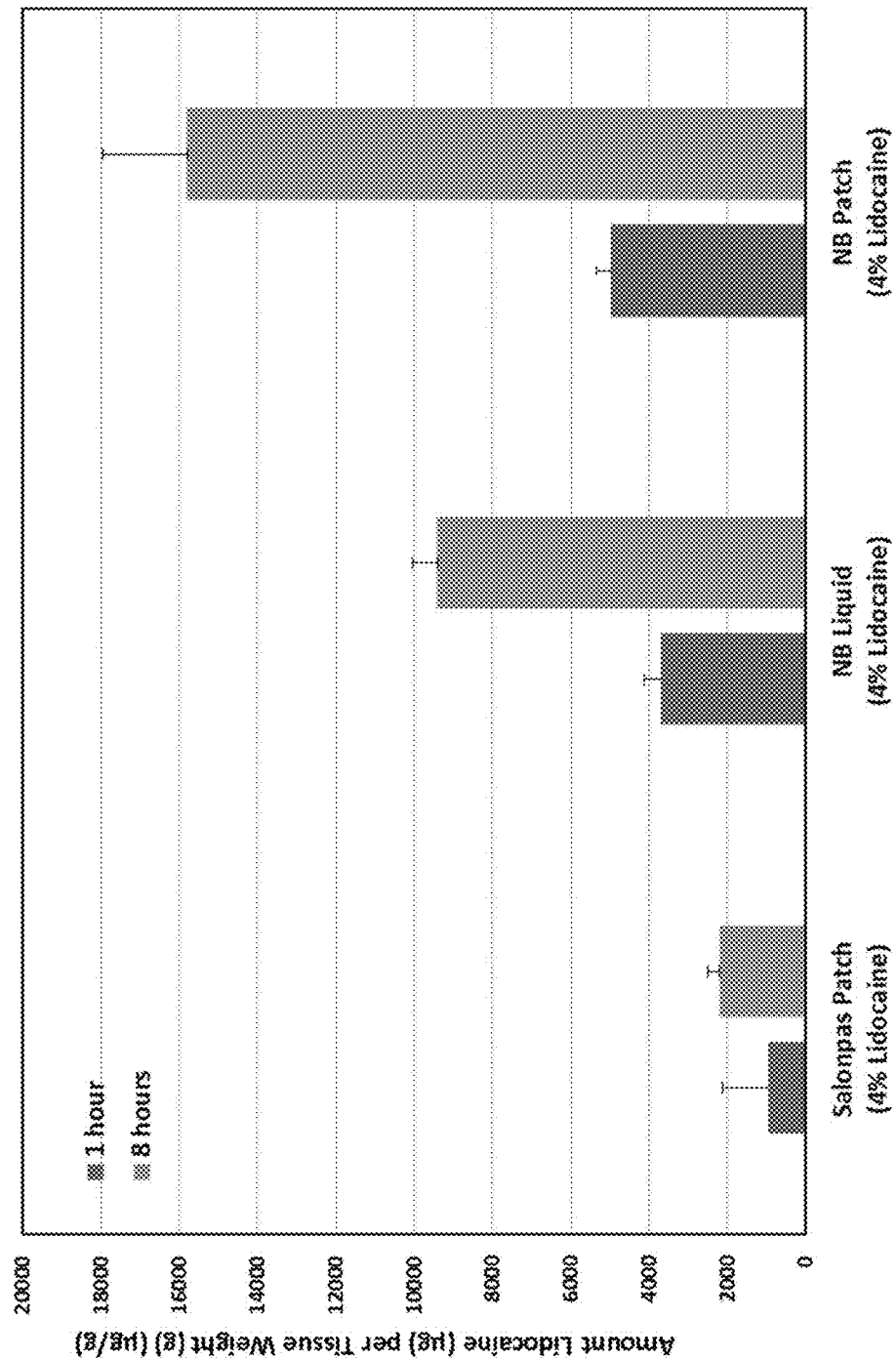
FIG. 40 shows epidermal levels of lidocaine delivered by Salonpas patch (left), nanoemulsion (NB liquid, center), and nanoemulsion patch (NB patch, right).

FIG. 38 shows epidermal permeability results, and FIG. 39 shows dermal permeability results, for nanoemulsion formulations falling within the disclosure and formulations outside the scope of the disclosure, relative to the formulation's stability (as measured by change in mean droplet size) following prolonged centrifugation. Nanoemulsions of the present disclosure are shown in the shaded box show significant and dramatic increased permeability as compared to the nanoemulsion formulations outside the claimed range (e.g., 80% and 100% nanoemulsion (NE)) and a current commercial formulation (Purell®).

The unexpected and dramatic cutaneous permeation properties of the nanoemulsions encompassed by the present invention are also demonstrated by studies measuring dermal permeation of nanoemulsion formulations for each of the five attributes examined in the Examples above. Figures for each of these attributes showing dermal permeability results for nanoemulsion formulations falling within the disclosure and outside the scope of the disclosure are shown in FIGS. 4, 5, and 31-40, and in each case, demonstrate that nanoemulsions outside the disclosed ranges show significant and dramatically reduced permeability.

Example 19—Lidocaine Permeation Study

Cryopreserved, dermatomed human cadaver male thigh skin from a donor was used in permeation studies and obtained from Science Care (Tucson, Ariz.) tissue organ donor bank. Cadaver skin was stored in aluminum foil pouches at −70° C. until use. At the time of use, the skin was thawed by placing the sealed pouch in 37° C. water for approximately five minutes. Thawed skin was removed from the pouch and cut into circular discs (30 mm diameter) to fit between the donor and receiver sides of the permeation chambers.

The receptor compartment was filled with 7.0 mL of distilled water, and was placed in the donor compartment. The receptor compartment spout was covered with a Teflon screw cap to minimize evaporation of the receptor solution. Correctly-sized human cadaver skin was placed onto the opening on the permeation cell. All cells were individually clamped with a clamp-support and placed in a heating bath which was maintained at 37° C. by a circulating water bath on the outside of the cells. The receptor compartment was maintained at 37° C. with the water bath and magnetic stirring. The surface temperature of the skin was appropriately 32° C. as determined by an IR surface temperature probe.

The test articles included the following: Salonpas Gel Patch with 4% Lidocaine, NDC #46581-830-06 (Hisamitsu, Japan), Salonpas Roll on Liquid with 4% Lidocaine, 10% Benzyl Alcohol, NDC #55328-901-03, (Hisamitsu, Japan), 20% NE with 0.13% BZK and 4% Lidocaine (non-occluded), 20% NE with 0.13% BZK and 4% Lidocaine (occluded). The composition of the NE is shown in Table 29.

TABLE 29

NE formulation with 0.13% BZK and 4% Lidocaine

| Formulation Excipients | Percentage in NE (wt/wt) (Surfactant Blend Ratio: 1:9) |
|------|------|
| Purified Water | 73.4 |
| BZK | 0.13 |
| Poloxamer 407 | 1.184 |
| Glycerol | 2.016 |
| Soybean Oil | 12.558 |
| EDTA | 0.0148 |
| Lidocaine | 4.0 |
| Ethanol | 6.7 |
| Total | 100% |

The skin was equilibrated for a period of 30 minutes before dosing. A 113 µL (over a dosing area of 1.13 cm$^2$) dose of the liquid test formulations were topically applied onto the epidermal surface of the cadaver skin mounted on the donor chamber of the diffusion cells using a positive displacement pipette. Half of the cells with the NE formulation was left non-occluded and half were occluded with a parafilm film placed over the donor cap to stop any evaporation of the NE from the skin surface. With respect to the Salonpas Gel Patch, a piece of the patch was cut to fit a surface area of 1.13 cm$^2$ area and the donor cap was clamped into the cell.

At one and eight hours after the application of the topical dose, anything from the surface was removed (e.g. patch) and the surface of the skin was rinsed with 1 ml of 70% ethanol/water solution and then cleaned with a 70% ethanol-soaked cotton swab, four times. Following alcohol swabbing, the donor cap was removed, and the skin was removed from the apparatus. The epidermis was removed from the dermis via a scraping method and placed in a tared scintillation vial. A punch biopsy was taken through the dermis and placed in a tared scintillation vial. Weights of dermis and epidermis were recorded. The excess skin portion was placed in scintillation vial with the surface swabs.

Two mL of the receptor solution was also sampled at 8 hours from the receptor of each cell and filtered through a 0.45 µm PTFE (25 mm) membrane syringe filter. The filtrates were collected in HPLC snap cap vials.

Skin samples were then collected after removal of the diffusion chamber. Briefly, the epidermis was removed from the dermis in the dosing area via a scraping technique, placed in a tared vial and weighed. The epidermal and dermal tissues were extracted with a 200-proof ethanol solution, sonicated for 30 minutes, filtered through a 25 mm, 0.45 µm PTFE membrane syringe filter into HPLC vials and assayed using HPLC.

Assay of the active agent (Lidocaine) extracted from human skin samples was determined by BlueWillow Biologics, Ann Arbor, Mich. This determination was performed on HPLC equipped with UV detector. See Table 30, below for experimental HPLC conditions for Lidocaine.

Figure 41:
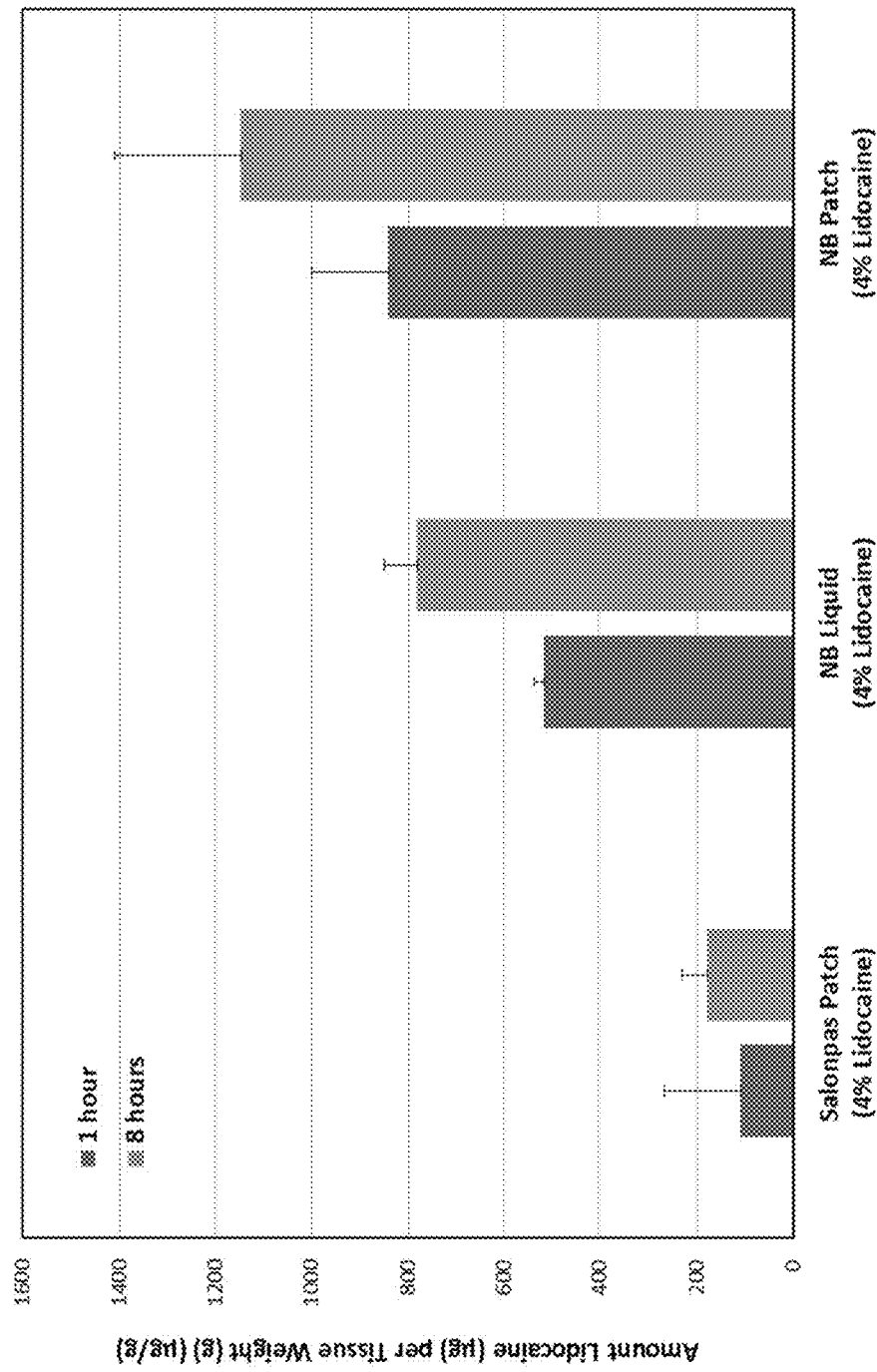
FIG. 41 shows dermal levels of lidocaine delivered by Salonpas patch (left), nanoemulsion (NB liquid, center), and nanoemulsion patch (NB patch, right).
Figure 42:
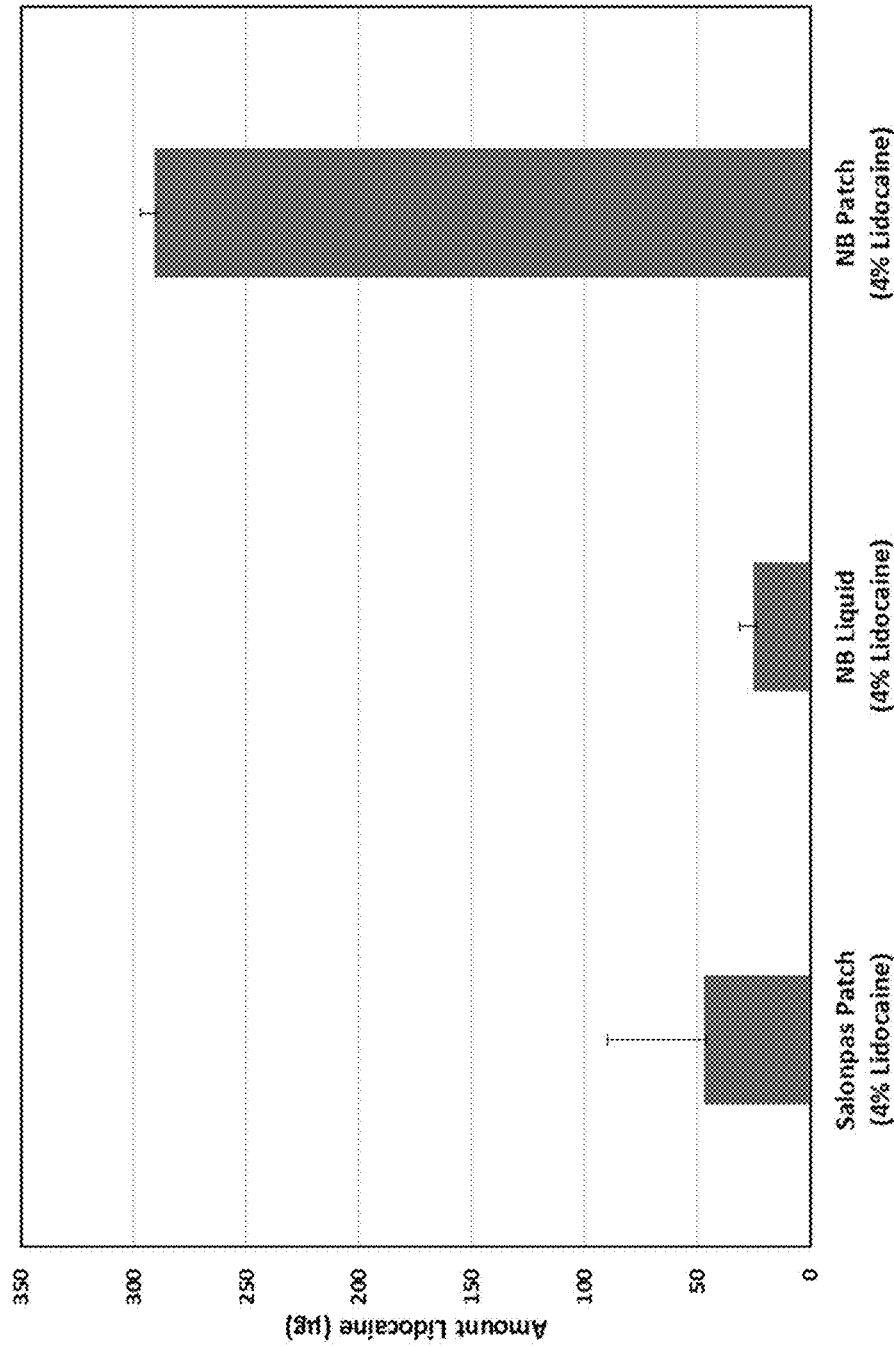
FIG. 42 shows levels of transdermal lidocaine delivered to the receptor by Salonpas patch (left), nanoemulsion (NB liquid, center), and nanoemulsion patch (NB patch, right).
Figure 43:
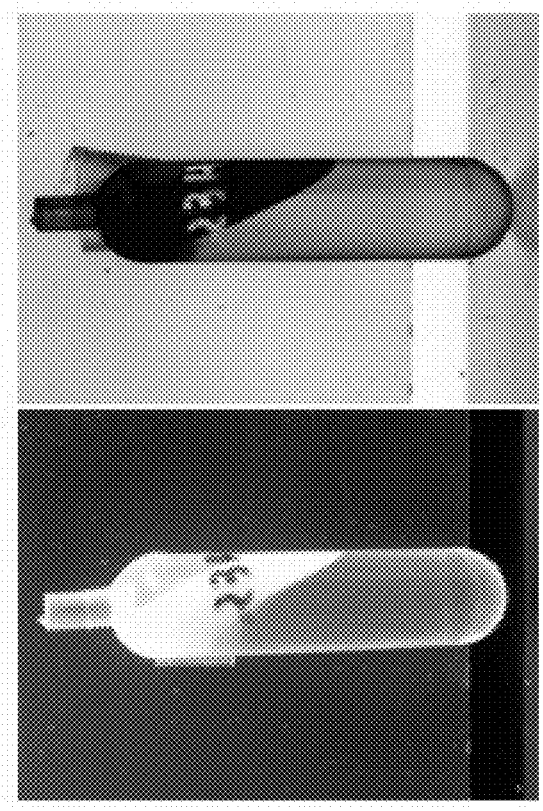
FIG. 43 shows images depicting nanoemulsion sample after centrifugation. Image taken under normal lighting conditions (left) and corresponding negative image (right).

The amount of active agent (Lidocaine) that permeated into the epidermis (at 1 and 8 hours, see FIG. 40), dermis (at 1 and 8 hours, see FIG. 41) and the receptor compartment (at 8 hours, see FIG. 42) was determined by HPLC. The levels of the active agent (Lidocaine) in each skin area are represented as the amount per wet tissue weight (µg/grams)±the standard deviation. The number of replicas used in the calculation was 4 or 5 for each formulation.

TABLE 30

Experimental conditions for HPLC analysis of actives extracted from human skin samples.

| Actives | Benzalkonium Chloride (BZK) | Benzethonium chloride (BEC) | Terbinafine Hydrochloride | Miconazole Nitrate | Hydrocortisone |
|---|---|---|---|---|---|
| HPLC System | LC System: Shimadzu LC-20AT Software: LC Solutions Communications Bus Module: Shimadzu CBM-20A UV-VIS Detector: Shimadzu SPD-20AV Column Oven: CTO-20AC | | LC System: Waters Software: Empower Detector: 2497 Dual λ Absorbance Detector Separation Module: Waters 2695 | | |
| Mobile Phase (v/v or v/v/v) | Acetate Buffer: ACN (48:52) | PO4 Buffer: MeOH: THF (52:40:8) | Acetate Buffer: ACN: MeOH: (2:3:5) | | ACN: Water (40:60) |
| Column | Phenomenex, Luna 5 μ, CN, 100 Å 250 × 4 mm | | Agilent, Zorbax 300 SB C-18, 150 × 4.6 mm 3.5 μm | Waters Symmetry C8 5 μ, 3.9 × 150 mm | Waters Symmetry C18 5 μm, 3.9 × 150 mm |
| Detector Wavelength | 254 nm | 215 nm | 220 nm | 230 nm | 254 nm |
| Column Temperature | 30° C. | 30° C. | 35° C. | 25° C. | 25° C. |
| Injection Volume | 100 μL | 100 μL | 20 μL | 20 μL | 20 μL |
| Flow Rate | 2 mL/min | 2 mL/min | 1 mL/min | 1 mL/min | 1 mL/min |
| Run Time | 15 minutes | 12 minutes | 10 minutes | 10 minutes | 10 minutes |
| Standard | 160 μg/mL | 50 μg/mL | 12.5 μg/mL | 60 μg/mL | 12 μg/mL |

| Actives | Salicylic Acid | Adapalene | PCMX | Chlorhexidine Gluconate | Lidocaine |
|---|---|---|---|---|---|
| HPLC System | LC System: Waters Software: Empower Detector: 2497 Dual λ Absorbance Detector Separation Module: Waters 2695 | | | | |
| Mobile Phase (v/v or v/v/v) | Water: MeOH HAc (60:40:1) | ACN:THF. TFA:Water (350:430: 0.3:220) | ACN:Water: H3PO4 (100:100:0.2) | PO4 Buffer: ACN (70:30) | PO4 Buffer: ACN (50:50) |
| Column | Thermo Hypersil ODS 5 μm, 4.6 × 100 mm | Thermo Hypersil ODS 5 μm, 4.6 × 250 mm | Waters Symmetry C18 5 μm, 3.9 × 150 mm | Waters Symmetry C18 5 μm, 3.9 × 150 mm | Waters Symmetry C18 5 μm, 3.9 × 150 mm |
| Detector Wavelength | 234 nm | 235 nm | 280 nm | 239 nm | 210 nm |
| Column Temperature | 35° C. | 45° C. | 25° C. | 40° C. | 25° C. |
| Injection Volume | 20 μL | 20 μL | 50 μL | 10 μL | 10 μL |
| Flow Rate | 0.7 mL/min | 1 mL/min | 1 mL/min | 1 mL/min | 0.5 mL/min |
| Run Time | 10 minutes | 10 minutes | 10 minutes | 6 minutes | 5 minutes |
| Standard | 60 μg/mL | 40 μg/mL | 100 μg/mL | 40 μg/mL | 100 μg/mL |

$PO_4$ Buffer = Phosphate Buffer
ACN = Acetonitrile
MeOH = Methanol
HAc = Acetic Acid
THF = Tetrahydrofuran
$H_3PO_4$ = Phosphoric Acid Example 20—Persistence Evaluation for Topical Antimicrobial Composition The purpose of this example was to evaluate the antimicrobial properties of a commercially available, nonprescription product, NanoBio® Protect Nasal.

NanoBio® Protect Nasal (BlueWillow Biologics, Ann Arbor, Mich.) is a nanoemulsion with a mean droplet diameter of approximately 350 nm. The nanoemulsion components are depicted above in Table 5 and shown again below. The composition has a surfactant blend ratio of 1:5.

TABLE 31

NE-1 formulation with 0.13% BZK.

| Formulation Excipients | NE-1 (Surfactant Blend Ratio: 1:5) |
|---|---|
| Purified Water | 91.805 |
| BZK | 0.13 |
| Poloxamer 407 | 0.592 |
| Glycerol | 1.008 |
| Soybean Oil | 6.279 |
| EDTA | 0.186 |
| Total | 100% |

The above percentages are wt/wt, unless otherwise noted.

The active agent in the nanoemulsion is benzalkonium chloride (BZK), a quaternary ammonium compound, which has antimicrobial activity and is a skin antiseptic under the FDA skin antiseptic monograph (Department of Health and Huma Services, Food and Drug Administration Safety and Effectiveness for Health Care Antiseptics; Topical Antimicrobial Drug Products for Over-the-Counter Human Use: Proposed Amendment of the Tentative Final Monograph; Reopening of Administrative Record Docket No. FDA-2015-N-0101.)

BZK resides at the interface between the oil and water phases of the nanodroplets with the hydrophobic tail distributed in the oil core and the polar cationic head group residing at the water phase as shown in FIG. 1.

Materials

Virus Strains (isolates): SARS-CoV-2 Victoria/1/2020 strain (Public Health England (PHE), Porton Down, Salisbury, UK); Human coronavirus 229E (ATCC: VR-740); Influenza B (VR-1931); Respiratory Syncytial Virus (BlueWillow Biologics in-house strain: NBL-14-001-2UC). The virus growth media was either Minimum Essential Medium—Eagle with Earle's BSS (MEM Eagle EBSS) from Lonza (Rochester, N.Y.) or Dulbecco's Modified Eagle's Medium (DMEM) from Corning Inc (Corning, N.Y.).

The cells used in the virus studies were obtained from ATTC (Manassas, Va.): vero E6 cells (ATCC #CRL 1586) for SARS-CoV2, MRC-5 cells for HCoV229E (CCL-171 ATCC), MDCK cells for Influenza B (CCL-34 ATCC) and vero cells for RSV (CCL-81 ATCC).

Bacteria: *Staphylococcus aureus* (ATCC: 6538), *Enterococcus faecium* (ATCC: 51559), *Staphylococcus epidermidis* (ATCC: 12228). Methicillin Resistant *Staphylococcus aureus* (MRSA, USA 300), *Pseudomonas aeruginosa* (ATCC: 9027), *Serratia marcescens* (ATCC: 14756), *Acinetobacter baumannii* (ATCC: 19606), *Klebsiella pneumoniae* (ATCC: 13883).

Tryptic Soy Agar (TSA) plates were purchased from Ward's Science (Rochester, N.Y.). Fetal Bovine Serum (FBS) was purchased from Corning, Inc. (Corning, N.Y.). The neutralizing buffer used was Butterfield's Buffer and was obtained from Hardy Diagnostics (Santa Maria, Calif.). Incubators (CO2, oxygen controls and temperate monitoring) for bacterial and viral studies were obtained from ThermoFisher Scientific (Waltham, Mass.).

Cryopreserved, dermatomed human cadaver abdominal skin from a caucasian donors was obtained from Science Care organ donor bank (Phoenix, Ariz.).

A Shimadzu (West Chicago, Ill.) reverse phase high performance liquid chromatography (RP-HPLC) system equipped with a degasser, autosampler, UV-VIS detector, column oven was used in the skin permeation studies. The HPLC column Luna Conn., 250×4 mm was purchased from Phenomenex (Torrance, Calif.). All the other analytical reagents were purchased from Sigma or VRW. An infrared surface temperature thermometer was purchased from VRW Scientific (Radnor, Pa.) to measure skin surface temperatures.

Exposure of Bacteria and Viruses to Nanoemulsion Antiseptic

The nanoemulsion antiseptic was inoculated with test organisms at 10% or 50% (v/v), and incubated at RT for 1, 5, 15 and 30 minutes. Bacterial and viral loads of treated samples were determined by plating the serial dilutions of samples onto TSA plates for bacteria or appropriate host cells for viruses.

In Vitro Determination of Antiviral Activity

Using the time kill procedures described in the Standard Guide ASTM E1052-11, the antiviral activity of the nanoemulsion was assessed by inoculating the formulation with a suspension of viral particles (final concentration of 1.5-3.1× 106 PFU/ml) (ASTM E1052-11, Standard Test method to assess the activity of microbicides against viruses in suspension, ASTM International, West Conshohocken, Pa., 2020, astm.org.) At a predetermined exposure time, an aliquot was removed and neutralized to remove residual effect of the product by diluting at 1:100 dilution in virus growth media containing 1-2% FBS. HCoV 229E was also evaluated at no dilution, as well as a 1/10, 1/20 dilution and 1/40 dilution, and compared against an aqueous BZK (0.13%) test sample. Concentration of active virus particles was determined quantitively by plaque or TCID50 assay. Briefly, serially diluted samples were plated onto 80-90% confluent vero E6 cells for SARS-CoV-2, MRC-5 cells for HCoV229E, MDCK for Influenza B and vero cells for RSV. Plates were incubated for 5-7 days at 35° C. for human corona viruses and influenza B, and at 37° C. for RSV, under 5% CO2. After completion of incubations, plates were fixed, stained and counted for plaques. TCID50 was calculated by the Karber method as referenced by Lambert (Titration of Human Coronaviruses, HCoV-229E and HCoV-OC43, by an Indirect Immunoperoxidase Assay, Lambert, F., Hélène Jacomy, H., Marceau, G. and Pierre J. Talbot. Methods in Molecular Biology, vol. 454: SARS- and Other Coronaviruses, 93, Edited by: D. Cavanagh, DOI: 10.1007/978-1-59745-181-9 C_8, Humana Press, New York, N.Y.), based on the presence of cytopathic effect in host cells. Number of PFU recovered from the test sample was converted into log 10 format and compared to an initial starting concentration to determine a log reduction (Clinical and Laboratory Standards Institute (NCCLS: Methods for Determining Bacterial Activity of Antimicrobial Agents: Approved Guideline Document MS26-1, 1999).

In Vitro Determination of Antimicrobial Activity

Using the time kill procedures described in the Standard Guide ASTM E2315-16, a nanoemulsion sample was inoculated with a suspension of bacteria at a final concentration 1×107 to 1×109 CFU/ml (ASTM E2315-16, Standard Guide for Assessment of Antimicrobial Activity Using a Time-Kill Procedure, ASTM International, West Conshohocken, Pa., 2016, astm.org.) At pre-determined exposure time, an aliquot was removed, serially diluted and plated on to TSA agar to determine the surviving test microorganisms. The nanoemulsion was diluted 1:100 in a neutralizing buffer to remove residual activity of the product. The plates were incubated at 35° C. for 24 to 48 hours and the numbers of CFU per plate were counted, converted into log 10 and compared to an initial starting population to determine log reduction. The active agent is considered bactericidal at the concentration and contact time that demonstrates a 3-log 10 (99.9%) or greater reduction in bacterial viability for the strains tested.

Ex Vivo Substantiality on Human Skin after Washing Procedure

Two formulations were tested: (1) nanoemulsion (0.13% BZK) and (2) an aqueous solution with 0.13% BZK. A single dose of 1 mL of each test formulation was topically applied to forearm (2" by 6" surface area) of three human volunteer and allowed to permeate into the skin under non-occluded conditions. The skin delineated into four sections (1" by 3") and at four or eight hours after the topical application, the 1) 1'×3" skin surface was rinsed with 75 mL water and dried or 2) 1 mL of a 5% soap-water solution was applied to the 1"×3" surface area and rubbed for 20 seconds and then rinsed with 75 mL of water and dried.

Three areas on each test site skin surface (1 cm² surface area) was tape stripped with D-Squame® adhesive tape (CuDerm Corp, Dallas, Tex.) ten times and each set of ten strips were placed in separate vials. D-Squame tape uniformly removes a sample from a fixed surface area on the stratum corneum on the skin surface (Serup, J., Winter, C., Blichmann, A. simple method for the study of scale pattern and effects of a moisture-qualitative and quantitative evaluation by D-Squame® tape compared with parameters of epidermal hydration. Clinical and Experimental Dermatology, 1365-2230 (1989).)

The BZK in the stripes in each vial were extracted with a 70% ethanol solution, sonication for 30 minutes and then filtered through a 0.45 µm PTFE membrane syringe filter into HPLC vials. The amount of BZK (µg/cm² surface area) was measured by HPLC, 4 or 8 hours after each washing procedure by reverse phase-high performance liquid chromatography (RP-HPLC). The HPLC was equipped with UV detector set at 254 nm, column Luna Conn., 250×4 mm, 5 µm at 55° C., mobile phase; acetate buffer and acetonitrile (ACN) in the ratio of 40:60 (v/v) in isocratic mode.

Ex Vivo Persistence of Coronavirus Antiviral Activity and MRSA Antimicrobial Activity on Human Skin The permeation and retention of each antiseptic preparation in human skin was determined using ex vivo permeation technique described by Franz (Franz, T J, "Percutaneous absorption: on the relevance of in vitro data," *J. Invest. Dermatol.*, 64:190-195 (1975)). Human skin was placed onto a Franz diffusion cell chamber and secured. The skin was maintained at a temperature and humidity that match typical in vivo conditions with a receptor phase maintained at 37° C. with the water bath and magnetic stirring. The surface temperature of the skin was appropriately 32° C. as determined by an Infrared surface temperature thermometer.

Human skin was placed onto a Franz diffusion cell chambers and a dose of either the nanoemulsion antiseptic (NE-BZK) or aqueous BZK solution (AQ-BZK) was applied at a single dose of 100 mL/cm². Sterile water for injection (WFI) was used as a control. At either 4 or 8 hours after the topical application, a dose of viral particles in suspension (final concentration of 1-3×10⁵ PFU/ml) was applied to the skin surface for a contact time of 20 minutes. The skin surface was then washed 2-3 times with 100 µL (each wash volume) of growth media. The washes were pooled and neutralized to remove residual effect of the test formulation by diluting at 1:100 dilution in virus growth media containing 1-2% FBS. Concentration of active virus particles was determined quantitively by plaque or TCID50 assay. Briefly, serially diluted samples were plated onto 80-90% confluent MRC-5 cells. Plates were incubated for 4-6 days at 35° C. under 5% $CO_2$. After the completion of incubation, plates were observed for cytopathic effect and the TCID50 was calculated by the Karber method as reference by Lambert (Titration of Human Coronaviruses, HCoV-229E and HCoV-OC43, by an Indirect Immunoperoxidase Assay, Lambert, F., Hélène Jacomy, H., Marceau, G. and Pierre J. Talbot. Methods in Molecular Biology, vol. 454: SARS- and Other Coronaviruses, 93, Edited by: D. Cavanagh, DOI: 10.1007/978-1-59745-181-9 C_8, Humana Press, New York, N.Y., based on the presence of cytopathic effect in host cells. Number of PFU recovered from the test sample was converted into log 10 format and compared to an initial starting concentration to determine a log reduction (Clinical and Laboratory Standards Institute (NCCLS: Methods for Determining Bacterial Activity of Antimicrobial Agents: Approved Guideline Document MS26-1, 1999.)

For the MRSA studies, the same methodology was used as stated above, wherein the nanoemulsion antiseptic (NE-BZK), AQ-BZK (aqueous BZK) or alcohol-based nasal sanitizer (Nozin Nasal Sanitizer®, Global Life Technologies Corp, Bethesda, Md.) were applied at a single dose of 100 mL/cm². Sterile water for injection (WFI) was used as a control. At either 4, 8 and/or 12 hours after application, MRSA inoculum in saline (final concentration of 1×10⁷ to 1×10⁹ CFU/ml) were applied to the skin surfaces. After a contact time of 20 minutes, the skin surface was washed, the wash was removed and neutralized to remove residual effect of the products by diluting 1:100 in TAT neutralizing buffer. The samples were serially diluted and plated on to TSA agar to determine the surviving test microorganisms. The plates were incubated at 35° C. for 24 to 48 hours and the numbers of CFU per plate were counted, converted into $log^{10}$ and compared to an initial starting population to determine log reduction.

In Vivo Human Skin Hydration Evaluation

The hydration effect of applying NE-BZK on human skin was evaluated by measuring the moisture level of tested skin area on human forearm and back arm of 5 human volunteers (3 females and 2 males) ranging in age from 30 to 62 years. The Delfin Meter SC (Miami, Fla.) uses a precise (1.25 MHz) electromagnetic field to measure the skin's dielectric constant giving more accurate and reproducible results (Alanen et al., "Measurement of hydration in the stratum corneum with the Moisture Meter and comparison with the Corneometer," *Skin Res Technol*, 10:32-37 (2004)).

A volume of 1 mL of each of the NE-BZK, a hand sanitizing product containing 0.13% BZK (Purell® SF 607 Instant Hand Sanitizing Foam, GoJo Industries, Akron, Ohio) and a commercial alcohol-based (70% ethyl alcohol) gel hand sanitizer (Purell® Advanced Hand Sanitizing Soothing Gel, GoJo Industries, Akron, Ohio, were applied to the forearms of each volunteer (surface area: 5"×12") and rubbed onto the skin's surface for 20 seconds. Skin hydration was measured 5 times in three different areas of the dosing area with the Delfin Meter at 10, 20, 30, 60, 120, and/or 180 minutes after application.

Results

Rapid Antimicrobial Activity of Nanoemulsion Antiseptic after Brief Exposure

The antimicrobial activity of NE-BZK was tested using the in-vitro suspensions method with several respiratory and skin microbial pathogens. FIG. 48 illustrates the antiviral and antibacterial activity of NE-BZK against several common pathogens, including the novel coronavirus SARS-CoV-2. NE-BZK deactivated >99.99% of all viruses following five minutes of exposure (the earliest time point measured) and >99.99% of all bacterial pathogens following one minute of exposure.

The results of these studies demonstrate that NE-BZK has sustained broad-spectrum activity against multiple bacterial and viral pathogens, including SARS-CoV-2 and human coronaviruses.

Example 21—Human Coronavirus Antiviral and MRSA Antibacterial Activity of an Antibacterial Nanoemulsion The purpose of this example was to evaluate the antibacterial activity against human coronavirus and MRSA of an antibacterial nanoemulsion comprising BZK (NE-BZK) as compared to aqueous BZK (AQ-BZK).

AQ-BZK formulations are the most commonly marketed BZK skin antiseptics. Three different concentrations of NE-BZK, including full-strength (0.13% BZK), 1/10 dilution (0.013% BZK) and 1/20 dilution (0.0065% BZK), were tested for in vitro antiviral activity as compared to the same concentrations of AQ-BZK.

Antiviral activity was measured against human coronavirus (HCoV229E) in a time-kill study following 5 minutes exposure. As presented in Table 32, both the nanoemulsion antiseptic and AQ-BZK formulations achieved >99.99% killing when formulated at full strength or a 1/10 dilution. Notably, at a dilution of 1/20, the aqueous AQ-BZK formulation lost all activity while in dramatic contrast the nanoemulsion antiseptic continued to demonstrate 99.99% killing.

TABLE 32

In vitro log reduction of human coronavirus (HCoV 229E) treated for 5 minutes with NE-BZK verses AQ-BZK at three dilution levels

| | AQ-BZK | | NE-BZK | |
|---|---|---|---|---|
| Product (% BZK) | Log Reduction | % Killing | Log Reduction | % Killing |
| Full Strength (0.13%) | >4.49 | >99.99 | >4.49 | >99.99 |

TABLE 32-continued

In vitro log reduction of human coronavirus (HCoV 229E) treated for 5 minutes with NE-BZK verses AQ-BZK at three dilution levels

| | AQ-BZK | | NE-BZK | |
|---|---|---|---|---|
| Product (% BZK) | Log Reduction | % Killing | Log Reduction | % Killing |
| 1/10 Dilution (0.013%) | >4.49 | >99.99 | >4.49 | >99.99 |
| 1/20 Dilution (0.0065%) | <LOD* | <LOD* | >4.49 | >99.99 |

Limit of detection (LOD) = 1

Four different concentrations of NE-BZK from 1/10 to 1/100 dilution were tested for in vitro antimicrobial activity against MRSA as compared to the same concentrations of AQ-BZK following 5 minutes of exposure. As presented in Table 33, both the nanoemulsion antiseptic and AQ-BZK formulation achieved >99.9999% killing when formulated at 1/10 and 1/20 dilution. However, at a 1/50 and 1/100 dilution the AQ-BZK lost activity while nanoemulsion antiseptic continued to demonstrate >99.99% killing. Dilution is an inherent process when applying any antiseptic to skin given the sweat and sebaceous glands present.

TABLE 33

In vitro log reduction of MRSA treated for 5 minutes with the Nanoemulsion Antiseptic verses AQ-BZK at four different dilutions

| | AQ-BZK | | Nanoemulsion Antiseptic | |
|---|---|---|---|---|
| Product (% BZK) | Log Reduction | % Killing | Log Reduction | % Killing |
| 1/10 Dilution (0.013%) | >6.52 | >99.9999 | >6.52 | >99.9999 |
| 1/20 Dilution (0.0065%) | >6.52 | >99.9999 | >6.52 | >99.9999 |
| 1/50 Dilution (0.0026%) | 2.14 | >99 | >6.52 | >99.9999 |
| 1/100 Dilution (0.0013%) | 0.02 | <LOD* | 4.50 | >99.99 |

Limit of detection (LOD)

Substantivity of NE-BZK on Human Volunteers

FIG. 49 shows that the NE-BZK exhibited a 5.8 and 3.8 fold increase substantivity on volunteers' skin surface at 4 hours after two washing protocols (e.g. 1) water rinse and 2) soap rub+water rinse) and 16.5 and 7.3 fold increase, respectively, after 8 hours after a two washing protocols as compared to a 0.13% AQ-BZK solution. The data from FIG. 49 is shown below in Table 34.

TABLE 34

Amount of BZK per surface area on skin surface from NE-BZK and AQ-BZK

| Formulation | Washino Protocol | Subject 1* | Subject 2* | Subject 3* | Combined** |
|---|---|---|---|---|---|
| Timepoint: 4 Hours | | | | | |
| Aqueous BZK (0.13% BKZ) | Water (75 mL) | 2.80 ± 0.34 | 2.06 ± 0.36 | 3.05 ± 0.49 | 2.64 ± 0.62 |
| Aqueous BZK (0.13% BKZ) | Soap (20 seconds) + Water (75 mL) | 2.54 ± 0.06 | 1.50 ± 0.37 | 3.30 ± 0.38 | 2.45 ± 0.85 |

TABLE 34-continued

Amount of BZK per surface area on skin surface from NE-BZK and AQ-BZK

| Formulation | Washino Protocol | Subject 1* | Subject 2* | Subject 3* | Combined** |
|---|---|---|---|---|---|
| Nanoemulsion ((0.13% BZK) | Water (75 mL) | 16.5 ± 1.6 | 14.6 ± 0.4 | 73.5 ± 03.8 | 18.2 ± 4.5 |
| Nanoemulsion (0.13% BZK) | Soap (20 seconds) + Water (75 mL) | 9.8 ± 0.7 | 16.5 ± 1.5 | 20.6 ± 0.4 | 15.6 ± 5.0 |
| Timepoint: 8 Hours | | | | | |
| Aqueous BZK (0.13% BKZ) | Water (75 mL) | 0.92 ± 0.12 | 1.21 ± 0.22 | 1.28 ± 0.23 | 1.14 ± 0.26 |
| Aqueous BZK (0.13% BKZ) | Soap (20 seconds) + Water (75 mL) | 0.92 ± 0.31 | 0.73 ± 0.06 | 2.1 ± 0.61 | 1.25 ± 0.77 |
| Nanoemulsion (0.13% BZK) | Water (75 mL) | 15.2 ± 1.4 | 13.5 ± 2.1 | 7.9 ± 2.5 | 12.2 ± 4.0 |
| Nanoemulsion (0.13% BZK) | Soap (20 seconds) + Water (75 mL) | 6.7 ± 1.9 | 7.5 ± 1.5 | 11.0 ± 4.3 | 8.4 ± 3.4 |

*Number of Replicates: n = 3 sites
**Combined Replicates: n = 9 sites

Persistent Antimicrobial Action Against Human Coronavirus and MRSA

Antiviral activity of NE-BZK was measured against human coronavirus (HCoV229E) ex vivo in a time-kill study following 15 minutes exposure of skin pre-treated with the nanoemulsion antiseptic (0.13% BZK) or AQ-BZK for 4 and 8 hours. As presented in Table 35, NE-BZK achieved >4.70/log killing at both the 4- and 8 hour time points. AQ-BZK exhibited only 1.5 log killing at 4 hours and below the limit of detection at 8 hours.

TABLE 35

Ex vivo log reduction of HCoV 229E by Nanoemulsion Antiseptic (NE-BZK) verses an AQ-BZK at 1:10 dilutions after 4 and 8 hours post application on human skin.

| Product (% BZK) | 4 Hours Average Log Kill (PFU/skin sample) | 8-Hours Average Log Kill (PFU/skin sample) |
|---|---|---|
| NE-BZK (0.013% BZK) | >4.7 | >4.7 |
| AQ-BZK (0.013%) | 1.5 | <1* |

Virus killing is calculated based on recovery from WFI control samples (5.70 Logs per skin sample)
Limit of detection (LOD) = 1

The antimicrobial activity of NE-BZK was measured against MRSA ex vivo in a time-kill study following 15 minutes exposure of skin pre-treated and compared to AQ-BZK (0.13% BZK) and an alcohol-based nasal sanitizer (0.62% ethyl alcohol). As presented in Table 36, NE-BZK achieved >5.2%/log killing at 4, 8 and 12 hours. AQ-BZK formulation exhibited only 0.5 log killing at 4 hours and 0.21 log killing at 8 hours. The alcohol-based nasal sanitizer demonstrated no antimicrobial activity at either 8 or 12 hours after application.

TABLE 36

Ex vivo log kill reduction of MRSA by NE-BZK, AQ-BZK and Alcohol-based Nasal Sanitizer after 4, 8 and/or 12 hours post application on human skin.

| Product | 4 Hours Average Log Kill (PFU/skin sample) | 8-Hours Average Log Kill (PFU/skin sample) | 12-Hours Average Log Kill (PFU/skin sample) |
|---|---|---|---|
| NE-BZK (0.13% BZK) | >5.28 | >5.25 | >5.19 |
| AQ-BZK (0.13%) | 0.55 | 0.21 | ND |
| Alcohol-based Nasal Sanitizer (62% Alcohol) | ND | -0.10 | -0.02 |

Bacterial killing was calculated based on recovery from WFI control samples (7.31 Log/skin sample)
ND = not determined Example 22—Nanoemulsion Enhances Skin Hydration To evaluate the effect on skin hydration in vivo, 1 mL of NE-BZK was applied directly to the arms of human volunteers and hydration was measured with a Delfin Moisture Meter at specified time points after application. For comparative purposes, two other commercially available skin antiseptic products were assessed in parallel, one containing 0.13% BZK and one containing 70% ethyl alcohol. As shown in FIG. 50, NE-BZK significantly enhanced skin hydration for up to three hours after a single application compared to the other formulations tested.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims

---

What is claimed:

1. A method for preventing or for the reducing the risk of microbial infection at a target site in a subject in need thereof, comprising:
   (a) administering topically, mucosally, ocularly, or nasally a long-acting antimicrobial nanoemulsion to the target site of the subject in need, wherein following a single application the nanoemulsion kills about 99.9% or more of microorganisms present at the target site at the time of administration, and additionally the nanoemulsion kills 99.9% of microorganisms exposed to the target site for at least about 4 hours after administration of the nanoemulsion;
   (b) the nanoemulsion comprises droplets having an average or mean diameter of less than about 1 micron, and additionally, the nanoemulsion comprises:
      (i) an aqueous phase;
      (ii) an oil phase comprising at least one pharmaceutically acceptable oil:
      (iii) at least one pharmaceutically acceptable organic solvent;
      (iv) at least one nonionic surfactant; and
      (v) a quaternary ammonium compound selected from the group consisting of cetylpyridinium chloride, benzalkonium chloride (BZK), benzethonium chloride, dioctadecyl dimethyl ammonium chloride, octenidine dihydrochloride and a combination thereof; and
   (c) the concentration (w/w) of the quaternary ammonium compound and nonionic surfactant is in a ratio of about 1:2 to about 1:18;
   wherein the method prevents or reduces the risk of microbial infection in the subject caused by contact of the microorganism with the target site of the subject.

2. The method of claim 1, wherein the ratio of the concentration of the quaternary ammonium compound to nonionic surfactant (w/w) is:
   (a) selected from the group consisting of about 2:1, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, and about 1:27; and/or
   (b) selected from the group consisting of about 1:2, about 1:6, about 1:7, about 1:9, about 1:10, and about 1:12; and/or
   (c) about 1:5 to about 1:10; and/or
   (d) about 1:6 to about 1:9; and/or
   (e) about 1:2 up to about 1:18.

3. The method of claim 1, wherein following administration, the target site is flushed with water or another liquid at least once during a period of 4 hours after administration, and wherein:
   (a) following flushing with water or another liquid, the target area retains the 99.9% microbial killing activity of the nanoemulsion; and/or
   (b) flushing with water or another liquid comprises sweating, submersion or rinsing in freshwater, submersion or rinsing in salt water, and/or rinsing with soap and water; and/or
   (c) the flushing is for a time period selected from the group consisting of about 1 min, about 2 mins, about 3 mins, about 4 mins, about 5 mins, about 10 mins, about 15 mins, about 20 mins, about 25 mins, about 30 mins, about 45 mins, about 1 hour, about 1.5 hrs, about 2 hours, about 2.5 hours or about 3 hours; and/or
   (d) the flushing occurs about 0.5 min to about 1 min, about 1 min to about 5 min, about 5 min to about 10 min, about 10 min to about 30 min, about 30 min to about 1 hr, about 1 hr to about 2 hr, about 2 hr to about 4 hr, or about 4 hr to about 8 hr, after topical administration of the nanoemulsion.

4. The method of claim 1, wherein following a single application the nanoemulsion kills 99.9% of microorganisms exposed to the target site for about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, or greater than about 12 hours after administration of the nanoemulsion.

5. The method of claim 1, wherein:
   (a) the quaternary ammonium compound is BZK, which is present in an amount of about 0.05% to about 5.0%; or
   (b) the quaternary ammonium compound is BZK, which is present in an amount of about 0.13%.

6. The method of claim 1, wherein:
   (a) the target site comprises skin, epidermis, dermis, mucosa, squamous epithelium, or a combination thereof of the subject; and/or
   (b) the nanoemulsion is bioadhesive with the target site.

7. The method of claim 1, wherein following application of the nanoemulsion to a target area, the nanoemulsion does not result in any noticeable irritation of the target site.

8. The method of claim 1, wherein when the nanoemulsion is applied to the target site, the nanoemulsion results in increased hydration as compared to a composition comprising the same quaternary ammonium compound at the same concentration but lacking a nanoemulsion, measured at any suitable time period after administration to the target area, and
optionally wherein the increase in target site hydration is about 50%, about 75%, about 100%, about 125%, about 150%, about 175%, about 200%, about 225%, about 250%, about 275%, about 300%, about 325%, about 350%, about 375%, about 400%, about 425%, about 450%, about 475%, about 500%, about 525%, about 550%, about 575%, about 600%, about 625%, about 650%, about 675%, about 700%, about 725%, about 750%, about 775%, about 800%, about 825%, about 850%, about 875%, about 900%, about 925%, about 950%, about 975%, or about 1000%.

9. The method of claim 1, wherein:
(a) the microorganism is a bacteria, virus, yeast, fungus, or any combination thereof; and/or
(b) the microorganism is a bacteria or virus; and/or
(c) the microorganism is a virus.

10. The method of claim 1, wherein:
(a) the microorganism is selected from the group consisting of SARS-CoV-2, Human coronavirus 229E, human coronavirus OC43, SARS-CoV, HCoV NL63, HKU1, MERS-CoV, SARS-CoV-2, and any combination thereof; and/or
(b) the microorganism is a coronavirus and the coronavirus comprises (i) a polynucleotide comprising the SARS-CoV-2 genome sequence, (ii) an immunogenic fragment of the SARS-CoV-2 genome sequence, or (iii) a polynucleotide having at least about 80%, at least about 90%, at least about 95%, or at least about 99% sequence identity to the polynucleotide comprising the SARS-CoV-2 genome sequence; and/or
(c) the microorganism is selected from the group consisting of Influenza, B Respiratory Syncytial Virus, Staphylococcus aureus, Enterococcus faecium, Staphylococcus epidermidis, Methicillin Resistant Staphylococcus aureus (MRSA), Pseudomonas aeruginosa, Serratia marcescens, Acinetobacter baumannii, Klebsiella pneumonia, and any combination thereof; and/or
(d) the microorganism is selected from the group consisting of an Alphacoronavirus; a Colacovirus; a Decacovirus; a Duvinacovirus; a Luchacovirus; a Minacovirus; a Minunacovirus; a Myotacovirus; a nyctacovirus; a Pedacovirus; a Rhinacovirus; a Setracovirus; a Tegacovirus; a Betacoronavirus; a Embecovirus; a Hibecovirus; a Merbecovirus; a Nobecovirus, a Sarbecovirus; a Deltacoronavirus; an Andecovirus; a Buldecovirus; a Herdecovirus; a Moordecovirus; a Gammacoronavirus; a Cegacovirus; and an Igacovirus.

11. The method of claim 1, wherein the quaternary ammonium compound is:
(a) benzalkonium chloride (BZK); and/or
(b) BZK present in a concentration of from about 0.05% to about 0.40%; BZK present in a concentration of from about 0.10% to about 0.20%; or BZK present in a concentration of about 0.13%; and/or
(c) cetylpyridinium chloride (CPC); and/or
(d) CPC present in a concentration of from about 0.05% to about 0.40%; CPC present in a concentration of from about 0.15% to about 0.30%; or CPC present in a concentration of about 0.20%; and/or
(e) benzethonium chloride (BEC); and/or
(f) BEC present in a concentration of from about 0.05% to about 1%; BEC present in a concentration of from about 0.10% to about 0.30%; or BEC present in a concentration of about 0.20%; and/or
(g) dioctadecyl dimethyl ammonium chloride (DODAC); and/or
(h) DODAC present in a concentration of from about 0.05% to about 1%; DODAC present in a concentration of from about 0.10% to about 0.40%; or DODAC present in a concentration of about 0.20%; and/or
(i) octenidine dihydrochloride (OCT); and/or
(j) OCT present in a concentration of from about 0.05% to about 1%; OCT present in a concentration of from about 0.10% to about 0.40%; or (u)OCT present in a concentration of about 0.20%.

12. The method of claim 1, wherein:
(a) the nanoemulsion particles have an average or mean diameter of less than or equal to about 900 nm, less than or equal to about 800 nm, less than or equal to about 700 nm, less than or equal to about 600 nm, less than or equal to about 500 nm, less than or equal to about 400 nm, less than or equal to about 300 nm, less than or equal to about 200 nm, less than or equal to about 150 nm, less than or equal to about 100 nm, or less than or equal to about 50 nm; and/or
(b) the nanoemulsion particles have an average or mean diameter of about 350 nm.

13. The method of claim 1, wherein the nanoemulsion is diluted resulting in a formulation of about 0.5% to about 60% nanoemulsion, and wherein:
(a) the concentration ratio of the quaternary ammonium compound to nonionic surfactant is about 5:1 to about 1:27, and the nanoemulsion enhances delivery of the quaternary ammonium compound into tissue by at least about 25% as compared to a solution with the same concentration of the same quaternary ammonium compound but lacking a nanoemulsion and as compared to a nanoemulsion with a concentration ratio of the quaternary ammonium compound to nonionic surfactant outside of the range from about 5:1 to about 1:27; or
(b) the viscosity of the nanoemulsion is less than about 1000 cp, and the nanoemulsion enhances delivery of the quaternary ammonium compound into tissue by at least about 25% as compared to a solution with the same concentration of the same quaternary ammonium compound but lacking a nanoemulsion and as compared to a nanoemulsion with a viscosity greater than about 1000 cp; or
(c) the zeta potential of nanoemulsion is greater than about 20 mV, and the nanoemulsion enhances delivery of the quaternary ammonium compound into tissue by at least about 25% as compared to a solution with the same concentration of the same quaternary ammonium compound but lacking a nanoemulsion and as compared to a nanoemulsion with a zeta potential less than about 20 mV; or
(d) at least about 33% of the quaternary ammonium compound is entrapped in the oil phase of the nanoemulsion and at least about 0.2% of the weight of the oil phase of the nanoemulsion is attributed to the quaternary ammonium compound; and the nanoemulsion enhances delivery of the quaternary ammonium compound into tissue by at least about 25% as compared to a solution with the same concentration of the same quaternary ammonium compound but lacking a nanoemulsion and as compared to a nanoemulsion with less than about 0.2% of the weight of the oil phase of the nanoemulsion attributed to the quaternary ammonium compound; or (e) the mean droplet size of the nanoemulsion does not change by more than about 10% after centrifuging the nanoemulsion at a speed of 200,000 rpm for one hour; and the nanoemulsion enhances delivery of the quaternary ammonium compound into tissue by at least about 25% as compared to a solution with the same concentration of the same quaternary ammonium compound but lacking a nanoemulsion and as compared to a nanoemulsion with a mean droplet size that changes by more than about 10% after centrifuging the nanoemulsion at a speed of 200,000 rpm for one hour.

14. The method of claim 1, wherein:
(a) the nonionic surfactant is:
   (i) selected from the group consisting of a poloxamer surfactant, polysorbate surfactant, nonoxynol-9, and any combination thereof; and/or
   (ii) selected from the group consisting of polysorbate 20, polysorbate 21, polysorbate 40, polysorbate 60, polysorbate 61, polysorbate 65, polysorbate 80, polysorbate 81, and polysorbate 85; and/or
   (iii) selected from the group consisting of poloxamer 407, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, Poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 408, poloxamer 105 Benzoate, and poloxamer 182 Dibenzoate; and/or
(b) the organic solvent:
   (i) comprises a C1-C12 alcohol, diol, or triol, a dialkyl phosphate, a trialkyl phosphate or a combination thereof; and/or
   (ii) comprises an alcohol selected from the group consisting of ethanol, isopropyl alcohol, glycerol or a combination thereof; and/or
(c) the oil:
   (i) comprises soybean oil, mineral oil, avocado oil, squalene oil, olive oil, canola oil, corn oil, rapeseed oil, safflower oil, sunflower oil, fish oils, flavor oils, cinnamon bark, coconut oil, cottonseed oil, flaxseed oil, pine needle oil, silicon oil, essential oils, water insoluble vitamins, other plant oil, or a combination thereof; and/or
   (ii) comprises soybean oil.

15. The method of claim 1, wherein the nanoemulsion further comprises a chelating agent, and optionally wherein the chelating agent is:
(a) ethylenediaminetetraacetic acid (EDTA), ethylene glycol-bis(β-aminoethyl ether)-N,N,N',N'-tetraacetic acid (EGTA), or a combination thereof; and/or
(b) ethylenediaminetetraacetic acid (EDTA); and/or
(c) EDTA and EDTA is present at a concentration of about 0.0005% to about 1% (w/w).

16. The method of claim 1, wherein the nanoemulsion comprises:
(a) about 5 vol. % to about 50 vol. % (w/w) of aqueous phase;
(b) about 30 vol. % to about 90 vol. % (w/w) of a pharmaceutically acceptable oil phase;
(c) about 0.1% up to about 20% of a pharmaceutically acceptable organic solvent;
(d) about 3 vol. % to about 15 vol. % (w/w) of a nonionic surfactant; and
(e) about 0.05% to about 3 vol. % (w/w) of a quaternary ammonium compound.

17. The method of claim 1, wherein the nanoemulsion comprises:
(a) about 5 vol. % to about 50 vol. % (w/w) of aqueous phase;
(b) about 30 vol. % to about 90 vol. % (w/w) soybean oil;
(c) about 0.1% up to about 20% (w/w) glycerol;
(d) about 3 vol. % to about 15 vol. % (w/w) poloxamer 407;
(e) benzalkonium chloride at a concentration of about 0.13% (w/w); and
(f) about 0.0005% to about 1% (w/w) EDTA.

18. The method of claim 1, wherein the nanoemulsion:
(a) is non-toxic in humans and animals; and/or
(b) is thermostable; and/or
(c) is stable for at least 3 months at about 50° C.; and/or
(d) is stable for at least 3 months at 40° C.; and/or
(e) is stable for at least 3 months at 25° C.; and/or
(f) is stable for at least 3 months at 5° C.; and/or
(g) is stable at 5° C. for up to at least 60 months; and/or
(h) is stable at 50° C. for up to at least 12 months; and/or
(i) has been autoclaved, and optionally wherein the nanoemulsion retains its structural and/or chemical integrity following autoclaving;
(j) is formulated in soap, hand sanitizer, lotion, cream, or spray dosage form; and/or
(k) is formulated in liquid dosage form, solid dosage form, or semisolid dosage form; and/or
(l) is formulated in a nasal spray.

19. The method of claim 10, wherein the Colacovirus comprises Bat coronavirus CDPHE15; wherein the Decacovirus comprises Bat coronavirus HKU10 or Rhinolophus ferrumequinum alphacoronavirus HuB-2013; wherein the Duvinacovirus comprises Human coronavirus 229E; wherein the Luchacovirus comprises Lucheng Rn rat coronavirus; wherein the Minacovirus comprises a Ferret coronavirus or Mink coronavirus 1; wherein the Minunacovirus comprises Miniopterus bat coronavirus 1 or Miniopterus bat coronavirus HKU8; wherein the Myotacovirus comprises Myotis ricketti alphacoronavirus Sax-2011; wherein the nyctacovirus comprises Nyctalus velutinus alphacoronavirus SC-2013; wherein the Pedacovirus comprises Porcine epidemic diarrhea virus or Scotophilus bat coronavirus 512; wherein the Rhinacovirus comprises Rhinolophus bat coronavirus HKU2; wherein the Setracovirus comprises Human coronavirus NL63 or NL63-related bat coronavirus strain BtKYNL63-9b; wherein the Tegacovirus comprises Alphacoronavirus 1; wherein the Embecovirus comprises Betacoronavirus 1, Human coronavirus OC43, China Rattus coronavirus HKU24, Human coronavirus HKU1 or Murine coronavirus; wherein the Hibecovirus comprises Bat Hp-betacoronavirus Zhejiang2013; wherein the Merbecovirus comprises Hedgehog coronavirus 1, Middle East respiratory syndrome-related coronavirus (MERS-CoV), Pipistrellus bat coronavirus HKU5 or Tylonycteris bat coronavirus HKU4; wherein the Nobecovirus comprises Rousettus bat coronavirus GCCDC1 or Rousettus bat coronavirus HKU9; wherein the Sarbecovirus comprises a Severe acute respiratory syndrome-related coronavirus, Severe acute respiratory syndrome coronavirus (SARS-CoV) or Severe acute respiratory syndrome coronavirus 2 (SARS-CoV-2, COVID-19); wherein the Andecovirus comprises Wigeon coronavirus HKU20; wherein the Buldecovirus comprises Bulbul coronavirus HKU11, Porcine coronavirus HKU15, Munia coronavirus HKU13 or White-eye coronavirus HKU16; wherein the Herdecovirus comprises Night heron coronavirus HKU19; wherein the Moordecovirus comprises Common moorhen coronavirus HKU21; wherein the Cegacovirus comprises Beluga whale coronavirus SW1; and wherein the Igacovirus comprises Avian coronavirus.

* * * * *

SEQUENCE LISTING

```
<160> NUMBER OF SEQ ID NOS: 1

<210> SEQ ID NO 1
<211> LENGTH: 29903
<212> TYPE: DNA
<213> ORGANISM: Severe acute respiratory syndrome coronavirus 2

<400> SEQUENCE: 1
attaaaggtt tataccttcc caggtaacaa accaaccaac tttcgatctc ttgtagatct      60
gttctctaaa cgaactttaa aatctgtgtg gctgtcactc ggctgcatgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaagatgga gagccttgtc cctggtttca acgagaaaac     300
acacgtccaa ctcagtttgc ctgttttaca ggttcgcgac gtgctcgtac gtggctttgg     360
agactccgtg gaggaggtct tatcagaggc acgtcaacat cttaaagatg gcacttgtgg     420
cttagtagaa gttgaaaaag gcgttttgcc tcaacttgaa cagccctatg tgttcatcaa     480
acgttcggat gctcgaactg cacctcatgg tcatgttatg gttgagctgg tagcagaact     540
cgaaggcatt cagtacggtc gtagtggtga cacttggt gtccttgtcc ctcatgtggg      600
cgaaatacca gtggcttacc gcaaggttct tcttcgtaag aacggtaata aaggagctgg     660
tggccatagt tacggcgccg atctaaagtc atttgactta ggcgacgagc ttggcactga     720
tccttatgaa gattttcaag aaaactggaa cactaaacat agcagtggtg ttacccgtga     780
actcatgcgt gagcttaacg gaggggcata cactcgctat gtcgataaca acttctgtga     840
ccctgatggc taccctcttg agtgcattaa agaccttcta gcacgtgctg gtaaagcttc     900
```

```
atgcactttg tccgaacaac tggactttat tgacactaag aggggtgtat actgctgccg    960
tgaacatgag catgaaattg cttggtacac ggaacgttct gaaaagagct atgaattgca   1020
gacaccttt  gaaattaaat tggcaaagaa atttgacacc ttcaatgggg aatgtccaaa   1080
ttttgtattt cccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata atgaatctgg   1440
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat cttttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat tgtcacgca    2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttacttt  ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
```

```
agagatggaa cttacaccag ttgttcagac tattgaagtg aatagtttta gtggttattt    3360
aaaacttact gacaatgtat acattaaaaa tgcagacatt gtggaagaag ctaaaaaggt    3420
aaaaccaaca gtggttgtta atgcagccaa tgtttacctt aaacatggag gaggtgttgc    3480
aggagcctta aataaggcta ctaacaatgc catgcaagtt gaatctgatg attacatagc    3540
tactaatgga ccacttaaag tgggtggtag ttgtgtttta agcggacaca atcttgctaa    3600
acactgtctt catgttgtcg gcccaaatgt taacaaaggt gaagacattc aacttcttaa    3660
gagtgcttat gaaaatttta atcagcacga agttctactt gcaccattat tatcagctgg    3720 tattttggt gctgaccctaa tacattcttt aagagtttgt gtagatactg ttcgcacaaa    3780
tgtctactta gctgtctttg ataaaaatct ctatgacaaa cttgtttcaa gcttttggga    3840
aatgaagagt gaaaagcaag ttgaacaaaa gatcgctgag attcctaaag aggaagttaa    3900
gccatttata actgaaagta aaccttcagt tgaacagaga aaacaagatg ataagaaaat    3960
caaagcttgt gttgaagaag ttacaacaac tctggaagaa actaagttcc tcacagaaaa    4020
cttgttactt tatattgaca ttaatggcaa tcttcatcca gattctgcca ctcttgttag    4080
tgacattgac atcactttct taagaaaga tgctccatat atagtgggtg atgttgttca    4140
agagggtgtt ttaactgctg tggttatacc tactaaaaag gctggtggca ctactgaaat    4200
gctagcgaaa gctttgagaa aagtgccaac agacaattat ataaccactt acccgggtca    4260
gggtttaaat ggttacactg tagaggaggc aaagacagtg cttaaaaagt gtaaaagtgc    4320 ctttacatt ctaccatcta ttatctctaa tgagaagcaa gaaattcttg gaactgtttc    4380
ttggaatttg cgagaaatgc ttgcacatgc agaagaaaca cgcaaattaa tgcctgtctg    4440
tgtggaaact aaagccatag tttcaactat acagcgtaaa tataagggta ttaaaataca    4500
agagggtgtg gttgattatg gtgctagatt ttactttac accagtaaaa caactgtagc    4560
gtcacttatc aacacactta acgatctaaa tgaaactctt gttacaatgc cacttggcta    4620
tgtaacacat ggcttaaatt tggaagaagc tgctcggtat atgagatctc tcaaagtgcc    4680
agctacagtt tctgttttctt cacctgatgc tgttacagcg tataatggtt atcttacttc    4740
ttcttctaaa acacctgaag aacattttat tgaaaccatc tcacttgctg ttcctataa    4800 agattggtcc tattctggac aatctacaca actaggtata gaatttctta agagaggtga    4860
taaaagtgta tattacacta gtaatcctac cacattccac ctagatggtg aagttatcac    4920
ctttgacaat cttaagacac ttctttcttt gagagaagtg aggactatta aggtgtttac    4980
aacagtagac aacattaacc tccacacgca agttgtggca atgtcaatga catatggaca    5040
acagtttggt ccaacttatt tggatggagc tgatgttact aaaataaaac ctcataattc    5100
acatgaaggt aaaacatttt atgttttacc taatgatgac actctacgtg ttgaggcttt    5160
tgagtactac cacacaactg atccctagttt tctgggtagg tacatgtcag cattaaatca    5220
cactaaaaag tggaaatacc cacaagttaa tggtttaact tctattaaat gggcagataa    5280
caactgttat cttgccactg cattgttaac actccaacaa atagagttga gtttaatcc    5340 acctgctcta caagatgctt attacagagc aagggctggt gaagctgcta acttttgtgc    5400
acttatctta gcctactgta taaagacagt aggtgagtta ggtgatgtta gagaaacaat    5460
gagttacttg tttcaacatg ccaatttaga ttcttgcaaa agagtcttga acgtggtgtg    5520
taaaacttgt ggacaacagc agacaaccct taagggtgta gaagctgtta tgtacatggg    5580
cacactttct tatgaacaat ttaagaaagg tgttcagata ccttgtacgt gtggtaaaca    5640
```

```
agctacaaaa tatctagtac aacaggagtc acctttgtt atgatgtcag caccacctgc    5700
tcagtatgaa cttaagcatg gtacatttac ttgtgctagt gagtcactg gtaattacca    5760 gtgtggtcac tataaacata taacttctaa agaaactttg tattgcatag acggtgcttt    5820
acttacaaag tcctcagaat acaaaggtcc tattacggat gttttctaca agaaaacag    5880 ttacacaaca accataaaac cagttactta taaattggat ggtgttgttt gtacagaaat    5940
tgaccctaag ttggacaatt attataagaa agacaattct tatttcacag agcaaccaat    6000
tgatcttgta ccaaaccaac catatccaaa cgcaagcttc gataattta agtttgtatg    6060 tgataatatc aaatttgctg atgatttaaa ccagttaact ggttataaga aacctgcttc    6120
aagagagctt aaagttacat ttttccctga cttaaatggt gatgtggtgg ctattgatta    6180
taaacactac acaccctctt taagaaagg agctaaattg ttacataaac ctattgtttg    6240
gcatgttaac aatgcaacta ataaagccac gtataaacca atacctggt gtatacgttg    6300 tctttggagc acaaaaccag ttgaaacatc aaattcgttt gatgtactga agtcagagga    6360
cgcgcaggga atggataatc ttgcctgcga agatctaaaa ccagtctctg aagaagtagt    6420
ggaaaatcct accatacaga aagacgttct tgagtgtaat gtgaaaacta ccgaagttgt    6480
aggagacatt atacttaaac cagcaaataa tagtttaaaa attacagaag aggttggcca    6540
cacagatcta atggctgctt atgtagacaa ttctagtctt actattaaga aacctaatga    6600
attatctaga gtattaggtt tgaaaaccct tgctactcat ggtttagctg ctgttaatag    6660
tgtcccttgg gatactatag ctaattatgc taagccttt cttaacaaag ttgttagtac    6720
aactactaac atagttacac ggtgtttaaa ccgtgtttgt actaattata tgccttattt    6780 ctttactta ttgctacaat tgtgtactt tactagaagt acaaattcta gaattaaagc    6840
atctatgccg actactatag caaagaatac tgttaagagt gtcggtaaat tttgtctaga    6900
ggcttcattt aattatttga agtcacctaa ttttttctaaa ctgataaata ttataattg    6960 gttttacta ttaagtgttt gcctaggttc tttaatctac tcaaccgctg ctttaggtgt    7020
tttaatgtct aatttaggca tgccttctta ctgtactggt tacagagaag gctatttgaa    7080
ctctactaat gtcactattg caacctactg tactggttct ataccttgta gtgtttgtct    7140
tagtggttta gattctttag acacctatcc ttctttagaa actatacaaa ttaccatttc    7200 atctttaaa tgggatttaa ctgcttttgg cttagttgca gagtggtttt ggcatatat    7260 tcttttcact aggttttct atgtacttgg attggctgca atcatgcaat gtttttcag    7320 ctatttgca gtacatttta ttagtaattc ttggcttatg tggttaataa ttaatcttgt    7380
acaaatggcc ccgatttcag ctatggttag aatgtacatc ttctttgcat catttatta    7440 tgtatgaaaa agttatgtgc atgttgtaga cggttgtaat tcatcaactt gtatgatgtg    7500
ttacaaacgt aatagagcaa caagagtcga atgtacaact attgttaatg gtgttagaag    7560
gtccttttat gtctatgcta atggaggtaa aggctttgc aaactacaca attggaattg    7620
tgttaattgt gatacattct gtgctggtag tacatttat agtgatgaag ttgcgagaga    7680
cttgtcacta cagtttaaaa gaccaataaa tcctactgac cagtcttctt acatcgttga    7740
tagtgttaca gtgaagaatg gttccatcca tctttacttt gataaagctg gtcaaaagac    7800
ttatgaaaga cattctctct ctcatttgt taacttagac aacctgagag ctaataacac    7860
taaaggttca ttgcctatta tgttatagt ttttgatggt aaatcaaaat gtgaagaatc    7920
atctgcaaaa tcagcgtctg tttactacag tcagcttatg tgtcaaccta tactgttact    7980
agatcaggca ttagtgtctg atgttggtga tagtgcggaa gttgcagtta aatgtttga    8040
```

```
tgcttacgtt aatacgtttt catcaactttt taacgtacca atggaaaaac tcaaaacact  8100
agttgcaact gcagaagctg aacttgcaaa gaatgtgtcc ttagacaatg tcttatctac  8160
ttttatttca gcagctcggc aagggtttgt tgattcagat gtagaaacta agatgttgt   8220
tgaatgtctt aaattgtcac atcaatctga catagaagtt actggcgata gttgtaataa  8280
ctatatgctc acctataaca aagttgaaaa catgacaccc cgtgaccttg gtgcttgtat  8340
tgactgtagt gcgcgtcata ttaatgcgca ggtagcaaaa agtcacaaca ttgctttgat  8400
atggaacgtt aaagatttca tgtcattgtc tgaacaacta cgaaaacaaa tacgtagtgc  8460
tgctaaaaag aataacttac cttttaagtt gacatgtgca actactagac aagttgttaa  8520
tgttgtaaca acaaagatag cacttaaggg tggtaaaatt gttaataatt ggttgaagca  8580
gttaattaaa gttacacttg tgttccttt tgttgctgct attttctatt taataacacc    8640
tgttcatgtc atgtctaaac atactgactt ttcaagtgaa atcataggat acaaggctat  8700
tgatggtggt gtcactcgtg acatagcatc tacagatact tgttttgcta acaaacatgc  8760
tgattttgac acatggttta gccagcgtgg tggtagttat actaatgaca aagcttgccc  8820
attgattgct gcagtcataa caagagaagt gggttttgtc gtgcctggtt tgcctggcac  8880
gatattacgc acaactaatg gtgactttt gcatttctta cctagagttt ttagtgcagt    8940
tggtaacatc tgttcacac catcaaaact tatagagtac actgactttg caacatcagc    9000
ttgtgttttg gctgctgaat gtacaatttt taaagatgct tctggtaagc cagtaccata  9060
ttgttatgat accaatgtac tagaaggttc tgttgcttat gaaagtttac gccctgacac  9120
acgttatgtg ctcatggatg gctctattat tcaatttcct aacacctacc ttgaaggttc  9180
tgttagagtg gtaacaactt ttgattctga gtactgtagg cacggcactt gtgaaagatc  9240
agaagctggt gtttgtgtat ctactagtgg tagatgggta cttaacaatg attattacag  9300
atctttacca ggagttttct gtggtgtaga tgctgtaaat ttacttacta atatgtttac  9360
accactaatt caacctattg gtgctttgga catatcagca tctatagtag ctggtggtat  9420
tgtagctatc gtagtaacat gccttgccta ctattttatg aggttagaa gagcttttgg    9480
tgaatacagt catgtagttg cctttaatac tttactattc cttatgtcat tcactgtact  9540
ctgtttaaca ccagtttact cattcttacc tggtgtttat tctgttattt acttgtactt  9600
gacatttat cttactaatg atgtttcttt tttagcacat attcagtgga tggttatgtt    9660
cacacccttta gtaccttct ggataacaat tgcttatatc atttgtattt ccacaaagca    9720
tttctattgg ttctttagta attacctaaa gagacgtgta gtctttaatg gtgtttcctt  9780
tagtacttt gaagaagctg cgctgtgcac cttttgtta aataaagaaa tgtatctaaa     9840
gttgcgtagt gatgtgctat tacctcttac gcaatataat agatacttag ctctttataa  9900
taagtacaag tattttagtg gagcaatgga tacaactagc tacagagaag ctgcttgttg  9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaacct aattatgaag atttactcat tcgtaagtct aatcataatt cttggtaca    10260
ggctggtaat gttcaactca gggttattgg acattctatg caaaattgtg tacttaagct  10320
taaggttgat acagccaatc ctaagacacc taagtataag tttgttcgca ttcaaccagg  10380
```

```
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggacctttg ttgacaggca  10620 aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca ccttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520 gttttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg caaaccttg   11820 tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgtttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaattga   12240 ccgtgatgca gccatgcaac gtaagttgga aaagatggct gatcaagcta tgacccaaat  12300
gtataaacag ctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaaactg cttgcactgat gacaatgcgt tagcttacta  12780
```

```
caacacaaca aagggaggta ggtttgtact tgcactgtta tccgatttac aggatttgaa    12840
atgggctaga ttccctaaga gtgatggaac tggtactatc tatacagaac tggaaccacc    12900
ttgtaggttt gttacagaca cacctaaagg tcctaaagtg aagtatttat actttattaa    12960
aggattaaac aacctaaata gaggtatggt acttggtagt ttagctgcca cagtacgtct    13020
acaagctggt aatgcaacag aagtgcctgc caattcaact gtattatctt tctgtgcttt    13080
tgctgtagat gctgctaaag cttacaaaga ttatctagct agtggggac aaccaatcac     13140 taattgtgtt aagatgttgt gtacacacac tggtactggt caggcaataa cagttacacc    13200
ggaagccaat atggatcaag aatcctttgg tggtgcatcg tgttgtctgt actgccgttg    13260
ccacatagat catccaaatc ctaaaggatt ttgtgactta aaaggtaagt atgtacaaat    13320
acctacaact tgtgctaatg accctgtggg ttttacactt aaaaacacag tctgtaccgt    13380
ctgcggtatg tggaaaggtt atggctgtag ttgtgatcaa ctccgcgaac ccatgcttca    13440
gtcagctgat gcacaatcgt ttttaaacgg gtttgcggtg taagtgcagc ccgtcttaca    13500
ccgtgcggca caggcactag tactgatgtc gtatacaggg cttttgacat ctacaatgat    13560
aaagtagctg ttttgctaa attcctaaaa actaattgtt gtcgcttcca agaaaaggac      13620
gaagatgaca atttaattga ttcttacttt gtagttaaga gacacacttt ctctaactac    13680
caacatgaag aaacaattta taatttactt aaggattgtc cagctgttgc taaacatgac    13740
ttctttaagt ttagaataga cggtgacatg gtaccacata tatcacgtca acgtcttact    13800
aaatacacaa tggcagacct cgtctatgct ttaaggcatt ttgatgaagg taattgtgac    13860
acattaaaag aaatacttgt cacatacaat tgttgtgatg atgattattt caataaaaag    13920
gactggtatg attttgtaga aaacccagat atattacgcg tatacgccaa cttaggtgaa    13980
cgtgtacgcc aagctttgtt aaaaacagta caattctgtg atgccatgcg aaatgctggt    14040
attgttggtg tactgacatt agataatcaa gatctcaatg gtaactggta tgatttcggt    14100
gatttcatac aaaccacgcc aggtagtgga gttcctgttg tagattctta ttattcattg    14160
ttaatgccta tattaacctt gaccagggct ttaactgcag agtcacatgt tgacactgac    14220
ttaacaaagc cttacattaa gtgggatttg ttaaaatatg acttcacgga agagaggtta    14280
aaactctttg accgttattt taaatattgg gatcagacat accacccaaa ttgtgttaac    14340
tgtttggatg acagatgcat tctgcattgt gcaaacttta atgttttatt ctctacagtg    14400
ttcccaccta caagttttgg accactagtg agaaaaatat ttgttgatgg tgttccattt    14460
gtagtttcaa ctggatacca cttcagagag ctaggtgttg tacataatca ggatgtaaac    14520
ttacatagct ctagacttag ttttaaggaa ttacttgtgt atgctgctga ccctgctatg    14580
cacgctgctt ctgtaatct attactagat aaacgcacta cgtgctttc agtagctgca    14640 cttactaaca atgttgcttt tcaaactgtc aaacccggta atttttaacaa agacttctat    14700 gactttgctg tgtctaaggg tttctttaag gaaggaagtc tgttgaatt aaaacacttc    14760 ttctttgctc aggatggtaa tgctgctatc agcgattatg actactatcg ttataatcta    14820
ccaacaatgt gtgatatcag acaactacta tttgtagttg aagttgttga taagtacttt    14880
gattgttacg atggtggctg tattaatgct aaccaagtca tcgtcaacaa cctagacaaa    14940
tcagctggtt ttccatttaa taaatggggt aaggctagac tttattatga ttcaatgagt    15000
tatgaggatc aagatgcact tttcgcatat acaaaacgta atgtcatccc tactataact    15060
caaatgaatc ttaagtatgc cattagtgca aagaatagag ctcgcaccgt agctggtgtc    15120
```

```
tctatctgta gtactatgac caatagacag tttcatcaaa aattattgaa atcaatagcc    15180
gccactagag gagctactgt agtaattgga acaagcaaat tctatggtgg ttggcacaac    15240
atgttaaaaa ctgtttatag tgatgtagaa aaccctcacc ttatgggttg ggattatcct    15300
aaatgtgata gagccatgcc taacatgctt agaattatgg cctcacttgt tcttgctcgc    15360
aaacatacaa cgtgttgtag cttgtcacac cgtttctata gattagctaa tgagtgtgct    15420
caagtattga gtgaaatggt catgtgtggc ggttcactat atgttaaacc aggtggaacc    15480
tcatcaggag atgccacaac tgcttatgct aatagtgttt ttaacatttg tcaagctgtc    15540
acggccaatg ttaatgcact tttatctact gatggtaaca aaattgccga taagtatgtc    15600
cgcaatttac aacacagact ttatgagtgt ctctatagaa atagagatgt tgacacagac    15660
tttgtgaatg agttttacgc atatttgcgt aaacatttct caatgatgat actctctgac    15720
gatgctgttg tgtgtttcaa tagcacttat gcatctcaag gtctagtggc tagcataaag    15780
aactttaagt cagttcttta ttatcaaaac aatgttttta tgtctgaagc aaaatgttgg    15840
actgagactg accttactaa aggacctcat gaattttgct ctcaacatac aatgctagtt    15900
aaacagggtg atgattatgt gtaccttcct tacccagatc catcaagaat cctaggggcc    15960
ggctgttttg tagatgatat cgtaaaaaca gatggtacac ttatgattga acggttcgtg    16020
tctttagcta tagatgctta cccacttact aaacatccta atcaggagta tgctgatgtc    16080
tttcatttgt acttacaata cataagaaag ctacatgatg agttaacagg acacatgtta    16140
gacatgtatt ctgttatgct tactaatgat aacacttcaa ggtattggga acctgagttt    16200
tatgaggcta tgtacacacc gcatacagtc ttacaggctg ttggggcttg tgttctttgc    16260
aattcacaga cttcattaag atgtggtgct tgcatacgta gaccattctt atgttgtaaa    16320
tgctgttacg accatgtcat atcaacatca cataaattag tcttgtctgt taatccgtat    16380
gtttgcaatg ctccaggttg tgatgtcaca gatgtgactc aactttactt aggaggtatg    16440
agctattatt gtaaatcaca taaaccaccc attagttttc cattgtgtgc taatggacaa    16500 gttttttggtt tatataaaaa tacatgtgtt ggtagcgata atgttactga ctttaatgca    16560
attgcaacat gtgactggac aaatgctggt gattacattt tagctaacac ctgtactgaa    16620
agactcaagc ttttttgcagc agaaacgctc aaagctactg aggagacatt taaactgtct    16680
tatggtattg ctactgtacg tgaagtgctg tctgacagag aattacatct ttcatgggaa    16740
gttggtaaac ctagaccacc acttaaccga aattatgtct ttactggtta tcgtgtaact    16800
aaaaacagta agtacaaat aggagagtac acctttgaaa aaggtgacta tggtgatgct    16860
gttgtttacc gaggtacaac aacttacaaa ttaaatgttg gtgattattt tgtgctgaca    16920
tcacatacag taatgccatt aagtgcacct acactagtgc cacaagagca ctatgttaga    16980
attactggct tatacccaac actcaatatc tcagatgagt tttctagcaa tgttgcaaat    17040
tatcaaaagg ttggtatgca aaagtattct acactccagg gaccacctgg tactggtaag    17100
agtcattttg ctattggcct agctctctac taccctctg ctcgcatagt gtatacagct    17160
tgctctcatg ccgctgttga tgcactatgt gagaaggcat taaaatattt gcctatagat    17220
aaatgtagta gaattatacc tgcacgtgct cgtgtagagt gttttgataa attcaaagtg    17280
aattcaacat tagaacagta tgtctttttgt actgtaaatg cattgcctga cgacagca    17340 gatatagttg tctttgatga aatttcaatg gccacaaatt atgatttgag tgttgtcaat    17400
gccagattac gtgctaagca ctatgtgtac attggcgacc ctgctcaatt acctgcacca    17460
cgcacattgc taactaaggg cacactagaa ccagaatatt tcaattcagt gtgtagactt    17520
```

```
atgaaaacta taggtccaga catgttcctc ggaacttgtc ggcgttgtcc tgctgaaatt   17580
gttgacactg tgagtgcttt ggtttatgat aataagctta aagcacataa agacaaatca   17640
gctcaatgct ttaaaatgtt ttataagggt gttatcacgc atgatgtttc atctgcaatt   17700
aacaggccac aaataggcgt ggtaagagaa ttccttacac gtaaccctgc ttggagaaaa   17760
gctgtcttta tttcacctta taattcacag aatgctgtag cctcaaagat tttgggacta   17820
ccaactcaaa ctgttgattc atcacagggc tcagaatatg actatgtcat attcactcaa   17880
accactgaaa cagctcactc ttgtaatgta aacagattta atgttgctat taccagagca   17940
aaagtaggca tactttgcat aatgtctgat agagacctt  atgacaagtt gcaatttaca   18000
agtcttgaaa ttccacgtag gaatgtggca actttacaag ctgaaaatgt aacaggactc   18060
tttaaagatt gtagtaaggt aatcactggg ttacatccta cacaggcacc tacacacctc   18120
agtgttgaca ctaaattcaa aactgaaggt ttatgtgttg acatacctgg catacctaag   18180
gacatgacct atagaagact catctctatg atgggtttta aaatgaatta tcaagttaat   18240
ggttacccta acatgtttat cacccgcgaa gaagctataa gacatgtacg tgcatggatt   18300
ggcttcgatg tcgaggggtg tcatgctact agagaagctg ttggtaccaa tttacctta   18360 cagctaggtt tttctacagg tgttaaccta gttgctgtac ctacaggtta tgttgataca   18420
cctaataata cagatttttc cagagttagt gctaaaccac cgcctggaga tcaatttaaa   18480
cacctcatac cacttatgta caaggactt  ccttggaatg tagtgcgtat aaagattgta   18540
caaatgttaa gtgacacact taaaaatctc tctgacagag tcgtatttgt cttatgggca   18600
catggctttg agttgacatc tatgaagtat tttgtgaaaa taggacctga gcgcacctgt   18660
tgtctatgtg atagacgtgc cacatgcttt tccactgctt cagacactta tgcctgttgg   18720
catcattcta ttggatttga ttacgtctat aatccgttta tgattgatgt tcaacaatgg   18780
ggttttacag gtaacctaca agcaaccat  gatctgtatt gtcaagtcca tggtaatgca   18840
catgtagcta gttgtgatgc aatcatgact aggtgtctag ctgtccacga gtgctttgtt   18900
aagcgtgttg actggactat tgaatatcct ataattggtg atgaactgaa gattaatgcg   18960
gcttgtagaa aggttcaaca catggttgtt aaagctgcat tattagcaga caaattccca   19020
gttcttcacg acattggtaa ccctaaagct attaagtgtg tacctcaagc tgatgtagaa   19080
tggaagttct atgatgcaca gccttgtagt gacaaagctt ataaaataga agaattattc   19140
tattcttatg ccacacattc tgacaaattc acagatggtg tatgcctatt ttggaattgc   19200
aatgtcgata gatatcctgc taattccatt gtttgtagat tgacactag agtgctatct   19260 aaccttaact tgcctggttg tgatggtggc agtttgtatg taaataaaca tgcattccac   19320
acaccagctt ttgataaaag tgcttttgtt aatttaaaac aattaccatt tttctattac   19380
tctgacagtc catgtgagtc tcatggaaaa caagtagtgt cagatataga ttatgtacca   19440
ctaaagtctg ctacgtgtat aacacgttgc aatttaggtg gtgctgtctg tagacatcat   19500
gctaatgagt acagattgta tctcgatgct tataacatga tgatctcagc tggctttagc   19560
ttgtgggttt acaaacaatt tgatacttat aacctctgga acacttttac aagacttcag   19620
agtttagaaa atgtggcttt taatgttgta aataaggaca ctttgatgg  acaacaggt   19680 gaagtaccag tttctatcat taataacact gtttacacaa agttgatgg tgttgatgta   19740 gaattgtttg aaaataaaac aacattacct gttaatgtag catttgagct ttgggctaag   19800
cgcaacatta aaccagtacc agaggtgaaa atactcaata atttgggtgt ggacattgct   19860
```

```
gctaatactg tgatctggga ctacaaaaga gatgctccag cacatatatc tactattggt    19920
gtttgttcta tgactgacat agccaagaaa ccaactgaaa cgatttgtgc accactcact    19980
gtcttttttg atggtagagt tgatggtcaa gtagacttat ttagaaatgc ccgtaatggt    20040
gttcttatta cagaaggtag tgttaaaggt ttacaaccat ctgtaggtcc caaacaagct    20100
agtcttaatg gagtcacatt aattggagaa gccgtaaaaa cacagttcaa ttattataag    20160
aaagttgatg gtgttgtcca acaattacct gaaacttact ttactcagag tagaaattta    20220
caagaattta aacccaggag tcaaatggaa attgatttct tagaattagc tatggatgaa    20280
ttcattgaac ggtataaatt agaaggctat gccttcgaac atatcgttta tggagatttt    20340
agtcatagtc agttaggtgg tttacatcta ctgattggac tagctaaacg ttttaaggaa    20400 tcacctttg aattagaaga ttttattcct atggacagta cagttaaaaa ctatttcata    20460
acagatgcgc aaacaggttc atctaagtgt gtgtgttctg ttattgattt attacttgat    20520
gattttgttg aaataataaa atcccaagat ttatctgtag tttctaaggt tgtcaaagtg    20580
actattgact atacagaaat ttcatttatg ctttggtgta agatggcca tgtagaaaca    20640 ttttacccaa aattcaaatc tagtcaagcg tggcaaccgg tgttgctat gcctaatctt    20700 tacaaaatgc aaagaatgct attagaaaag tgtgaccttc aaaattatgg tgatagtgca    20760
acattaccta aaggcataat gatgaatgtc gcaaaatata ctcaactgtg tcaatattta    20820
aacacattaa cattagctgt accctataat atgagagtta tacattttgg tgctggttct    20880
gataaaggag ttgcaccagg tacagctgtt ttaagacagt ggttgcctac gggtacgctg    20940
cttgtcgatt cagatcttaa tgactttgtc tctgatgcag attcaacttt gattggtgat    21000
tgtgcaactg tacatacagc taataaatgg gatctcatta ttagtgatat gtacgaccct    21060
aagactaaaa atgttacaaa agaaaatgac tctaaagagg gttttttcac ttacatttgt    21120
gggtttatac aacaaagct agctcttgga ggttccgtgg ctataaagat aacagaacat    21180
tcttggaatg ctgatcttta taagctcatg ggacacttcg catggtggac agcctttgtt    21240
actaatgtga atgcgtcatc atctgaagca ttttttaattg gatgtaatta tcttggcaaa    21300
ccacgcgaac aaatagatgg ttatgtcatg catgcaaatt acatattttg gaggaataca    21360
aatccaattc agttgtcttc ctattctta tttgacatga gtaaatttcc ccttaaatta    21420 agggtactg ctgttatgtc tttaaaagaa ggtcaaatca atgatatgat ttatctctt    21480 cttagtaaag gtagacttat aattagagaa acaacagag ttgttatttc tagtgatgtt    21540
cttgttaaca actaaacgaa caatgttgt ttttcttgtt ttattgccac tagtctctag    21600
tcagtgtgtt aatcttacaa ccagaactca attacccct gcatacacta attctttcac    21660
acgtggtgtt tattaccctg acaaagtttt cagatcctca gttttacatt caactcagga    21720
cttgttctta cctttcttt ccaatgttac ttggttccat gctatacatg tctctgggac    21780
caatggtact aagaggtttg ataaccctgt cctaccattt aatgatggtg tttatttgc    21840 ttccactgag aagtctaaca taataagagg ctggattttt ggtactactt tagattcgaa    21900
gacccagtcc ctacttattg ttaataacgc tactaatgtt gttattaaag tctgtgaatt    21960 tcaatttgt aatgatccat ttttgggtgt ttattaccac aaaaacaaca aaagttggat    22020
ggaaagtgag ttcagagttt attctagtgc gaataattgc acttttgaat atgtctctca    22080
gccttttctt atggaccttg aaggaaaaca gggtaatttc aaaaatctta gggaatttgt    22140
gtttaagaat attgatggtt attttaaaat atattctaag cacacgccta ttaatttagt    22200
gcgtgatctc cctcagggtt tttcggcttt agaaccattg gtagatttgc caataggtat    22260
```

```
taacatcact aggtttcaaa ctttacttgc tttacataga agttatttga ctcctggtga    22320
ttcttcttca ggttggacag ctggtgctgc agcttattat gtgggttatc ttcaacctag    22380
gacttttcta ttaaaatata atgaaaatgg aaccattaca gatgctgtag actgtgcact    22440
tgaccctctc tcagaaacaa agtgtacgtt gaaatccttc actgtagaaa aaggaatcta    22500
tcaaacttct aactttagag tccaaccaac agaatctatt gttagatttc ctaatattac    22560
aaacttgtgc cctttggtg aagttttaa cgccaccaga tttgcatctg tttatgcttg       22620
gaacaggaag agaatcagca actgtgttgc tgattattct gtcctatata attccgcatc    22680 atttccact tttaagtgtt atggagtgtc tcctactaaa ttaaatgatc tctgctttac      22740
taatgtctat gcagattcat ttgtaattag aggtgatgaa gtcagacaaa tcgctccagg    22800
gcaaactgga aagattgctg attataatta taaattacca gatgatttta caggctgcgt    22860
tatagcttgg aattctaaca atcttgattc taaggttggt ggtaattata attacctgta    22920
tagattgttt aggaagtcta atctcaaacc ttttgagaga gatatttcaa ctgaaatcta    22980
tcaggccggt agcacacctt gtaatggtgt tgaaggtttt aattgttact tcccttaca    23040 atcatatggt ttccaaccca ctaatggtgt tggttaccaa ccatacagag tagtagtact    23100
ttcttttgaa cttctacatg caccagcaac tgtttgtgga cctaaaaagt ctactaattt    23160
ggttaaaaac aaatgtgtca atttcaactt caatggttta acaggcacag gtgttcttac    23220
tgagtctaac aaaaagtttc tgcctttcca acaatttggc agagacattg ctgacactac    23280
tgatgctgtc cgtgatccac agacacttga gattcttgac attacaccat gttcttttgg    23340
tggtgtcagt gttataacac caggaacaaa tacttctaac caggttgctg ttctttatca    23400
ggatgttaac tgcacagaag tccctgttgc tattcatgca gatcaactta ctcctacttg    23460
gcgtgtttat tctacaggtt ctaatgtttt tcaaacacgt gcaggctgtt taataggggc    23520
tgaacatgtc aacaactcat atgagtgtga catacccatt ggtgcaggta tatgcgctag    23580
ttatcagact cagactaatt ctcctcggcg ggcacgtagt gtagctagtc aatccatcat    23640
tgcctacact atgtcacttg gtgcagaaaa ttcagttgct tactctaata actctattgc    23700
catacccaca aatttactta ttagtgttac cacagaaatt ctaccagtgt ctatgaccaa    23760
gacatcagta gattgtacaa tgtacatttg tggtgattca actgaatgca gcaatctttt    23820
gttgcaatat ggcagttttt gtacacaatt aaaccgtgct ttaactggaa tagctgttga    23880
acaagacaaa aacacccaag aagttttgc acaagtcaaa caaatttaca aaacaccacc    23940
aattaaagat tttggtggtt ttaattttc acaaatatta ccagatccat caaaaccaag    24000
caagaggtca tttattgaag atctacttt caacaaagtg acacttgcag atgctggctt    24060
catcaaacaa tatggtgatt gccttggtga tattgctgct agagacctca tttgtgcaca    24120
aaagtttaac ggccttactg ttttgccacc tttgctcaca gatgaaatga ttgctcaata    24180
cacttctgca ctgttagcgg gtacaatcac ttctggttgg accttggtg caggtgctgc    24240 attacaaata ccatttgcta tgcaaatggc ttataggttt aatggtattg gagttacaca    24300
gaatgttctc tatgagaacc aaaaattgat tgccaaccaa tttaatagtg ctattggcaa    24360
aattcaagac tcactttctt ccacagcaag tgcacttgga aaacttcaag atgtggtcaa    24420
ccaaaatgca caagctttaa acacgcttgt taaacaactt agctccaatt ttggtgcaat    24480
ttcaagtgtt ttaaatgata tcctttcacg tcttgacaaa gttgaggctg aagtgcaaat    24540
tgataggttg atcacaggca gacttcaaag tttgcagaca tatgtgactc aacaattaat    24600
```

```
tagagctgca gaaatcagag cttctgctaa tcttgctgct actaaaatgt cagagtgtgt   24660
acttggacaa tcaaaaagag ttgatttttg tggaaagggc tatcatctta tgtccttccc   24720
tcagtcagca cctcatggtg tagtcttctt gcatgtgact tatgtccctg cacaagaaaa   24780
gaacttcaca actgctcctg ccatttgtca tgatggaaaa gcacactttc ctcgtgaagg   24840
tgtctttgtt tcaaatggca cacactggtt tgtaacacaa aggaattttt atgaaccaca   24900
aatcattact acagacaaca catttgtgtc tggtaactgt gatgttgtaa taggaattgt   24960
caacaacaca gtttatgatc cttttgcaacc tgaattagac tcattcaagg aggagttaga   25020
taaatatttt aagaatcata catcaccaga tgttgattta ggtgacatct ctggcattaa   25080
tgcttcagtt gtaaacattc aaaaagaaat tgaccgcctc aatgaggttg ccaagaattt   25140
aaatgaatct ctcatcgatc tccaagaact tggaaagtat gagcagtata taaaatggcc   25200
atggtacatt tggctaggtt ttatagctgg cttgattgcc atagtaatgg tgacaattat   25260
gctttgctgt atgaccagtt gctgtagttg tctcaagggc tgttgttctt gtggatcctg   25320
ctgcaaattt gatgaagacg actctgagcc agtgctcaaa ggagtcaaat tacattacac   25380
ataaacgaac ttatggattt gtttatgaga atcttcacaa ttggaactgt aactttgaag   25440
caaggtgaaa tcaaggatgc tactccttca gattttgttc gcgctactgc aacgataccg   25500
atacaagcct cactcccttt cggatggctt attgttggcg ttgcacttct tgctgttttt   25560
cagagcgctt ccaaaatcat aaccctcaaa agagatggc aactagcact ctccaagggt   25620
gttcactttg tttgcaactt gctgttgttg tttgtaacag tttactcaca ccttttgctc   25680
gttgctgctg gccttgaagc ccctttctc tatcttatg ctttagtcta cttcttgcag   25740
agtataaact ttgtaagaat aataatgagg ctttggcttt gctggaaatg ccgttccaaa   25800
aacccattac tttatgatgc caactatttt ctttgctggc atactaattg ttacgactat   25860
tgtataccct acaatagtgt aacttcttca attgtcatta cttcaggtga tggcacaaca   25920
agtcctattt ctgaacatga ctaccagatt ggtggttata ctgaaaaatg ggaatctgga   25980
gtaaaagact gtgttgtatt acacagttac ttcacttcag actattacca gctgtactca   26040
actcaattga gtacagacac tggtgttgaa catgttacct tcttcatcta caataaaatt   26100
gttgatgagc ctgaagaaca tgtccaaatt cacacaatcg acggttcatc cggagttgtt   26160
aatccagtaa tggaaccaat ttatgatgaa ccgacgacga ctactagcgt gcctttgtaa   26220
gcacaagctg atgagtacga acttatgtac tcattcgttt cggaagagac aggtacgtta   26280
atagttaata gcgtacttct ttttcttgct ttcgtggtat tcttgctagt tacactagcc   26340
atccttactg cgcttcgatt gtgtgcgtac tgctgcaata ttgttaacgt gagtcttgta   26400
aaaccttctt tttacgttta ctctcgtgtt aaaaatctga attcttctag agttcctgat   26460
cttctggtct aaacgaacta aatattatat tagttttct gtttggaact ttaattttag   26520
ccatggcaga ttccaacggt actattaccg ttgaagagct aaaaagctc cttgaacaat   26580
ggaacctagt aataggtttc ctattcctta catggatttg tcttctacaa tttgcctatg   26640
ccaacaggaa taggtttttg tatataatta agttaatttt cctctggctg ttatggccag   26700
taactttagc ttgttttgtg cttgctgctg tttacagaat aaattggatc accgtggaa   26760
ttgctatcgc aatggcttgt cttgtaggct tgatgtggct cagctacttc attgcttctt   26820
tcagactgtt tgcgcgtacg cgttccatgt ggtcattcaa tccagaaact aacattcttc   26880
tcaacgtgcc actccatggc actattctga ccagaccgct tctagaaagt gaactcgtaa   26940
tcggagctgt gatccttcgt ggacatcttc gtattgctgg acaccatcta ggacgctgtg   27000
```

```
acatcaagga cctgcctaaa gaaatcactg ttgctacatc acgaacgctt tcttattaca   27060
aattgggagc ttcgcagcgt gtagcaggtg actcaggttt tgctgcatac agtcgctaca   27120
ggattggcaa ctataaatta aacacagacc attccagtag cagtgacaat attgctttgc   27180
ttgtacagta agtgacaaca gatgtttcat ctcgttgact ttcaggttac tatagcagag   27240
atattactaa ttattatgag gacttttaaa gtttccattt ggaatcttga ttacatcata   27300
aacctcataa ttaaaaattt atctaagtca ctaactgaga ataaatattc tcaattagat   27360
gaagagcaac caatggagat tgattaaacg aacatgaaaa ttattctttt cttggcactg   27420
ataacactcg ctacttgtga gctttatcac taccaagagt gtgttagagg tacaacagta   27480
cttttaaaag aaccttgctc ttctggaaca tacgagggca attccaccatt tcatcctcta   27540
gctgataaca aatttgcact gacttgcttt agcactcaat tgcttttgc ttgtcctgac   27600
ggcgtaaaac acgtctatca gttacgtgcc agatcagttt cacctaaact gttcatcaga   27660
caagaggaag ttcaagaact ttactctcca attttttctta ttgttgcggc aatagtgttt   27720
ataacacttt gcttcacact caaaagaaag acagaatgat tgaactttca ttaattgact   27780
tctatttgtg ctttttagcc tttctgctat tccttgtttt aattatgctt attatctttt   27840
ggttctcact tgaactgcaa gatcataatg aaacttgtca cgcctaaacg aacatgaaat   27900
ttcttgttttt cttaggaatc atcacaactg tagctgcatt tcaccaagaa tgtagtttac   27960
agtcatgtac tcaacatcaa ccatatgtag ttgatgaccc gtgtcctatt cacttctatt   28020
ctaaatggta tattagagta ggagctagaa aatcagcacc tttaattgaa ttgtgcgtgg   28080
atgaggctgg ttctaaatca cccattcagt acatcgatat cggtaattat acagtttcct   28140
gtttaccttt tacaattaat tgccaggaac ctaaattggg tagtcttgta gtgcgttgtt   28200
cgttctatga agactttta gagtatcatg acgttcgtgt tgttttagat ttcatctaaa   28260
cgaacaaact aaaatgtctg ataatggacc ccaaaatcag cgaaatgcac cccgcattac   28320
gtttggtgga ccctcagatt caactggcag taaccagaat ggagaacgca gtggggcgcg   28380
atcaaaacaa cgtcggcccc aaggtttacc caataatact gcgtcttggt tcaccgctct   28440
cactcaacat ggcaaggaag accttaaatt ccctcgagga caaggcgttc caattaacac   28500
caatagcagt ccagatgacc aaattggcta ctaccgaaga gctaccagac gaattcgtgg   28560
tggtgacggt aaaatgaaag atctcagtcc aagatggtat ttctactacc taggaactgg   28620
gccagaagct ggacttccct atggtgctaa caaagacggc atcatatggg ttgcaactga   28680
gggagccttg aatacaccaa aagatcacat tggcacccgc aatcctgcta acaatgctgc   28740
aatcgtgcta caacttcctc aaggaacaac attgccaaaa ggcttctacg cagaagggag   28800
cagaggcggc agtcaagcct cttctcgttc ctcatcacgt agtcgcaaca gttcaagaaa   28860
ttcaactcca ggcagcagta ggggaacttc tcctgctaga atggctggca atggcggtga   28920
tgctgctctt gctttgctgc tgcttgacag attgaaccag cttgagagca aaatgtctgg   28980
taaaggccaa caacaacaag gccaaactgt cactaagaaa tctgctgctg aggcttctaa   29040
gaagcctcgg caaaaacgta ctgccactaa agcatacaat gtaacacaag ctttcggcag   29100
acgtggtcca gaacaaaccc aaggaaattt tggggaccag gaactaatca gacaaggaac   29160
tgattacaaa cattggccgc aaattgcaca atttgccccc agcgcttcag cgttcttcgg   29220
aatgtcgcgc attggcatgg aagtcacacc ttcgggaacg tggttgacct acacaggtgc   29280
catcaaattg gatgacaaag atccaaattt caaagatcaa gtcattttgc tgaataagca   29340
```

-continued

```
tattgacgca tacaaaacat tcccaccaac agagcctaaa aaggacaaaa agaagaaggc    29400
tgatgaaact caagccttac cgcagagaca gaagaaacag caaactgtga ctcttcttcc    29460
tgctgcagat ttggatgatt tctccaaaca attgcaacaa tccatgagca gtgctgactc    29520
aactcaggcc taaactcatg cagaccacac aaggcagatg ggctatataa acgttttcgc    29580
ttttccgttt acgatatata gtctactctt gtgcagaatg aattctcgta actacatagc    29640
acaagtagat gtagttaact ttaatctcac atagcaatct ttaatcagtg tgtaacatta    29700
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aaaaaaaaaa aaaaaaaaaa aaa                                            29903
```